United States Patent
Reeves et al.

(10) Patent No.: US 12,410,163 B2
(45) Date of Patent: Sep. 9, 2025

(54) COMPOUNDS AS GLP-IR AGONISTS

(71) Applicant: Terns Pharmaceuticals, Inc., Foster City, CA (US)

(72) Inventors: Corey Reeves, Foster City, CA (US); Christopher T. Jones, Foster City, CA (US); Kevin Quinn, Foster City, CA (US); Gary W. Luehr, Foster City, CA (US)

(73) Assignee: Terns Pharmaceuticals, Inc.

( * ) Notice: Subject to any disclaimer, the term of this patent is extended or adjusted under 35 U.S.C. 154(b) by 85 days.

(21) Appl. No.: 18/173,426

(22) Filed: Feb. 23, 2023

(65) Prior Publication Data

US 2023/0322758 A1    Oct. 12, 2023

Related U.S. Application Data

(60) Provisional application No. 63/313,160, filed on Feb. 23, 2022.

(51) Int. Cl.
| | | |
|---|---|---|
| *C07D 417/14* | (2006.01) | |
| *A61P 1/16* | (2006.01) | |
| *C07D 403/14* | (2006.01) | |
| *C07D 405/14* | (2006.01) | |

(52) U.S. Cl.
CPC .............. *C07D 417/14* (2013.01); *A61P 1/16* (2018.01); *C07D 403/14* (2013.01); *C07D 405/14* (2013.01)

(58) Field of Classification Search
CPC .. C07D 417/14; C07D 403/14; C07D 405/14; C07D 401/14; A61P 1/16; A61P 3/00; A61P 9/00; A61P 3/04; A61P 3/10; A61K 31/444; A61K 31/498
See application file for complete search history.

(56) References Cited

U.S. PATENT DOCUMENTS

| | | |
|---|---|---|
| 5,665,732 A | 9/1997 | Baker et al. |
| 5,714,498 A | 2/1998 | Kulagowski et al. |
| 5,763,263 A | 6/1998 | Dehlinger |
| 5,780,475 A | 7/1998 | Baker et al. |
| 9,764,003 B2 | 9/2017 | Jensen |
| 10,208,019 B2 | 2/2019 | Aspnes et al. |
| 10,335,462 B2 | 7/2019 | Jensen |
| 10,669,259 B2 | 6/2020 | Aspnes et al. |
| 10,844,049 B2 | 11/2020 | Zhong |
| 10,851,081 B2 | 12/2020 | Aspnes et al. |
| 11,512,070 B2 | 11/2022 | Aspnes et al. |
| 11,584,751 B1 | 2/2023 | Ren et al. |
| 11,918,623 B2 | 3/2024 | Corvari et al. |
| 12,024,507 B2 | 7/2024 | Reeves et al. |
| 2003/0162790 A1 | 8/2003 | Cowart et al. |
| 2003/0176438 A1 | 9/2003 | Arienti et al. |
| 2004/0127504 A1 | 7/2004 | Cowart et al. |
| 2005/0004114 A1 | 1/2005 | Whitehouse et al. |
| 2007/0244126 A1 | 10/2007 | Edwards et al. |
| 2008/0280933 A1 | 11/2008 | Efremov et al. |
| 2012/0028959 A1 | 2/2012 | Thunuguntla et al. |
| 2018/0170908 A1 | 6/2018 | Aspnes et al. |
| 2019/0119255 A1 | 4/2019 | Aspnes et al. |
| 2020/0071306 A1 | 3/2020 | Esler et al. |
| 2021/0047298 A1 | 2/2021 | Aspnes et al. |
| 2022/0089578 A1 | 3/2022 | Romero et al. |
| 2022/0348564 A1 | 11/2022 | Ren et al. |
| 2023/0124938 A1 | 4/2023 | Aspnes et al. |
| 2023/0150998 A1 | 5/2023 | Reeves et al. |
| 2023/0159512 A1 | 5/2023 | Reeves et al. |
| 2023/0322744 A1 | 10/2023 | Romero et al. |
| 2024/0360122 A1 | 10/2024 | Bian et al. |
| 2024/0368120 A1 | 11/2024 | Luehr et al. |
| 2024/0391910 A1 | 11/2024 | Reeves et al. |

FOREIGN PATENT DOCUMENTS

| | | | |
|---|---|---|---|
| CN | 113480534 A | 10/2021 | |
| CN | 113493447 A | 10/2021 | |
| EP | 3555064 B1 | 11/2022 | |
| JP | 2019099571 A | 6/2019 | |
| TW | 202128659 A | 8/2021 | |
| WO | WO-2010114957 A1 | 10/2010 | |
| WO | WO-2011143365 A1 | 11/2011 | |
| WO | WO-2015166398 A1 | 11/2015 | |
| WO | WO-2018056453 A1 | 3/2018 | |
| WO | WO-2018109607 A1 | 6/2018 | |

(Continued)

OTHER PUBLICATIONS

International Preliminary Report on Patentability, mailed Mar. 2, 2023, for International Application No. PCT/US2021/047015, 8 pages.
International Search Report and Written Opinion for International Application No. PCT/US2021/047015, mailed Jan. 13, 2022, 11 Pages.
International Search Report and Written Opinion for International Application No. PCT/US2022/047687 dated Feb. 16, 2023, 13 pages.
International Search Report and Written Opinion, mailed Dec. 5, 2022, for International Application No. PCT/US2022/044915 (13 total pages).
Invitation to Pay Additional Fees and, Where Applicable, Protest Fee, dated Oct. 25, 2021, for International Application No. PCT/US2021/047015 (2 total pages).

(Continued)

*Primary Examiner* — Joseph K McKane
*Assistant Examiner* — Anna Grace Kuckla
(74) *Attorney, Agent, or Firm* — Cooley LLP

(57) ABSTRACT

The present application provides compounds that may be used as a glucagon-like peptide-1 receptors (GLP-1R) agonist, or pharmaceutically acceptable salts thereof. Also provided are pharmaceutical compositions containing such compounds, or pharmaceutically acceptable salts thereof. Methods of preparing these compounds and compositions, and methods of using these compounds and compositions to treat or prevent a disease or a condition mediated by GLP-1R, are also provided.

23 Claims, No Drawings

(56) References Cited

FOREIGN PATENT DOCUMENTS

| | | |
|---|---|---|
| WO | WO-2019239319 A1 | 12/2019 |
| WO | WO-2019239371 A1 | 12/2019 |
| WO | WO-2020103815 A1 | 5/2020 |
| WO | WO-2020207474 A1 | 10/2020 |
| WO | WO-2020263695 A1 | 12/2020 |
| WO | WO-2021018023 A1 | 2/2021 |
| WO | WO-2021081207 A1 | 4/2021 |
| WO | WO-2021096284 A1 | 5/2021 |
| WO | WO-2021096304 A1 | 5/2021 |
| WO | WO-2021112538 A1 | 6/2021 |
| WO | WO-2021116874 A1 | 6/2021 |
| WO | WO-2021154796 A1 | 8/2021 |
| WO | WO-2021155841 A1 | 8/2021 |
| WO | WO-2021160127 A1 | 8/2021 |
| WO | WO-2021187886 A1 | 9/2021 |
| WO | WO-2021197464 A1 | 10/2021 |
| WO | WO-2021219019 A1 | 11/2021 |
| WO | WO-2021242817 A1 | 12/2021 |
| WO | WO-2021244391 A1 | 12/2021 |
| WO | WO-2021244645 A1 | 12/2021 |
| WO | WO-2021249492 A1 | 12/2021 |
| WO | WO-2021254470 A1 | 12/2021 |
| WO | WO-2021259309 A1 | 12/2021 |
| WO | WO-2022007979 A1 | 1/2022 |
| WO | WO-2022017338 A1 | 1/2022 |
| WO | WO-2022028572 A1 | 2/2022 |
| WO | WO-2022031994 A1 | 2/2022 |
| WO | WO-2022040600 A1 | 2/2022 |
| WO | WO-2022042691 A1 | 3/2022 |
| WO | WO-2022048665 A1 | 3/2022 |
| WO | WO-2022052958 A1 | 3/2022 |
| WO | WO-2022068772 A1 | 4/2022 |
| WO | WO-2022078152 A1 | 4/2022 |
| WO | WO-2022078352 A1 | 4/2022 |
| WO | WO-2022078380 A1 | 4/2022 |
| WO | WO-2022078407 A1 | 4/2022 |
| WO | WO-2022109182 A1 | 5/2022 |
| WO | WO-2022111624 A1 | 6/2022 |
| WO | WO-2022116693 A1 | 6/2022 |
| WO | WO-2022135572 A1 | 6/2022 |
| WO | WO-2022165076 A1 | 8/2022 |
| WO | WO-2022192428 A1 | 9/2022 |
| WO | WO-2022192430 A1 | 9/2022 |
| WO | WO-2022199458 A1 | 9/2022 |
| WO | WO-2022199661 A1 | 9/2022 |
| WO | WO-2022202864 A1 | 9/2022 |
| WO | WO-2022207950 A1 | 10/2022 |
| WO | WO-2022216094 A1 | 10/2022 |
| WO | WO-2022219495 A1 | 10/2022 |
| WO | WO-2022225941 A1 | 10/2022 |
| WO | WO-2022228490 A1 | 11/2022 |
| WO | WO-2022235717 A1 | 11/2022 |
| WO | WO-2022246019 A1 | 11/2022 |
| WO | WO-2022258805 A1 | 12/2022 |
| WO | WO-2022268152 A1 | 12/2022 |
| WO | WO-2023000834 A1 | 1/2023 |
| WO | WO-2023001237 A1 | 1/2023 |
| WO | WO-2023011539 A1 | 2/2023 |
| WO | WO-2023016546 A1 | 2/2023 |
| WO | WO-2023028606 A1 | 3/2023 |
| WO | WO-2023029380 A1 | 3/2023 |
| WO | WO-2023031741 A1 | 3/2023 |
| WO | WO-2023038039 A1 | 3/2023 |
| WO | WO-2023049518 A1 | 3/2023 |
| WO | WO-2023057414 A1 | 4/2023 |
| WO | WO-2023057427 A1 | 4/2023 |
| WO | WO-2023057429 A1 * | 4/2023 |
| WO | WO-2023066356 A1 | 4/2023 |
| WO | WO-2023076237 A1 | 5/2023 |
| WO | WO-2023103310 A1 | 6/2023 |
| WO | WO-2023106310 A1 | 6/2023 |
| WO | WO-2023111144 A1 | 6/2023 |
| WO | WO-2023111145 A1 | 6/2023 |
| WO | WO-2023124824 A1 | 7/2023 |
| WO | WO-2023138684 A1 | 7/2023 |
| WO | WO-2023151574 A1 | 8/2023 |
| WO | WO-2023151575 A1 | 8/2023 |
| WO | WO-2023152698 A1 | 8/2023 |
| WO | WO-2023164050 A1 | 8/2023 |
| WO | WO-2023164358 A1 | 8/2023 |
| WO | WO-2023169456 A1 | 9/2023 |
| WO | WO-2023179542 A1 | 9/2023 |
| WO | WO-2023198140 A1 | 10/2023 |
| WO | WO-2023222084 A1 | 11/2023 |
| WO | WO-2023222124 A1 | 11/2023 |
| WO | WO-2024041609 A1 | 2/2024 |
| WO | WO-2024046342 A1 | 3/2024 |
| WO | WO-2024051700 A1 | 3/2024 |
| WO | WO-2024063140 A1 | 3/2024 |
| WO | WO-2024063143 A1 | 3/2024 |
| WO | WO-2024102625 A1 | 5/2024 |
| WO | WO-2024107781 A1 | 5/2024 |
| WO | WO-2024131869 A1 | 6/2024 |
| WO | WO-2024149080 A1 | 7/2024 |
| WO | WO-2024206647 A1 | 10/2024 |
| WO | WO-2024206878 A1 | 10/2024 |

OTHER PUBLICATIONS

1H-Benzimidazole-6-carboxylic acid, 2-[[4-[(2S)-2-(5-chloro-2-pyridinyl)-2-methyl-1,3-benzodioxol-4-yl]-1-piperidinyl]methyl]-1-[(2S)-2-oxetanylmethyl]-, Chemical Book, 2017, 2 pages.

Ahmad, I., et al., "Xanthine oxidase/tyrosinase inhibiting, antioxidant, and antifungal oxindole alkaloids from Isatis costata," Pharmaceutical Biology, 2010, 48(6), pp. 716-721.

Arshad, M. F., et al., "Thiazole: A Versatile Standalone Moiety Contributing to the Development of Various Drugs and Biologically Active Agents," Molecules 2022, 27, 3994, https://doi.org/10.3390/molecules27133994, 54 pages.

Balaban, A. T., et al., Aromaticity as a Cornerstone of Heterocyclic Chemistry, Chem. Rev. 2004, 104, 2777-2812.

Beker, W, et al., "Reactivity Patterns of Imidazole, Oxazole, and Thiazole as Reflected by the Polarization Justified Fukui Functions," J. Phys. Chem. A 2013, 117, 1596-1600.

Belaidi, S., et al., "Electronic Structure and Physico-Chemical Property Relationship for Thiazole Derivatives," Asian Journal of Chemistry, 2013, vol. 25, No. 16, 9241-9245.

Beulah, K., et al., "Design, Synthesis and Biological Evaluation of Benzimidazole-pyridine-Piperidine Hybrids as a New Class of Potent Antimicrobial Agents," Letters in Drug Design & Discovery, 2015, vol. 12, No. 1, pp. 38-45.

Blanco, F. J., et al., "Effect of Antiinflammatory Drugs on COX-1 and COX-2 Activity in Human Articular Chondrocytes," The Journal of Rheumatology, 1999, 26:6, pp. 1366-1373.

Blanpied, T. A., et al., "Trapping Channel Block of NMDA-Activated Responses by Amantadine and Memantine," The American Physiological Society, 1997, pp. 309-323.

Chen, L., et al., "Discovery of Novel 5,6-Dihydro-1,2,4-triazine Derivatives as Efficacious Glucagon-Like Peptide-1 Receptor Agonists," Journal of Medicinal Chemistry 2023, 66, pp. 7988-8010.

U.S. Appl. No. 18/629,151, filed Apr. 8, 2024, by Jones et al.

Davies, D. T., Aromatic Heterocyclic Chemistry, Chapters 3 and 4, Oxford University Press 1992, 21 pages.

Dorwald, Side Reactions in Organic Synthesis. Wiley-VCH, 1-16 (2005).

Griffith, D. A., et al., "A Small-Molecule Oral Agonist of the Human Glucagon-like Peptide-1 Receptor," Journal of Medicinal Chemistry, 2022, 65, pp. 8208-8226.

Haake, P., et al., "A Comparison of Thiazoles and Oxazoles," Communications to the Editor, vol. 85, Dec. 20, 1963, pp. 4044-4045.

Haberhauer, G., et al., "Structural Investigation of Westiellamide Analogues," Tetrahedron 2008, 64, 1853-1859.

Hampp, C. et al., "Use of Antidiabetic Drugs in the U.S., 2003-2012," Diabetes Care, May 2014, vol. 37, pp. 1367-1374, DOI: 10.2337/dc13-2289.

(56) References Cited

OTHER PUBLICATIONS

Holst, J. J., et al., "The Physiology of Glucagon-like Peptide 1," Physiological Reviews, 2007, vol. 87, pp. 1409-1439, doi:10.1152/physrev.00034.2006.

Horner, K. E., et al., "Shielding in and around Oxazole, Imidazole, and Thiazole: How Does the Second Heteroatom Affect Aromaticity and Bonding?," J. Org. Chem. 2015, 80, 7150-7157.

International Preliminary Report on Patentability for International Application No. PCT/US2022/047687, mailed May 10, 2024, 8 pages.

International Preliminary Report on Patentability for International Application No. PCT/US2023/013700 mailed Sep. 6, 2024 8 pages.

International Preliminary Report on Patentability, mailed Apr. 11, 2024, for International Application No. PCT/US2022/044915, 8 pages.

International Search Report and Written Opinion for International Application No. PCT/US2024/021994 mailed Jul. 30, 2024, 16 pages.

International Search Report and Written Opinion for International Application No. PCT/US2024/022311 mailed Aug. 14, 2024, 19 pages.

International Search Report and Written Opinion, mailed Apr. 28, 2023, for International Application No. PCT/US2023/013700, 11 pages.

Invitation to Pay Additional Fees and, Where Applicable, Protest Fee for International Application No. PCT/US2024/022311, mailed Jun. 24, 2024, 14 pages.

Kaspady, M., et al., "Synthesis, Antibacterial Activity of 2,4-Disubstituted Oxazoles and Thiazoles as Bioisosteres," Letters in Drug Design & Discovery, 2009, 6, pp. 21-28.

Meier, J. J., et al., "Glucagon-like Peptide 1 and Gastric Inhibitory Polypeptide: Potential Applications in Type 2 Diabetes Mellitus," BioDrugs, 2003, vol. 17(2), pp. 93-102.

Meier, J. J., "GLP-1 receptor agonists for individualized treatment of type 2 diabetes mellitus," Nature Reviews Endocrinology, Dec. 2012, vol. 8, p. 728-742, Published online Sep. 4, 2012, doi:10.1038/nrendo.2012.140.

Nauck, M. A., et al., "Another milestone in the evolution of GLP-1-based diabetes therapies," Nature Medicine, vol. 27, Jun. 2021, pp. 949-953.

Ognyaov, V. I., et al., "Design of Potent, Orally Available Antagonists of the Transient Receptor Potential Vanilloid 1. Structure-Activity Relationships of 2-Piperazin-1-yl-1H-benzimidazoles," J. Med Chem, 2006, vol. 49, No. 12, pp. 3719-3742.

Partial Supplementary European Search Report for European Application No. 21859247.5 dated Sep. 6, 2024, 16 pages.

Pathway: HSA04911, Insulin secretion—*Homo sapiens* (human), KEGG, Jun. 6, 2017, 6 pages.

Saxena, A. R., et al., "Danuglipron (PF-06882961) in type 2 diabetes: a randomized, placebo-controlled, multiple ascending-dose phase 1 trial," Nature Medicine, vol. 27, Jun. 2021, pp. 1079-1087, doi: 10.1038/s41591-021-01391-w.

Saxena, A. R., et al., "Efficacy and Safety of Oral Small Molecule Glucagon-Like Peptide 1 Receptor Agonist Danuglipron for Glycemic Control Among Patients With Type 2 Diabetes: A Randomized Clinical Trial," JAMA Network Open, May 22, 2023, vol. 6(5), e2314493, 12 pages, doi:10.1001/jamanetworkopen.2023.14493.

Shaffer, A. A, et al., "Comparison of Computational Methods Applied to Oxazole, Thiazole, and Other Heterocyclic Compounds," Journal of Computational Chemistry, vol. 14, No. 1, pp. 75-88 (1993).

Sharma, M. C., "QSAR studies of novel 1-(4-methoxyphenethyl)-1H-benzimidazole-5-carboxylic acid derivatives and their precursors as antileukaemic agents," Journal of Taibah University for Science, 2016, vol. 10, pp. 122-130.

Sloop, K. W., et al., "Novel Small Molecules Glucagon-Like Peptide-1 Receptor Agonist Stimulates Isulin Secretion in Rodents and From Human Islets," Diabetes, vol. 59, Dec. 2010, p. 3099.

Stevens, E., Medicinal Chemistry: The Modern Drug Discovery Process, 2013, Chapter 10, Lead Discovery, pp. 247-272.

Teague, S. J., et al., "The Design of Leadlike Combinatorial Libraries," Communications, Angew. Chem. Int. Ed., 1999, 38, No. 24, pp. 3743-3748.

Vilsbøll, T., et al., "Reduced postprandial concentrations of intact biologically active glucagon-like peptide 1 in type 2 diabetic patients," Diabetes, Mar. 2001, vol. 50, pp. 609-613.

Zhang, X. et al., "Differential GLP-1R Binding and Activation by Peptide and Non-peptide Agonists," Molecular Cell 80, Nov. 5, 2020; pp. 485-500 & 485-500.e1-e7, doi: 10.1016/j.molcel.2020.09.020.

Bjerregaard, L. G., et al., "Change in Overweight from Childhood to Early Adulthood and Risk of Type 2 Diabetes," The New England Journal of Medicine, Apr. 5, 2018, 378(14):1302-1312, DOI: 10.1056/NEJMoa1713231 doi:10.1056/NEJMoa1713231.

Coll, B., et al., "A Phase 1b/2a Study of the Safety and Tolerability of GSBR-1290, a Novel Oral Small Molecule Glucagon-Like Peptide 1 Receptor Agonist (GLP-1RA), in Healthy Overweight/Obese Volunteers (HOV) and Participants with Type 2 Diabetes Mellitus (T2DM)," ADA Poster Presentation, Jun. 23, 2024, Abstract 767-P, 1 page.

Dolomanov, O. V., et al., "OLEX2: a complete structure solution, refinement and analysis program," J. Appl. Cryst. 2009, 42, 339-341, doi:10.1107/S0021889808042726.

Escobar-Morreale, H. F., "Polycystic ovary syndrome: definition, aetiology, diagnosis and treatment," Nature Reviews Endocrinology, May 2018, vol. 14, pp. 270-284, doi:10.1038/nrendo.2018.24.

Extended European Search Report for European Application No. 21859247.5 mailed Nov. 27, 2024, 15 pages.

Farrugia, L. J., "WinGX and ORTEP for Windows: an update," Applied Crystallography 2012, 45, 849-854, doi:10.1107/S0021889812029111.

FLACK, H. D., "On Enantiomorph-Polarity Estimation," Acta Cryst. 1983, A39, 876-881.

Flack, H. D., et al., "The Use of X-ray Crystallography to Determine Absolute Configuration," CHIRALITY 20:681-690, 2008, DOI: 10.1002/chir.20473.

Guerrero-Pepinosa, N. Y., et al., "Antiproliferative activity of thiazole and oxazole derivatives: A systematic review of in vitro and in vivo studies," Biomedicine & Pharmacotherapy 138 (2021) 111495, https://doi.org/10.1016/j.biopha.2021.111495, 15 pages.

Guidance for Industry: Estimating the Maximum Safe Starting Dose in Initial Clinical Trials for Therapeutics in Adult Healthy Volunteers. US Department of Health and Human Services, Food and Drug Administration (FDA), Center for Drug Evaluation and Research, Jul. 2005, 30 pages, https://www.fda.gov/media/72309/download.

Guidance for Industry: Toxicity Grading Scale for Healthy Adult and Adolescent Volunteers Enrolled in Preventive Vaccine Clinical Trials. U.S. Department of Health and Human Services, Food and Drug Administration, Center for Biologics Evaluation and Research, Sep. 2007, 10 pages.

Hamdan, F., et al., "Synthesis of novel cyclopeptides containing heterocyclic skeletons," RSC Advances 2018, 8, 33893-33926, DOI: 10.1039/c8ra03899f.

Hooft, R. W. W., et al., "Determination of absolute structure using Bayesian statistics on Bijvoet differences," J. Appl. Cryst. 2008, 41, 96-103, doi:10.1107/S0021889807059870.

Huang, K.-P., et al., "Dissociable hindbrain GLP1R circuits for satiety and aversion," Nature, Aug. 15, 2024, vol. 632, pp. 585-593, including Methods, Extended Data & Reporting Summary, 25 pages, https://doi.org/10.1038/s41586-024-07685-6.

Kalra, S., et al., "Consensus Recommendations on GLP-1 RA Use in the Management of Type 2 Diabetes Mellitus: South Asian Task Force," Diabetes Ther 2019, 10: 1645-1717, https://doi.org/10.1007/s13300-019-0669-4.

Krieger, J.-P., "Intestinal glucagon-like peptide-1 effects on food intake: Physiological relevance and emerging mechanisms," Peptides 2020, 131:170342, 8 pages, https://doi.org/10.1016/j.peptides.2020.170342.

Lega, I. C., et al., "Review: Diabetes, Obesity, and Cancer-Pathophysiology and Clinical Implications," Endocrine Reviews, Feb. 2020, 41(1):35-52, doi:10.1210/endrev/bnz014.

(56) References Cited

OTHER PUBLICATIONS

Macrae, C. F., et al., "Mercury: visualization and analysis of crystal structures," J. Appl. Cryst. 2006, 39, 453-457, doi: 10.1107/S002188980600731X.
Muller, T.D., et al., "Anti-Obesity Therapy: from Rainbow Pills to Polyagonists," Pharmacological Reviews, Oct. 2018, 70: 712-746, doi:10.1124/pr.117.014803.
NCT01237119: "Liraglutide Efficacy and Action in Non-Alcoholic Steatohepatitis (LEAN)," Aug. 2010, Phase 2, 7 pages, Retrieved on Feb. 13, 2025, Retrieved from https://clinicaltrials.gov/study/NCT01237119.
NCT03590626. "Effect of Dulaglutide on Liver Fat in Patients With Type 2 Diabetes and Nonalcoholic Fatty Liver Disease (D-LIFT)," Jan. 1, 2019, 11 pages, Retrieved on Feb. 13, 2025, Retrieved from https://clinicaltrials.gov/study/NCT03590626.
Pfizer Press release—Pfizer Announces Topline Phase 2b Results of Oral GLP-1R Agonist, Danuglipron, in Adults with Obesity, Dec. 1, 2023, 4 pages, businesswire.com: https://www.businesswire.com/news/home/20231130108413/en/.
Plamoeck, A., et al., "The effect of exogenous GLP-1 on food intake is lost in male truncally vagotomized subjects with pyloroplasty," Am J Physiol Gastrointest Liver Physiol 304: G1117-G1127, 2013, https://doi.org/10.1152/ajpgi.00035.2013.
Polyzos, S. A., et al., "Obesity and nonalcoholic fatty liver disease: From pathophysiology to therapeutics," Metabolism Clinical and Experimental 2019, 92:82-97, doi:10.1016/j.metabol.2018.11.014.
Priner, M. et al., "94-LB: A Phase 1, Double-Blind, Placebo-Controlled Multiple Escalating Dose Study of RGT-075 Novel Small-Molecule Oral GLP-1 Receptor Agonist in Adults with Type 2 Diabetes," Diabetes 2022;71 (Supplement_1):94-LB, 1 page, https://doi.org/10.2337/db22-94-LB.
PUBCHEM "Danuglipron," CID: 134611040, Created Jun. 23, 2018; Modified Feb. 8, 2025, 32 pages, Retrieved on Feb. 13, 2025, Retrieved from https://pubchem.ncbi.nlm.nih.gov/compound/134611040#section=Information-Sources.
Roche, Ad hoc announcement pursuant to Art. 53 LR, "Roche announces positive Phase I results of its oral GLP-1 receptor agonist CT-996 for the treatment of people with obesity," Jul. 17, 2024, 5 pages, https://www.roche.com/media/releases/med-cor-2024-07-17.
Saxena, A., et al., "Tolerability, safety and pharmacodynamics of oral, small-molecule glucagon-like peptide-1 receptor agonist danuglipron for type 2 diabetes: A 12-week, randomized, placebo-controlled, Phase 2 study comparing different dose-escalation schemes," Diabetes Obes Metab. 2023;25:2805-2814, DOI: 10.1111/dom.15168.
SAXENDA® (liraglutide) injection, for subcutaneous use. United States Prescribing Information (USPI). 2022. Accessed: Feb. 2, 2023. 13 pages. https://www.novo-pi.com/saxenda.pdf.
Sheldrick, G. M., "Crystal structure refinement with SHELXL," ActaCryst. 2015, C71, 3-8, doi:10.1107/S2053229614024218.
Sheldrick, G. M., "Shelxl—Integrated space-group and crystal-structure determination" ActaCryst. 2015, A71, 3-8, doi:10.1107/S2053273314026370.
Sloop, K. W., et al., "Novel Small Molecules Glucagon-Like Peptide-1 Receptor Agonist Stimulates Isulin Secretion in Rodents and From Human Islets," Diabetes, vol. 59, Dec. 2010, p. 3099-3107.
Stas, M., et al., "Thiazole-amino acids: influence of thiazole ring on conformational properties of amino acid residues," Amino Acids 2021, 53: 673-686, https://doi.org/10.1007/s00726-021-02974-0.
Stemmer, K., et al., "CNS-targeting pharmacological interventions for the metabolic syndrome," The Journal of Clinical Investigation, Oct. 2019, 129(10), pp. 4058-4071, https://www.jci.org/articles/view/129195/pdf.
Structure Therapeutics Corporate Presentation, GSBR-1290 Phase 1b MAD Results. Sep. 29, 2023, 24 pages.
Terns Pharmaceuticals Announces Positive Phase 1 Clinical Trial Results with TERN-601 Once-Daily Oral GLP-1R Agonist for the Treatment of Obesity, Sep. 9, 2024, 3 pages, retrieved on Feb. 12, 2025, retrieved from URL: https://ir.ternspharma.com/news-releases/news-release-details/terns-pharmaceuticals-announces-positive-phase-1-clinical-trial.
Twig, G., et al., "Body-Mass Index in 2.3 Million Adolescents and Cardiovascular Death in Adulthood," The New England Journal of Medicine, Jun. 23, 2016, 374;25: 2430-2440, DOI: 10.1056/NEJMoa1503840.
Waise, T. M. Z., et al., The metabolic role of vagal afferent innervation, Nature Reviews Gastroenterology & Hepatology, vol. 15, Oct. 2018, pp. 625-636, https://doi.org/10.1038/s41575-018-0062-1.
WEGOVY® (semaglutide) injection, for subcutaneous use. United States Prescribing Information (USPI). 2023. Accessed: Feb. 2, 2023. 15 pages. https://www.novo-pi.com/wegovy.pdf.

\* cited by examiner

COMPOUNDS AS GLP-IR AGONISTS

CROSS-REFERENCE TO RELATED APPLICATIONS

This application claims priority to and the benefit of U.S. Provisional Application No. 63/313,160, filed on Feb. 23, 2022, which is incorporated by reference herein in their entirety for all purposes.

FIELD

This invention relates to compositions for modulating glucagon-like peptide-1 (GLP-1) receptors and methods thereof.

BACKGROUND

Diabetes is a major public health concern because of its increasing prevalence and associated health risks. The disease is characterized by high levels of blood glucose resulting from defects in insulin production, insulin action, or both. Two major forms of diabetes are recognized, Type 1 and Type 2. Type 1 diabetes (T1D) develops when the body's immune system destroys pancreatic beta cells, the only cells in the body that make the hormone insulin that regulates blood glucose. To survive, people with Type 1 diabetes must have insulin administered by injection or a pump. Type 2 diabetes mellitus (T2DM) usually begins with either insulin resistance or when there is insufficient production of insulin to maintain an acceptable glucose level.

Currently, various pharmacological approaches are available for treating hyperglycemia and subsequently, T2DM (Hampp, C. et al. Use of Antidiabetic Drugs in the U.S., 2003-2012, Diabetes Care 2014, 37, 1367-1374). One of them is glucagon-like peptide-1 receptor (GLP-1R) agonists (e.g., liraglutide, albiglutide, exenatide, lixisenatide, dulaglutide, semaglutide), which enhance secretion of insulin by acting on the pancreatic beta-cells. Marketed GLP-1R agonists are peptides administered by subcutaneous injection. Liraglutide is additionally approved for the treatment of obesity.

GLP-1 is a 30 amino acid long incretin hormone secreted by the L-cells in the intestine in response to ingestion of food. GLP-1 has been shown to stimulate insulin secretion in a physiological and glucose-dependent manner, decrease glucagon secretion, inhibit gastric emptying, decrease appetite, and stimulate proliferation of beta-cells. In non-clinical experiments GLP-1 promotes continued beta-cell competence by stimulating transcription of genes important for glucose-dependent insulin secretion and by promoting beta-cell neogenesis (Meier et al. Biodrugs. 2003; 17 (2): 93-102).

In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying and slows small bowel motility delaying food absorption. In people with T2DM, the normal post-prandial rise in GLP-1 is absent or reduced (Vilsboll T, et al. Diabetes. 2001. 50; 609-613).

Holst (Physiol. Rev. 2007, 87, 1409) and Meier (Nat. Rev. Endocrinol. 2012, 8, 728) describe that GLP-1 receptor agonists, such as liraglutide and exendin-4, have 3 major pharmacological activities to improve glycemic control in patients with T2DM by reducing fasting and postprandial glucose (FPG and PPG): (i) increased glucose-dependent insulin secretion (improved first- and second-phase), (ii) glucagon suppressing activity under hyperglycemic conditions, (iii) delay of gastric emptying rate resulting in retarded absorption of meal-derived glucose.

There remains a need of developing GLP-1 receptor agonists for an easily-administered prevention and/or treatment for cardiometabolic and associated diseases.

SUMMARY

Disclosed are compounds that can be used as glucagon-like peptide-1 receptor (GLP-1R) agonists, compositions containing these compounds, and methods for treating diseases and/or conditions mediated by GLP-1R.

In one aspect, provided is a compound of Formula (0), Formula (1), including compounds of Formula (2)-(10), or a subformula of any of the foregoing, or a compound selected from the group consisting of the compounds listed in Table 1, or a pharmaceutically acceptable salt thereof, as detailed herein.

Further provided is a pharmaceutical composition comprising a compound of Formula (0), Formula (1), including compounds of Formula (2)-(10), or a subformula of any of the foregoing, or a compound selected from the group consisting of the compounds listed in Table 1, or a pharmaceutically acceptable salt thereof, and a pharmaceutically acceptable carrier or excipient.

In another aspect, provided is a method of treating a disease or a condition mediated by GLP-1R in a subject in need thereof comprises administering to the subject a therapeutically effective amount of a compound of Formula (0), Formula (1), including compounds of Formula (2)-(10), or a subformula of any of the foregoing, or a compound selected from the group consisting of the compounds listed in Table 1, or a pharmaceutically acceptable salt thereof. In some embodiments, the disease or the condition is a cardiometabolic disease. In some embodiments, the disease or the condition is diabetes. In some embodiments, the disease or the condition is a liver disease.

Also provided is a compound of Formula (0), Formula (1), including compounds of Formula (2)-(10), or a subformula of any of the foregoing, or a compound selected from the group consisting of the compounds listed in Table 1, or a pharmaceutically acceptable salt thereof, as detailed herein, for the treatment.

Also provided is use of a compound of Formula (0), Formula (1), including compounds of Formula (2)-(10), or a subformula of any of the foregoing, or a compound selected from the group consisting of the compounds listed in Table 1, or a pharmaceutically acceptable salt thereof, as detailed herein, in the manufacture of a medicament for the treatment.

Further provided is a kit comprising a compound of Formula (0), Formula (1), including compounds of Formula (2)-(10), or a subformula of any of the foregoing, or a compound selected from the group consisting of the compounds listed in Table 1, or a pharmaceutically acceptable salt thereof. In some embodiments, the kit comprises instructions for use according to a method described herein.

In yet another aspect, provided is a method of making a compound of Formula (0), Formula (1), including compounds of Formula (2)-(10), or a subformula of any of the foregoing, or a compound selected from the group consisting of the compounds listed in Table 1, or a pharmaceutically acceptable salt thereof. Also provided are compound intermediates useful in synthesis of a compound of Formula (0), Formula (1), including compounds of Formula (2)-(10), or a subformula of any of the foregoing, or a compound selected from the group consisting of the compounds listed in Table 1, or a pharmaceutically acceptable salt thereof.

DETAILED DESCRIPTION

Definitions

As used herein, the following definitions shall apply unless otherwise indicated. Further, if any term or symbol used herein is not defined as set forth below, it shall have its ordinary meaning in the art.

As used herein and in the appended claims, the singular forms "a," "an" and "the" include plural forms, unless the context clearly dictates otherwise.

As used herein, and unless otherwise specified, the terms "about" and "approximately," when used in connection with doses, amounts, or weight percent of ingredients of a composition or a dosage form, mean a dose, amount, or weight percent that is recognized by those of ordinary skill in the art to provide a pharmacological effect equivalent to that obtained from the specified dose, amount, or weight percent. Specifically, the terms "about" and "approximately," when used in connection with a value, contemplate a variation within ±15%, within ±10%, within +5%, within ±4%, within ±3%, within ±2%, within ±1%, or within ±0.5% of the specified value. Reference to "about" a value or parameter herein includes (and describes) embodiments that are directed to that value or parameter per se. For example, description referring to "about X" includes description of "X".

"Comprising" is intended to mean that the compositions and methods include the recited elements, but not exclude others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of, e.g., other ingredients and substantial method steps recited. Embodiments defined by each of these transition terms are within the scope of this invention.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Pharmaceutically acceptable" refers to safe and non-toxic, preferably for in vivo, more preferably, for human administration.

"Pharmaceutically acceptable salt" refers to a salt that is pharmaceutically acceptable. A compound described herein may be administered as a pharmaceutically acceptable salt.

"Salt" refers to an ionic compound formed between an acid and a base. When the compound provided herein contains an acidic functionality, such salts include, without limitation, alkali metal, alkaline earth metal, and ammonium salts. As used herein, ammonium salts include, salts containing protonated nitrogen bases and alkylated nitrogen bases. Exemplary and non-limiting cations useful in pharmaceutically acceptable salts include Na, K, Rb, Cs, NH4, Ca, Ba, imidazolium, and ammonium cations based on naturally occurring amino acids. When the compounds utilized herein contain basic functionality, such salts include, without limitation, salts of organic acids, such as carboxylic acids and sulfonic acids, and mineral acids, such as hydrogen halides, sulfuric acid, phosphoric acid, and the likes. Exemplary and non-limiting anions useful in pharmaceutically acceptable salts include oxalate, maleate, acetate, propionate, succinate, tartrate, chloride, sulfate, bisulfate, mono-, di-, and tribasic phosphate, mesylate, tosylate, and the likes.

"Stereoisomer" or "stereoisomers" refer to compounds that differ in the stereogenicity of the constituent atoms such as, without limitation, in the chirality of one or more stereocenters or related to the cis or trans configuration of a carbon-carbon or carbon-nitrogen double bond. Stereoisomers include enantiomers and diastereomers.

As used herein, the term "subject" refers to an animal, including, but are not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

As used herein, "treatment" or "treating" is an approach for obtaining beneficial or desired results including clinical results. For purposes of this disclosure, beneficial or desired results include, but are not limited to, one or more of the following: decreasing one or more symptoms resulting from the disease or disorder, diminishing the extent of the disease or disorder, stabilizing the disease or disorder (e.g., preventing or delaying the worsening of the disease or disorder), delaying the occurrence or recurrence of the disease or disorder, delaying or slowing the progression of the disease or disorder, ameliorating the disease or disorder state, providing a remission (whether partial or total) of the disease or disorder, decreasing the dose of one or more other medications required to treat the disease or disorder, enhancing the effect of another medication used to treat the disease or disorder, delaying the progression of the disease or disorder, increasing the quality of life, and/or prolonging survival of a patient. Also encompassed by "treatment" is a reduction of pathological consequence of the disease or disorder. The methods of this disclosure contemplate any one or more of these aspects of treatment.

"Therapeutically effective amount" or dose of a compound or a composition refers to that amount of the compound or the composition that results in reduction or inhibition of symptoms or a prolongation of survival in a patient. The results may require multiple doses of the compound or the composition.

"Alkyl" refers to monovalent saturated aliphatic hydrocarbyl groups having from 1 to 12 carbon atoms, preferably from 1 to 10 carbon atoms, and more preferably from 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—). Cx alkyl refers to an alkyl group having x number of carbon atoms.

"Alkylene" refers to a divalent saturated aliphatic hydrocarbyl group having from 1 to 12 carbon atoms, preferably from 1 to 10 carbon atoms, and more preferably from 1 to 6 carbon atoms. This term includes, by way of example, linear and branched hydrocarbyl groups such as methylene (—$CH_2$—), ethylene (—$CH_2CH_2$— or —CH(Me)-), propylene (—$CH_2CH_2CH_2$— or —CH(Me)$CH_2$—, or —CH(Et)-) and the likes.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Aryl" refers to a monovalent aromatic carbocyclic group of from 6 to 14 carbon atoms having a single ring (e.g., phenyl (Ph)) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Cyano" refers to the group —CN.

"Cycloalkyl" refers to saturated or unsaturated but non-aromatic cyclic alkyl groups of from 3 to 10 carbon atoms, preferably from 3 to 8 carbon atoms, and more preferably from 3 to 6 carbon atoms, having single or multiple cyclic rings including fused, bridged, and spiro ring systems. Cx cycloalkyl refers to a cycloalkyl group having x number of ring carbon atoms. Examples of suitable cycloalkyl groups include, for instance, adamantyl, cyclopropyl, cyclobutyl, cyclopentyl, and cyclooctyl. One or more the rings can be aryl, heteroaryl, or heterocyclic provided that the point of attachment is through the non-aromatic, non-heterocyclic ring saturated carbocyclic ring. "Substituted cycloalkyl" refers to a cycloalkyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO3H, substituted sulfonyl, sulfonyloxy, thioacyl, thiol, alkylthio, and substituted alkylthio, wherein said substituents are defined herein.

"Halo" or "halogen" refers to fluoro, chloro, bromo and iodo and preferably is fluoro or chloro.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include 5 or 6 membered heteroaryls such as pyridinyl, pyrrolyl, thiophenyl, and furanyl. Other preferred heteroaryls include 9 or 10 membered heteroaryls, such as indolyl, quinolinyl, quinolonyl, isoquinolinyl, and isoquinolonyl.

"Heterocycle" or "heterocyclic" or "heterocycloalkyl" or "heterocyclyl" refers to a saturated or partially saturated, but not aromatic, group having from 1 to 10 ring carbon atoms, preferably from 1 to 8 carbon atoms, and more preferably from 1 to 6 carbon atoms, and from 1 to 4 ring heteroatoms, preferably from 1 to 3 heteroatoms, and more preferably from 1 to 2 heteroatoms selected from the group consisting of nitrogen, sulfur, or oxygen. Cx heterocycloalkyl refers to a heterocycloalkyl group having x number of ring atoms including the ring heteroatoms. Heterocycle encompasses single ring or multiple condensed rings, including fused bridged and spiro ring systems. In fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl (S(O)), sulfonyl (S(O)2) moieties.

Examples of heterocyclyl and heteroaryl include, but are not limited to, azetidinyl, pyrrolyl, imidazolyl, pyrazolyl, pyridyl, pyrazyl, pyrimidyl, pyridazyl, indolizyl, isoindolyl, indolyl, dihydroindolyl, indazolyl, purinyl, quinolizinyl, isoquinolinyl, quinolinyl, phthalazinyl, naphthylpyridinyl, quinoxalinyl, quinazolinyl, cinnolinyl, pteridinyl, carbazolyl, carbolinyl, phenanthridinyl, acridinyl, phenanthrolinyl, isothiazolyl, phenazinyl, isoxazolyl, phenoxazinyl, phenothiazinyl, imidazolidinyl, imidazolinyl, piperidinyl, piperazinyl, indolinyl, phthalimidyl, 1,2,3,4-tetrahydroisoquinolinyl, 4,5,6,7-tetrahydrobenzo[b]thiophenyl, thiazolyl, thiazolidinyl, thiophenyl, benzo[b]thiophenyl, morpholinyl, thiomorpholinyl (also referred to as thiamorpholinyl), 1,1-dioxothiomorpholinyl, piperidinyl, pyrrolidinyl, and tetrahydrofuranyl.

"Oxo" refers to the atom (=O) or (O).

The terms "optional" or "optionally" as used throughout the specification means that the subsequently described event or circumstance may but need not occur, and that the description includes instances where the event or circumstance occurs and instances in which it does not. For example, "the nitrogen atom is optionally oxidized to provide for the N-oxide (N→O) moiety" means that the nitrogen atom may but need not be oxidized, and the description includes situations where the nitrogen atom is not oxidized and situations where the nitrogen atom is oxidized.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4, 1 to 5, 2 to 3, 2 to 4, or 2 to 5 substituents. In one embodiment, an optionally substituted group is unsubstituted.

It is understood that an optionally substituted moiety can be substituted with more than five substituents, if permitted by the number of valences available for substitution on the moiety. For example, a propyl group can be substituted with seven halogen atoms to provide a perhalopropyl group. The substituents may be the same or different.

Compounds

In one aspects, provided is a compound of Formula (0):

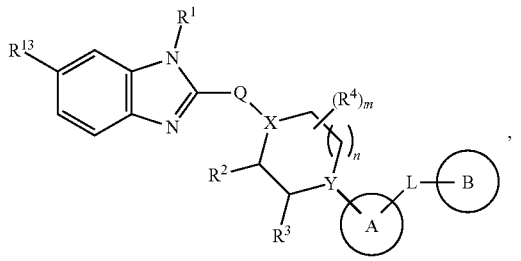

(0)

or a pharmaceutically acceptable salt, wherein:
$R^{13}$ is —C(O)OH or

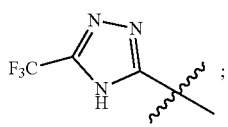

;

X is N or $CR^x$, wherein $R^x$ is hydrogen, OH or $C_1$-$C_6$ alkyl;
Y is N or $CR^y$, wherein $R^y$ is hydrogen, OH or $C_1$-$C_6$ alkyl;
n is 0 or 1;
Q is selected from the group consisting of —C($R^7$)($R^8$)—, —O—, —N($R^9$)—, and —S—, wherein
  $R^7$ and $R^8$ are independently hydrogen, halogen, or $C_1$-$C_6$ alkyl; and
  $R^9$ is hydrogen or $C_1$-$C_6$ alkyl;
$R^1$ is optionally substituted —$C_1$-$C_6$ alkylene or —$C_1$-$C_6$ alkylene-$R^5$, wherein $R^5$ is $C_3$-$C_6$ cycloalkyl, 3- to 6-membered heterocyclyl, or 5- to 6-membered heteroaryl, each of which is independently optionally substituted by one to three substituents independently selected from the group consisting of halo, oxo, CN, $C_1$-$C_6$ alkyl, $C_3$-$C_6$ cycloalkyl, and —O$C_1$-$C_6$ alkyl, wherein each $C_1$-$C_6$ alkyl, $C_3$-$C_6$ cycloalkyl, and —O$C_1$-$C_6$ alkyl substituent is independently optionally substituted by halo or CN;

$R^2$ and $R^3$ are taken together with the carbon atoms to which they are attached to form an optionally substituted $C_3$-$C_4$ cycloalkyl ring; or
$R^2$ and $R^x$, when present, are taken together with the carbon atoms to which they are attached to form an optionally substituted $C_3$-$C_5$ cycloalkyl ring, and $R^3$ is hydrogen, oxo, or $C_1$-$C_6$ alkyl;
m is 0, 1, 2, or 3;
$R^4$ is oxo or $C_1$-$C_6$ alkyl;
Ring A is $C_6$-$C_{14}$ aryl, 5- to 12-membered heterocyclyl or 5- to 12-membered heteroaryl, each of which is independently optionally substituted by halo, OH, CN, $C_3$-$C_6$ cycloalkyl, or $C_1$-$C_6$ alkyl optionally substituted by halo or OH;
L is a bond, —O—, $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-**, wherein * represents the point of attachment to ring A and ** represents the point of attachment to ring B, and wherein:
  when L is $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-**, L is optionally substituted by one to three $R^L$ substituents, wherein each $R^L$ is independently halo, OH, or $C_1$-$C_6$ alkyl; or two $R^L$ are taken together with the carbon atom or atoms to which they are attached to form $C_3$-$C_6$ cycloalkyl or 3- to 6-membered heterocyclyl;
$R^6$, when present, is hydrogen or $C_1$-$C_6$ alkyl; and Ring B is $C_3$-$C_{10}$ cycloalkyl, $C_6$-$C_{14}$ aryl, 4- to 12-membered heterocyclyl, or 5- to 12-membered heteroaryl, each of which is independently optionally substituted by one to three substituents independently selected from the group consisting of halo, CN, oxo, $C_1$-$C_6$ alkyl optionally substituted by halo or CN, —O$C_1$-$C_6$ alkyl optionally substituted by halo or CN, —COCH$_3$, —CONH$_2$, —S(O)$_2$CH$_3$, and phenyl optionally substituted by halo or CN.

In one aspect, provided is a compound of Formula (1):

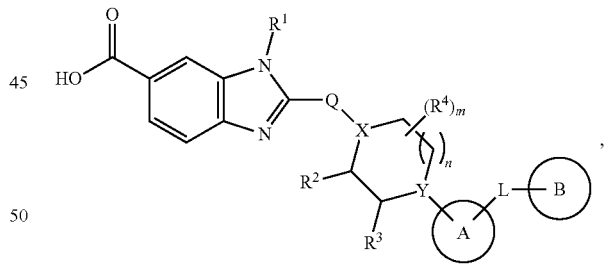

(1)

or a pharmaceutically acceptable salt thereof, wherein:
X is N or $CR^x$, wherein $R^x$ is hydrogen, OH or $C_1$-$C_6$ alkyl, and
Y is N or $CR^Y$, wherein $R^Y$ is hydrogen, OH or $C_1$-$C_6$ alkyl;
n is 0 or 1;
Q is selected from the group consisting of —C($R^7$)($R^8$)—, —O—, —N($R^9$)—, and —S—, wherein
  $R^7$ and $R^8$ are independently hydrogen, halogen, or $C_1$-$C_6$ alkyl, and
  $R^9$ is hydrogen or $C_1$-$C_6$ alkyl;
$R^1$ is —$C_1$-$C_6$ alkylene-$R^5$, wherein $R^5$ is 3- to 6-membered heterocyclyl or 5- to 6-membered heteroaryl, each of which is independently optionally substituted by one to three substituents independently selected from the group consisting of halo, oxo, CN, $C_1$-$C_6$ alkyl, $C_3$-$C_6$ cycloalkyl, and —$OC_1$-$C_6$ alkyl, wherein each $C_1$-$C_6$ alkyl, $C_3$-$C_6$ cycloalkyl, and —$OC_1$-$C_6$ alkyl substituent is independently optionally substituted by halo or CN;

$R^2$ and $R^3$ are taken together with the carbon atoms to which they are attached to form an optionally substituted $C_3$-$C_4$ cycloalkyl ring; or $R^2$ and $R^x$, when present, are taken together with the carbon atoms to which they are attached to form an optionally substituted $C_3$-$C_5$ cycloalkyl ring, and $R^3$ is hydrogen, oxo, or $C_1$-$C_6$ alkyl;

m is 0, 1, 2, or 3;

$R^4$ is oxo or $C_1$-$C_6$ alkyl;

Ring A is $C_6$-$C_{14}$ aryl, 5- to 12-membered heterocyclyl or 5- to 12-membered heteroaryl, each of which is independently optionally substituted by halo, OH, CN, $C_3$-$C_6$ cycloalkyl, or $C_1$-$C_6$ alkyl optionally substituted by halo or OH;

L is a bond, —O—, $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-**, wherein * represents the point of attachment to ring A and ** represents the point of attachment to ring B, and wherein:

when L is $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-**, L is optionally substituted by one to three $R^L$ substituents, wherein each $R^L$ is independently halo, OH, or $C_1$-$C_6$ alkyl; or two $R^L$ are taken together with the carbon atom or atoms to which they are attached to form $C_3$-$C_6$ cycloalkyl or 3- to 6-membered heterocyclyl; and $R^6$, when present, is hydrogen or $C_1$-$C_6$ alkyl; and Ring B is $C_3$-$C_{10}$ cycloalkyl, $C_6$-$C_{14}$ aryl, 4- to 12-membered heterocyclyl, or 5- to 12-membered heteroaryl, each of which is independently optionally substituted by one to three substituents independently selected from the group consisting of halo, CN, oxo, $C_1$-$C_6$ alkyl optionally substituted by halo or CN, —$OC_1$-$C_6$ alkyl optionally substituted by halo or CN, —$COCH_3$, —$CONH_2$, —$S(O)_2CH_3$, and phenyl optionally substituted by halo or CN.

In some embodiments of Formula (0) or Formula (1), at least one of X and Y is N. In other embodiments of Formula (0) or Formula (1), both X and Y are N.

In some embodiments of Formula (0) or Formula (1), $R^2$ and $R^3$ are taken together with the carbon atoms to which they are attached to form an optionally substituted $C_3$-$C_4$ cycloalkyl ring. In some embodiments, provided is a compound of Formula (2):

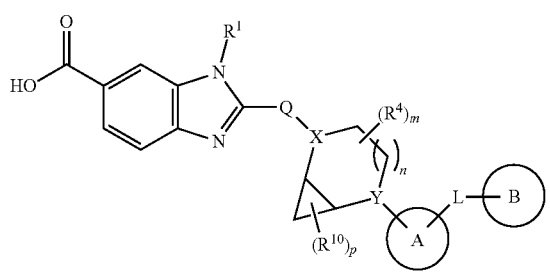

or a pharmaceutically acceptable salt thereof, wherein p is 0, 1, or 2; each $R^{10}$ is halo; and X, Y, n, Q, $R^1$, m, $R^4$, Ring A, L, and Ring B are as detailed herein for Formula (0) or Formula (1).

In some embodiments of Formula (2), at least one of X and Y is N. In other embodiments of Formula (2), both X and Y are N.

In some embodiments of Formula (2), L is *—$OCH_2$—** and Ring B is phenyl. In some embodiments, provided is a compound of Formula (3):

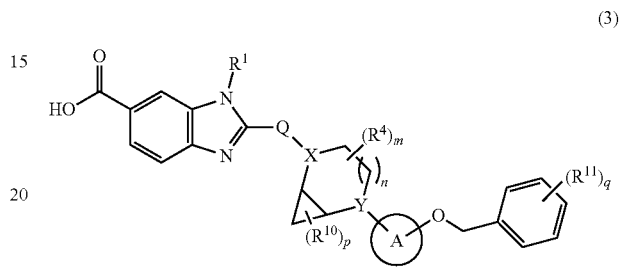

or a pharmaceutically acceptable salt thereof, wherein q is 0, 1, 2, or 3; $R^{11}$ is selected from the group consisting of halo, CN, $C_1$-$C_6$ alkyl optionally substituted by halo or CN, —$OC_1$-$C_6$ alkyl optionally substituted by halo or CN, —$COCH_3$, —$CONH_2$, —$S(O)_2CH_3$, and phenyl optionally substituted by halo or CN; p and $R^{10}$ are as detailed herein for Formula (2); and X, Y, n, Q, $R^1$, m, $R^4$, and Ring A are as detailed herein for Formula (0) or Formula (1).

In some such embodiments, each $R^{11}$ is independently selected from halo and CN. In some embodiments of Formula (3), at least one of X and Y is N. In other embodiments of Formula (3), both X and Y are N.

In some embodiments of Formula (3), Ring A is pyridinyl. In some embodiments, provided is a compound of Formula (4):

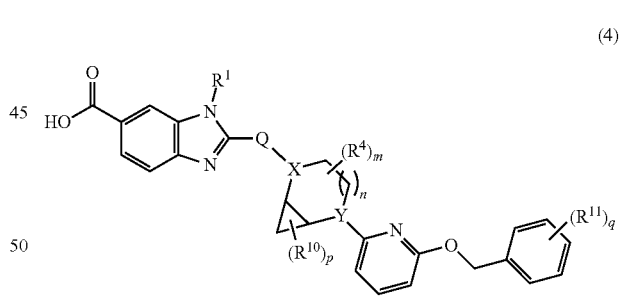

or a pharmaceutically acceptable salt thereof, wherein q and $R^{11}$ are as detailed herein for Formula (3), p and $R^{10}$ are as detailed herein for Formula (2), and X, Y, n, Q, $R^1$, m, and $R^4$ are as detailed herein for Formula (0) or Formula (1).

In some such embodiments, each $R^{11}$ is independently selected from halo and CN. In some embodiments of Formula (4), at least one of X and Y is N. In other embodiments of Formula (4), both X and Y are N.

In some embodiments of a compound of Formula (0) or Formula (1) (including compounds of Formula (2) and subformulae thereof, if applicable), or a pharmaceutically acceptable salt thereof, $R^1$ is —$C_1$-$C_6$ alkylene-$R^5$, wherein $R^5$ is 3- to 6-membered heterocyclyl or 5- to 6-membered heteroaryl, each of which is independently optionally substituted by one to three substituents independently selected from the group consisting of halo, oxo, CN, $C_1$-$C_6$ alkyl, $C_3$-$C_6$ cycloalkyl, and —$OC_1$-$C_6$ alkyl, wherein each $C_1$-$C_6$ alkyl, $C_3$-$C_6$ cycloalkyl, and —$OC_1$-$C_6$ alkyl substituent is independently optionally substituted by halo or CN. In some embodiments, $R^1$ is —$CH_2$—$R^5$.

In some embodiments, provided is a compound of Formula (5):

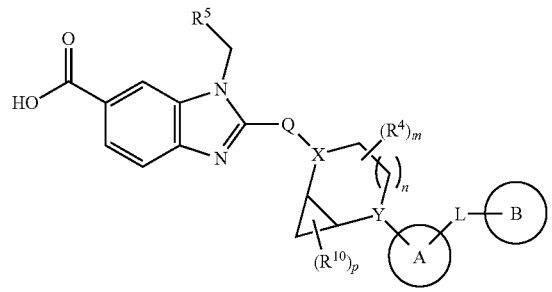

(5)

or a pharmaceutically acceptable salt thereof, wherein p and $R^{10}$ are as detailed herein for Formula (2), and X, Y, n, Q, $R^5$, m, $R^4$, Ring A, L, and Ring B are as detailed herein for Formula (0) or Formula (1).

In some embodiments of Formula (5), at least one of X and Y is N. In other embodiments of Formula (5), both X and Y are N.

In some embodiments of Formula (5), L is *—$OCH_2$—** and Ring B is phenyl. In some embodiments, provided is a compound of Formula (6):

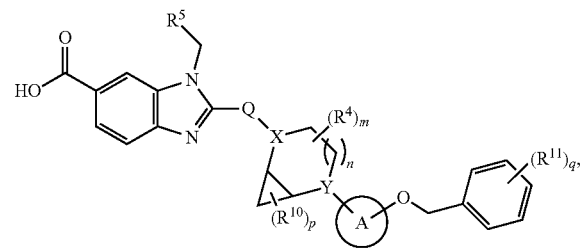

(6)

wherein q is 0, 1, 2, or 3; $R^{11}$ is halo, CN, $C_1$-$C_6$ alkyl optionally substituted by halo or CN, —$OC_1$-$C_6$ alkyl optionally substituted by halo or CN, —$COCH_3$, —$CONH_2$, —$S(O)_2CH_3$, or phenyl optionally substituted by halo or CN; p and $R^{10}$ are as detailed herein for Formula (2); and X, Y, n, Q, $R^5$, m, $R^4$, and Ring A are as detailed herein for Formula (0) or Formula (1).

In some such embodiments, each $R^{11}$ is independently selected from halo and CN. In some embodiments of Formula (6), at least one of X and Y is N. In other embodiments of Formula (6), both X and Y are N.

In some embodiments of Formula (6), Ring A is pyridinyl. In some embodiments, provided is a compound of Formula (7):

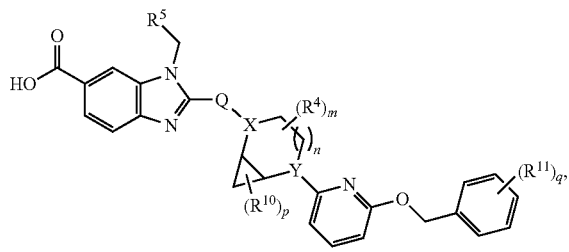

(7)

wherein q and $R^{11}$ are as defined herein for Formula (6); p and $R^{10}$ are as detailed herein for Formula (2); and X, Y, n, Q, $R^5$, m, and $R^4$ are as detailed herein for Formula (0) or Formula (1).

In some such embodiments, each $R^{11}$ is independently selected from halo and CN. In some embodiments of Formula (7), at least one of X and Y is N. In other embodiments of Formula (7), both X and Y are N.

In some embodiments of a compound of Formula (0) or Formula (1), X is $CR^x$, and $R^2$ and $R^x$ are taken together with the carbon atoms to which they are attached to form an optionally substituted $C_3$-$C_5$ cycloalkyl ring. In some embodiments, the compound is of Formula (8):

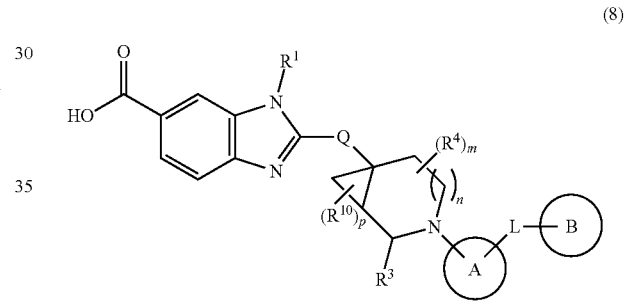

(8)

or a pharmaceutically acceptable salt thereof, wherein p is 0, 1, or 2; each $R^{10}$ is halo; and n, Q, $R^1$, $R^3$, m, $R^4$, Ring A, L, and Ring B are as detailed herein for Formula (0) or Formula (1).

In some embodiments of Formula (8), $R^2$ and $R^x$ are taken together with the carbon atoms to which they are attached to form an optionally substituted $C_3$ cycloalkyl ring. In other embodiments of Formula (8), $R^2$ and $R^x$ are taken together with the carbon atoms to which they are attached to form an optionally substituted $C_3$ cycloalkyl ring.

In some embodiments of a compound of Formula (8), L is *—$OCH_2$—** and Ring B is phenyl. In some embodiments, the compound is of Formula (9):

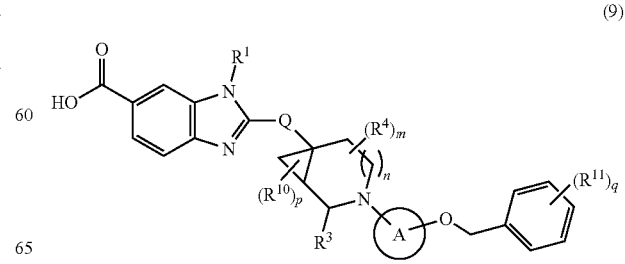

(9)

or a pharmaceutically acceptable salt thereof, wherein q is 0, 1, 2, or 3; $R^{11}$ is halo, CN, $C_1$-$C_6$ alkyl optionally substituted by halo or CN, —$OC_1$-$C_6$ alkyl optionally substituted by halo or CN, —$COCH_3$, —$CONH_2$, —$S(O)_2CH_3$, or phenyl optionally substituted by halo or CN; p and $R^{10}$ are as detailed herein for Formula (8); and n, Q, $R^1$, $R^3$, m, $R^4$, and Ring A are as detailed herein for Formula (0) or Formula (1).

In some embodiments of a compound of Formula (9), Ring A is pyridinyl. In some embodiments, the compound is of Formula (10):

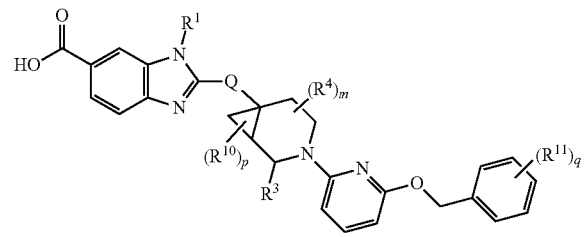

(10)

or a pharmaceutically acceptable salt thereof, wherein p and $R^{10}$ are as detailed herein for Formula (8); q and $R^{11}$ are as detailed herein for Formula (9); and n, Q, $R^1$, $R^3$, m, and $R^4$ are as detailed herein for Formula (0) or Formula (1).

In some embodiments of a compound of Formula (0) or Formula (1) (including compounds of Formula (2)-(10) and subformulae thereof), $R^5$ is optionally substituted 3- to 6-membered heterocyclyl. In some embodiments, $R^5$ is

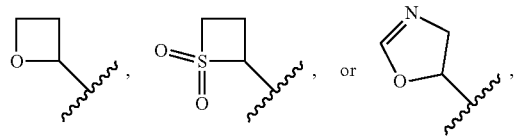 [SMILES: *C1CCO1 ; *C1CCS1(=O)=O ; *C1CN=CO1]

each of which is optionally substituted. In some embodiments, $R^5$ is

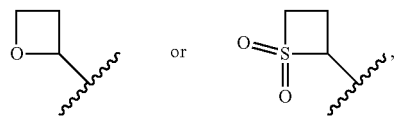 [SMILES: *C1CCO1 ; *C1CCS1(=O)=O]

each of which is optionally substituted. In some embodiments of any of the foregoing, $R^5$ is optionally substituted by one to three substituents independently selected from the group consisting of halo, oxo, CN, $C_1$-$C_6$ alkyl, $C_3$-$C_6$ cycloalkyl, and —$OC_1$-$C_6$ alkyl, wherein each $C_1$-$C_6$ alkyl, $C_3$-$C_6$ cycloalkyl, and —$OC_1$-$C_6$ alkyl substituent is independently optionally substituted by halo or CN. In some such embodiments, $R^5$ is optionally substituted by one to three substituents independently selected from the group consisting of halo, oxo, CN, $C_1$-$C_6$ alkyl, $C_3$-$C_6$ cycloalkyl, and —$OC_1$-$C_6$ alkyl. In some such embodiments, $R^5$ is optionally substituted by one to three substituents independently selected from the group consisting of halo, oxo, CN, $C_1$-$C_6$ alkyl, and —$OC_1$-$C_6$ alkyl. In some such embodiments, $R^5$ is optionally substituted by one to three substituents independently selected from the group consisting of halo, oxo, CN, $C_1$-$C_3$ alkyl, and —$OC_1$-$C_3$ alkyl. In some such embodiments, $R^5$ is optionally substituted by one to three substituents independently selected from the group consisting of Cl, F, Br, oxo, CN, $C_1$-$C_3$ alkyl, and —$OC_1$-$C_3$ alkyl. In some such embodiments, $R^5$ is optionally substituted by one to three substituents independently selected from the group consisting of Cl, F, Br, $C_1$-$C_3$ alkyl, and —$OC_1$-$C_3$ alkyl. In some such embodiments, $R^5$ is optionally substituted by one to three substituents independently selected from the group consisting of Cl, F, Br, and $C_1$-$C_3$ alkyl. In some embodiments, $R^5$ is unsubstituted.

In some embodiments of a compound of Formula (0) or Formula (1) (including compounds of Formula (2)-(10) and subformulae thereof), $R^5$ is an optionally substituted 5- to 6-membered heteroaryl. In some embodiments, $R^5$ is an optionally substituted 5-membered heteroaryl. In some embodiments, $R^5$ is pyrrolyl, oxazolyl, imidazolyl, triazolyl, thiazolyl, or isothiazolyl, each of which is optionally substituted. In some embodiments, $R^5$ is oxazolyl, triazolyl, or thiazolyl, each of which is optionally substituted. In some embodiments, $R^5$ is optionally substituted triazolyl. In some embodiments, $R^5$ is optionally substituted thiazolyl. In some embodiments, $R^5$ is

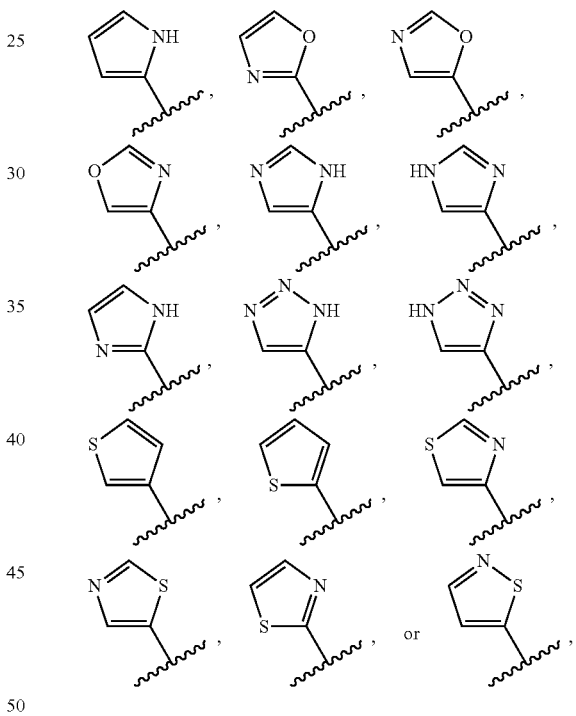

each of which is optionally substituted. In some embodiments, $R^5$ is

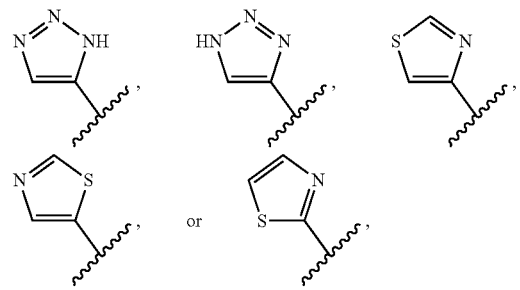

or each of which is optionally substituted. In some embodiments, $R^5$ is

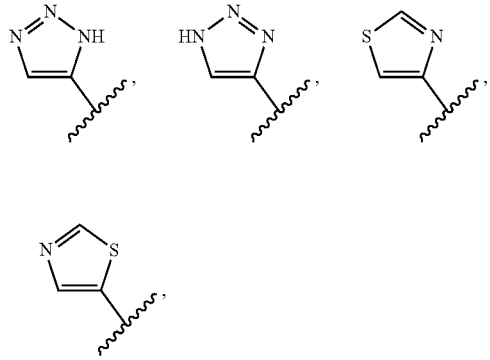

each of which is optionally substituted. In some embodiments, $R^5$ is

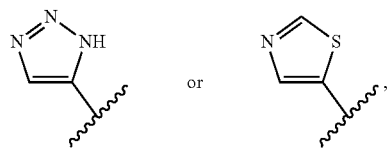 [SMILES: *c1cnn[nH]1 ; *c1cncs1]

each of which is optionally substituted. In some embodiments, $R^5$ is

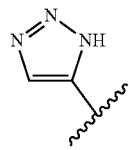

which is optionally substituted. In some embodiments, $R^5$ is

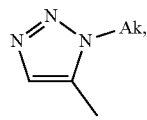

wherein Ak is an alkyl group (e.g., $C_{1-4}$ alkyl group). In some embodiments, $R^5$ is

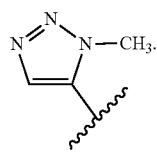

In some embodiments, $R^5$ is

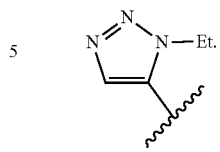

In some embodiments, $R^5$ is

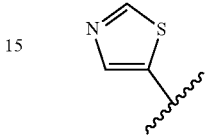

which is optionally substituted. In some embodiments of any of the foregoing, $R^5$ is optionally substituted by one to three substituents independently selected from the group consisting of halo, oxo, CN, $C_1$-$C_6$ alkyl, $C_3$-$C_6$ cycloalkyl, and —O$C_1$-$C_6$ alkyl, wherein each $C_1$-$C_6$ alkyl, $C_3$-$C_6$ cycloalkyl, and —O$C_1$-$C_6$ alkyl substituent is independently optionally substituted by halo or CN. In some such embodiments, $R^5$ is optionally substituted by one to three substituents independently selected from the group consisting of halo, oxo, CN, $C_1$-$C_6$ alkyl, $C_3$-$C_6$ cycloalkyl, and —O$C_1$-$C_6$ alkyl. In some such embodiments, $R^5$ is optionally substituted by one to three substituents independently selected from the group consisting of halo, oxo, CN, $C_1$-$C_6$ alkyl, and —O$C_1$-$C_6$ alkyl. In some such embodiments, $R^5$ is optionally substituted by one to three substituents independently selected from the group consisting of halo, oxo, CN, $C_1$-$C_3$ alkyl, and —O$C_1$-$C_3$ alkyl. In some such embodiments, $R^5$ is optionally substituted by one to three substituents independently selected from the group consisting of Cl, F, Br, oxo, CN, $C_1$-$C_3$ alkyl, and —O$C_1$-$C_3$ alkyl. In some such embodiments, $R^5$ is optionally substituted by one to three substituents independently selected from the group consisting of Cl, F, Br, $C_1$-$C_3$ alkyl, and —O$C_1$-$C_3$ alkyl. In some such embodiments, $R^5$ is optionally substituted by one to three substituents independently selected from the group consisting of Cl, F, Br, and $C_1$-$C_3$ alkyl, such as methyl, ethyl, propyl, or isopropyl. In some embodiments, $R^5$ is unsubstituted.

In some embodiments of a compound of Formula (0) or Formula (1) (including compounds of Formula (2)-(10) and subformulae thereof, if applicable), X is N, Y is N, and $R^2$ and $R^3$ taken together with the carbon atoms to which they are attached form a $C_3$-$C_4$ cycloalkyl ring. In some embodiments, X is $CR^x$, wherein $R^x$ is hydrogen, OH or $C_1$-$C_6$ alkyl, Y is N, and $R^2$ and $R^3$ taken together with the carbon atoms to which they are attached form a $C_3$-$C_4$ cycloalkyl ring. In some embodiments, X is N, Y is $CR^y$ wherein $R^y$ is hydrogen, OH or $C_1$-$C_6$ alkyl, and $R^2$ and $R^3$ taken together with the carbon atoms to which they are attached form a $C_3$-$C_4$ cycloalkyl ring. In some embodiments, X is $CR^x$, $R^x$ is taken together with $R^2$ and the carbon atoms to which they are attached to form an optionally substituted $C_3$-$C_4$ cycloalkyl ring, Y is N, and $R^3$ is hydrogen, oxo, or $C_1$-$C_6$ alkyl. In some embodiments of any of the foregoing, Q is $CR^7R^8$.

In some embodiments, when Q is —O—, —N($R^9$)—, or —S—, X is $CR^x$, wherein $R^x$ is hydrogen, OH or $C_1$-$C_6$ alkyl, Y is N, and $R^2$ and $R^3$ taken together with the carbon atoms to which they are attached form a $C_3$-$C_4$ cycloalkyl ring. In some embodiments, when Q is —O—, —N($R^9$)—, or —S—, X is CR$^x$, R$^x$ is taken together with R$^2$ and the carbon atoms to which they are attached to form an optionally substituted C$_3$-C$_4$ cycloalkyl ring, Y is N, and R$^3$ is hydrogen, oxo, or C$_1$-C$_6$ alkyl.

In some embodiments of a compound of Formula (0) or Formula (1) (including compounds of Formula (2)-(10) and subformulae thereof), or a pharmaceutically acceptable salt thereof, n is 0. In other embodiments, n is 1.

In some embodiments of a compound of Formula (0) or Formula (1) (including compounds of Formula (2)-(10) and subformulae thereof, if applicable), or a pharmaceutically acceptable salt thereof, the moiety

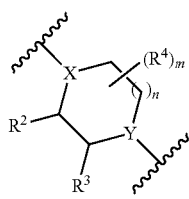 is 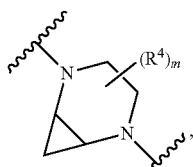,

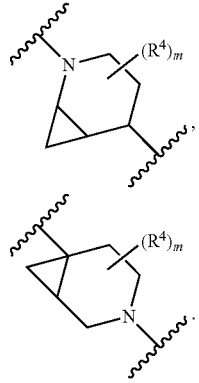

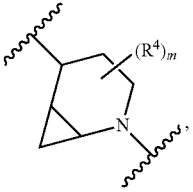, or

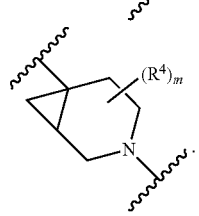

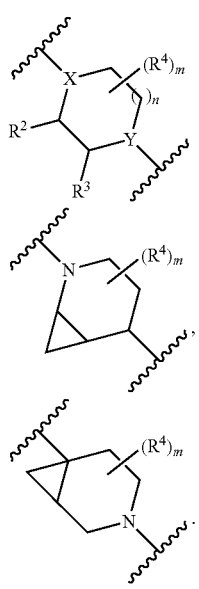

In some embodiments of a compound of Formula (0) or Formula (1) (including compounds of Formula (2)-(10) and subformulae thereof, if applicable), or a pharmaceutically acceptable salt thereof, Q is CR$^7$R$^8$ and the moiety

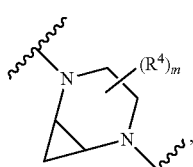 is 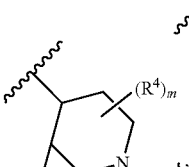,

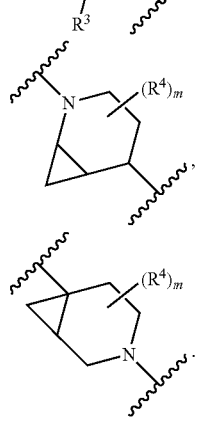

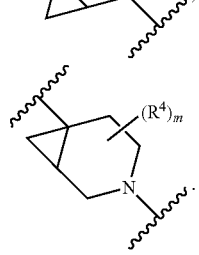, or

In some embodiments of a compound of Formula (0) or Formula (1) (including compounds of Formula (2)-(10) and subformulae thereof, if applicable), or a pharmaceutically acceptable salt thereof, Q is CR$^7$R$^8$ and the moiety

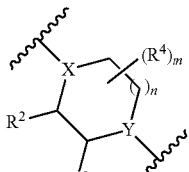 is 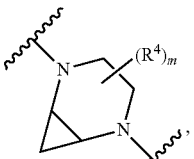,

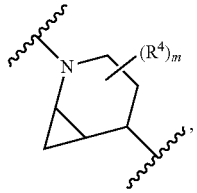 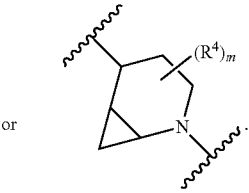, or

In some such embodiments, Q is CR$^7$R$^8$ and the moiety

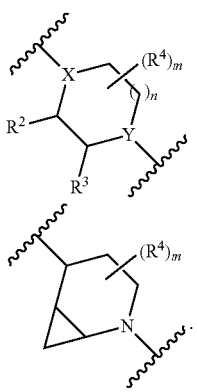 is 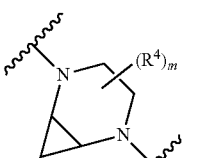 or

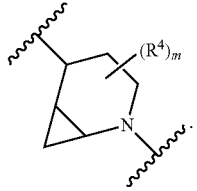

In some such embodiments, Q is CR$^7$R$^8$ and the moiety

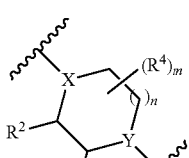 is 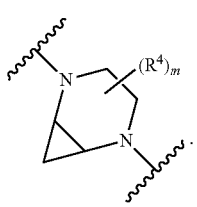.

In some such embodiments, Q is CR$^7$R$^8$ and the moiety

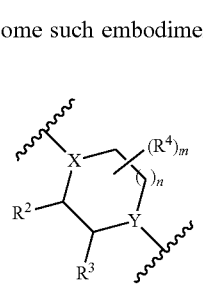 is 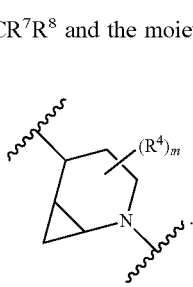.

In other embodiments of a compound of Formula (0) or Formula (1) (including compounds of Formula (2)-(10) and subformulae thereof, if applicable), or a pharmaceutically acceptable salt thereof, Q is —O—, —N(R⁹)—, or —S—, and the moiety

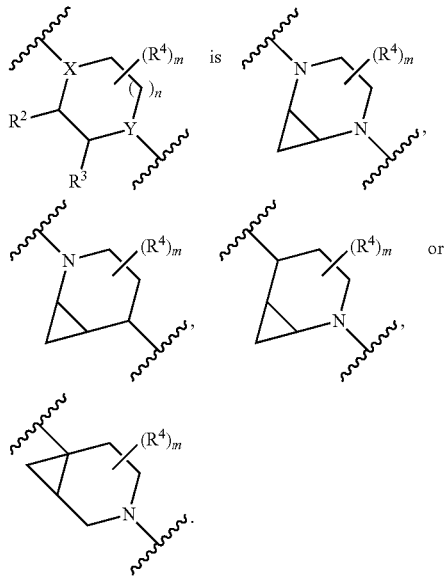

In some such embodiments, Q is —O—, —N(R⁹)—, or —S—, and the moiety

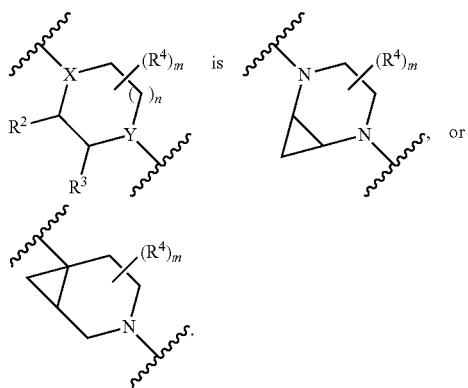

In some such embodiments, Q is —O—, —N(R⁹)—, or —S—, and the moiety

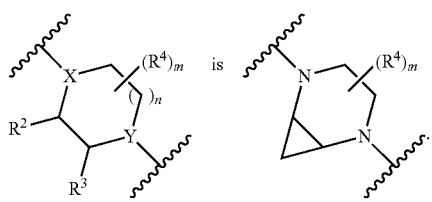

In some embodiments of a compound of Formula (0) or Formula (1) (including compounds of Formula (2)-(10) and subformulae thereof), or a pharmaceutically acceptable salt thereof, m is 0, 1, 2, or 3. In other embodiments, m is 0, 1, or 2. In other embodiments, m is 0 or 1. In some embodiments of any of the foregoing, each $R^4$ is oxo or $C_1$-$C_6$ alkyl. In some such embodiments, each $R^4$ is oxo or methyl. In some embodiments, m is 0.

In some embodiments of a compound of Formula (0) or Formula (1) (including compounds of Formula (2)-(10) and subformulae thereof, if applicable), Q is selected from the group consisting of —C(R⁷)(R⁸)—, —O—, —N(R⁹)—, and —S—, wherein R⁷ and R⁸ are independently hydrogen, halogen, or $C_1$-$C_6$ alkyl; and R⁹ is hydrogen or $C_1$-$C_6$ alkyl. In some embodiments, Q is selected from the group consisting of —C(R⁷)(R⁸)—, —O—, —N(R⁹)—, and —S—, wherein R⁷ is hydrogen, halogen, or $C_1$-$C_6$ alkyl, and R⁸ is halogen or $C_1$-$C_6$ alkyl; and R⁹ is hydrogen or $C_1$-$C_6$ alkyl. Examples of suitable Q groups include, but are not limited to, —CH₂—, —CHF—, —C(H)(CH₃)—, —CF₂—, —C(CH₃)₂—, —NH—, —N(CH₃)—, —O—, —S—, and the like. In some embodiments, Q is not —CH₂—.

In some embodiments of a compound of Formula (0) or Formula (1) (including compounds of Formula (2)-(10) and subformulae thereof), or a pharmaceutically acceptable salt thereof, Ring A is an optionally substituted 5- to 12-membered heterocyclyl. In some embodiments, Ring A is

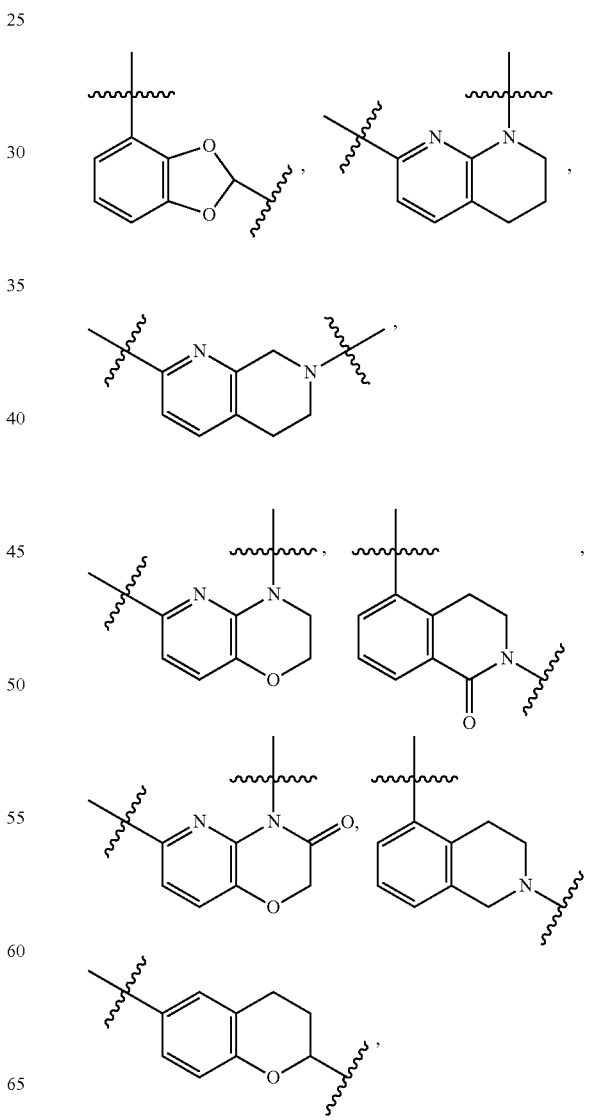

-continued

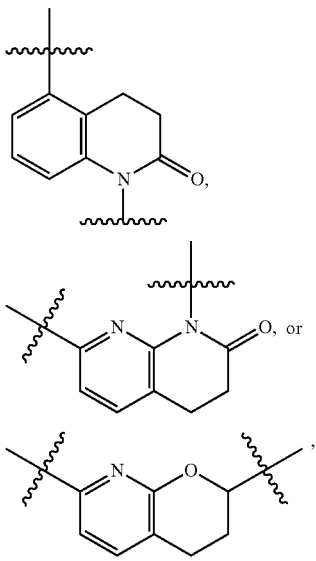

each of which is optionally substituted. In some embodiments, Ring A is

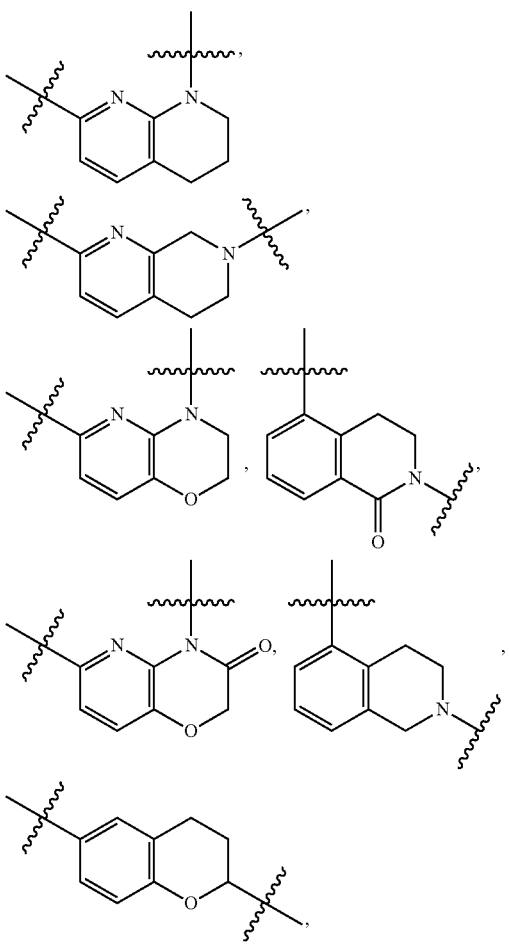

-continued

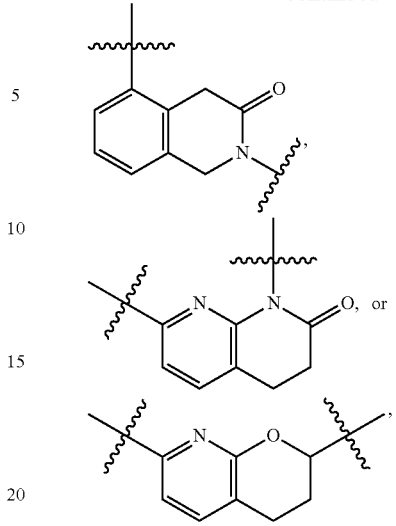

each of which is optionally substituted. In some embodiments of any of the foregoing, Ring A is optionally substituted by halo, OH, CN, $C_3$-$C_6$ cycloalkyl, or $C_1$-$C_6$ alkyl optionally substituted by halo or OH. In some such embodiments, Ring A is optionally substituted by halo or OH. In some such embodiments, Ring A is optionally substituted by halo. In some embodiments, Ring A is unsubstituted.

In some embodiments of a compound of Formula (0) or Formula (1) (including compounds of Formula (2)-(10) and subformulae thereof), or a pharmaceutically acceptable salt thereof, Ring A is optionally substituted 5- to 12-membered heteroaryl. In some embodiments, Ring A is

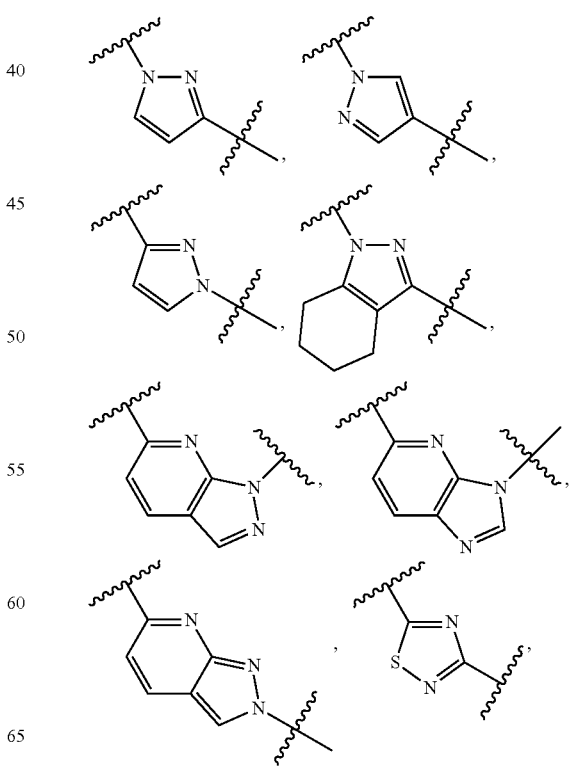

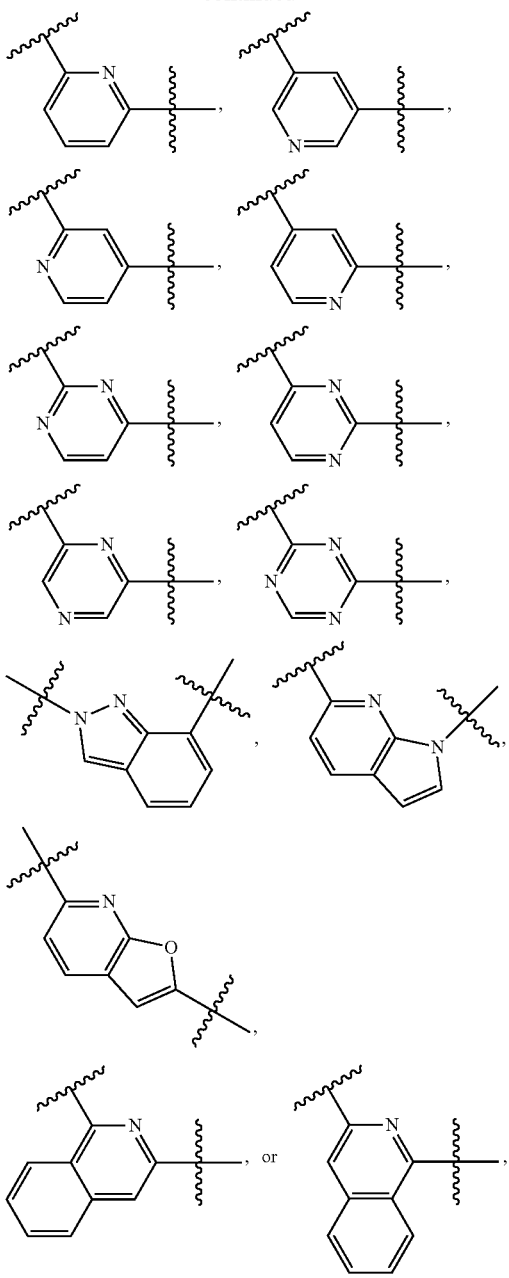

each of which is optionally substituted. In some embodiments, Ring A is

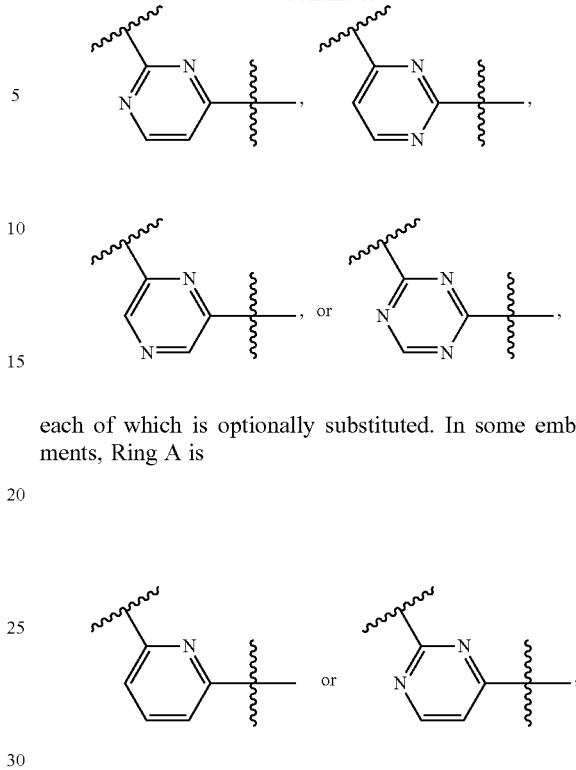

each of which is optionally substituted. In some embodiments, Ring A is each of which is optionally substituted. In some embodiments, Ring A is which is optionally substituted. In some embodiments of any of the foregoing, Ring A is optionally substituted by halo, OH, CN, $C_3$-$C_6$ cycloalkyl, or $C_1$-$C_6$ alkyl optionally substituted by halo or OH. In some such embodiments, Ring A is optionally substituted by halo or OH. In some such embodiments, Ring A is optionally substituted by halo. In some embodiments, Ring A is unsubstituted.

In some embodiments of a compound of Formula (0) or Formula (1) (including compounds of Formula (2)-(10) and subformulae thereof, if applicable), or a pharmaceutically acceptable salt thereof, L is a bond. In some embodiments, L is —O—. In some embodiments, L is $C_1$-$C_6$ alkylene. In some embodiments, L is unsubstituted $C_1$-$C_6$ alkylene. In some embodiments, L is $C_1$-$C_6$ alkylene optionally substituted by $R^L$, wherein each $R^L$ is independently halo, OH, oxo, or $C_1$-$C_6$ alkyl, or two $R^L$ are taken together with the carbon atom or atoms to which they are attached to form $C_3$-$C_6$ cycloalkyl or 3- to 6-membered heterocyclyl. In some embodiments, L is unsubstituted $C_1$-$C_2$ alkylene. In some embodiments, L is $C_1$-$C_2$ alkylene optionally substituted by $R^L$, wherein each $R^L$ is independently halo, OH, oxo, or $C_1$-$C_6$ alkyl. In some embodiments, L is unsubstituted $C_2$ alkylene. In some embodiments, L is $C_2$ alkylene optionally substituted by $R^L$, wherein each $R^L$ is independently halo, OH, oxo, or $C_1$-$C_6$ alkyl. In some such embodiments, L is

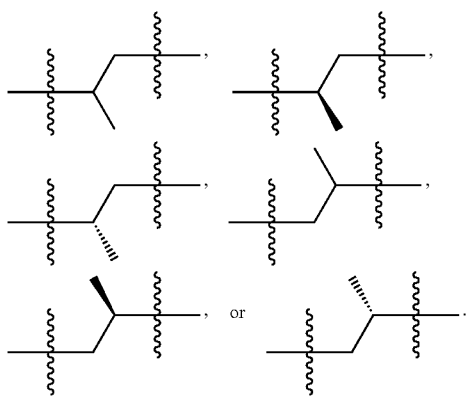

In some embodiments, L is $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-**, wherein * represents the point of attachment to ring A and ** represents the point of attachment to ring B, wherein $R^6$ is hydrogen or $C_1$-$C_6$ alkyl. For example, L can be *—$OCH_2$—**. In some embodiments, when L is $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-**, L is substituted by $R^L$, wherein each $R^L$ is independently $C_1$-$C_6$ alkyl or halo, or two $R^L$ are taken together with the carbon atom or atoms to which they are attached to form $C_3$-$C_6$ cycloalkyl or 3- to 6-membered heterocyclyl. To give a specific example, when L is *—$OC(R^L)_2$—**, two $R^L$ can be taken together with the carbon atom or atoms to which they are attached to form $C_3$-$C_6$ cycloalkyl or 3- to 6-membered heterocyclyl. In some embodiments, L is *—O—$C_1$-$C_6$ alkylene-**. In some embodiments, L is *—O—$C_1$-$C_3$ alkylene-**. In some embodiments, L is *—$OCH_2$—**.

In some embodiments of a compound of Formula (0) or Formula (1) (including compounds of Formula (0)-(10) and subformulae thereof, if applicable), Ring B is optionally substituted $C_3$-$C_{10}$ cycloalkyl. Exemplary $C_3$-$C_{10}$ cycloalkyl include, but are not limited to,

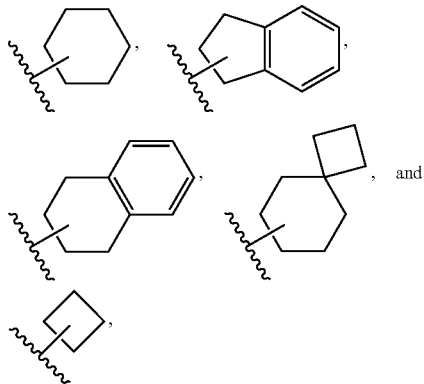

each of which is independently optionally substituted. In some embodiments of the foregoing, Ring B is optionally substituted by one to three substituents independently selected from the group consisting of halo, CN, oxo, $C_1$-$C_6$ alkyl optionally substituted by halo or CN, $OC_1$-$C_6$ alkyl optionally substituted by halo or CN, —$COCH_3$, —$CONH_2$, —$S(O)_2CH_3$ and phenyl optionally substituted by halo or CN. In some such embodiments, Ring B is optionally substituted by one to three substituents independently selected from the group consisting of halo and CN. In some embodiments, Ring B is substituted by two substituents independently selected from F, Cl, and CN.

In some embodiments of a compound of Formula (0) or Formula (1) (including compounds of Formula (0)-(10) and subformulae thereof, if applicable), Ring B is optionally substituted $C_6$-$C_{14}$ aryl. For example, the $C_6$-$C_{14}$ aryl can be

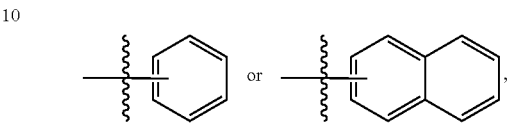

each of which is independently optionally substituted. In some embodiments, Ring B is phenyl, which is optionally substituted. In some embodiments of any of the foregoing, Ring B is optionally substituted by one to three substituents each independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl. In some such embodiments, Ring B is optionally substituted by one to three substituents independently selected from the group consisting of halo and CN. In some embodiments, Ring B is substituted by two substituents independently selected from F, Cl, and CN.

In some embodiments of a compound of Formula (0) or Formula (1) (including compounds of Formula (0)-(10) and subformulae thereof, if applicable), Ring B is optionally substituted 4- to 12-membered heterocyclyl. Exemplary 4- to 12-membered heterocyclyl include, but are not limited to,

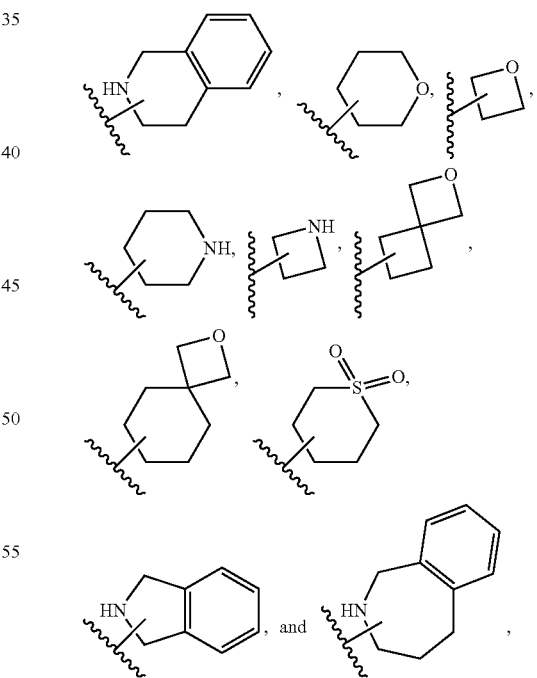

each of which is independently optionally substituted. In some embodiments of any of the foregoing, Ring B is optionally substituted by one to three substituents each independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl. In some such embodiments, Ring B is optionally substituted by one to three substituents independently selected from the group consisting of halo and CN. In some embodiments, Ring B is substituted by two substituents independently selected from F, Cl, and CN.

In some embodiments, Ring B is optionally substituted 5- to 12-membered heteroaryl. Exemplary 5- to 12-membered heteroaryl include, but are not limited to,

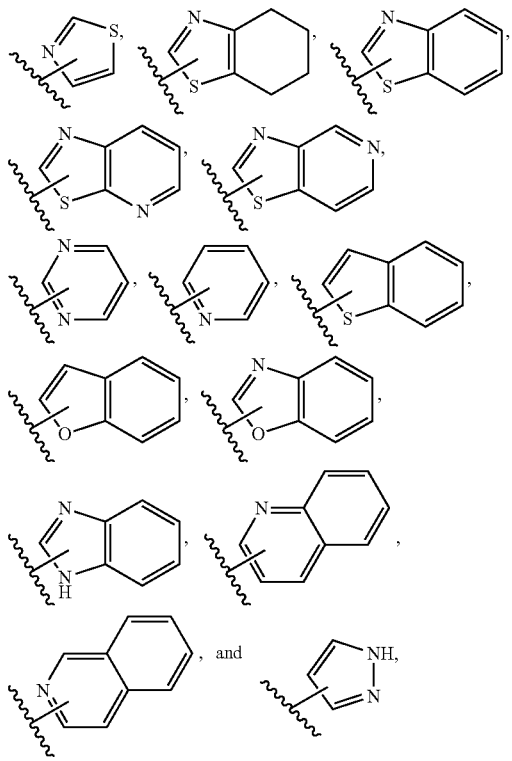

each of which is independently optionally substituted. In some embodiments of any of the foregoing, Ring B is optionally substituted by one to three substituents each independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$ and phenyl. In some such embodiments, Ring B is optionally substituted by one to three substituents independently selected from the group consisting of halo and CN.

In some embodiments of Formula (2)-(10), or subformulae thereof if applicable, p is 0, 1, or 2 and each $R^{10}$, when present, is halo. In some embodiments, p is 0. In some embodiments, p is 1. In some embodiments, p is 2. In some embodiments, p is 2 and each $R^{10}$ is halo. For instance, in some embodiments, the moiety

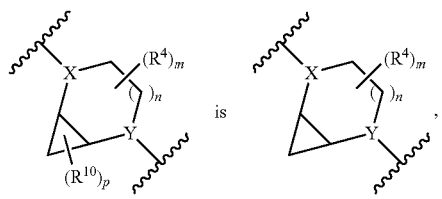

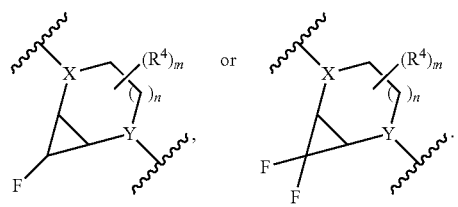

In some embodiments of Formula (3), (4), (6), (7), (9), and (10), or subformulae thereof if applicable, q is 0, 1, 2, or 3. In some embodiments, q is 2 or 3. In some embodiments, q is 0. In some embodiments, q is 1. In some embodiments, q is 2. In some embodiments, q is 3. In some embodiments, q is 2, and each $R^{11}$ is independently selected from halo or CN.

In the descriptions herein, it is understood that every description, variation, embodiment or aspect of a moiety/variable may be combined with every description, variation, embodiment or aspect of other moieties/variables the same as if each and every combination of descriptions is specifically and individually listed, for example, as shown in the subformulae below.

(1A)

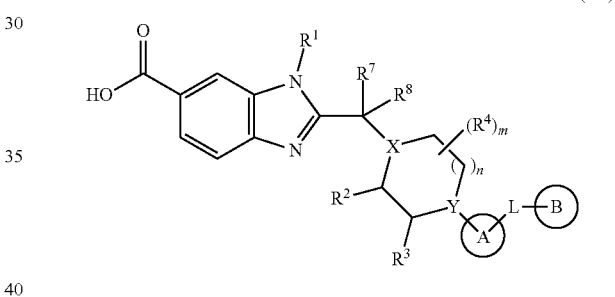

(1A-i)

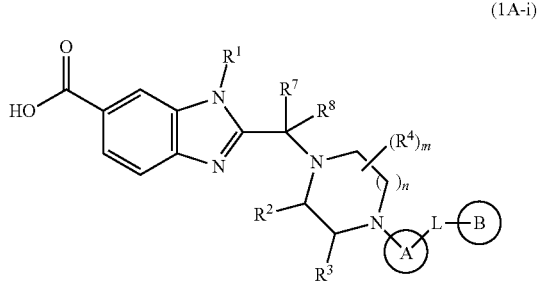

(1A-ii)

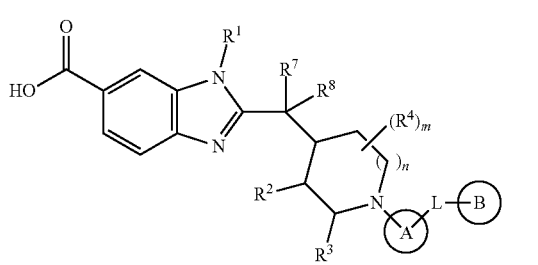

(1A-iii)
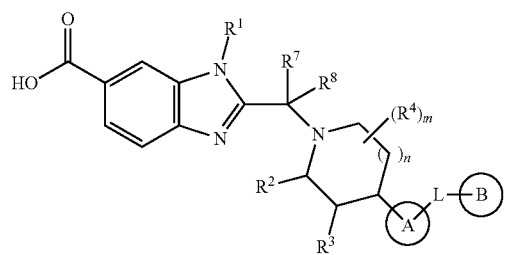
(1B)
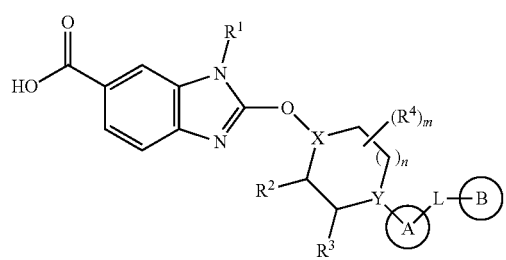
(1C)
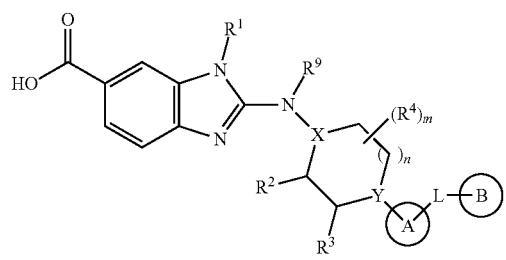
(1D)
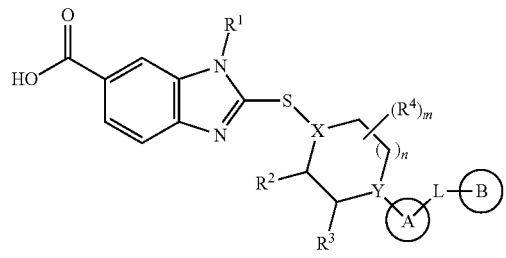
(2A)
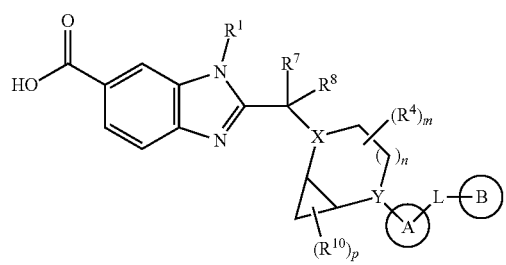
(2A-i)
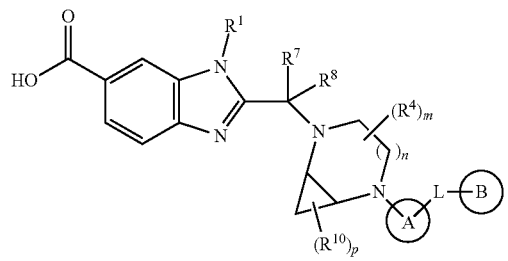
(2A-ii)
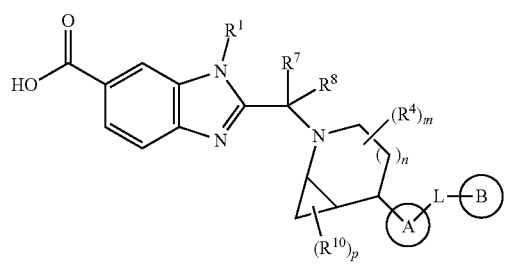
(2A-iii)
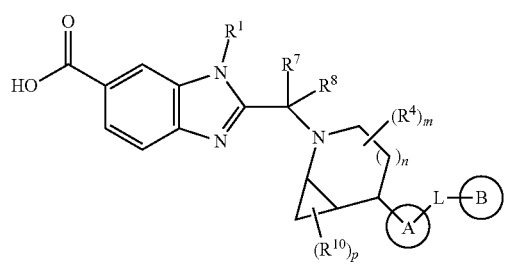
(2B)
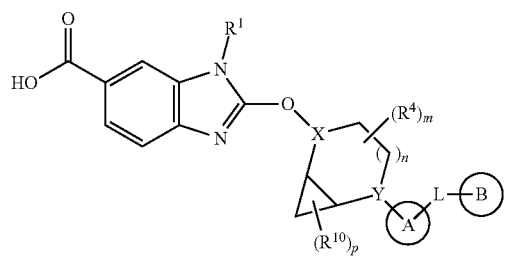
(2C)
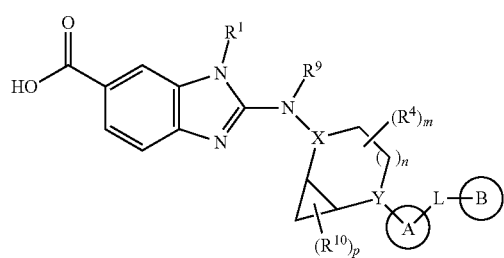

(2D)
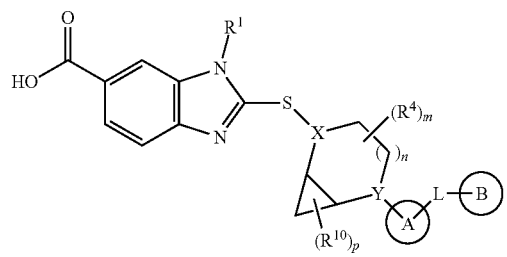
(3A)
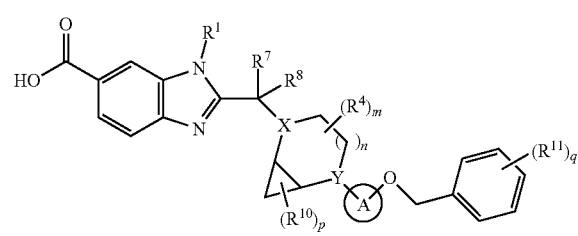
(3A-i)
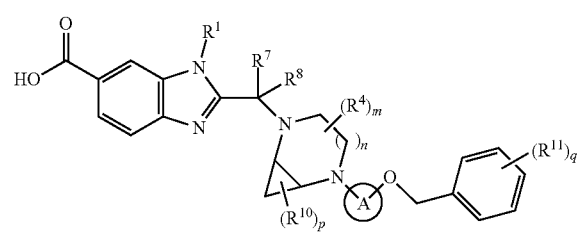
(3A-ii)
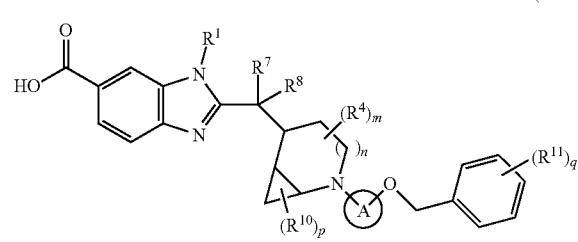
(3A-iii)
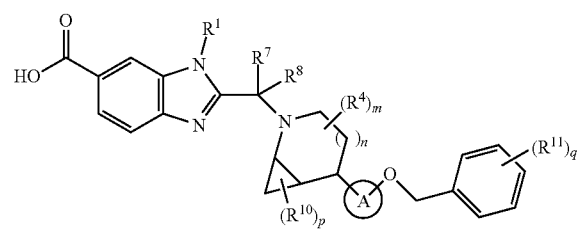
(3B)
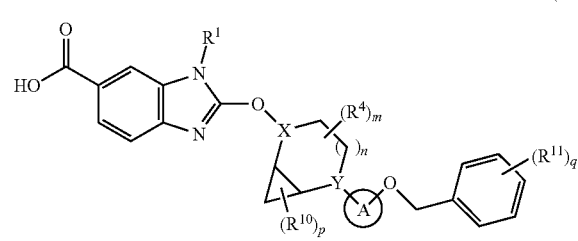
(3C)
(3D)
(4A)
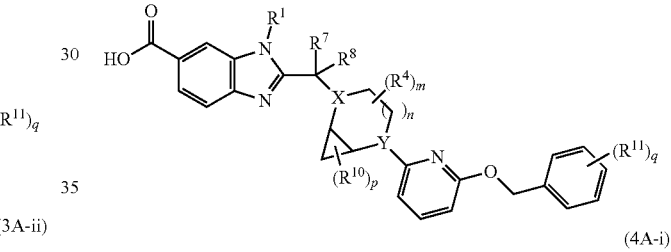
(4A-i)
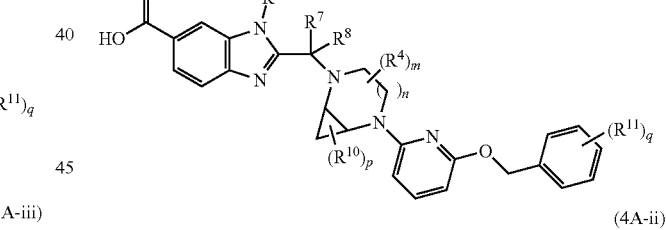
(4A-ii)
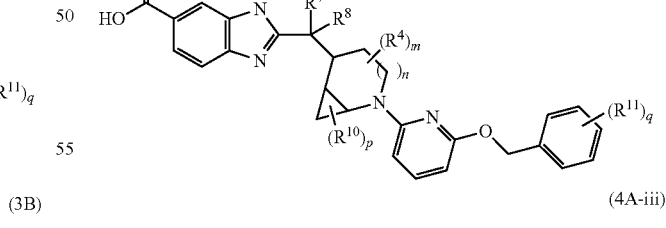
(4A-iii)
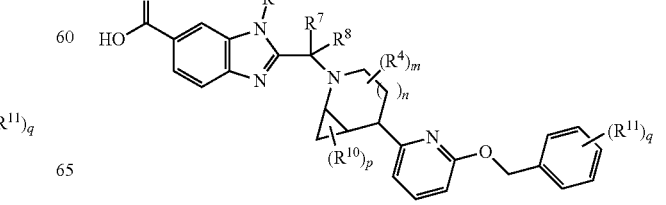

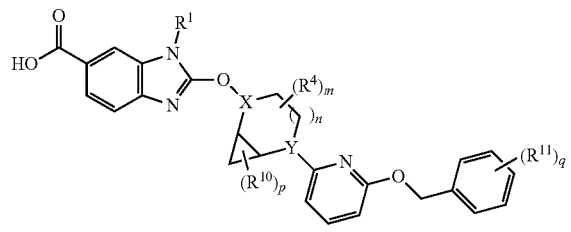
(4B)
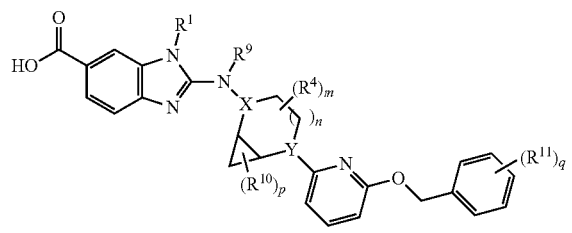
(4C)
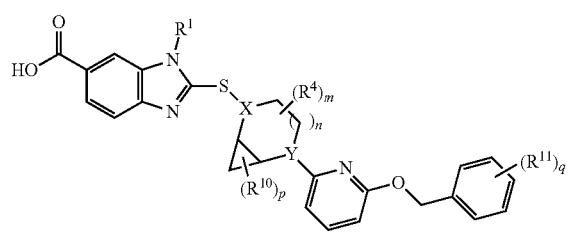
(4D)
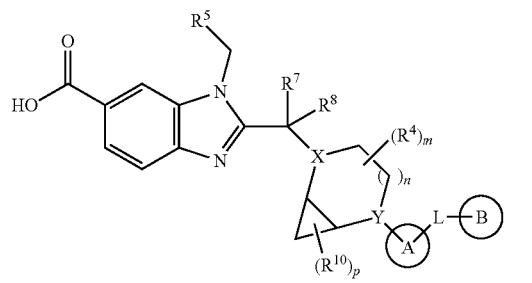
(5A)
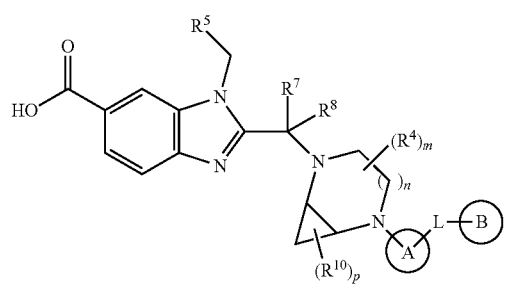
(5A-i)
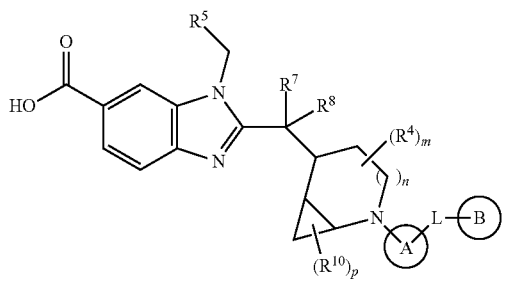
(5A-ii)
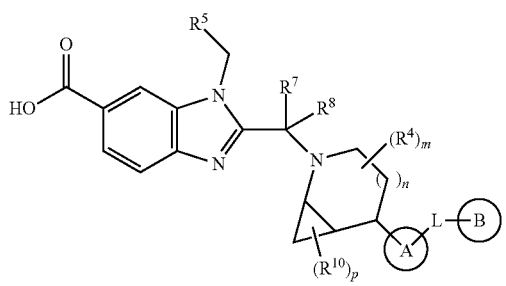
(5A-iii)
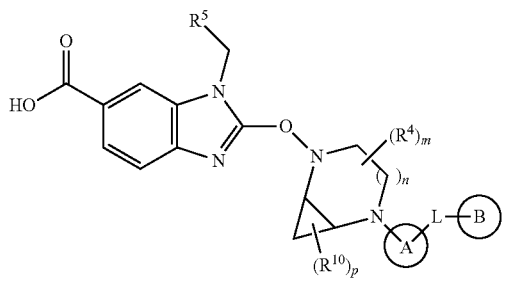
(5B)
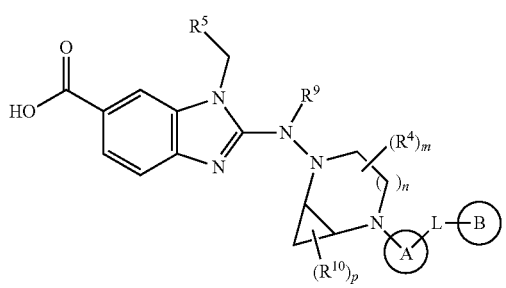
(5C)
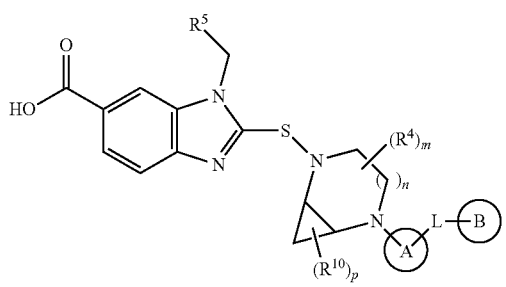
(5D)

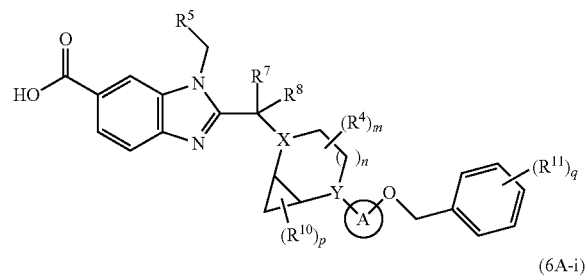
(6A)
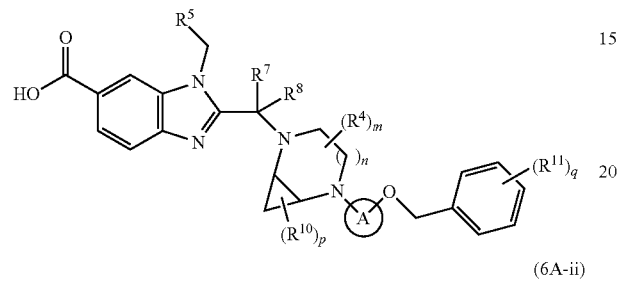
(6A-i)
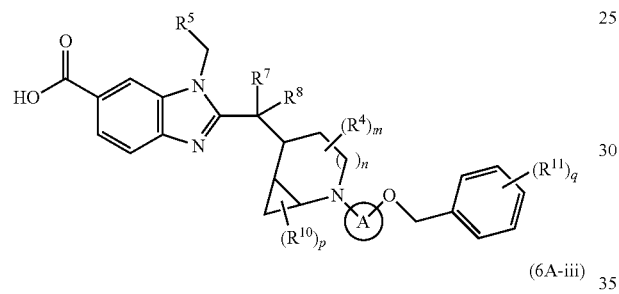
(6A-ii)

(6A-iii)
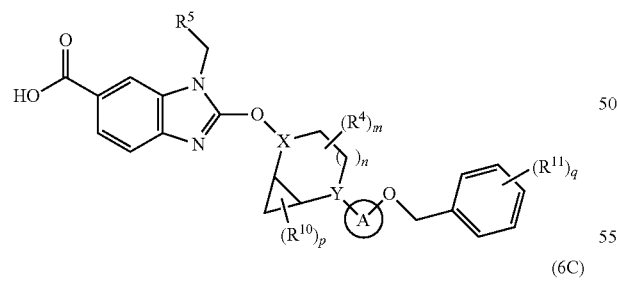
(6B)
(6C)
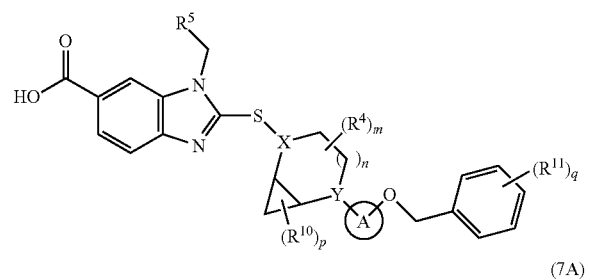
(6D)
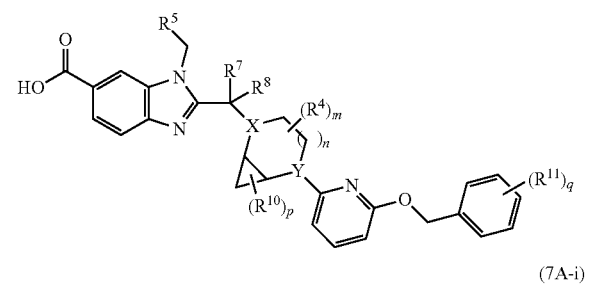
(7A)
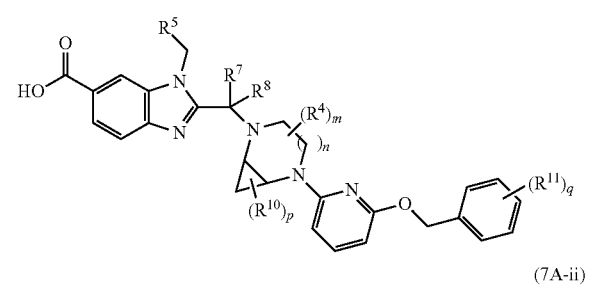
(7A-i)
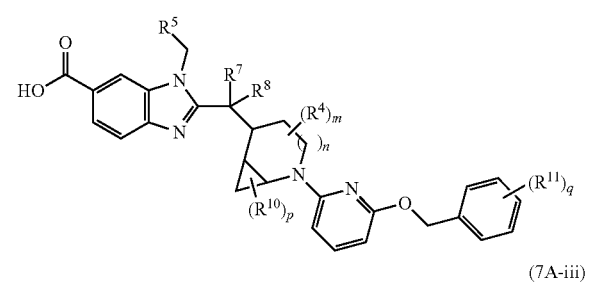
(7A-ii)
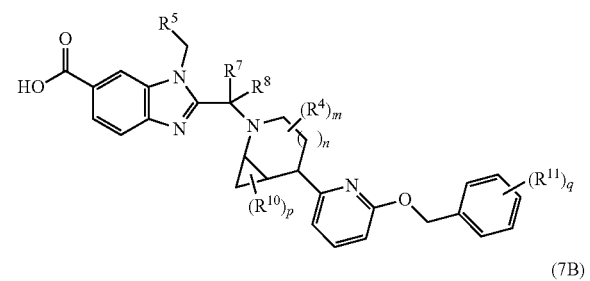
(7A-iii)
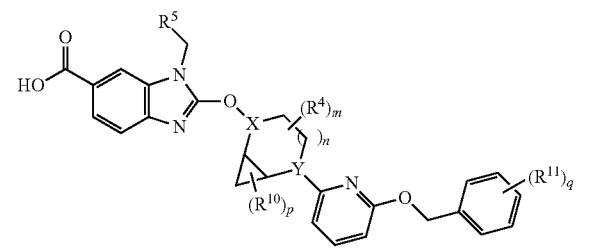
(7B)

(7C)
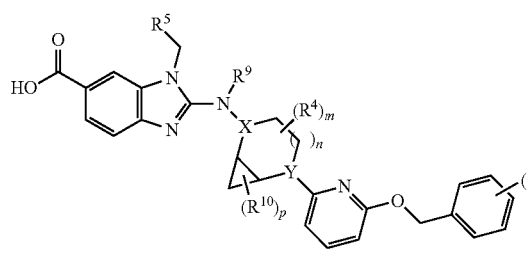
(7D)
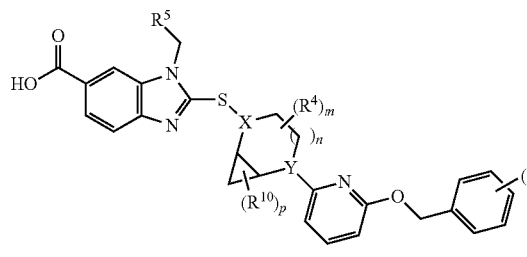
(8A)
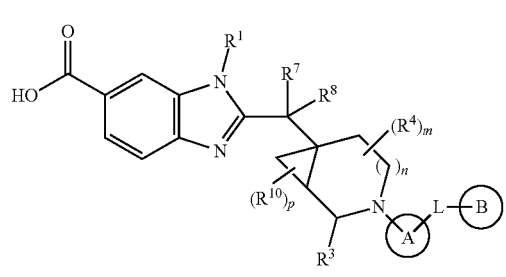
(8B)
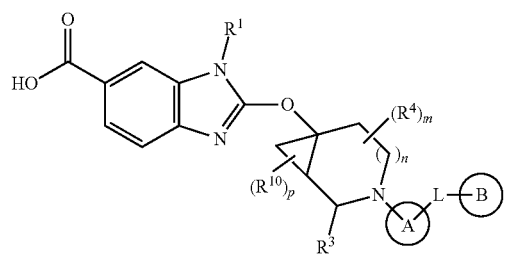
(8C)
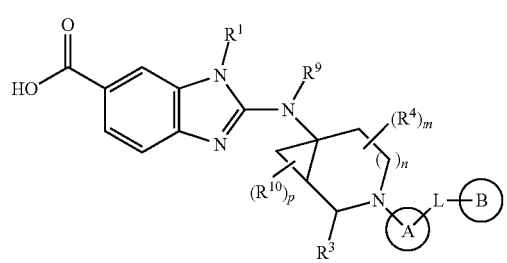
(8D)
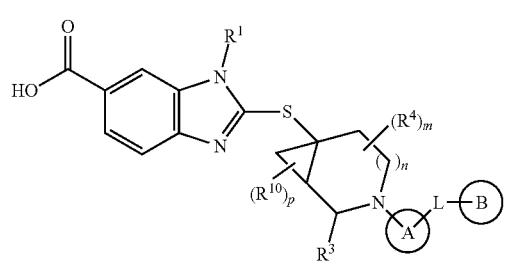
(9A)
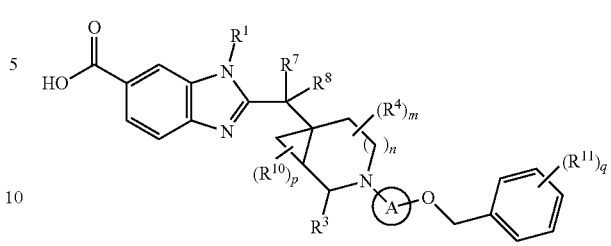
(9B)
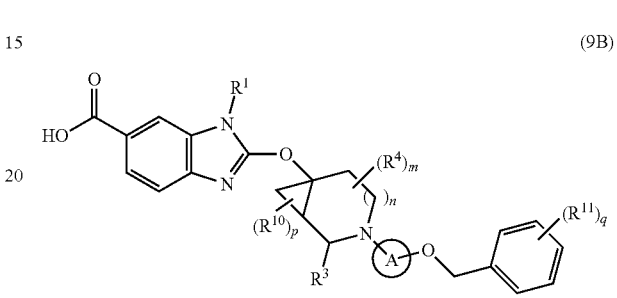
(9C)
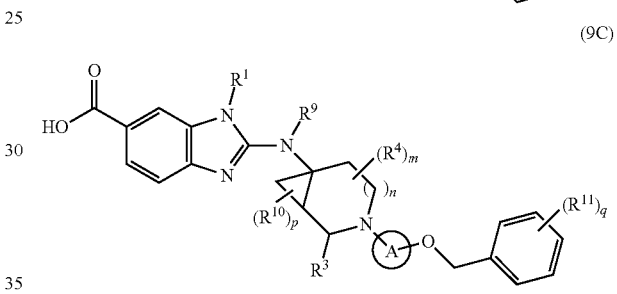
(9D)
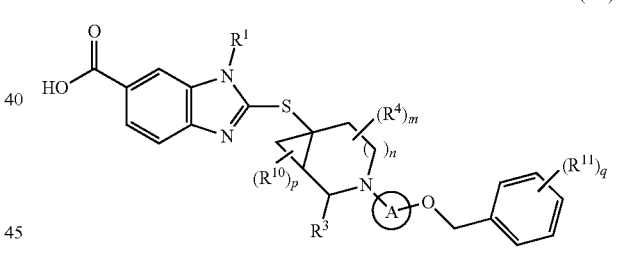
(10A)
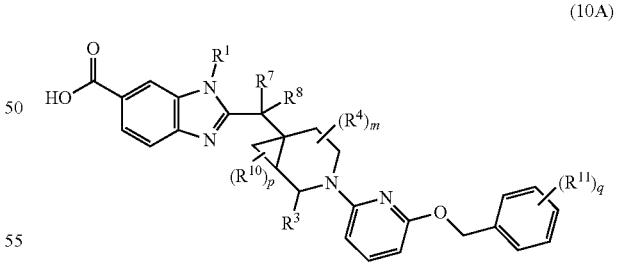
(10B)
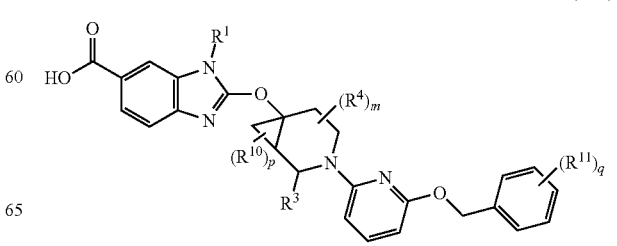

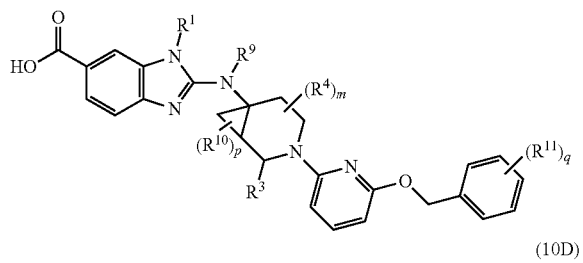

(10C)

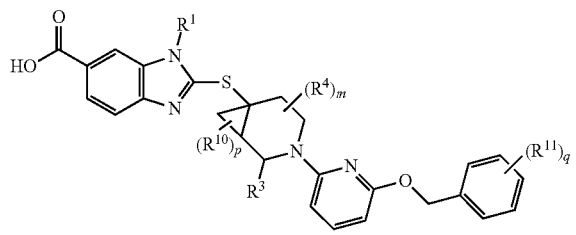

(10D)

In some embodiments of Formula (1A), (1A-i), (1A-ii), (1A-iii), (1), (1C), (1D), (2A), (2A-i), (2A-ii), (2A-iii), (2B), (2C), (2D), (3A), (3A-i), (3A-ii), (3A-iii), (3B), (3C), (3D), (4A), (4A-i), (4A-ii), (4A-iii), (4B), (4C), (4D), (5A), (5A-i), (5A-ii), (5A-iii), (5B), (5C), (5D), (6A), (6A-i), (6A-ii), (6A-iii), (6B), (6C), (6D), (7A), (7A-i), (7A-ii), (7A-iii), (7B), (7C), (7D), (8A), (8A-i), (8A-ii), (8A-iii), (8B), (8C), (8D), (9A), (9A-i), (9A-ii), (9A-iii), (9B), (9C), (9D), (10A), (10A-i), (10A-ii), (10A-iii), (10B), (10C), and (10D), $R^5$ is triazolyl or thiazolyl, each of which is optionally substituted. In some embodiments, $R^5$ is triazolyl which is unsubstituted. In some embodiments, $R^5$ is thiazolyl which is optionally substituted. In some embodiments of any of the foregoing, $R^5$ is optionally substituted by one to three substituents independently selected from the group consisting of halo, oxo, CN, $C_1$-$C_6$ alkyl, $C_3$-$C_6$ cycloalkyl, and —$OC_1$-$C_6$ alkyl, wherein each $C_1$-$C_6$ alkyl, $C_3$-$C_6$ cycloalkyl, and —$OC_1$-$C_6$ alkyl substituent is independently optionally substituted by halo or CN. In some such embodiments, $R^5$ is optionally substituted by one to three substituents independently selected from the group consisting of halo, oxo, CN, $C_1$-$C_6$ alkyl, $C_3$-$C_6$ cycloalkyl, and —$OC_1$-$C_6$ alkyl. In some such embodiments, $R^5$ is optionally substituted by one to three substituents independently selected from the group consisting of halo, oxo, CN, $C_1$-$C_6$ alkyl, and —$OC_1$-$C_6$ alkyl. In some such embodiments, $R^5$ is optionally substituted by one to three substituents independently selected from the group consisting of halo, oxo, CN, $C_1$-$C_3$ alkyl, and —$OC_1$-$C_3$ alkyl. In some such embodiments, $R^5$ is optionally substituted by one to three substituents independently selected from the group consisting of Cl, F, Br, oxo, CN, $C_1$-$C_3$ alkyl, and —$OC_1$-$C_3$ alkyl. In some such embodiments, $R^5$ is optionally substituted by one to three substituents independently selected from the group consisting of Cl, F, Br, $C_1$-$C_3$ alkyl, and —$OC_1$-$C_3$ alkyl. In some such embodiments, $R^5$ is optionally substituted by one to three substituents independently selected from the group consisting of Cl, F, Br, and $C_1$-$C_3$ alkyl, such as methyl, ethyl, propyl, or isopropyl. In some embodiments, $R^5$ is unsubstituted.

In some embodiments of Formula (1A), (1A-i), (1A-ii), (1A-iii), (1), (1C), (1D), (2A), (2A-i), (2A-ii), (2A-iii), (2B), (2C), (2D), (3A), (3A-i), (3A-ii), (3A-iii), (3B), (3C), (3D), (4A), (4A-i), (4A-ii), (4A-iii), (4B), (4C), (4D), (5A), (5A-i), (5A-ii), (5A-iii), (5B), (5C), (5D), (6A), (6A-i), (6A-ii), (6A-iii), (6B), (6C), (6D), (7A), (7A-i), (7A-ii), (7A-iii), (7B), (7C), (7D), (8A), (8A-i), (8A-ii), (8A-iii), (8B), (8C), (8D), (9A), (9A-i), (9A-ii), (9A-iii), (9B), (9C), (9D), (10A), (10A-i), (10A-ii), (10A-iii), (10B), (10C), and (10D), $R^5$ is

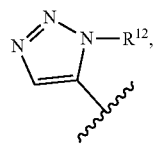

wherein $R^{12}$ is $C_1$-$C_6$ alkyl. In some such embodiments, $R^{12}$ is methyl. In other such embodiments, $R^{12}$ is ethyl. In other such embodiments, $R^{12}$ is isoproyl. In other such embodiments, $R^{12}$ is isobutyl.

The present disclosure also includes any or all of the stereochemical forms, including any enantiomeric or diastereomeric forms of the compounds described. Compounds of any formula given herein may have asymmetric centers and therefore exist in different enantiomeric or diastereomeric forms. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms, and mixtures thereof in any ratio, unless a specific stereochemistry is otherwise indicated. Where a formula or a compound of Table 1 is depicted with a particular stereochemical configuration, also provided herein is any alternative stereochemical configuration of the compound, as well as a mixture of stereoisomers of the compound in any ratio. For example, where a formula or a compound of Table 1 has a stereocenter that is in an "S" stereochemical configuration, also provided herein is the enantiomer of the compound wherein that stereocenter is in an "R" stereochemical configuration. Likewise, when a formula or a compound of Table 1 has a stereocenter that is in an "R" configuration, also provided herein is enantiomer of the compound in an "S" stereochemical configuration. Also provided are mixtures of the compound with both the "S" and the "R" stereochemical configuration. As another example, in Formula (0)-(7), and subformulae thereof, the moiety

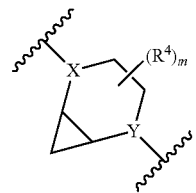

includes variations wherein the formula has the form

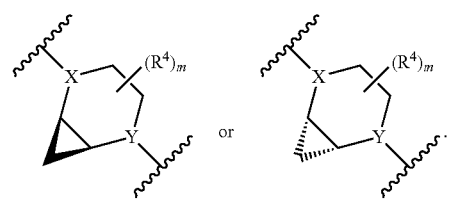

Also provided are mixtures comprising both forms

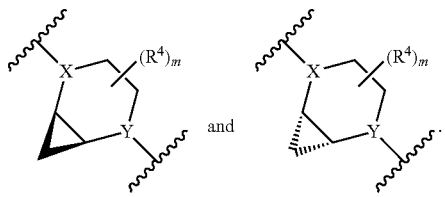

and

Similarly, the moiety

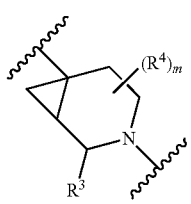

includes variations wherein the formula has the form

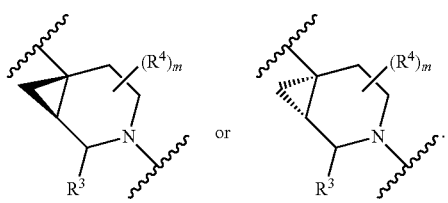

or

Also provided are mixtures comprising both forms

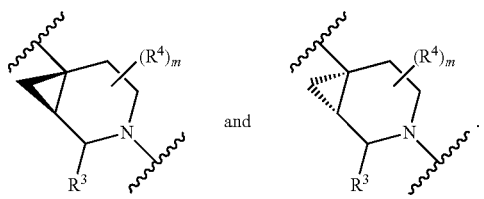

and

In some embodiments, one diastereomeric form may be preferred, for instance, compounds Formula (2) or subformulae thereof may be preferred with the configuration shown in Formula (2.1), Formula (2.1a), and Formula (2.1b) relative to the configuration shown in Formula (2.2), Formula (2.2a), and Formula (2.2b), respectively.

(2.1)

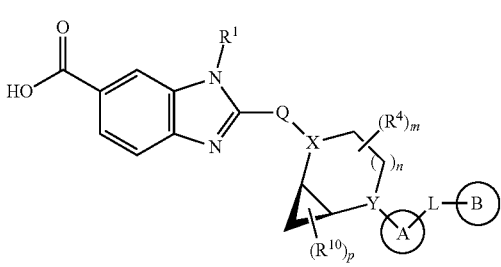

-continued (2.2)

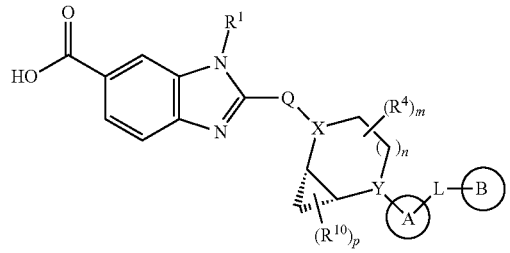

(2.1a)

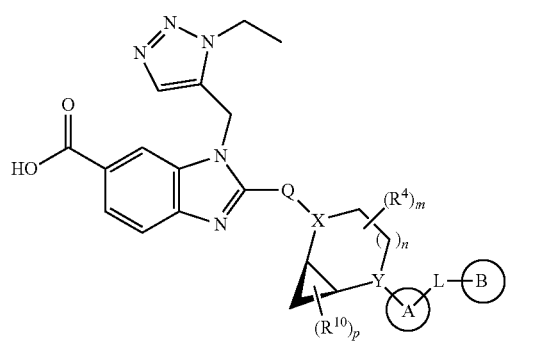

(2.2a)

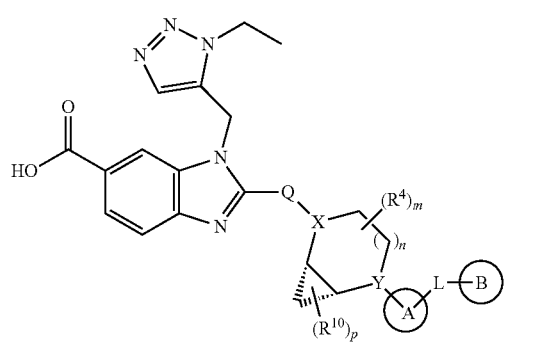

(2.1b)

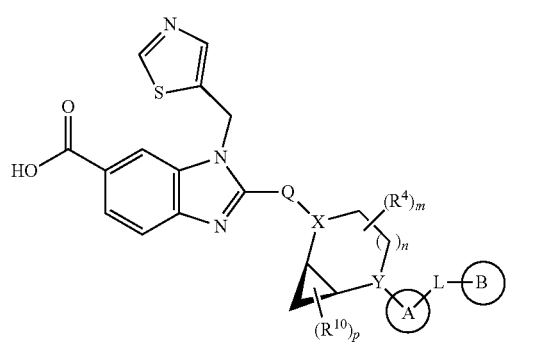

-continued (2.2b)

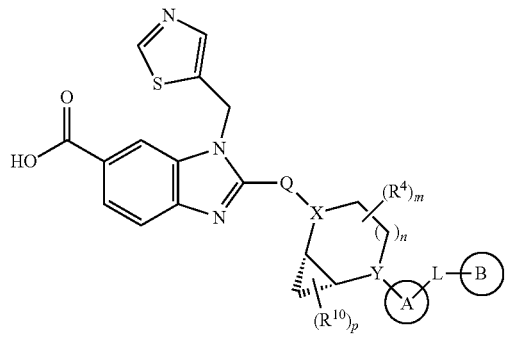

The compounds depicted herein may be present as salts even if salts are not depicted and it is understood that the present disclosure embraces all salts and solvates of the compounds depicted here, as well as the non-salt and non-solvate form of the compound, as is well understood by the skilled artisan. In some embodiments, the salts of the compounds provided herein are pharmaceutically acceptable salts.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of Formula (0), Formula (1), including compounds of Formula (2)-(10), or a subformula of any of the foregoing, or variations thereof described herein, where a fraction of one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^{2}H$, $^{3}H$, $^{11}C$, $^{13}C$, $^{14}C$, $^{13}N$, $^{15}O$, $^{17}O$, $^{32}P$, $^{35}S$, $^{18}F$, $^{36}Cl$. Certain isotope labeled compounds (e.g. $^{3}H$ and $^{14}C$) are useful in compound or substrate tissue distribution study. Incorporation of heavier isotopes such as deuterium ($^{2}H$) can afford certain therapeutic advantages resulting from greater metabolic stability, for example, increased in vivo half-life, or reduced dosage requirements and, hence may be preferred in some instances.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

The invention also includes any or all metabolites of any of the compounds described. The metabolites may include any chemical species generated by a biotransformation of any of the compounds described, such as intermediates and products of metabolism of the compound, such as would be generated in vivo following administration to a human.

Representative compounds are listed in Table 1 below. In some embodiments, provided is a compound, or a pharmaceutically acceptable salt thereof, which is selected from Compound Nos. 1-46 in Table 1. In some embodiments, provided is a compound, or a pharmaceutically acceptable salt thereof, which is Compound 1 in Table 1.

TABLE 1

| Compound No. | Structure |
|---|---|
| 1 | 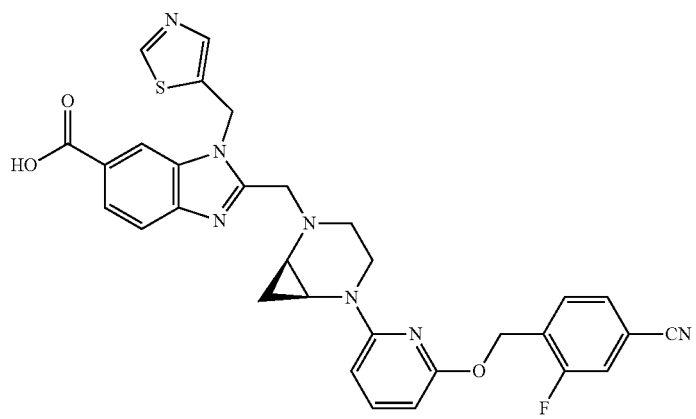 [SMILES: N#Cc1ccc(COc2cccc(N3CCN(Cc4nc5ccc(C(=O)O)cc5n4Cc4cncs4)[C@@H]4C[C@@H]43)n2)c(F)c1] |

TABLE 1-continued
| Compound No. | Structure |
|---|---|
| 2 | 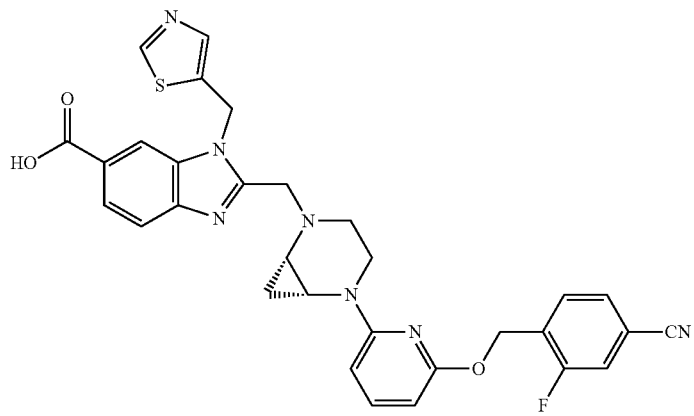 [SMILES: N#Cc1ccc(COc2cccc(N3CCN(Cc4nc5ccc(C(=O)O)cc5n4Cc4cncs4)[C@H]4C[C@H]43)n2)c(F)c1] |
| 3 | 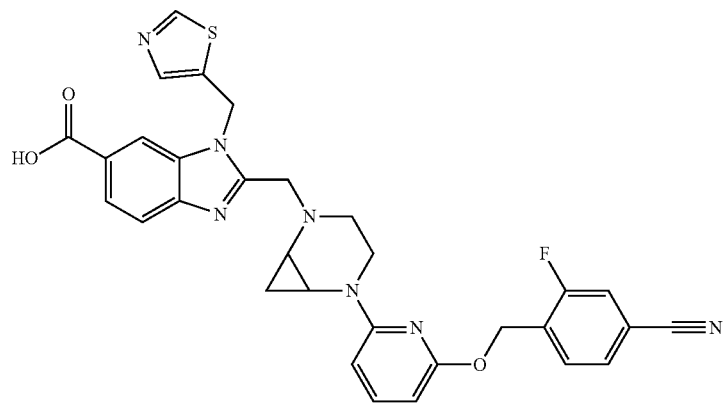 [SMILES: N#Cc1ccc(COc2cccc(N3CCN(Cc4nc5ccc(C(=O)O)cc5n4Cc4cncs4)C4CC43)n2)c(F)c1] |
| 4 | 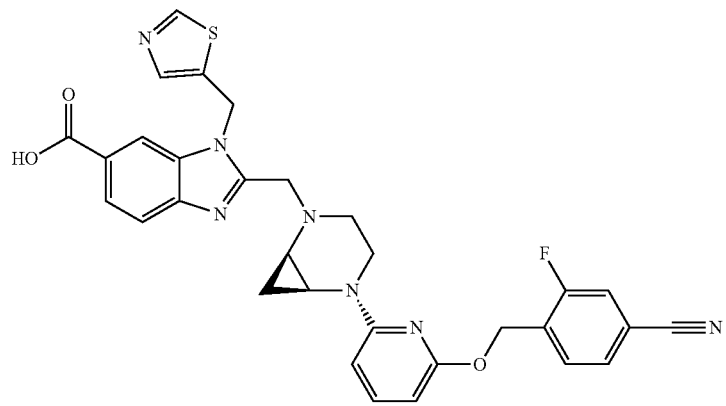 |

TABLE 1-continued
| Compound No. | Structure |
|---|---|
| 5 | 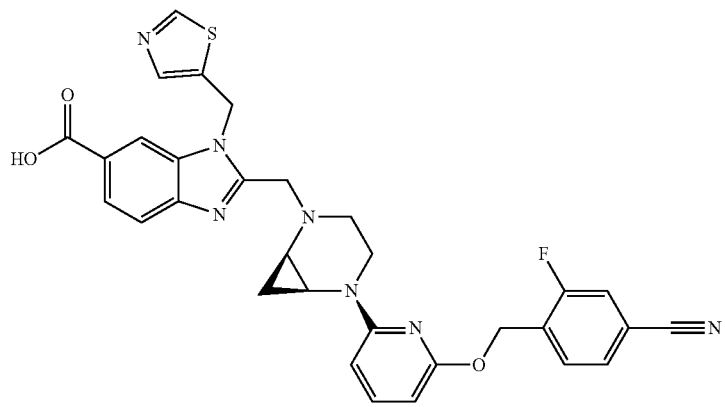 |
| 6 | 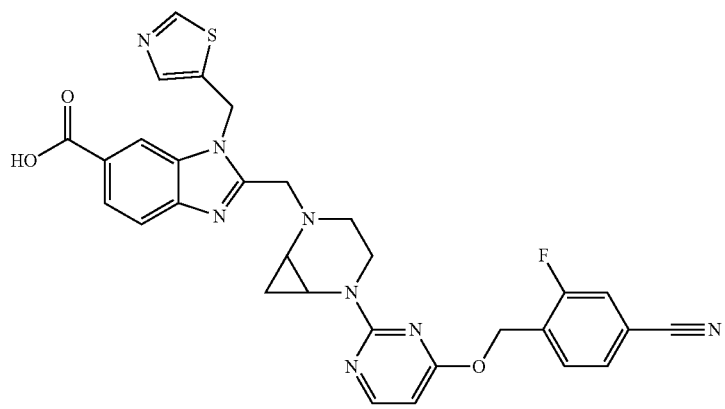 [SMILES: N#Cc1ccc(COc2ccnc(N3CCN(Cc4nc5ccc(C(=O)O)cc5n4Cc4cncs4)C4CC43)n2)c(F)c1] |
| 7 | 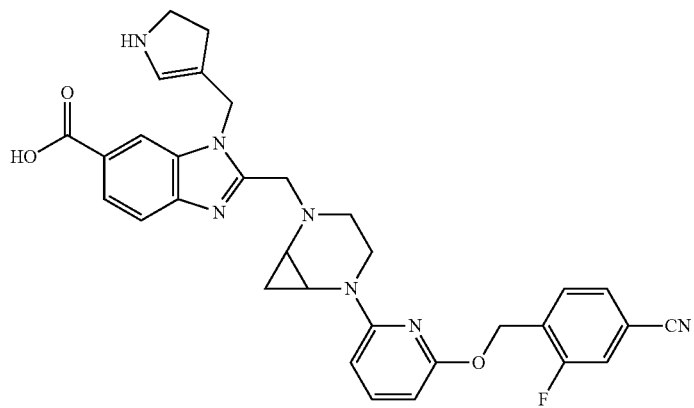 [SMILES: N#Cc1ccc(COc2cccc(N3CCN(Cc4nc5ccc(C(=O)O)cc5n4CC4=CNCC4)C4CC43)n2)c(F)c1] |

TABLE 1-continued
| Compound No. | Structure |
|---|---|
| 8 | 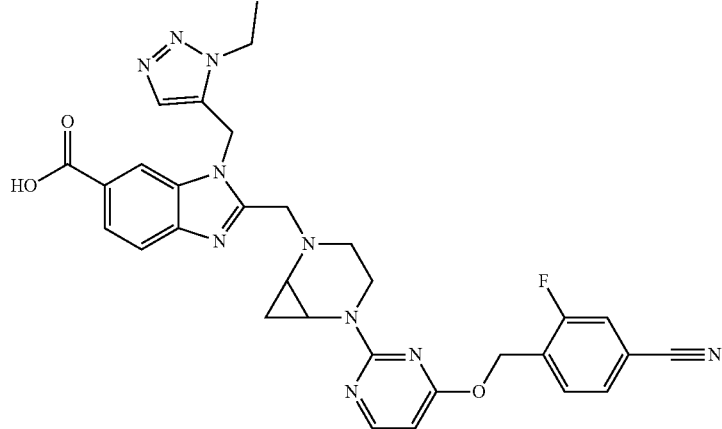 [SMILES: CCn1nncc1Cn1c(CN2CCN(c3nccc(OCc4ccc(C#N)cc4F)n3)C3CC32)nc2ccc(C(=O)O)cc21] |
| 9 | 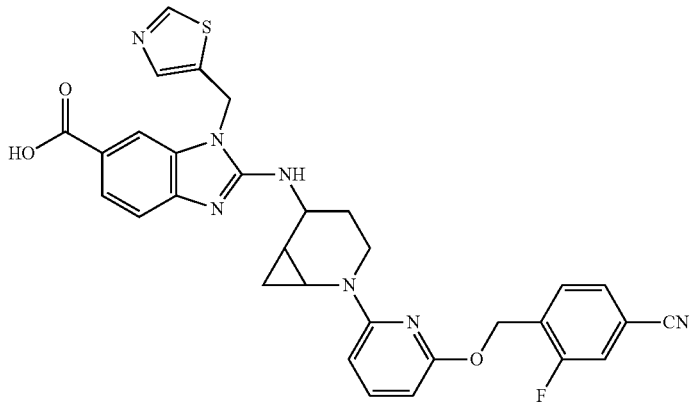 [SMILES: N#Cc1ccc(COc2cccc(N3CCC(Nc4nc5ccc(C(=O)O)cc5n4Cc4cncs4)C4CC43)n2)c(F)c1] |
| 10 | 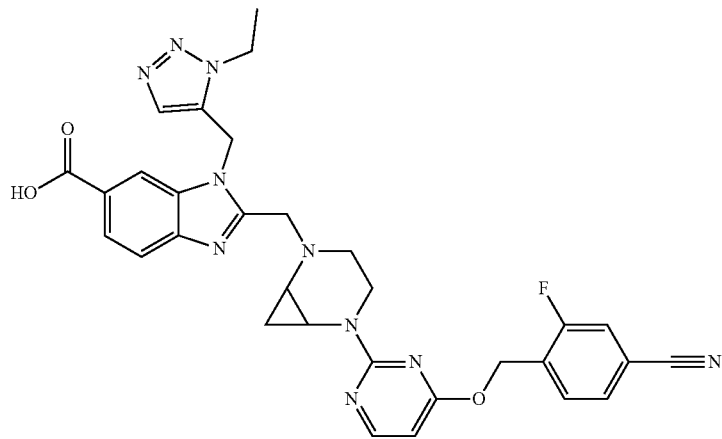 [SMILES: CCn1nncc1Cn1c(CN2CCN(c3nccc(OCc4ccc(C#N)cc4F)n3)C3CC32)nc2ccc(C(=O)O)cc21] |

TABLE 1-continued
| Compound No. | Structure |
|---|---|
| 11 | 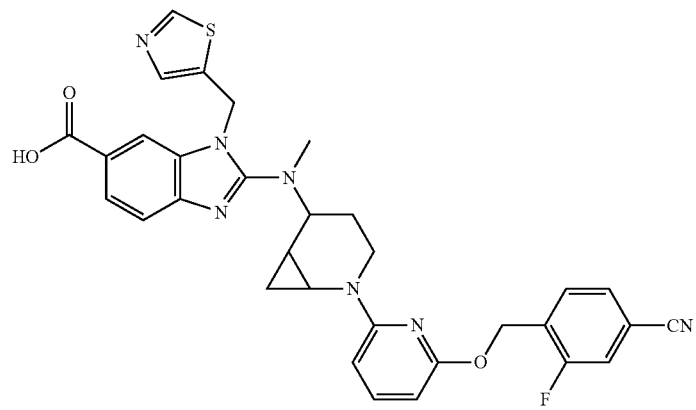 [SMILES: CN(c1nc2ccc(C(=O)O)cc2n1Cc1cncs1)C1CCN(c2cccc(OCc3ccc(C#N)cc3F)n2)C2CC12] |
| 12 | 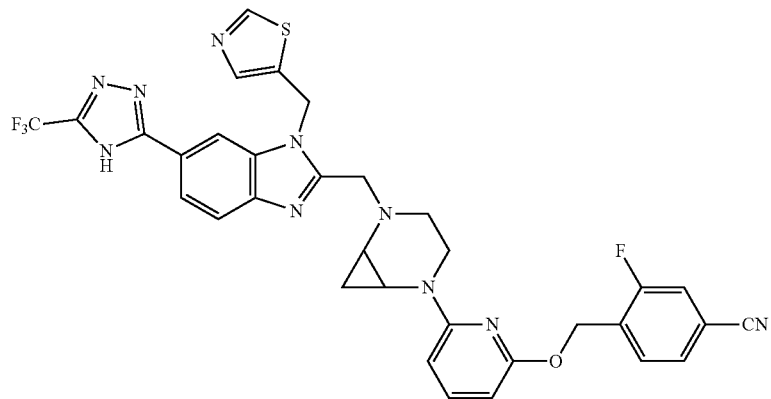 [SMILES: N#Cc1ccc(COc2cccc(N3CCN(Cc4nc5ccc(-c6nnc(C(F)(F)F)[nH]6)cc5n4Cc4cncs4)C4CC43)n2)c(F)c1] |
| 13 | 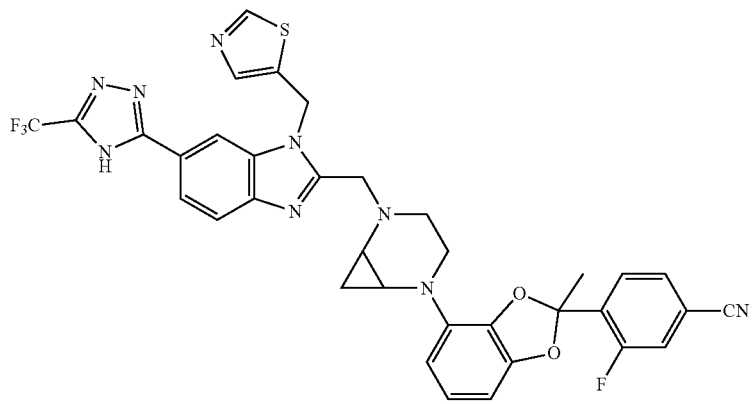 [SMILES: CC1(c2ccc(C#N)cc2F)Oc2cccc(N3CCN(Cc4nc5ccc(-c6nnc(C(F)(F)F)[nH]6)cc5n4Cc4cncs4)C4CC43)c2O1] |

TABLE 1-continued
| Compound No. | Structure |
|---|---|
| 14 | 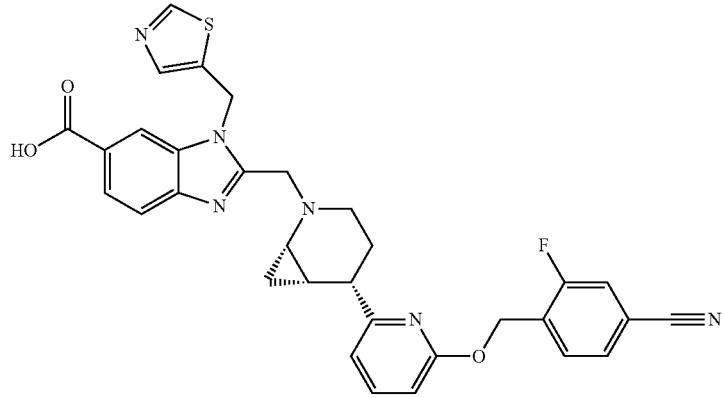 [SMILES: N#Cc1ccc(COc2cccc([C@H]3CCN(Cc4nc5ccc(C(=O)O)cc5n4Cc4cncs4)[C@H]4C[C@@H]34)n2)c(F)c1] |
| 15 | 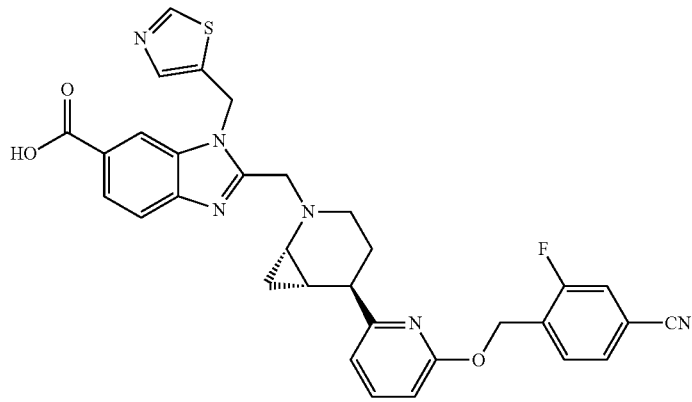 [SMILES: N#Cc1ccc(COc2cccc([C@@H]3CCN(Cc4nc5ccc(C(=O)O)cc5n4Cc4cncs4)[C@H]4C[C@@H]34)n2)c(F)c1] |
| 16 | 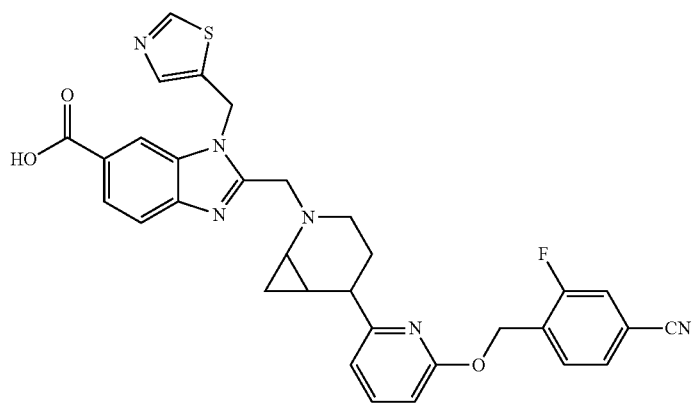 [SMILES: N#Cc1ccc(COc2cccc(C3CCN(Cc4nc5ccc(C(=O)O)cc5n4Cc4cncs4)C4CC34)n2)c(F)c1] |

TABLE 1-continued
| Compound No. | Structure |
|---|---|
| 17 | 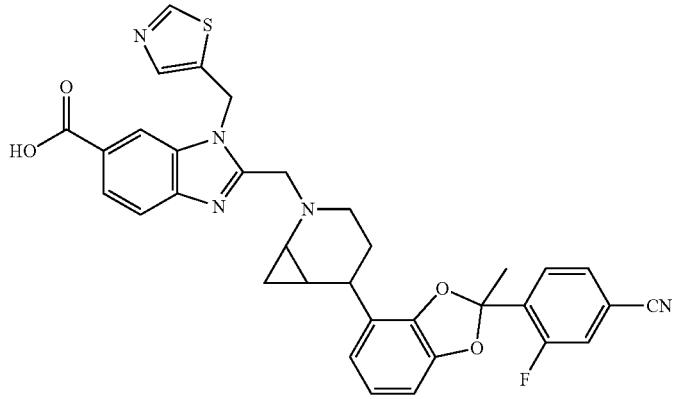 |
| 18 | 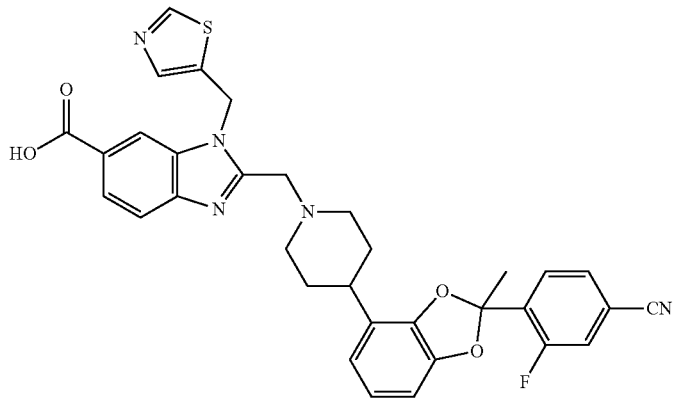 [SMILES: CC1(c2ccc(C#N)cc2F)Oc2cccc(C3CCN(Cc4nc5ccc(C(=O)O)cc5n4Cc4cncs4)CC3)c2O1] |
| 19 | 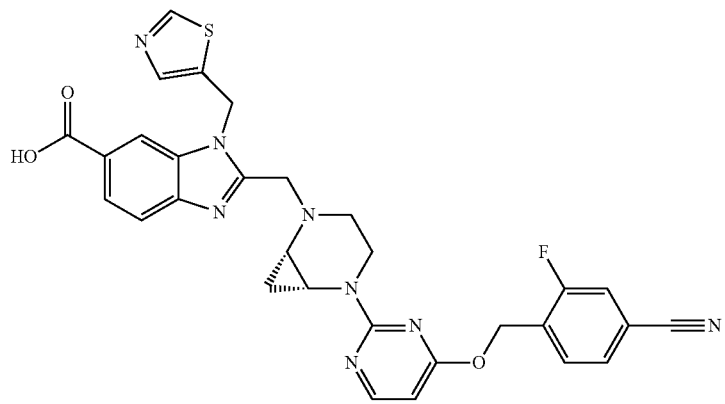 |

TABLE 1-continued
| Compound No. | Structure |
|---|---|
| 20 | 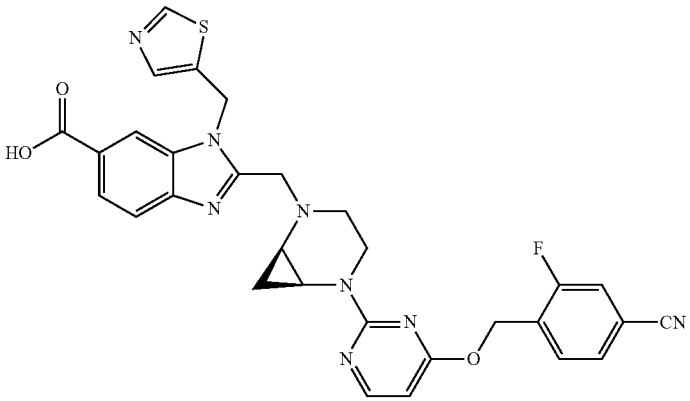 [SMILES: N#Cc1ccc(COc2ccnc(N3CCN(Cc4nc5ccc(C(=O)O)cc5n4Cc4cncs4)[C@@H]4C[C@@H]43)n2)c(F)c1] |
| 21 | 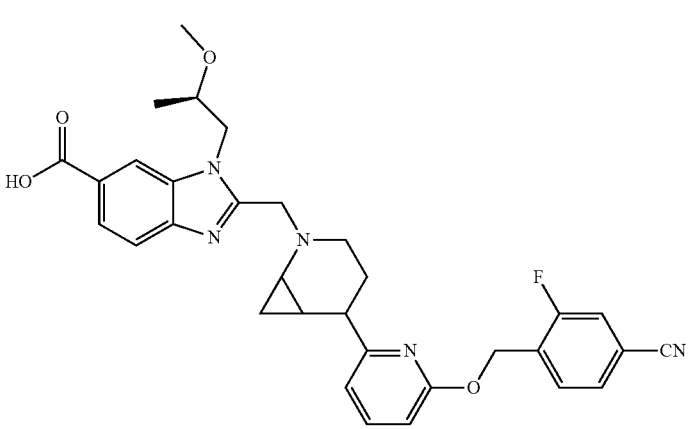 [SMILES: CO[C@H](C)Cn1c(CN2CCC(c3cccc(OCc4ccc(C#N)cc4F)n3)C3CC32)nc2ccc(C(=O)O)cc21] |
| 22 | 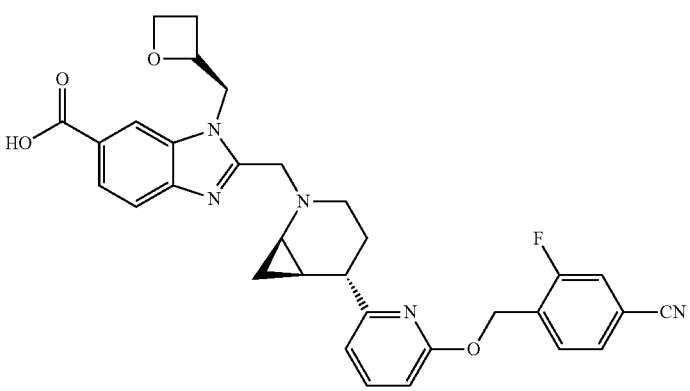 |
| 23 | 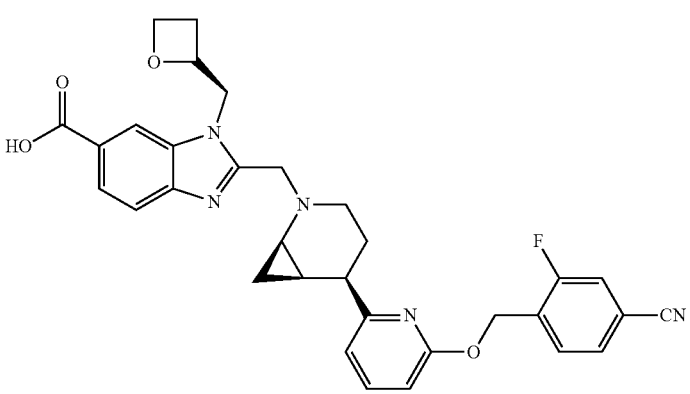 |

TABLE 1-continued

| Compound No. | Structure |
|---|---|
| 24 | 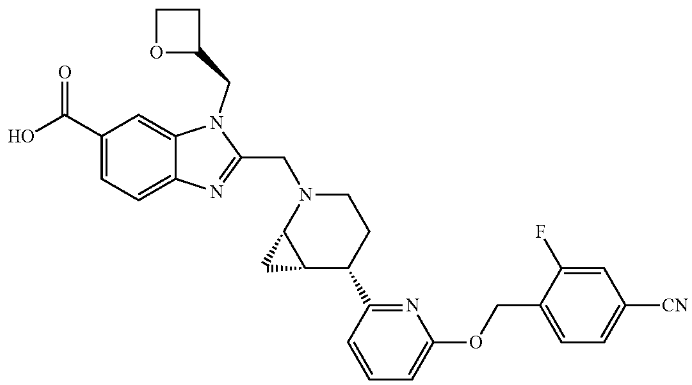 |
| 25 | 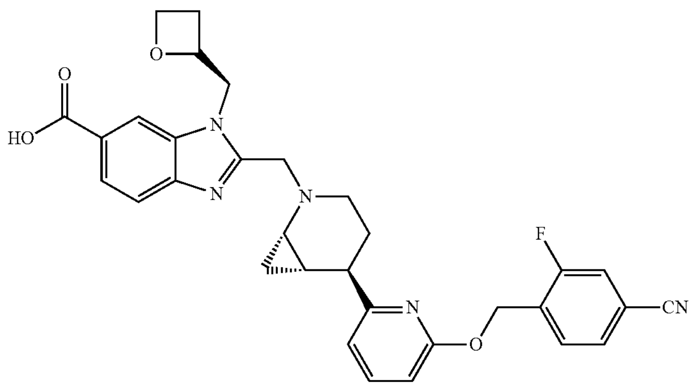 |
| 26 | 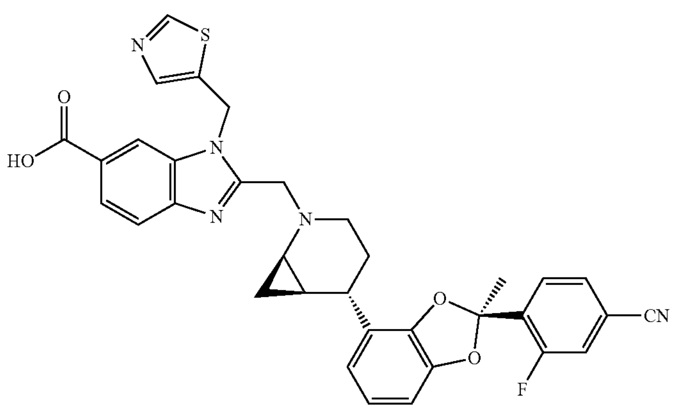 [SMILES: C[C@]1(c2ccc(C#N)cc2F)Oc2cccc([C@H]3CCN(Cc4nc5ccc(C(=O)O)cc5n4Cc4cncs4)[C@@H]4C[C@H]34)c2O1] |
| 27 | 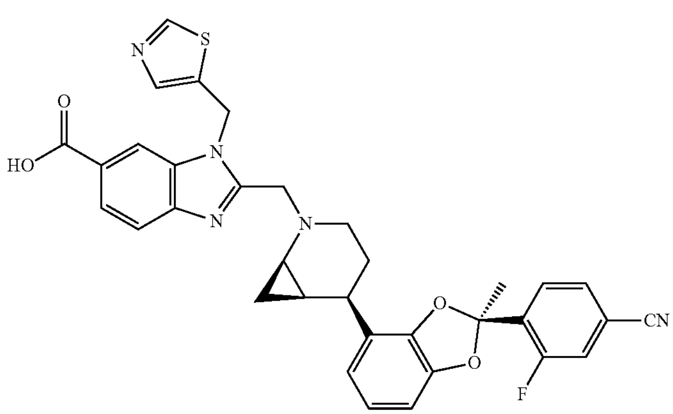 [SMILES: C[C@]1(c2ccc(C#N)cc2F)Oc2cccc([C@@H]3CCN(Cc4nc5ccc(C(=O)O)cc5n4Cc4cncs4)[C@@H]4C[C@@H]43)c2O1] |

TABLE 1-continued
| Compound No. | Structure |
|---|---|
| 28 | 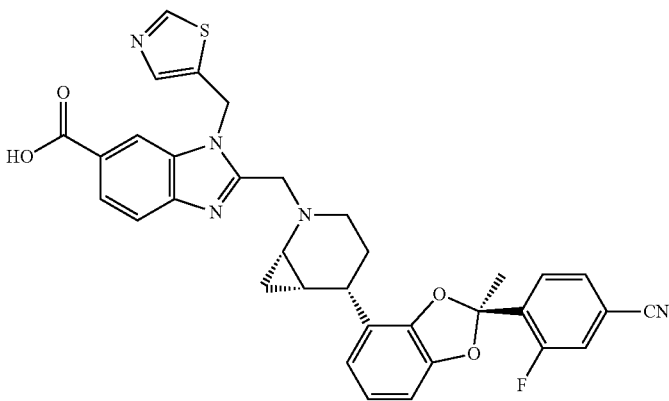 [SMILES: C[C@]1(c2ccc(C#N)cc2F)Oc2cccc([C@H]3CCN(Cc4nc5ccc(C(=O)O)cc5n4Cc4cncs4)[C@H]4C[C@@H]34)c2O1] |
| 29 | 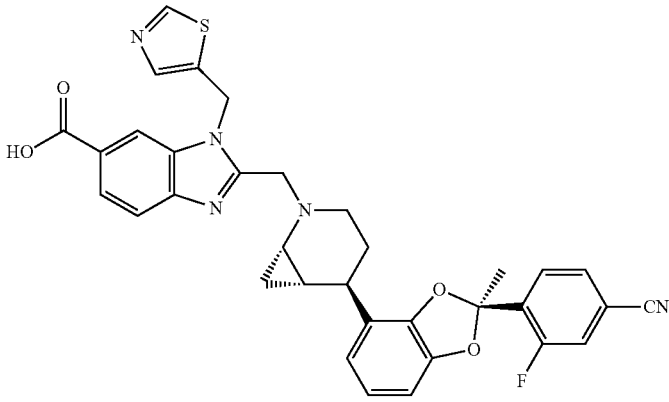 [SMILES: C[C@]1(c2ccc(C#N)cc2F)Oc2cccc([C@@H]3CCN(Cc4nc5ccc(C(=O)O)cc5n4Cc4cncs4)[C@H]4C[C@@H]34)c2O1] |
| 30 | 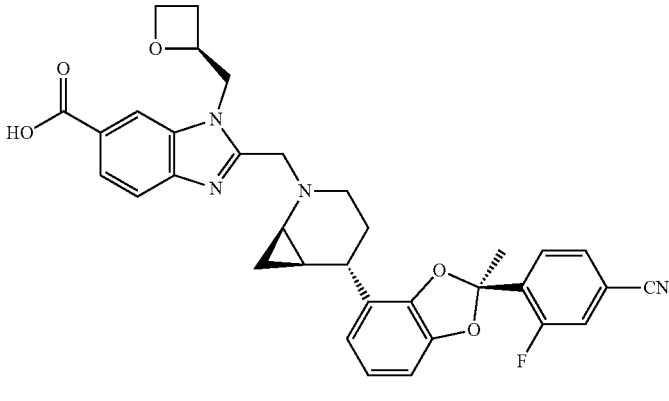 [SMILES: C[C@]1(c2ccc(C#N)cc2F)Oc2cccc([C@H]3CCN(Cc4nc5ccc(C(=O)O)cc5n4C[C@@H]4CCO4)[C@@H]4C[C@H]34)c2O1] |
| 31 | 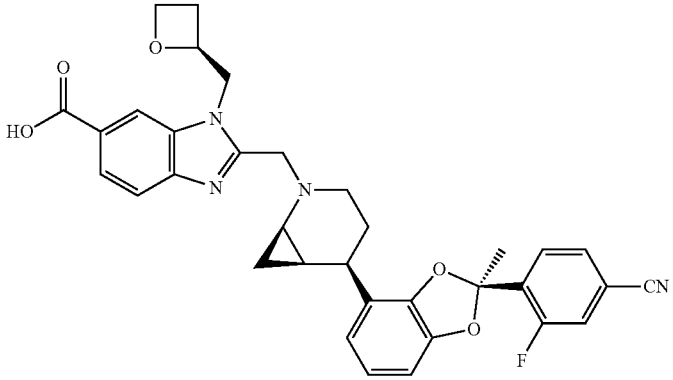 [SMILES: C[C@]1(c2ccc(C#N)cc2F)Oc2cccc([C@@H]3CCN(Cc4nc5ccc(C(=O)O)cc5n4C[C@@H]4CCO4)[C@@H]4C[C@@H]43)c2O1] |

TABLE 1-continued

| Compound No. | Structure |
|---|---|
| 32 | 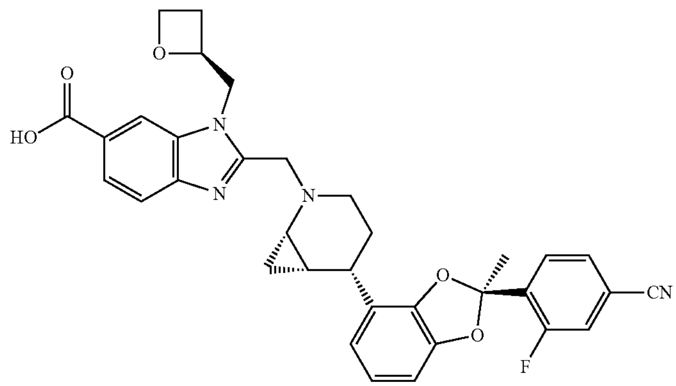 [SMILES: C[C@]1(c2ccc(C#N)cc2F)Oc2cccc([C@H]3CCN(Cc4nc5ccc(C(=O)O)cc5n4C[C@@H]4CCO4)[C@H]4C[C@@H]34)c2O1] |
| 33 | 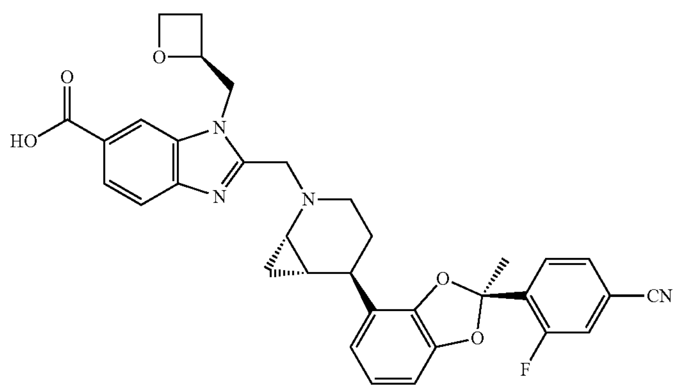 [SMILES: C[C@]1(c2ccc(C#N)cc2F)Oc2cccc([C@@H]3CCN(Cc4nc5ccc(C(=O)O)cc5n4C[C@@H]4CCO4)[C@H]4C[C@@H]34)c2O1] |
| 34 | 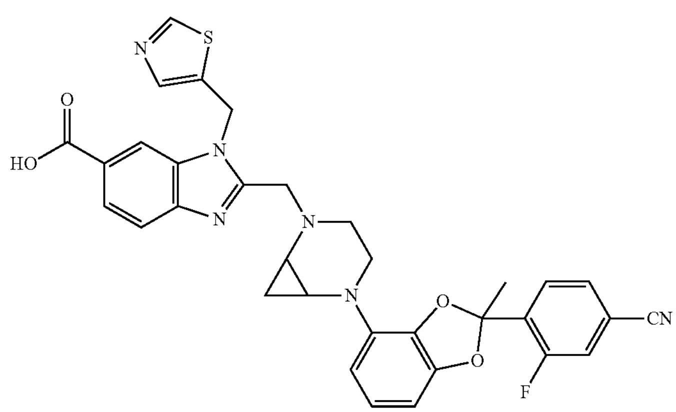 [SMILES: CC1(c2ccc(C#N)cc2F)Oc2cccc(N3CCN(Cc4nc5ccc(C(=O)O)cc5n4Cc4cncs4)C4CC43)c2O1] |
| 35 | 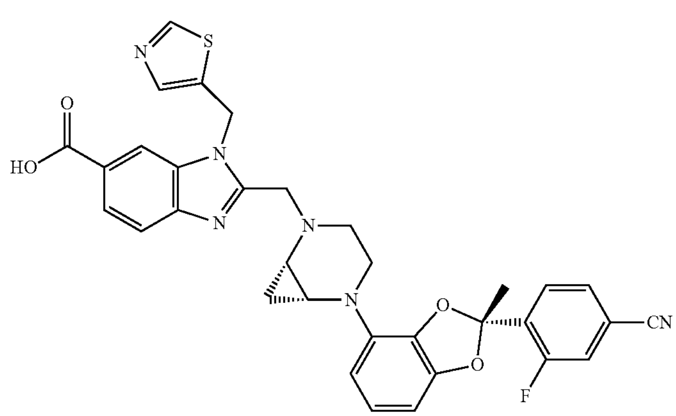 [SMILES: C[C@@]1(c2ccc(C#N)cc2F)Oc2cccc(N3CCN(Cc4nc5ccc(C(=O)O)cc5n4Cc4cncs4)[C@H]4C[C@H]43)c2O1] |

TABLE 1-continued
| Compound No. | Structure |
|---|---|
| 36 | 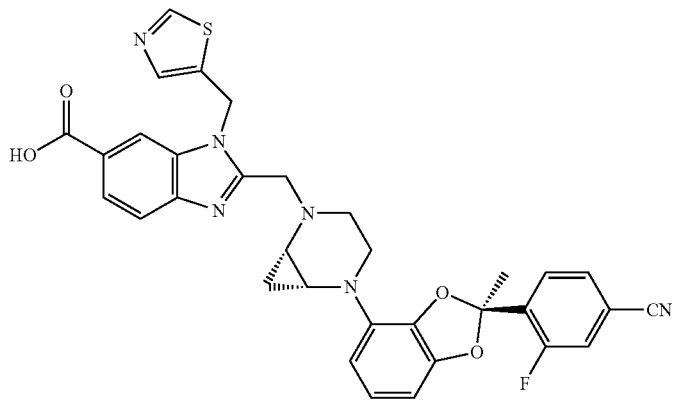 |
| 37 | 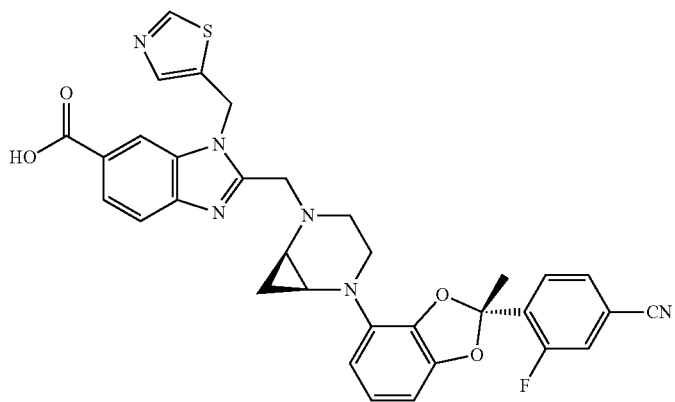 [SMILES: C[C@@]1(c2ccc(C#N)cc2F)Oc2cccc(N3CCN(Cc4nc5ccc(C(=O)O)cc5n4Cc4cncs4)[C@@H]4C[C@@H]43)c2O1] |
| 38 | 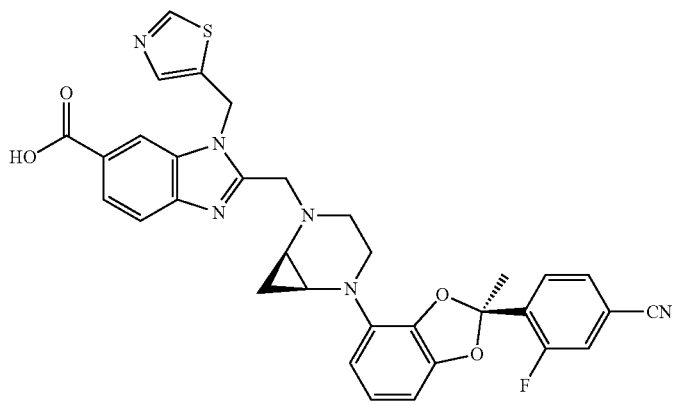 |

TABLE 1-continued
| Compound No. | Structure |
|---|---|
| 39 | 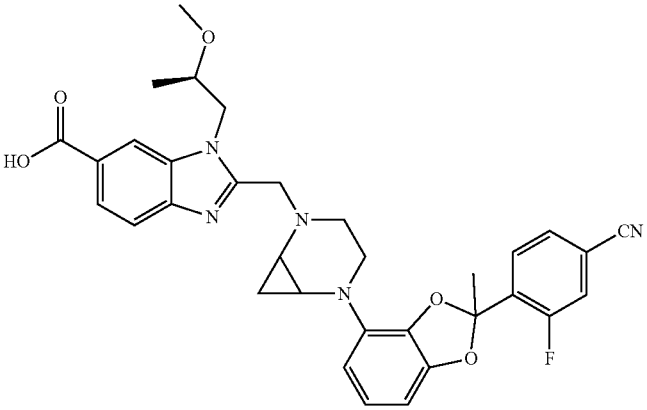 [SMILES: CO[C@H](C)Cn1c(CN2CCN(c3cccc4c3OC(C)(c3ccc(C#N)cc3F)O4)C3CC32)nc2ccc(C(=O)O)cc21] |
| 40 | 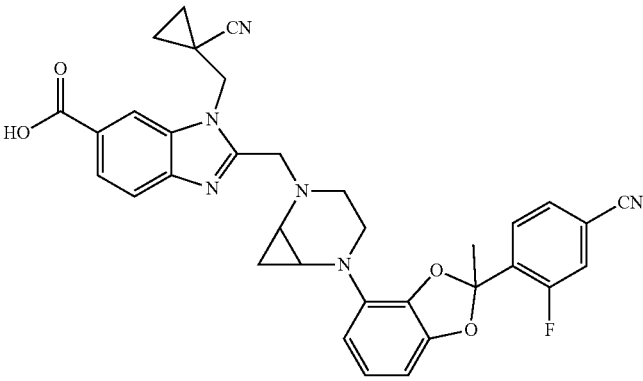 [SMILES: CC1(c2ccc(C#N)cc2F)Oc2cccc(N3CCN(Cc4nc5ccc(C(=O)O)cc5n4CC4(C#N)CC4)C4CC43)c2O1] |
| 41 | 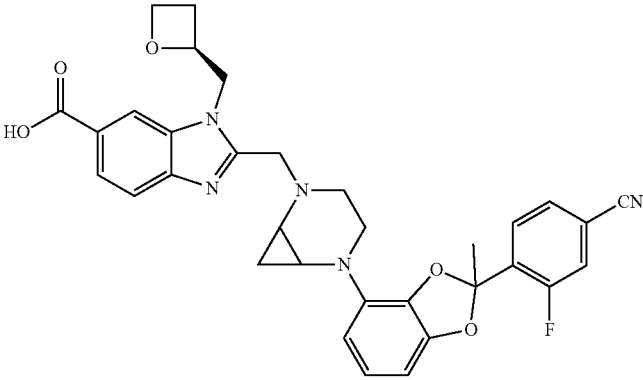 [SMILES: CC1(c2ccc(C#N)cc2F)Oc2cccc(N3CCN(Cc4nc5ccc(C(=O)O)cc5n4C[C@@H]4CCO4)C4CC43)c2O1] |
| 42 | 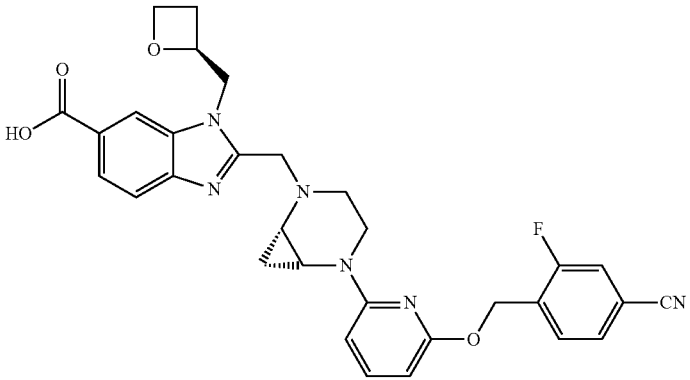 |

TABLE 1-continued
| Compound No. | Structure |
|---|---|
| 43 | 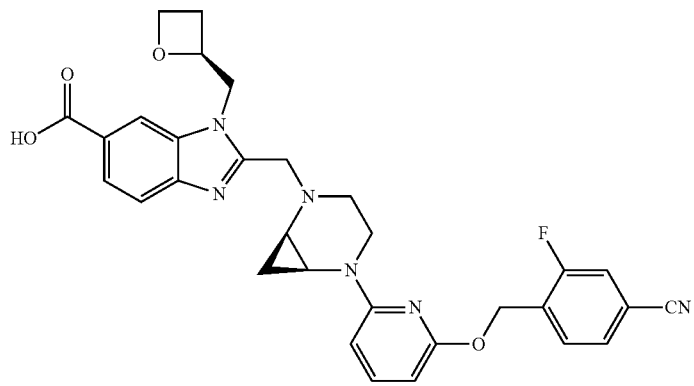 [SMILES: N#Cc1ccc(COc2cccc(N3CCN(Cc4nc5ccc(C(=O)O)cc5n4C[C@@H]4CCO4)[C@@H]4C[C@@H]43)n2)c(F)c1] |
| 44 | 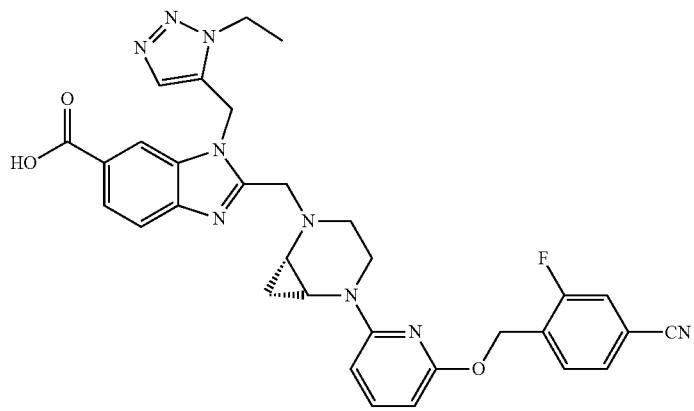 |
| 45 | 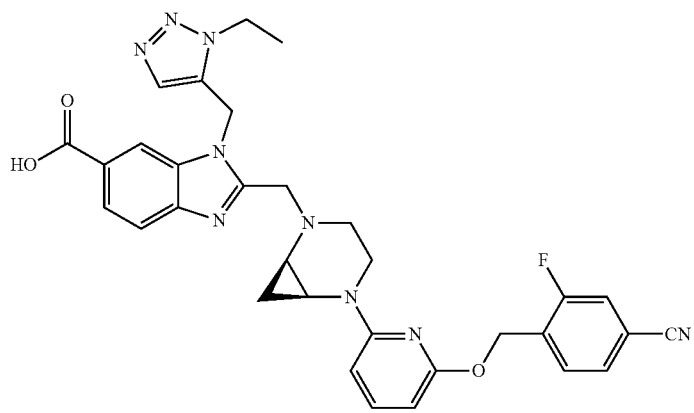 [SMILES: CCn1nncc1Cn1c(CN2CCN(c3cccc(OCc4ccc(C#N)cc4F)n3)[C@H]3C[C@H]32)nc2ccc(C(=O)O)cc21] |

TABLE 1-continued

| Compound No. | Structure |
|---|---|
| 46 | 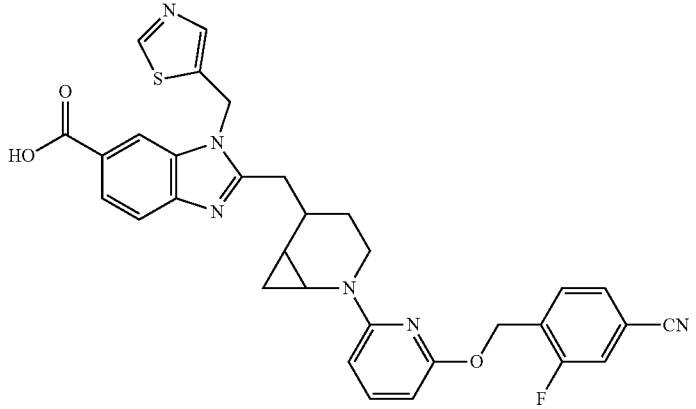 [SMILES: N#Cc1ccc(COc2cccc(N3CCC(Cc4nc5ccc(C(=O)O)cc5n4Cc4cncs4)C4CC43)n2)c(F)c1] |

Pharmaceutically Acceptable Compositions and Formulations

Pharmaceutically acceptable compositions or simply "pharmaceutical compositions" of any of the compounds detailed herein are embraced by this invention. Thus, the invention includes pharmaceutical compositions comprising a compound of Formula (0), Formula (1), including compounds of Formula (2)-(10), or a subformula of any of the foregoing, or a pharmaceutically acceptable salt thereof, and a pharmaceutically acceptable carrier or excipient.

In some embodiments, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. In one variation, "substantially pure" intends a composition that contains no more than 35% impurity, wherein the impurity denotes a compound other than the compound comprising the majority of the composition or a salt thereof. For example, a composition of a substantially pure compound intends a composition that contains no more than 35% impurity, wherein the impurity denotes a compound other than the compound or a salt thereof. In one variation, a composition of substantially pure compound or a salt thereof is provided wherein the composition contains no more than 25% impurity. In another variation, a composition of substantially pure compound or a salt thereof is provided wherein the composition contains or no more than 20% impurity. In still another variation, a composition of substantially pure compound or a salt thereof is provided wherein the composition contains or no more than 10% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity. In yet other variations, a composition of substantially pure compound means that the composition contains no more than 15% or preferably no more than 10% or more preferably no more than 5% or even more preferably no more than 3% and most preferably no more than 1% impurity, which impurity may be the compound in a different stereochemical form.

In one variation, the compounds herein are synthetic compounds prepared for administration to an individual such as a human. In another variation, compositions are provided containing a compound in substantially pure form. In another variation, the invention embraces pharmaceutical compositions comprising a compound detailed herein and a pharmaceutically acceptable carrier or excipient. In another variation, methods of administering a compound are provided. The purified forms, pharmaceutical compositions and methods of administering the compounds are suitable for any compound or form thereof detailed herein.

The compounds may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

Compounds described herein can be used in the preparation of a formulation, such as a pharmaceutical formulation, by combining the compounds as active ingredients with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in Remington: The Science and Practice of Pharmacy, Lippincott Williams & Wilkins, 21st ed. (2005), which is incorporated herein by reference.

Compounds as described herein may be administered to individuals (e.g., a human) in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid polyols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Compositions comprising two compounds utilized herein are described. Any of the compounds described herein can be formulated in a tablet in any dosage form described herein. In some embodiments, the composition comprises a compound of Formula (0), Formula (1), including compounds of Formula (2)-(10), or a subformula of any of the foregoing, or a pharmaceutically acceptable salt thereof, as described herein. In some embodiments, provided herein is a dosage form comprises a therapeutically effective amount of a compound of Formula (0), Formula (1), including compounds of Formula (2)-(10), or a subformula of any of the foregoing, or a pharmaceutically acceptable salt thereof. In some embodiments, the compound or a pharmaceutically acceptable salt thereof is selected from Compound Nos. 1-46 in Table 1

Methods of Use and Uses

Compounds and compositions described herein may in some aspects be used in treatment of diseases and/or conditions described herein, for example, diseases and/or conditions mediated by GLP-1R. In some embodiments, the method of treating a disease or condition in a subject in need thereof comprises administering to the subject a therapeutically effective amount of a compound of Formula (0), Formula (1), including compounds of Formula (2)-(10), or a subformula of any of the foregoing, or a pharmaceutically acceptable salt thereof. In some embodiments, the method of treating a disease or condition in a subject in need thereof comprises administering to the subject a therapeutically effective amount of a compound selected from Compound Nos. 1-46 in Table 1, or a pharmaceutically acceptable salt thereof.

In accordance with the present application, a disease or condition to be treated and/or prevented is selected from the group consisting of cardiometabolic and associated diseases including diabetes (T1 D and/or T2DM, including pre-diabetes), idiopathic T1 D (Type 1 b), latent autoimmune diabetes in adults (LADA), early-onset T2DM (EOD), youth-onset atypical diabetes (YOAD), maturity onset diabetes of the young (MODY), malnutrition-related diabetes, gestational diabetes, hyperglycemia, insulin resistance, hepatic insulin resistance, impaired glucose tolerance, diabetic neuropathy, diabetic nephropathy, kidney disease (e.g., acute kidney disorder, tubular dysfunction, proinflammatory changes to the proximal tubules), diabetic retinopathy, adipocyte dysfunction, visceral adipose deposition, sleep apnea, obesity (including hypothalamic obesity and monogenic obesity) and related comorbidities (e.g., osteoarthritis and urine incontinence), eating disorders (including binge eating syndrome, bulimia nervosa, and syndromic obesity such as Prader-Willi and Bardet-Biedl syndromes), weight gain from use of other agents (e.g., from use of steroids and antipsychotics), excessive sugar craving, dyslipidemia (including hyperlipidemia, hypertriglyceridemia, increased total cholesterol, high LDL cholesterol, and low HDL cholesterol), hyperinsulinemia, liver diseases such as NAFLD, steatosis, NASH, fibrosis, cirrhosis, and hepatocellular carcinoma, cardiovascular disease, atherosclerosis (including coronary artery disease), peripheral vascular disease, hypertension, endothelial dysfunction, impaired vascular compliance, congestive heart failure, myocardial infarction (e.g. necrosis and apoptosis), stroke, hemorrhagic stroke, ischemic stroke, traumatic brain injury, pulmonary hypertension, restenosis after angioplasty, intermittent claudication, postprandial lipemia, metabolic acidosis, ketosis, arthritis, osteoporosis, Parkinson's Disease, left ventricular hypertrophy, peripheral arterial disease, macular degeneration, cataract, glomerulosclerosis, chronic renal failure, metabolic syndrome, syndrome X, premenstrual syndrome, angina pectoris, thrombosis, atherosclerosis, transient ischemic attacks, vascular restenosis, impaired glucose metabolism, conditions of impaired fasting plasma glucose, hyperuricemia, gout, erectile dysfunction, skin and connective tissue disorders, psoriasis, foot ulcerations, ulcerative colitis, hyper apo B lipoproteinemia, Alzheimer's Disease, schizophrenia, impaired cognition, inflammatory bowel disease, short bowel syndrome, Crohn's disease, colitis, irritable bowel syndrome, Polycystic Ovary Syndrome and addiction (e.g., alcohol and/or drug abuse), prevention or treatment of Polycystic Ovary Syndrome and treatment of addiction (e.g., alcohol and/or drug abuse).

In some embodiments, provided herein is a method of treating a cardiometabolic disease in a subject (e.g., a human patient) in need thereof, comprising administering to the subject a therapeutically effective amount of a compound described herein, or a pharmaceutically acceptable salt thereof.

In some embodiments, provided herein is a method of treating diabetes in a subject (e.g., a human patient) in need thereof, comprising administering to the subject a therapeutically effective amount of a compound described herein, or a pharmaceutically acceptable salt thereof. Exemplary diabetes include, but are not limited to, T1 D, T2DM, pre-diabetes, idiopathic T1 D, LADA, EOD, YOAD, MODY, malnutrition-related diabetes, and gestational diabetes.

In some embodiments, provided herein is a method of treating a liver disorder in a subject (e.g., a human patient) in need thereof, comprising administering to the subject a therapeutically effective amount of a compound described herein, or a pharmaceutically acceptable salt thereof. Exemplary liver disorders include, without limitation, liver inflammation, fibrosis, and steatohepatitis. In some embodiments, the liver disorder is selected from the list consisting of primary biliary cirrhosis (PBC), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, viral hepatitis, alcoholic liver disease, nonalcoholic fatty liver disease (NAFLD), nonalcoholic steatohepatitis (NASH), graft versus host disease, transplant liver regeneration, congenital hepatic fibrosis, choledocholithiasis, granulomatous liver disease, intra- or extrahepatic malignancy, Sjogren's syndrome, sarcoidosis, Wilson's disease, Gaucher's disease, hemochromatosis, and oti-antitrypsin deficiency. In some embodiments, the liver disorder is selected from the list consisting of liver inflammation, liver fibrosis, alcohol induced fibrosis, steatosis, alcoholic steatosis, primary sclerosing cholangitis (PSC), primary biliary cirrhosis (PBC), non-alcoholic fatty liver disease (NAFLD), and non-alcoholic steatohepatitis (NASH). In some embodiments, the liver disorder is selected from the group consisting of liver fibrosis, alcohol induced fibrosis, steatosis, alcoholic steatosis, NAFLD, and NASH. In one embodiment, the liver disorder is NASH. In another embodiment, the liver disorder is liver inflammation. In another embodiment, the liver disorder is liver fibrosis. In another embodiment, the liver disorder is alcohol induced fibrosis. In another embodiment, the liver disorder is steatosis. In another embodiment, the liver disorder is alcoholic steatosis. In another embodiment, the liver disorder is NAFLD. In one embodiment, the treatment methods provided herein impedes or slows the progression of NAFLD to NASH. In one embodiment, the treatment methods provided herein impedes or slows the progression of NASH. NASH can progress, e.g., to one or more of liver cirrhosis, hepatic cancer, etc. In some embodiments, the liver disorder is NASH. In some embodiments, the patient has had a liver biopsy. In some embodiments, the method further comprising obtaining the results of a liver biopsy.

In accordance with the present application, a compound described herein, or a pharmaceutically acceptable salt thereof, can be administered by any suitable route in the form of a pharmaceutical composition adapted to such a route, and in a dose effective for the treatment intended. In some embodiments, it is a compound of any embodiment of Formula (0), Formula (1), including compounds of Formula (2)-(10), or a subformula of any of the foregoing, or selected from the compounds of Table 1, or a pharmaceutically acceptable salt thereof. The compounds and/or compositions described herein may be administered orally, rectally, vaginally, parenterally, or topically.

In some embodiments, the compounds and/or compositions may be administered orally. Oral administration may involve swallowing, so that the compound enters the gastrointestinal tract, or buccal or sublingual administration may be employed by which the compound enters the bloodstream directly from the mouth.

In some embodiments, the compounds and/or compositions may be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In some embodiments, the compounds and/or compositions may be administered topically to the skin or mucosa, that is, dermally or transdermally. In some embodiments, the compounds and/or compositions may be administered intranasally or by inhalation. In some embodiments, the compounds and/or compositions may be administered rectally or vaginally. In some embodiments, the compounds and/or compositions may be administered directly to the eye or ear.

The dosage regimen for the compounds and/or compositions described herein is based on a variety of factors, including the type, age, weight, sex and medical condition of the patient; the severity of the condition; the route of administration; and the activity of the particular compound employed. Thus the dosage regimen may vary widely. In some embodiments, the total daily dose of the compounds of the present application is typically from about 0.001 to about 100 mg/kg (i.e., mg compound per kg body weight) for the treatment of the indicated conditions discussed herein. In one embodiment, total daily dose of the compounds of the present application is from about 0.01 to about 30 mg/kg, and in another embodiment, from about 0.03 to about 10 mg/kg, and in yet another embodiment, from about 0.1 to about 3. It is not uncommon that the administration of the compounds of the present application will be repeated a plurality of times in a day (typically no greater than 4 times). Multiple doses per day typically may be used to increase the total daily dose, if desired.

For oral administration, the compounds and/or compositions described herein may be provided in the form of tablets containing 0.1, 0.5, 1.0, 2.5, 5.0, 10.0, 15.0, 25.0, 30.0 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.01 to about 10 mg/kg/minute during a constant rate infusion.

The compounds and/or compositions described herein can be used alone, or in combination with other therapeutic agents. The administration of two or more agents "in combination" means that all of the agents are administered closely enough in time that each may generate a biological effect in the same time frame. The presence of one agent may alter the biological effects of the other agent(s). The two or more agents may be administered simultaneously, concurrently or sequentially. Additionally, simultaneous administration may be carried out by mixing the agents prior to administration or by administering the compounds at the same point in time but as separate dosage forms at the same or different site of administration.

The present application provides any of the uses, methods or compositions as defined herein wherein a compound of any embodiment of Formula (0), Formula (1), including compounds of Formula (2)-(10), or a subformula of any of the foregoing, or selected from the compounds of Table 1 as described herein, or a pharmaceutically acceptable salt thereof, is used in combination with one or more other therapeutic agent. This would include a pharmaceutical composition comprising a compound of any embodiment of Formula (0), Formula (1), including compounds of Formula (2)-(10), or a subformula of any of the foregoing, or selected from the compounds of Table 1, or a pharmaceutically acceptable salt thereof, as defined in any of the embodiments described herein, in admixture with at least one pharmaceutically acceptable excipient and one or more other therapeutic agent.

In some embodiments, the one or more other therapeutic agent is an anti-diabetic agent including but not limited to a biguanide (e.g., metformin), a sulfonylurea (e.g., tolbutamide, glibenclamide, gliclazide, chlorpropamide, tolazamide, acetohexamide.glyclopyramide, glimepiride, or glipizide), a thiazolidinedione (e.g., pioglitazone, rosiglitazone, or lobeglitazone), a glitazar (e.g., saroglitazar, aleglitazar, muraglitazar or tesaglitazar), a meglitinide (e.g., nateglinide, repaglinide), a dipeptidyl peptidase 4 (DPP-4) inhibitor (e.g., sitagliptin, vildagliptin, saxagliptin, linagliptin, gemigliptin, anagliptin, teneligliptin, alogliptin, trelagliptin, dutogliptin, or omarigliptin), a glitazone (e.g., pioglitazone, rosiglitazone, balaglitazone, rivoglitazone, or lobeglitazone), a sodium-glucose linked transporter 2 (SGLT2) inhibitor (e.g., empagliflozin, canagliflozin, dapagliflozin, ipragliflozin, Ipragliflozin, tofogliflozin, sergliflozin etabonate, remogliflozin etabonate, or ertugliflozin), an SGLTL1 inhibitor, a GPR40 agonist (FFAR1/FFA1 agonist, e.g. fasiglifam), glucose-dependent insulinotropic peptide (GIP) and analogues thereof, an alpha glucosidase inhibitor (e.g. voglibose, acarbose, or miglitol), or an insulin or an insulin analogue, including the pharmaceutically acceptable salts of the specifically named agents and the pharmaceutically acceptable solvates of said agents and salts.

In some embodiments, the one or more other therapeutic agent is an antiobesity agent including but not limited to peptide YY or an analogue thereof, a neuropeptide Y receptor type 2 (NPYR2) agonist, a NPYR1 or NPYR5 antagonist, a cannabinoid receptor type 1 (CB1 R) antagonist, a lipase inhibitor (e.g., orlistat), a human proislet peptide (HIP), a melanocortin receptor 4 agonist (e.g., setmelanotide), a melanin concentrating hormone receptor 1 antagonist, a farnesoid X receptor (FXR) agonist (e.g. obeticholic acid), zonisamide, phentermine (alone or in combination with topiramate), a norepinephrine/dopamine reuptake inhibitor (e.g., buproprion), an opioid receptor antagonist (e.g., naltrexone), a combination of norepinephrine/dopamine reuptake inhibitor and opioid receptor antagonist (e.g., a combination of bupropion and naltrexone), a GDF-15 analog, sibutramine, a cholecystokinin agonist, amylin and analogues thereof (e.g., pramlintide), leptin and analogues thereof (e.g., metroleptin), a serotonergic agent (e.g., lorcaserin), a methionine aminopeptidase 2 (MetAP2) inhibitor (e.g., beloranib or ZGN-1061), phendimetrazine, diethylpropion, benzphetamine, an SGLT2 inhibitor (e.g., empagliflozin, canagliflozin, dapagliflozin, ipragliflozin, Ipragliflozin, tofogliflozin, sergliflozin etabonate, remogliflozin etabonate, or ertugliflozin), an SGLTL1 inhibitor, a dual SGLT2/SGLT1 inhibitor, a fibroblast growth factor receptor (FGFR) modulator, an AMP-activated protein kinase (AMPK) activator, biotin, a MAS receptor modulator, or a glucagon receptor agonist (alone or in combination with another GLP-1 R agonist, e.g., liraglutide, exenatide, dulaglutide, albiglutide, lixisenatide, or semaglutide), including the pharmaceutically acceptable salts of the specifically named agents and the pharmaceutically acceptable solvates of said agents and salts.

In some embodiments, the one or more other therapeutic agent is an agent to treat NASH including but not limited to PF-05221304, an FXR agonist (e.g., obeticholic acid), a PPAR a/d agonist (e.g., elafibranor), a synthetic fatty acid-bile acid conjugate (e.g., aramchol), a caspase inhibitor (e.g., emricasan), an anti-lysyl oxidase homologue 2 (LOXL2) monoclonal antibody (e.g., simtuzumab), a galectin 3 inhibitor (e.g., GR-MD-02), a MAPK5 inhibitor (e.g., GS-4997), a dual antagonist of chemokine receptor 2 (CCR2) and CCR5 (e.g., cenicriviroc), a fibroblast growth factor21 (FGF21) agonist (e.g., BMS-986036), a leukotriene D4 (LTD4) receptor antagonist (e.g., tipelukast), a niacin analogue (e.g., ARI 3037MO), an ASBT inhibitor (e.g., volixibat), an acetyl-CoA carboxylase (ACC) inhibitor (e.g., NDI 010976), a ketohexokinase (KHK) inhibitor, a diacylglyceryl acyltransferase 2 (DGAT2) inhibitor, a CB1 receptor antagonist, an anti-CB1 R antibody, or an apoptosis signal-regulating kinase 1 (ASK1) inhibitor, including the pharmaceutically acceptable salts of the specifically named agents and the pharmaceutically acceptable solvates of said agents and salts.

Articles of Manufacture and Kits

The present disclosure further provides articles of manufacture comprising a compound, or a pharmaceutically acceptable salt thereof in accordance with the present application, a composition described herein, or one or more unit dosages described herein in suitable packaging. In certain embodiments, the article of manufacture is for use in any of the methods described herein. Suitable packaging (e.g., containers) is known in the art and includes, for example, vials, vessels, ampules, bottles, jars, flexible packaging and the like. An article of manufacture may further be sterilized and/or sealed.

The kits may be in unit dosage forms, bulk packages (e.g., multi-dose packages) or sub-unit doses. For example, kits may be provided that contain sufficient dosages of a compound, or a pharmaceutically acceptable salt thereof in accordance with the present application, a composition described herein, and/or one or more other therapeutic agent useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds/compositions described herein and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present disclosure. The instructions included with the kit generally include information as to the components and their administration to an individual.

General Synthetic Schemes

Scheme A. Preparation of 5-(6-(Aryloxy)pyridine-2-yl)-2-azabicyclo[4.1.0]heptane Intermediate A7.

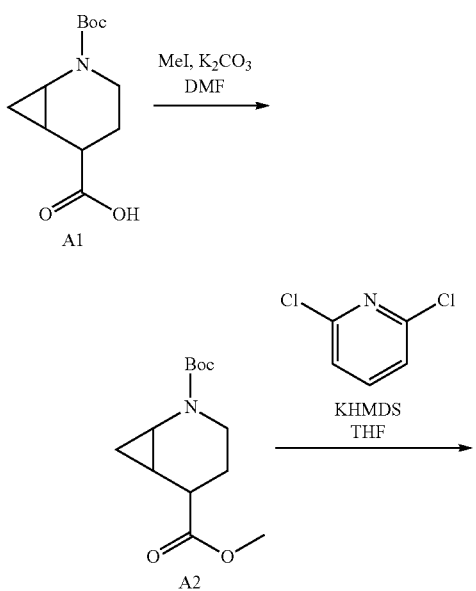

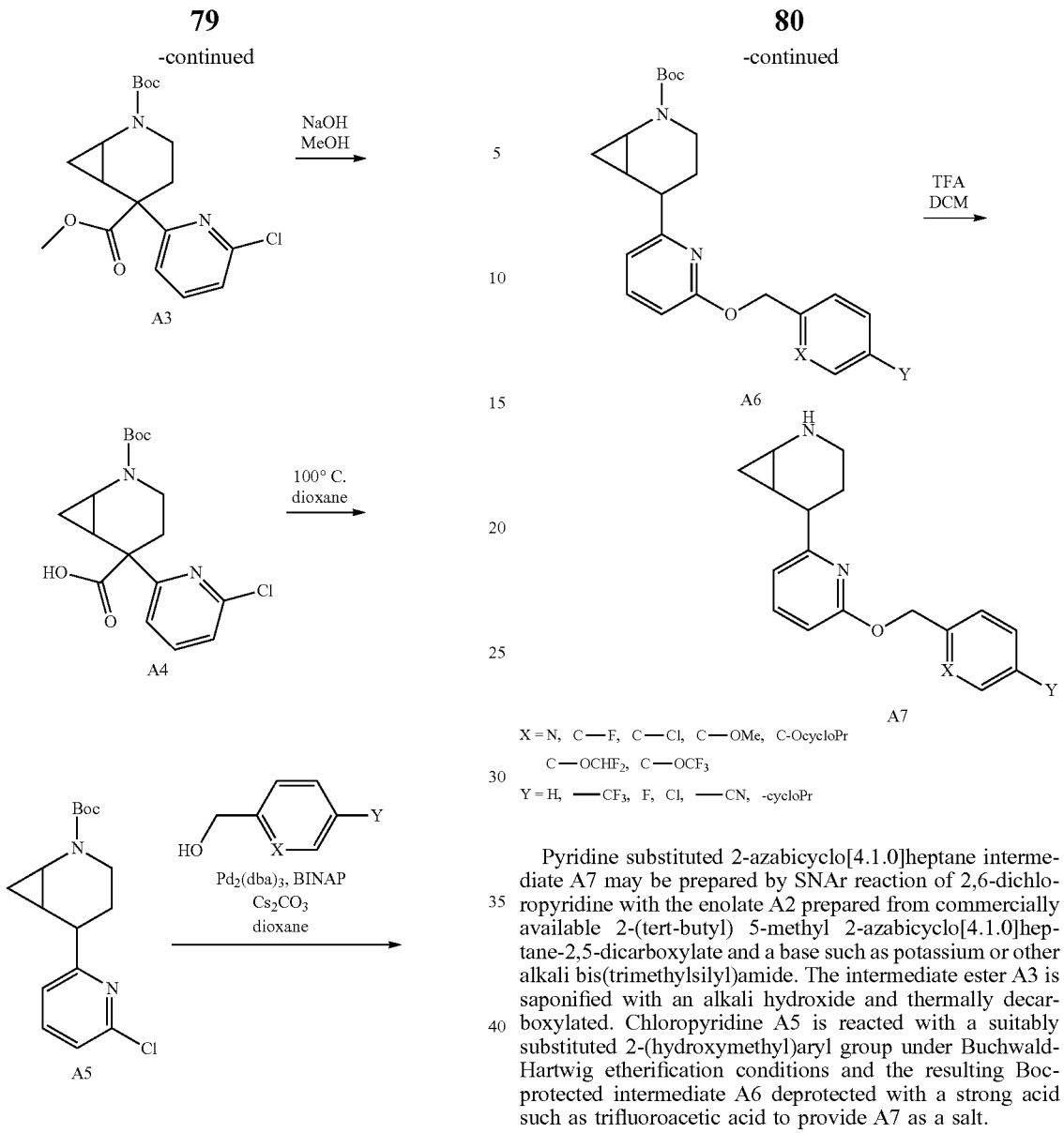

X = N, C—F, C—Cl, C—OMe, C-OcycloPr
C—OCHF₂, C—OCF₃
Y = H, —CF₃, F, Cl, —CN, -cycloPr Pyridine substituted 2-azabicyclo[4.1.0]heptane intermediate A7 may be prepared by SNAr reaction of 2,6-dichloropyridine with the enolate A2 prepared from commercially available 2-(tert-butyl) 5-methyl 2-azabicyclo[4.1.0]heptane-2,5-dicarboxylate and a base such as potassium or other alkali bis(trimethylsilyl)amide. The intermediate ester A3 is saponified with an alkali hydroxide and thermally decarboxylated. Chloropyridine A5 is reacted with a suitably substituted 2-(hydroxymethyl)aryl group under Buchwald-Hartwig etherification conditions and the resulting Boc-protected intermediate A6 deprotected with a strong acid such as trifluoroacetic acid to provide A7 as a salt.

Scheme B. Preparation of 5-(6-(Aryloxy)pyridine-2-yl)-2-azabicyclo[4.1.0]heptan-2-yl)methyl)-1-substituted-1H-benzo[d]imidazole-6-carboxylic acids B1, B2, B3 and B4.

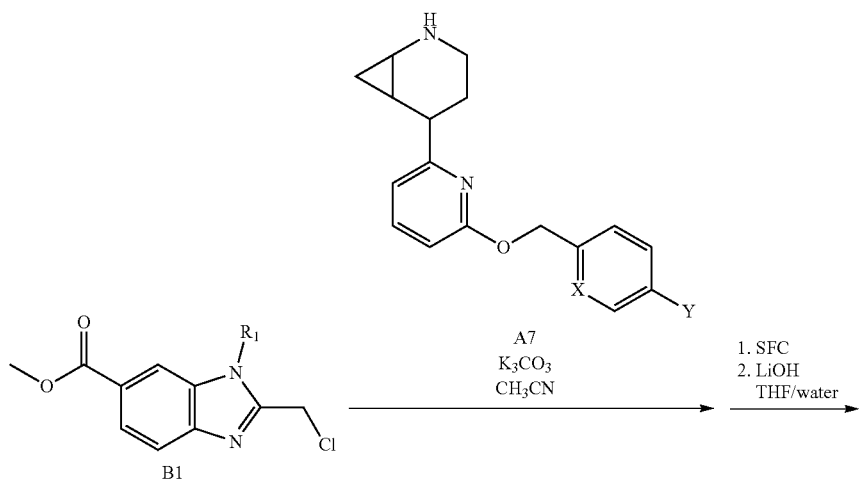

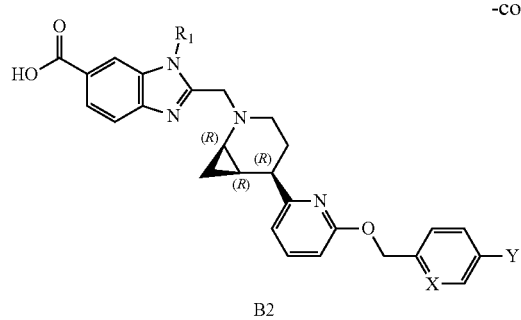

B2

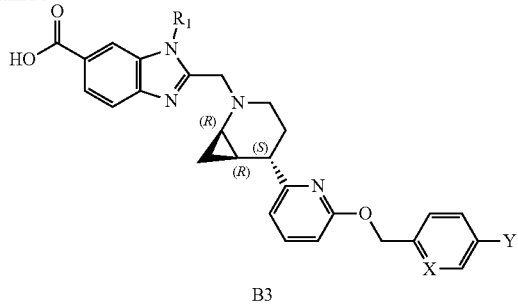

B3

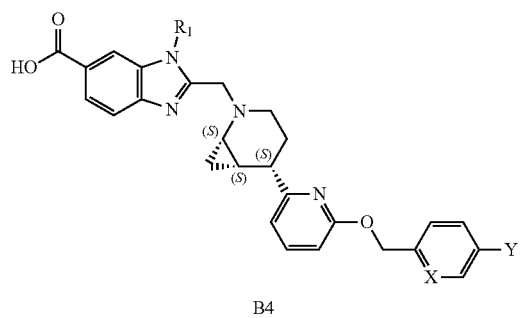

B4

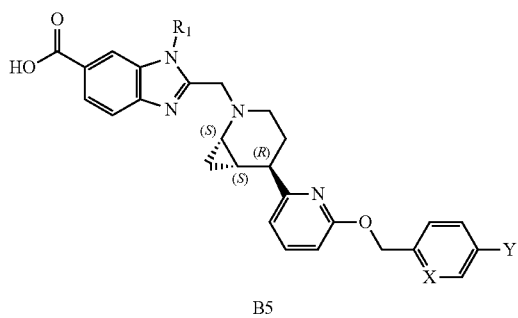

B5

5-(6-(Aryloxy)pyridine-2-yl)-2-azabicyclo[4.1.0]heptane intermediate A7 is reacted with an appropriately $R_1$-substituted benzimidazole-6-carboxylic acid ester B1 (prepared following various known synthetic methods such as those described in WO2019239371) in the presence of an acid scavenger such as an alkalki carbonate to provide a mixture of 4 diastereomers with (1R,5R,6R), (1R,5S,6R), (1S,5R, 6S) and (1S,5S,6S) configurations. The intermediate mixture of diastereomers is separated by supercritical fluid chromatography (SFC) and then each discrete compound saponified with an alkali hydroxide to provide final products B2, B3, B4 and B5. Alternatively, intermediate A7 may be prepared in a stereoselective synthesis or purified to obtain only the desired isomer for use in subsequent steps.

Scheme C. Preparation of 2-(6-(Aryloxy)pyridine-2-yl)-2,5-diazabicyclo[4.1.0]-heptane Intermediate C4.

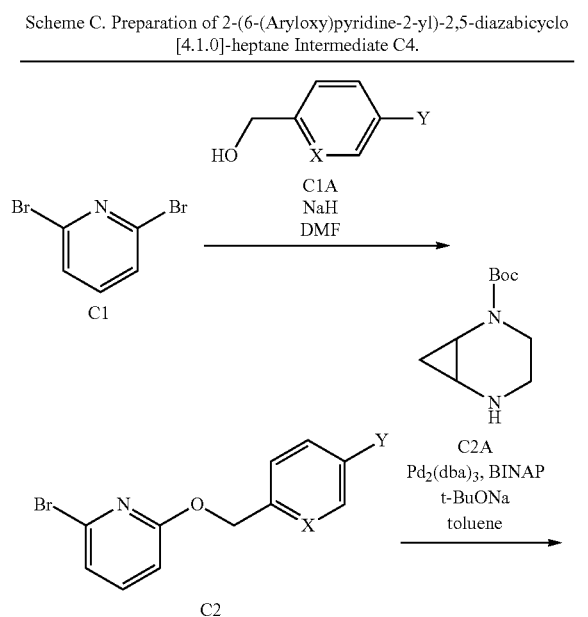

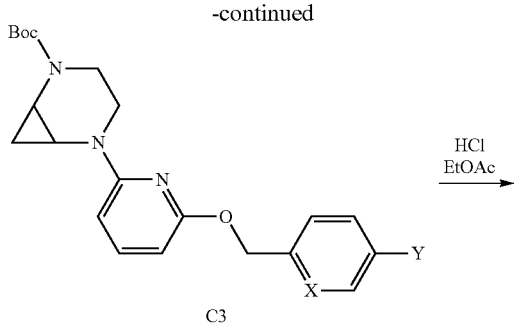

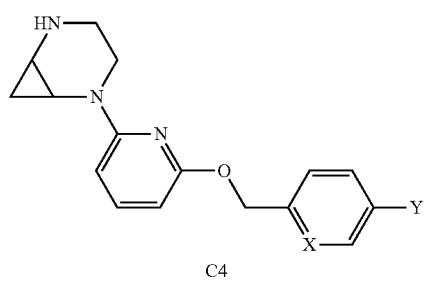

Pyridine substituted 2,5-diazabicyclo[4.1.0]heptane intermediate C3 may be prepared by nucleophilic substitution of a 2,6-dihalopyridine C1 with a suitably substituted 2-(hydroxymethyl)aryl group anion formed from C1A and a strong base such as sodium hydride. The 2-(aryloxy)-6-halopyridine C2 is reacted with commercially available tert-butyl 2,5-diazabicyclo[4.1.0]heptane-2-carboxylate C2A under Buchwald-Hartwig amination conditions and the resulting the resulting Boc-protected intermediate C3 deprotected with a strong acid such as hydrochloric acid to provide intermediate C4 as a salt.

Scheme D. Preparation of 2-((5-(6-(Aryloxy)pyridine-2-yl)-2,5-diazabicyclo[4.1.0]-heptan-2-yl)methyl)-1-substituted-1H-benzo[d]imidazole-6-carboxylic acids D1 and D2.

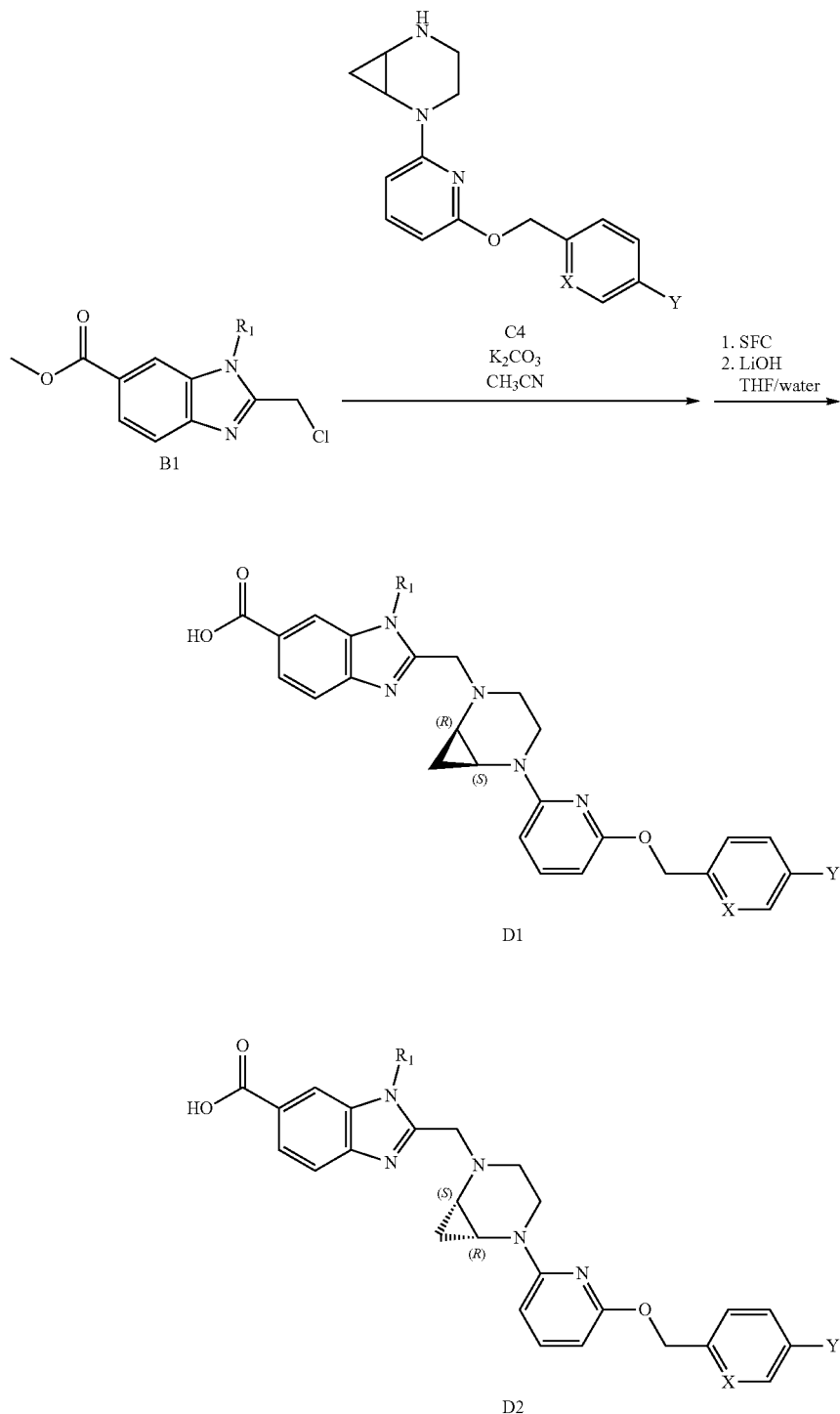

2-(6-(Aryloxy)pyridine-2-yl)-2,5-diazabicyclo[4.1.0] heptane Intermediate $C_4$ is reacted with an appropriately $R_1$-substituted benzimidazole-6-carboxylic acid ester B1 (prepared following various known synthetic methods such as those described in WO2019239371) in the presence of an acid scavenger such as an alkali carbonate to provide a mixture of 2 diastereomers with (1R,6S) and (1S,6R) configurations. The intermediate mixture of diastereomers is separated by supercritical fluid chromatography (SFC) and then each discrete compound saponified with an alkali hydroxide to provide final products D1 and D2. Alternatively, intermediate C4 may be prepared in a stereoselective synthesis or purified to obtain only the desired isomer for use in subsequent steps.

Scheme E. Preparation of (S)-4, 4, 5, 5-Tetramethyl-2-(2-methyl-2-(substituted-aryl)benzo[d][1,3]dioxol-4-yl)-1, 3, 2-dioxaborolane Intermediate E6.

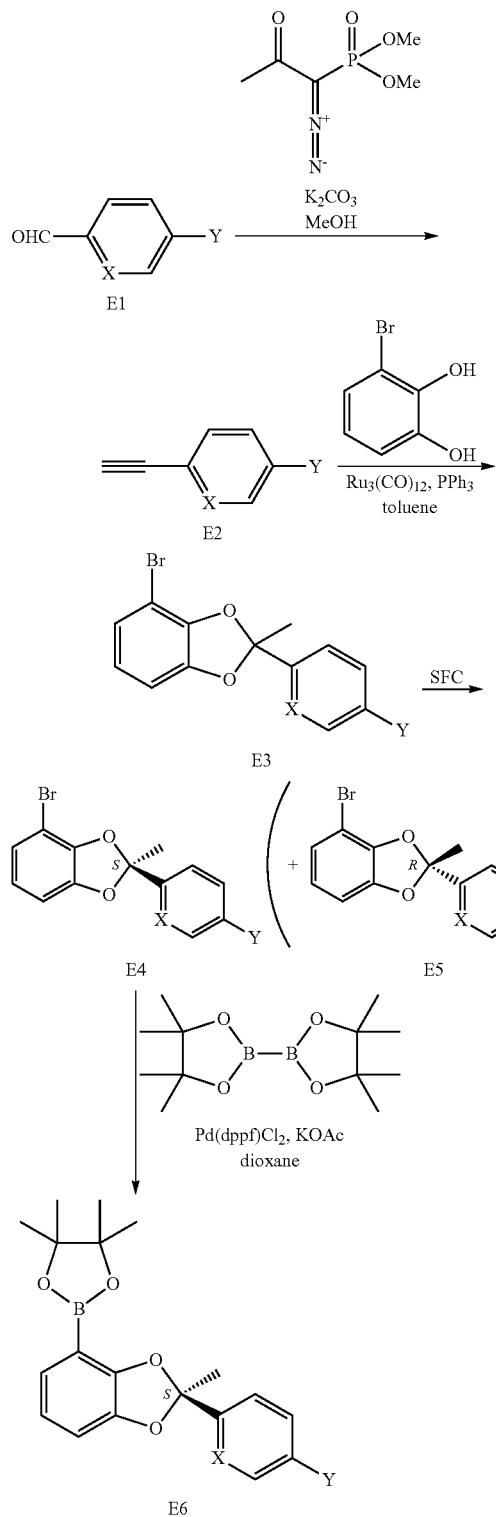

X = N, C—F, C—Cl, C—OMe, C-OcycloPr
C—OCHF$_2$, C—OCF$_3$

Y = —CF$_3$, F, Cl, —CN, -cycloPr

Seyferth-Gilbert homologation provides alkyne intermediate E2 from the appropriately substituted aryl aldehyde E1 and dimethyl (diazomethyl)phosphonate. The addition of 3-bromocatechol to alkyne E2 in the presence of triruthenium dodecacarbonyl provides 4-bromo-2-methyl-2-arylbenzo[d][1,3]dioxole as a mixture of enantiomers E4 and E5 which may be separated by super critical fluid chromatography (SFC) to provide the desired (S)-isomer.

Scheme F. Preparation of 5-((S)-2-Methyl-2-substituted-arylbenzo[d][1,3]dioxol-4-yl)-2-azabicyclo[4.1.0]heptane Intermediate F7.

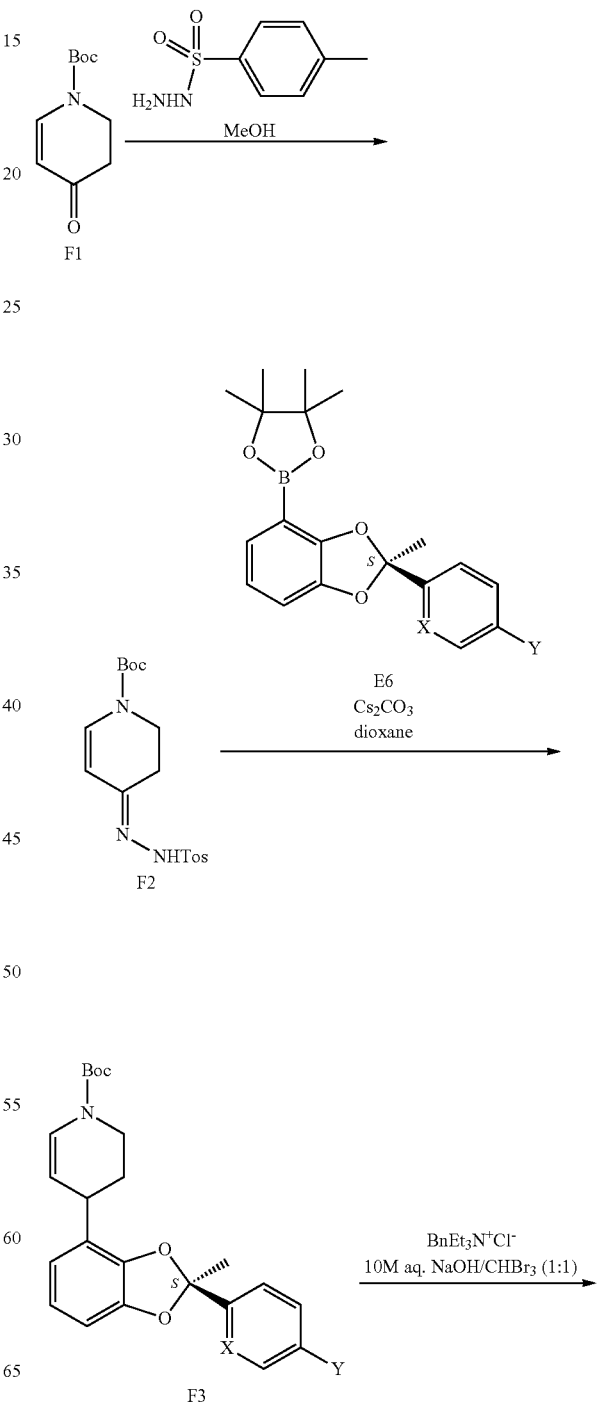

-continued

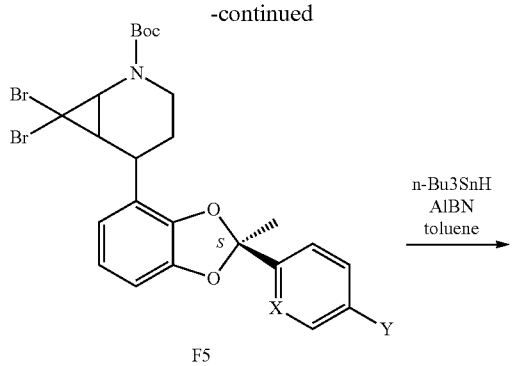
F5

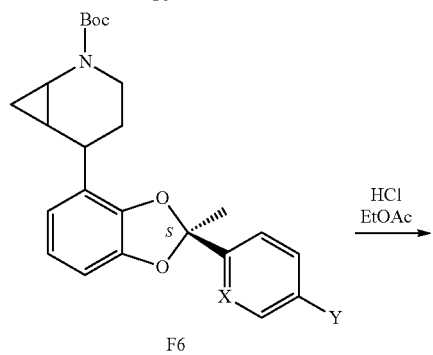
F6

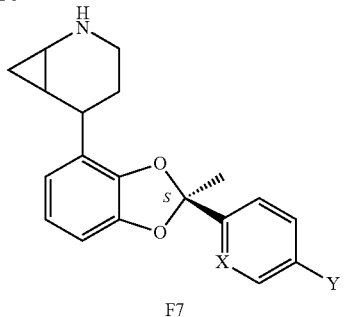
F7

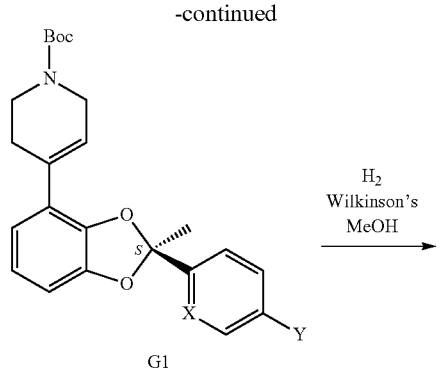
G1

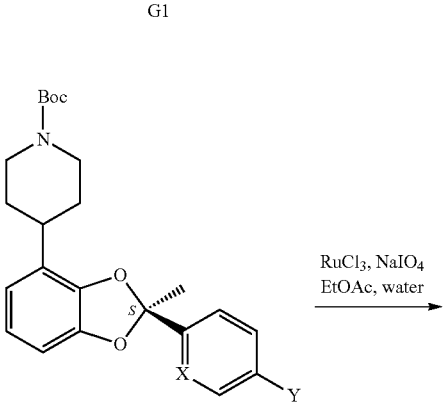
G2

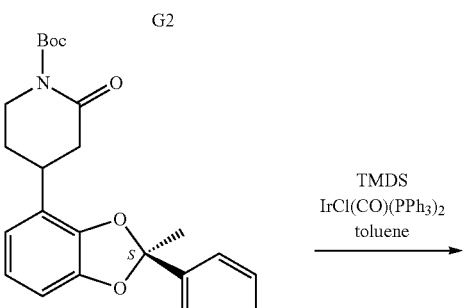
G3

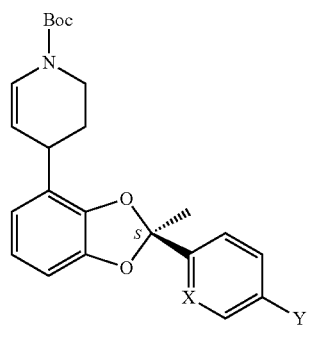
F3

Metal free cross-coupling between sulfonylhydrazine F2 and (S)-4,4,5,5-tetramethyl-2-(2-methyl-2-(substituted-aryl)benzo[d][1,3]dioxol-4-yl)-1,3,2-dioxaborolane intermediate E6 in the presence of a base, such as cesium carbonate, provides tert-butyl-((S)-2-methyl-2-substituted-arylbenzo[d][1,3]dioxol-4-yl)-3,4-dihydropyridine-1(2H)-carboxylate F3. Reaction of F3 with dibromocarbene, generated under phase transfer conditions, provides gem-dibromocyclopropane adduct F5 which is reductively dehalogenated with tri-n-butyltin hydride. Deprotection of F6 with strong acid, such as HCl or TFA, provides F7.

Scheme G. Alternate Preparation of tert-Butyl-((S)-2-methyl-2-substituted-arylbenzo[d][1,3]dioxol-4-yl)-3,4-dihydropyridine-1(2H)-carboxylate Intermediate F3.

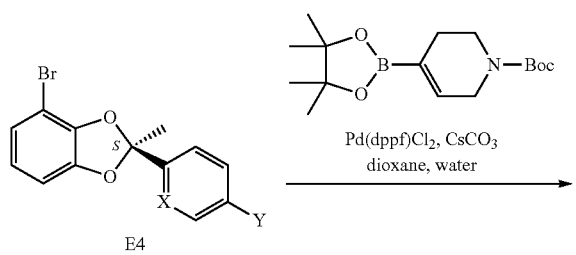

Alternatively, intermediate F3 may be prepared by Suzuki coupling of commercially available tert-butyl 4-(4,4,5,5-tetramethyl-1,3,2-dioxaborolan-2-yl)-3,6-dihydropyridine-1(2H)-carboxylate with intermediate E4. The resulting dihydropyridine G1 is reduced and oxidized with catalytic ruthenium (III) chloride and sodium periodate to provide lactam G3. Lactam G3 may be converted to dihydropyridine F3 by an organic silane such as tetramethyldisiloxane and catalytic Vaska's Reagent.

Scheme H. Alternate Preparation of tert-Butyl-((S)-2-methyl-2-substituted-arylbenzo[d][1,3]dioxol-4-yl)-3,4-dihydropyridine-1(2H)-carboxylate Intermediate F3.

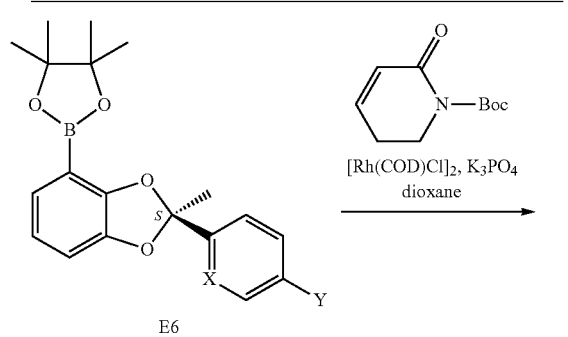

E6

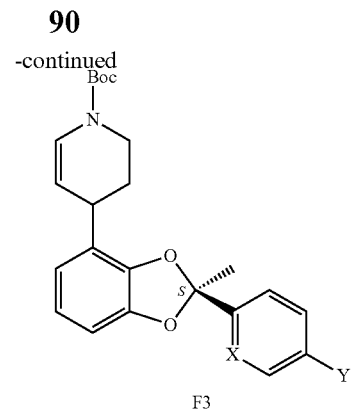

F3

Alternatively, intermediate F3 may be prepared by rhodium catalyzed cross-coupling of the commercial tert-butyl 6-oxo-3,6-dihydropyridine-1(2H)-carboxylate with intermediate E6. Reduction of lactam G3 provides hydroxypiperidine H1 which is treated with aqueous acid to provide intermediate F3.

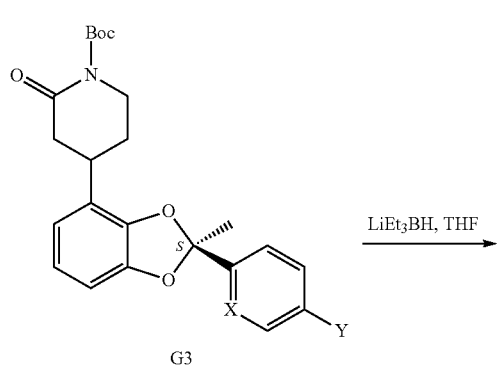

G3

Scheme I. Alternate Preparation of 5-((S)-2-Methyl-2-substituted-arylbenzo[d]-[1,3]dioxol-4-yl)-2-azabicyclo[4.1.0]heptane Intermediate F7.

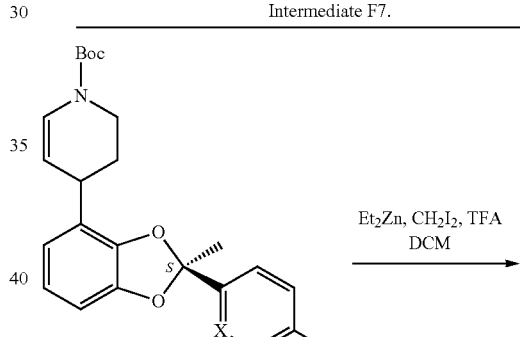

G4

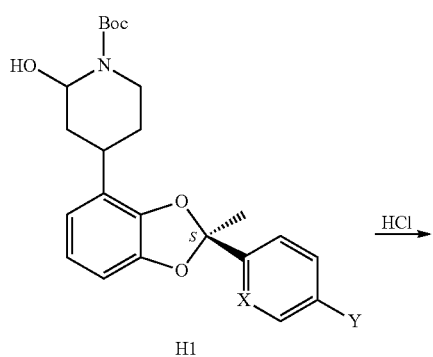

H1

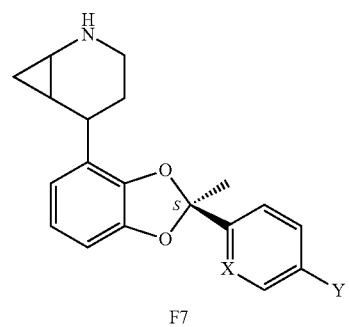

F7

Intermediate F7 may be obtained in very low yields from G4 under traditional Simmons-Smith reaction conditions.

Scheme J. Preparation of 1-Substituted-2-((5-((S)-2-methyl-2-substituted-phenylbenzo[d][1,3]dioxol-4-yl)-2-azabicyclo[4.1.0]heptan-2-yl)methyl)-1H-benzo[d]imidazole-6-carboxylic acids J1, J2, J3 and J4.

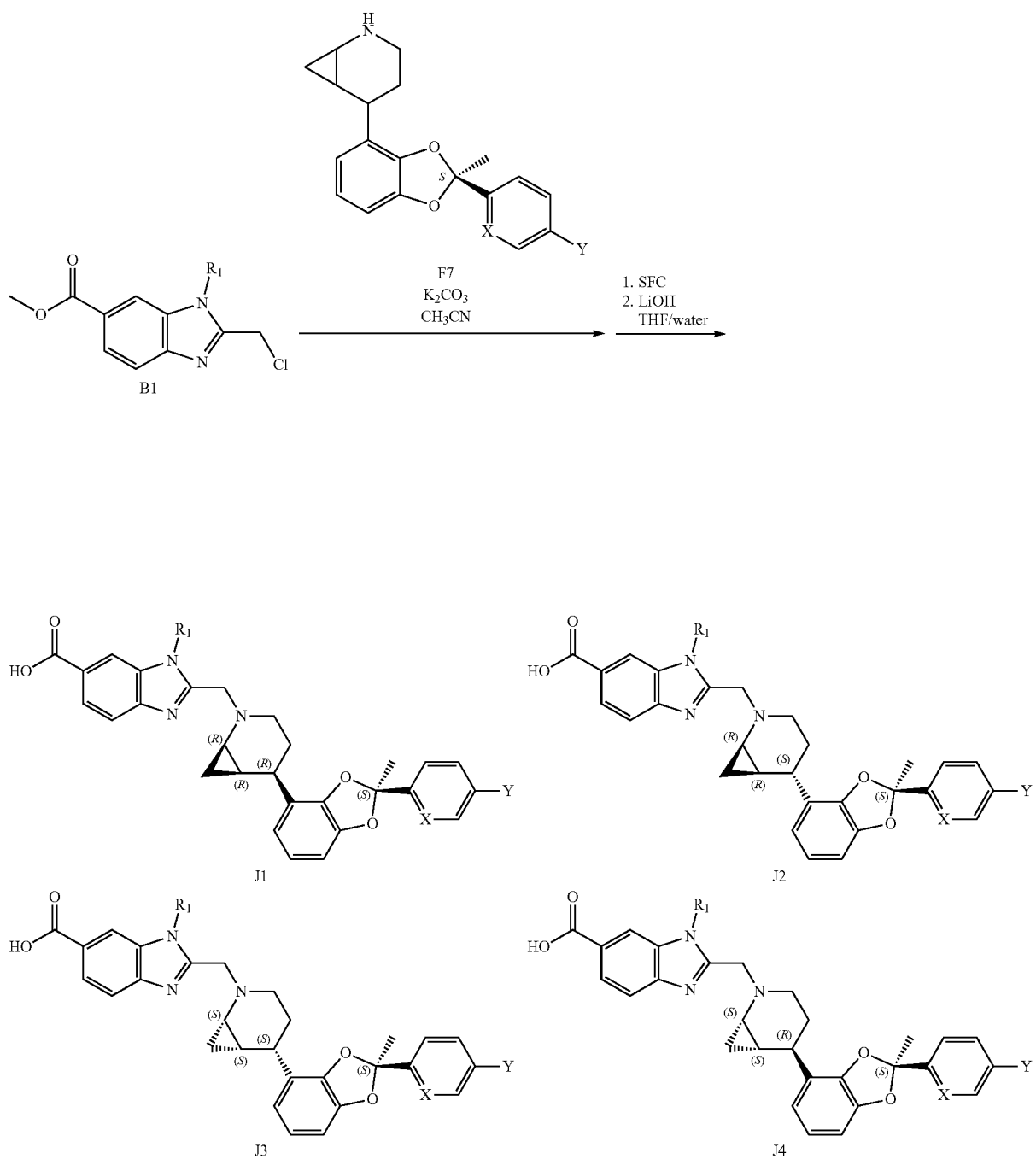

5-((S)-2-Methyl-2-substituted-arylbenzo[d][1,3]dioxol-4-yl)-2-azabicyclo[4.1.0]heptane Intermediate F7 is reacted with an appropriately $R_1$-substituted benzimidazole-6-carboxylic acid ester B1 (prepared following various known synthetic methods such as those described in WO2019239371) in the presence of an acid scavenger such as an alkali carbonate to provide a mixture of 4 diastereomers with (1R,5R,6R), (1R,5S,6R), (1S,5R,6S) and (1S,5S,6S) configurations. The intermediate mixture of diastereomers is separated by supercritical fluid chromatography (SFC) and then each discrete compound saponified with an alkali hydroxide to provide final products J1, J2, J3 and J4. Alternatively, intermediate F7 may be prepared in a stereoselective synthesis or purified to obtain only the desired isomer for use in subsequent steps.

Scheme K. Preparation of 2-((S))-2-Methyl-2-substituted-arylbenzo[d][1,3]dioxol-4-yl)-2,5-diazabicyclo[4.1.0]heptane Intermediate K2.

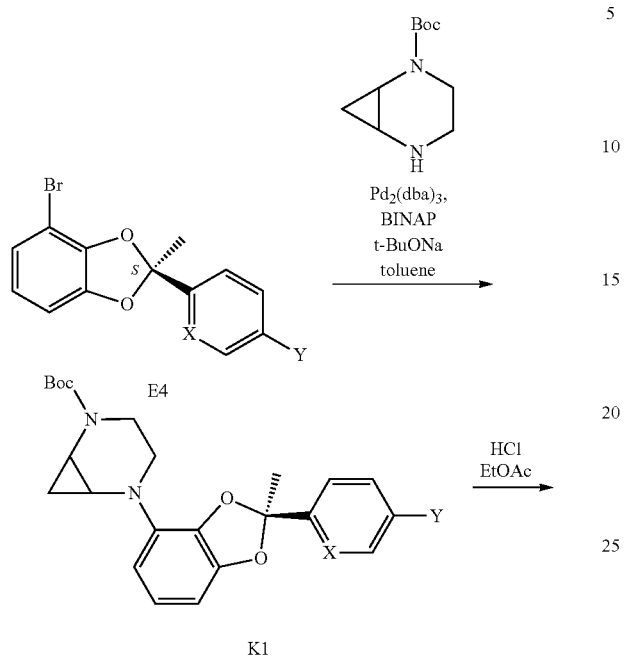

Commercially available tert-butyl 2,5-diazabicyclo[4.1.0]heptane-2-carboxylate is reacted with E4 under Buchwald amination conditions and the resulting intermediate deprotected with strong acid to provide K2.

Scheme L. 1-Substituted-2-((5-((S)-2-Methyl-2-substituted-arylbenzo[d][1,3]dioxol-4-yl)-2,5-diazabicyclo[4.1.0]heptn-2-yl)methyl)-1H-benzo[d]imidazole-6-carboxylic acids L1 and L2.

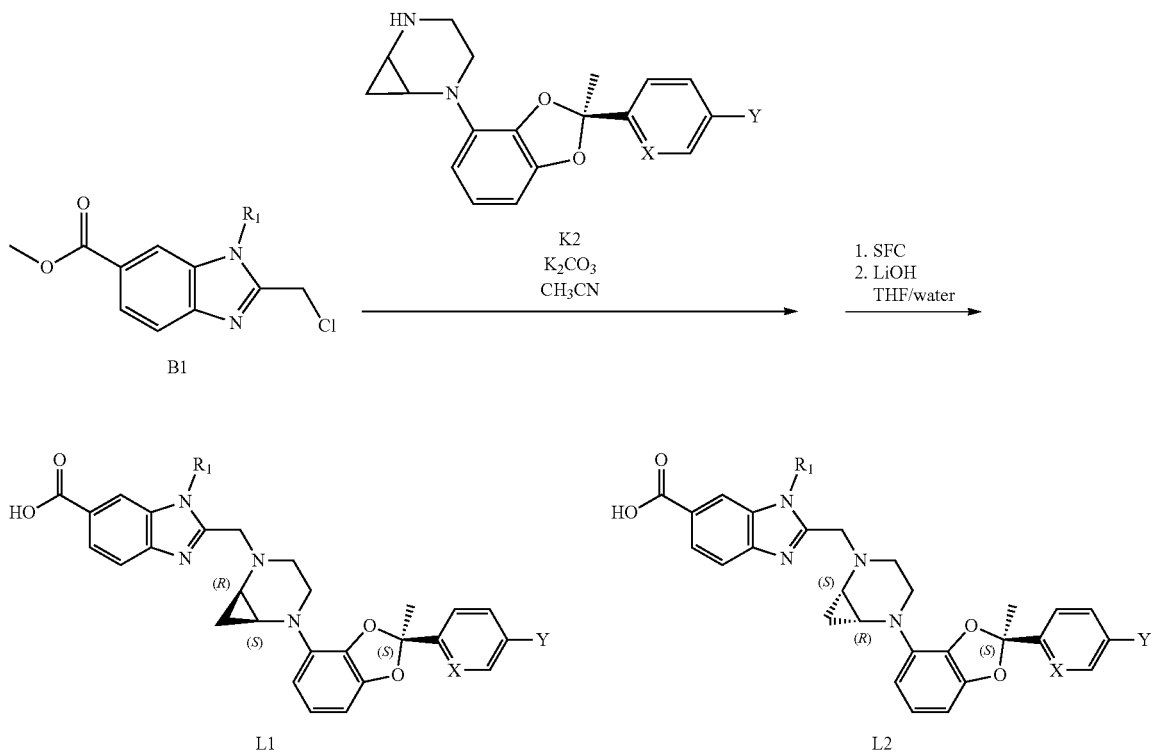

2-((S))-2-Methyl-2-substituted-arylbenzo[d][1,3]dioxol-4-yl)-2,5-diazabicyclo[4.1.0]heptane Intermediate K2 is reacted with an appropriately $R_1$-substituted benzimidazole-6-carboxylic acid ester B1 (prepared following various known synthetic methods such as those described in WO2019239371) in the presence of an acid scavenger such as an alkali carbonate to provide a mixture of 2 diastereomers with (1R,6S) and (1S,6R) configurations. The intermediate mixture of diastereomers is separated by supercritical fluid chromatography (SFC) and then each discrete compound saponified with an alkali hydroxide to provide final products L1 and L2. Alternatively, intermediate K2 may be prepared in a stereoselective synthesis or purified to obtain only the desired isomer for use in subsequent steps.

Scheme M. Preparation of 2-((2-(6-(Aryloxy)pyridine-2-yl)-2-azabicyclo[4.1.0]-heptan-5-yl)methyl)-1-substituted-1H-benzo[d]imidazole-6-carboxylic acids M7.

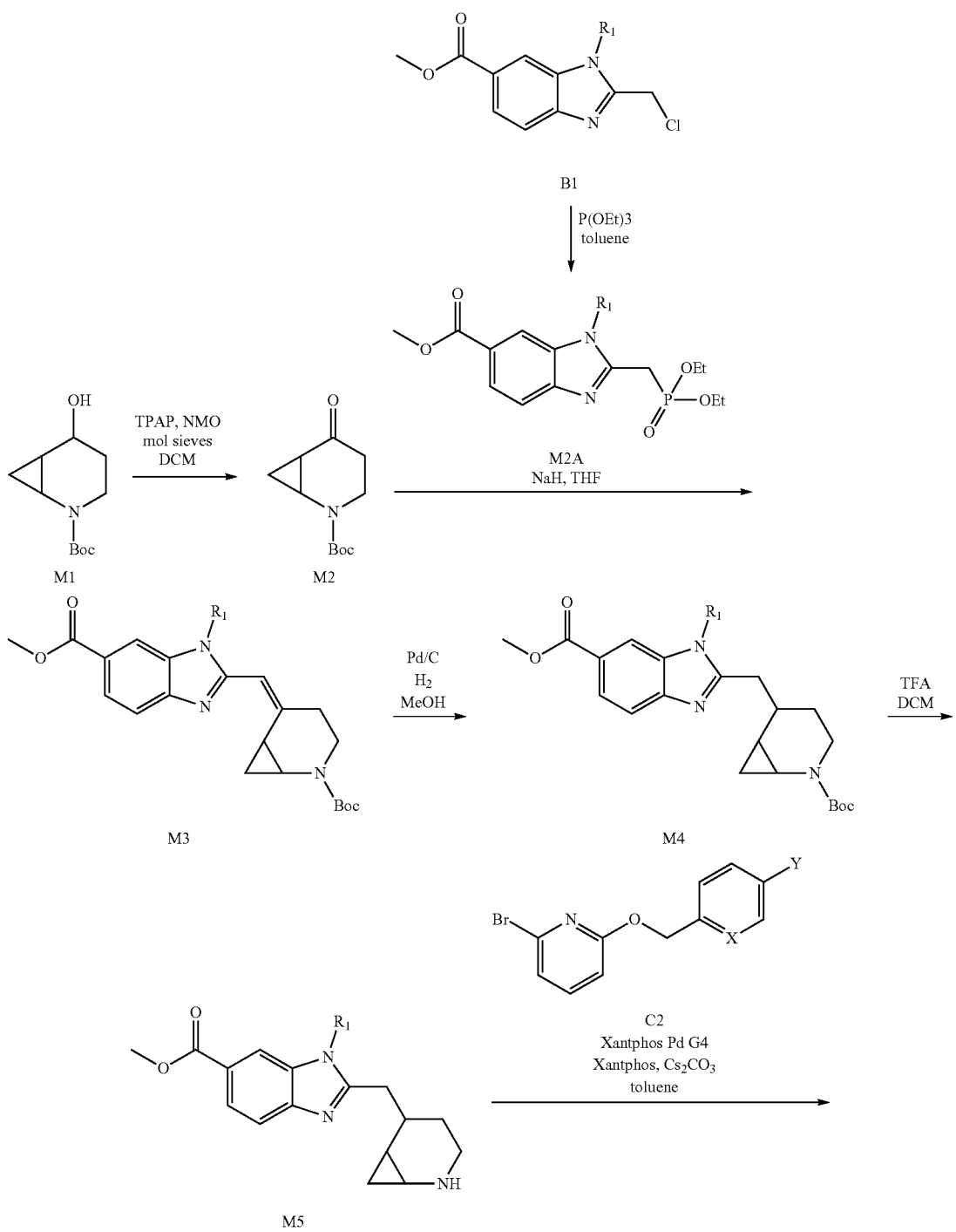

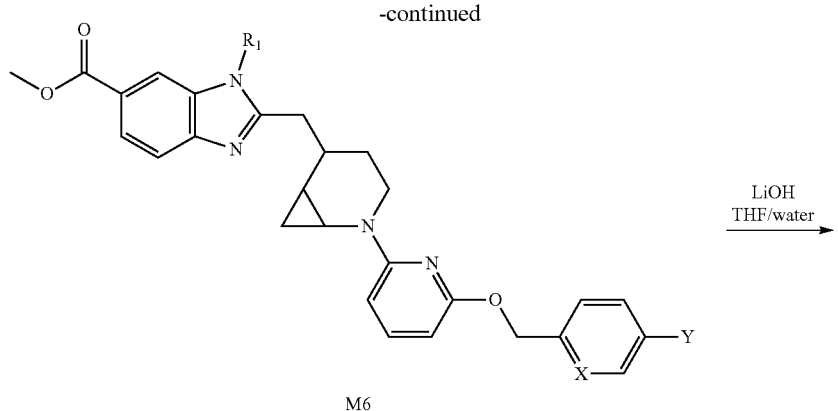

M6

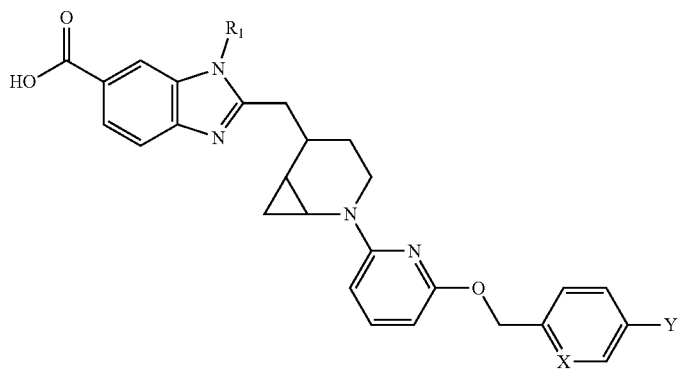

M7

Horner-Wadsworth-Emmons olefination of commercially available tert-butyl 5-oxo-2-azabicyclo[4.1.0]heptane-2-carboxylate and phosphonate M2A provides methyl 2-((2-(tert-butoxycarbonyl)-2azabicyclo[4.1.0]heptan-5-ylidene)methyl)-1-substituted-1H-benzo[d]imidazole-6-carboxylate M3 which is reduced and deprotected with strong acid. Amination of 2-(aryloxy)-6-bromopyridine C2 under Buchwald conditions provides M6 which is then saponified with an alkali hydroxide to provide M7 as a mixture of 4 diastereomers. Alternatively, M6 may be separated by supercritical fluid chromatography (SFC) to provide (1S,5R, 6S), (1S,5S,6S), (1R,5R,6R) and (1R,5S,6R) discrete isomers which may be saponified with an alkali hydroxide to provide final products. Alternatively, intermediate M6 may be prepared in a stereoselective synthesis or purified to obtain only the desired isomer for use in subsequent steps.

Scheme N. Preparation of 2-((5-(6-Substituted-aryloxy)pyridine-2-yl)-2-azabicyclo[4.1.0]heptan-2-yl)methyl)-1-substituted-6-(1H-tetrazol5-yl)-1H-benzo[d]imidazole N6.

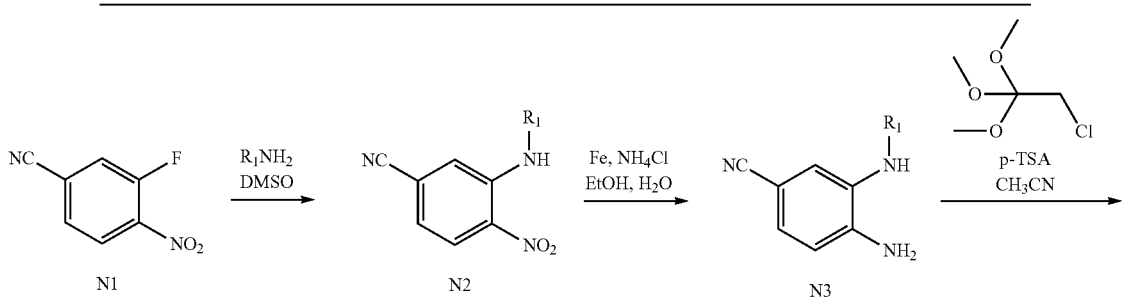

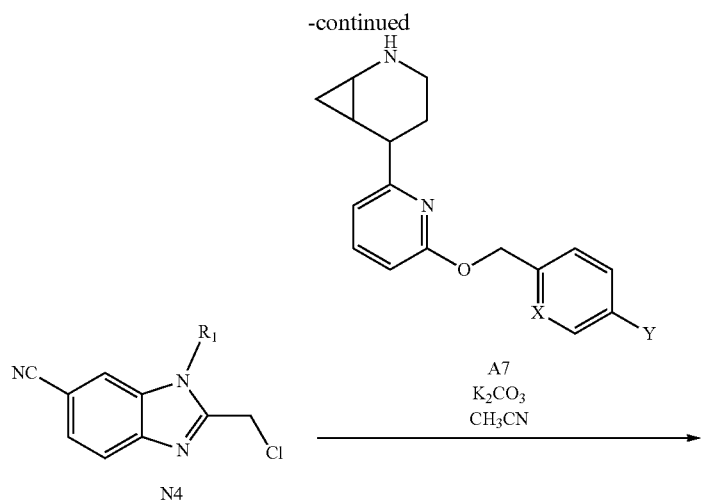

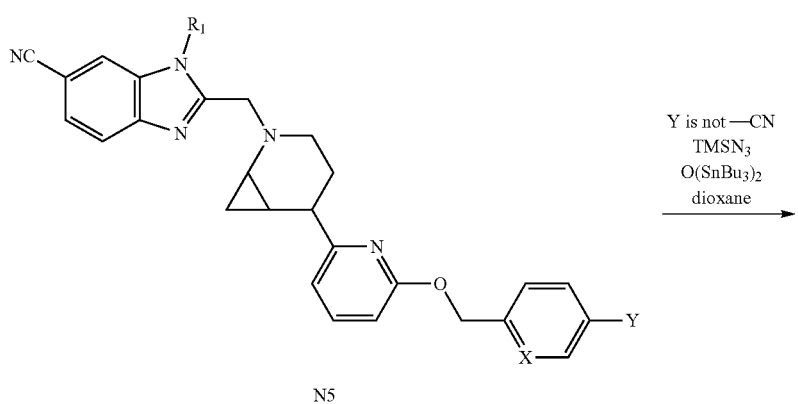

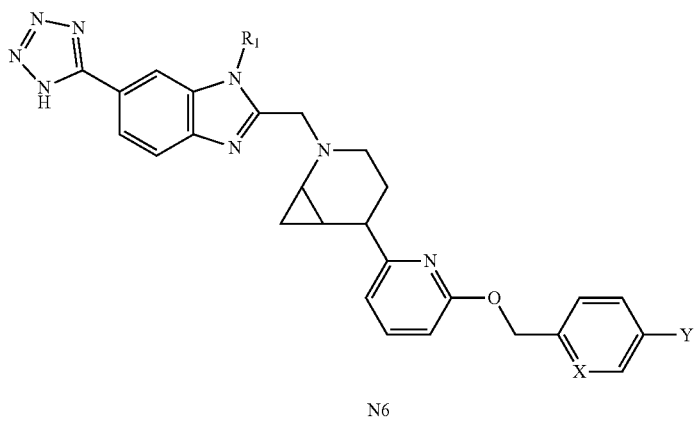

Nucleophilic substitution of commercially available 3-fluoro-4-nitrobenzonitrile with the desired amine, $R_1NH_2$, followed by reduction and condensation with 2-chloro-1,1,1-trimethoxyethane provides 2-(chloromethyl)-1-substituted-1H-benzo[d]imidazole-6-carbonitrile N4. N4 is reacted with 5-(6-(aryloxy)pyridine-2-yl)-2-azabicyclo[4.1.0]heptane intermediate A7 in the presence of an acid scavenger such as an alkali carbonate to provide N5. Cycloaddition of N5 with azidotrimethylsilane in the presence of a catalyst such as tri-n-butyltin oxide provides N6 as a mixture of 4 diastereomers. The mixture of diastereomers may be separated, if desired, by supercritical fluid chromatography (SFC).

Scheme O. Preparation of 3-(2-((5-(6-(Substituted-aryloxy)pyridine-2-yl)-2-azabicyclo[4.1.0]heptan-2-yl)methyl)-1-substituted-1H-benzo[d]imidazole-6-yl)-1, 2, 4-oxadiazol-5(4H)-one O2.

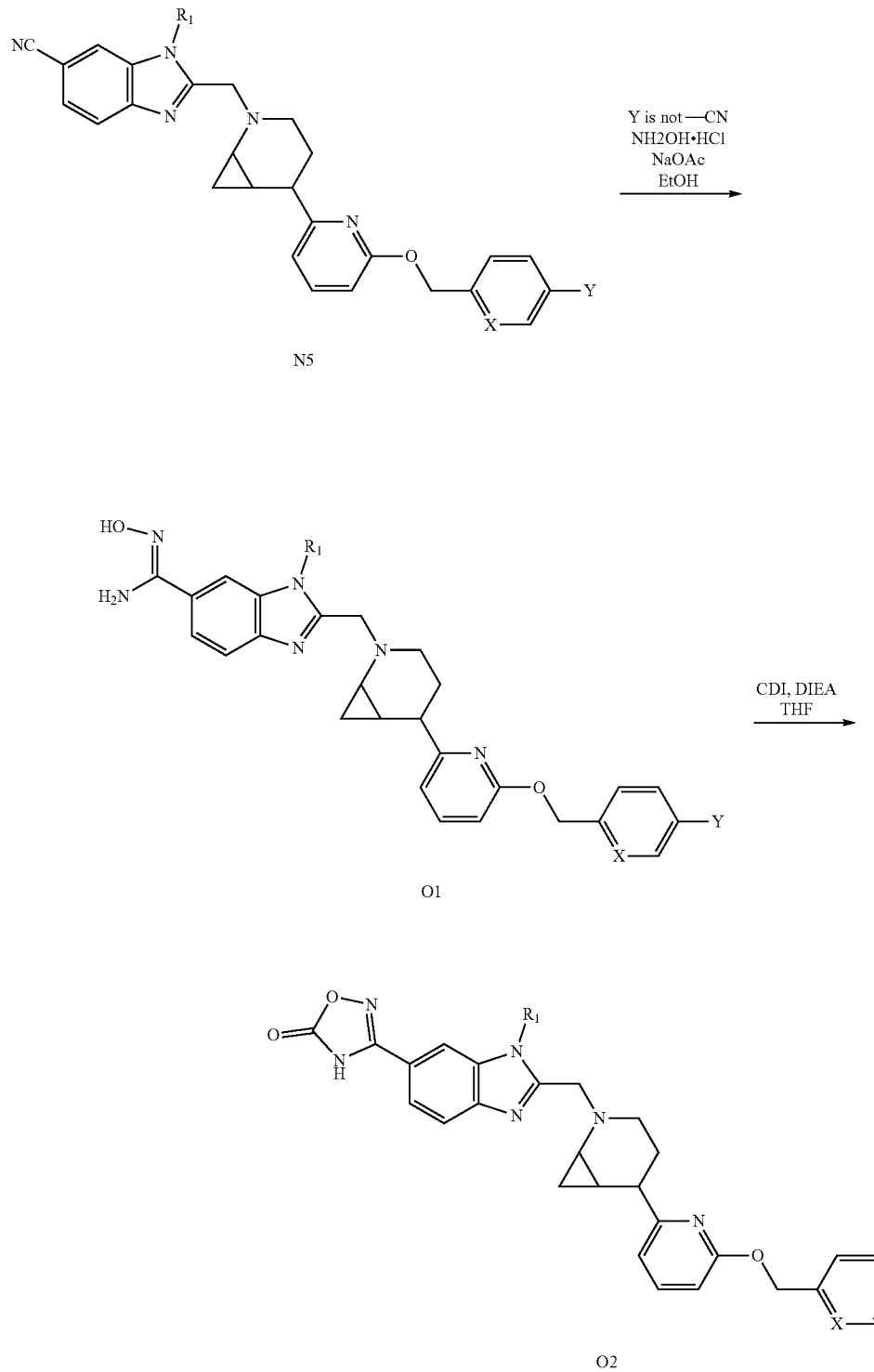

Reaction of hydroxylamine with N5 yields 2-((5-(6-(substituted-aryloxy)pyridine-2-yl)-2-azabicyclo[4.1.0]heptan-2-yl)methyl)-N'-hydroxy-1-substituted-1H-benzo[d]imidazole-6-carboximidamide O1 which is further cyclized with 1,1'-carbonyldiimidazole or phosgene in the presence of a base to provide O2. The reaction may be conducted with discrete diastereomer N5 or the mixture of 4 diastereomers separated by supercritical fluid chromatography (SFC).

Scheme P. Preparation of 5-(2-((5-(6-(Substituted-aryloxy)pyridin-2-yl)-2-azabicyclo[4.1.0]-heptan-2-yl)-1-substituted-1H-benzo[d]imidazol-6-yl)isoxazole-3(2H)-one P10.
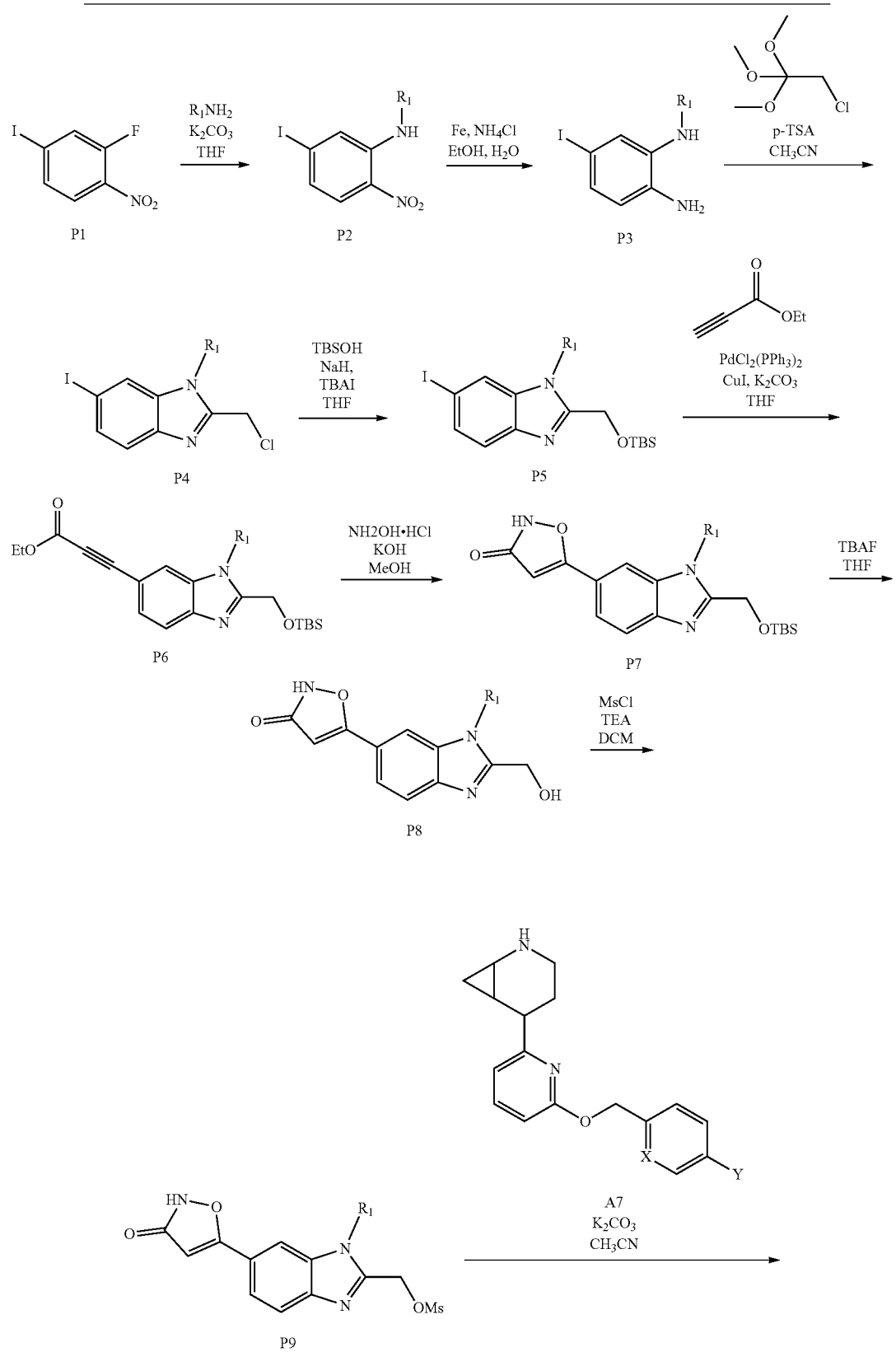

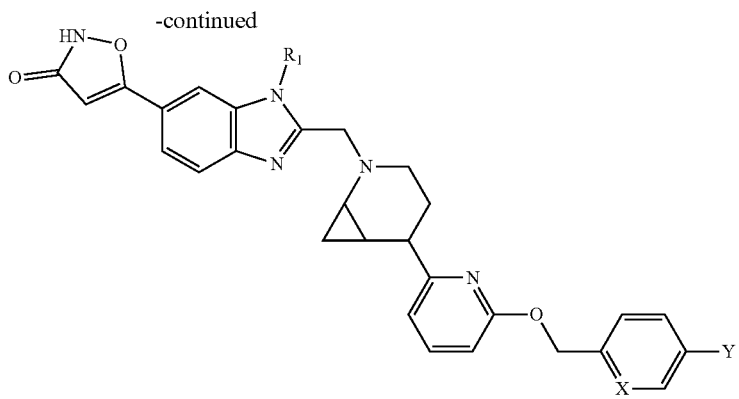

P10

2-(Chloromethyl)-6-iodo-1-substituted-1H-benzo[d]imidazole P4 is prepared following similar methods used to synthesize N4. Conversion to the TBS ether and Sonogashira coupling with ethyl propiolate yields alkyne P6 which is cyclized with hydroxylamine to provide isoxazol-3-one P7. Deprotection, mesylation and reaction with 5-(6-(aryloxy)pyridine-2-yl)-2-azabicyclo[4.1.0]heptane intermediate A7 in the presence of an acid scavenger such as an alkali carbonate provides P10. The reaction may be conducted with discrete diastereomer A7 or the mixture of 4 diastereomers separated by supercritical fluid chromatography (SFC).

Scheme Q. Alternative Preparation of 2-((5-(6-Substituted-aryloxy)pyridine-2-yl)-2-azabicyclo[4.1.0]heptan-2-yl)methyl)-1-substituted-6-(1H-tetrazol5-yl)-1H-benzo[d]imidazole N6.

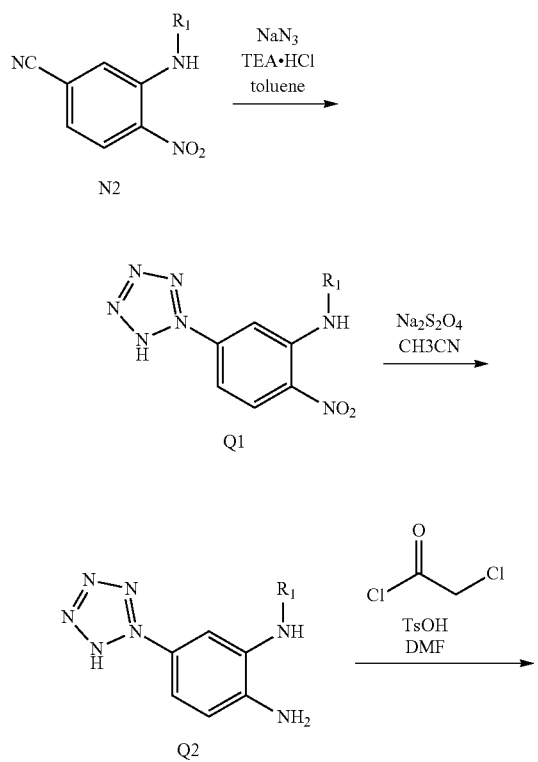

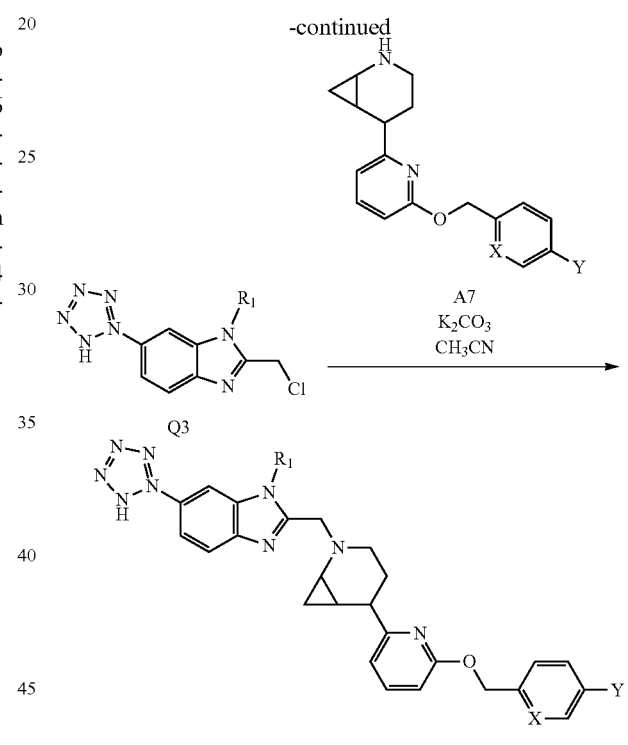

When Y=CN, it is advantageous to install the tetrazole heterocycle at an earlier stage in the synthesis. Azide cycloaddition of N2 provides N-substituted-2-nitro-5-(1H-tetrazol-5-yl)aniline Q1 which is reduced and condensed with 2-chloro-1,1,1-trimethoxyethane to provide 2-(chloromethyl)-1-substituted-6-(1H-tetrazol-5-yl)-1H-benzo[d]imidazole Q3. Q3 is reacted with 5-(6-(aryloxy)pyridine-2-yl)-2-azabicyclo[4.1.0]heptane intermediate A7 in the presence of an acid scavenger such as an alkali carbonate to provide N6.

GLP-1R Cell Assay

Stable cell lines expressing high and low GLP-1R surface expression are generated in CHO-K1 cells transfected (Fugene 6) with a puromycin selectable DNA plasmid encoding human GLP-1R receptor (accession number: NM_002062.5) under control of an EF1A promoter. Transfected cells are seeded into 24-well plates (9,000 cells/well) containing complete medium and incubated in a humidified incubator at 37° C. with 5% carbon dioxide. After overnight incubation, medium is replaced with complete medium supplemented with puromycin (6 μg/mL) and refreshed every 2-3 days to select for stably transfected cells. Individual pools of selected cells are expanded prior to analysis for responsiveness to GLP-1 control peptide using a TR-FRET assay to detect cAMP (LANCE Ultra cAMP Assay, Perkin Elmer). Briefly, cells are collected in Versene solution, plated in 384-well plates (1,000 cells/well) and combined with serially diluted GLP-1R control peptide (10 nL) using an acoustic dispenser (ECHO). Plates are incubated for 30 minutes at 25° C. prior to the addition of EU-cAMP tracer (5 μL) and Ulight-anti-cAMP (5 μL) reagents to each well, followed by 15 minutes incubation at 25° C. TR-FRET signal is detected using an EnVision Multimode Plate Reader (excitation=320 nm; emission=615 and 655 nm). Dose-response curves are used to generate $EC_{50}$ values as a measure of responsiveness to the GLP-1R control peptide. Selected cell lines are monitored for responsiveness over multiple passages to ensure stability. CHO-K1_hGLP-1Rhigh_clone16 and CHO-K1_hGLP-1Rlow_clone10 showed consistently high and low responsiveness to GLP-1R control peptide, respectively, and are chosen for further analysis to determine relative levels of GLP-1R surface expression. Briefly, GLP-1R expression is analyzed by flow cytometry using a fluorescein-labeled Exendin-4 peptide fluorescent probe (FLEX). Cells are harvested in Versene solution and washed 3-times with PBS+0.5% BSA before incubation with FLEX reagent (10 μM) for 2 hours at room temperature. After incubation, cells are washed 3-times in PBS+0.5% BSA before final resuspension in PBS prior to analysis by flow cytometry to measure FLEX mean fluorescence intensity (MFI) as a measure of GLP-1R expression on the cell surface.

For compound testing in the CHO-K1_hGLP-1Rlow_clone10 cell lines, cells are seeded in 384-well plates (1,000 cells/well). Test compounds are serially diluted in DMSO (10-point, 3-fold dilution), added to wells using an ECHO dispenser (10 nL/well) and plates are centrifuged for 1 min and agitated for 2 min at room temperature prior to 30-minute incubation at 25° C. After incubation, Eu-cAMP (5 μL) and Ulight-anti-cAMP (5 μL) reagents are added to each well, followed by centrifugation for 1 minute, agitation for 2 minutes at room temperature, and final incubation of the plates at 25° C. for 15 minutes. Plates are read using an EnVision microplate reader (excitation=320 nm; emission=615 and 655 nm). Dose-response curves are generated from duplicate wells based on percent activation calculated relative to a control GLP-1 peptide agonist that was run in parallel. $EC_{50}$ values are determined by fitting percent activation as a function of compound concentration using the Hill equation (XLfit).

The EC50 values of exemplary compounds 1 and 2 in the low expression assay are shown in the table below. The EC50 values are compared to Reference Compound A and Reference Compound B. The compounds tested were compound samples prepared according to the General Procedures described in the Examples section.

Metabolic Stability in Hepatocytes

Test compounds are incubated in human hepatocytes and stability is assessed from the substrate depilation approach. Test compounds are dissolved in dimethyl sulfoxide (DMSO) to create a 10 mM Stock, and then further diluted to create a 1000× Working Stock of 1 mM with DMSO in 96-well plates for test compounds and the positive control (midazolam). Vials containing cryopreserved hepatocytes are removed from the liquid nitrogen tank and immediately immersed in a 37° C. water bath. The vials are shaken gently until the contents had thawed and were then immediately emptied into 48 mL of pre-warmed HT Medium in a 50 mL conical tube. Cells remaining in the vial are resuspended with 1.0 mL of pre-warmed HT Medium and added to the conical tube. The tube is capped and then gently inverted several times to resuspend the hepatocytes. The cell suspension is centrifuged at 50×g at room temperature for 5 minutes and the supernatant discarded. The cell pellet is loosened by gently swirling the centrifuge tube and is re-suspended in 4 mL of warm Dulbecco's Modified Eagle medium (DMEM). Cell density is determined by a cell counter by Nexcelom, and DMEM medium is added to obtain a target density of 1×10⁶ cells/mL. The assay is carried out in 96-well microtiter plates. Test Compounds are incubated at 1 μM with 1×10⁶ cells/mL hepatocytes in DMEM for 0, 30, 60, 120 and 240 minutes. The incubation is carried out with gentle shaking at 37° C. under a humid atmosphere of 95% air/5% $CO_2$. The volume of the incubation mixture is 37 μL with a final 0.1% DMSO. At each of the time points, the incubation is stopped by adding 150 μL quenching solution (100% acetonitrile, 0.1% formic acid containing bucetin as an internal standard for positive ESI mode). Subsequently, the mixtures are vortexed for 20 min and centrifuged at 4,000 RPM at 10° C. The supernatant (80 μL) is transferred to a clean 96-well plate and analyzed by LC-MS/MS. Midazolam at 1 μM with a final 0.1% DMSO is included as a positive control to verify assay performance. The percent parent remaining, intrinsic and predicted hepatic clearance and $t_{1/2}$ are calculated. All samples are analyzed by LC-MS/MS using an AB Sciex API 4000 instrument, coupled to a Shimadzu LC-20AD LC Pump system. Separation is achieved using a Waters Atlantis T3 dC18 reverse phase HPLC column (20 mm×2.1 mm) at a flow rate of 0.5 mL/min. The mobile phase consisted of 0.1% formic acid in water (solvent A) and 0.1% formic acid in 100% acetonitrile (solvent B). Elution conditions are detailed below.

| Time (min) | Flow (μL/min) | % A | % B |
|---|---|---|---|
| 0 | 500 | 98 | 2 |
| 0.30 | 500 | 98 | 2 |
| 1.40 | 500 | 2 | 98 |
| 2.20 | 500 | 2 | 98 |
| 2.21 | 500 | 98 | 2 |
| 3.00 | 500 | 98 | 2 |

The ion optics of each test compound are optimized for their declustering potential (DP), collection energy (CE), collision-cell exit potential (CXP) and used in a selected ion monitoring experiment in the positive ion mode. The peak area ratio of each test compound to internal standard is then evaluated for stability. The extent of metabolism is calculated based on the disappearance of the test compound, compared to its initial concentration. The initial rates of clearance of the test compound are calculated using the linear regression plot of semi-log % remaining of the compound versus time. The elimination rate constant (k) of the linear regression plot is then used to determine $t_{1/2}$ and the intrinsic clearance ($CL_{int}$) using the following formula, where $C_{hepatocyte}$ (million cells/mL) is the cell density of the incubation:

$k = -\text{slope}$ $t_{1/2} = 0.693/k$ $CL_{int} = k/C_{hepatocyte}$

This method of intrinsic clearance determination assumes that the test compound concentration is far below the Michaelis-Menten constant of the compound to its metabolizing enzymes.

The predicted hepatic clearance ($CL_{hep}$) was calculated using the well stirred method with the following formula with $CL_{int(in\ vivo)}$ normalized based on liver weight:

$$CL_{int(in\ vivo)} = CL_{int} \times \text{Hepatocellularity} \times \text{liver weight}$$

$$CL_{hep\ predicted} = (CL_{int(in\ vivo)} \times Q_{liver})/(CL_{int}(\text{in vivo}) + Q_{liver})$$

Where $Q_{liver}$ ((ml/min/kg) is Liver Blood Flow

The relevant physiological parameters of liver weight, blood flow, and hepatocellularity for humans are listed below:

| Liver Weight (g liver/kg body weight) | Hepatocellularity (106 cells/g liver) | Liver Blood Flow ($Q_{liver}$, mL/min/kg) |
|---|---|---|
| 25.7 | 135 | 20.7 |

Passive Permeability and Efflux Ratio

Caco-2 cells (clone C2BBe1) are obtained, e.g., from American Type Culture Collection (Manassas, VA). Cell monolayers are grown to confluence on collagen-coated, microporous membranes in 12-well assay plates. The permeability assay buffer is Hanks' balanced salt solution containing 10 mM HEPES and 15 mM glucose at a pH of 7.4. The buffer in the receiver chamber also contains 1% bovine serum albumin. The dosing solution concentration is 5 µM of test article in the assay buffer. Cell monolayers are dosed on the apical side (A-to-B) or basolateral side (B-to-A) and incubated at 37° C. with 5% $CO_2$ in a humidified incubator. Samples are taken from the donor and receiver chambers at 120 minutes. Each determination is performed in duplicate. The flux of lucifer yellow is also measured post-experimentally for each monolayer to ensure no damage is inflicted to the cell monolayers during the flux period. All samples are assayed by LC-MS/MS using electrospray ionization. The apparent permeability ($P_{app}$) and percent recovery were calculated as follows:

$$P_{app} = (dC_r/dt) \times V_r/(A \times C_A) \qquad (1)$$

$$\text{Percent Recovery} = 100 \times ((V_r \times C_r^{final}) + (V_d \times C_d^{final}))/(V_d \times C_N) \qquad (2),$$

where, $dC_r/dt$ is the slope of the cumulative receiver concentration versus time in µM s$^{-1}$; $V_r$ is the volume of the receiver compartment in cm$^3$; $V_d$ is the volume of the donor compartment in cm$^3$; A is the area of the insert (1.13 cm$^2$ for 12-well); $C_A$ is the average of the nominal dosing concentration and the measured 120-minute donor concentration in µM; CN is the nominal concentration of the dosing solution in µM; $C_r^{final}$ is the cumulative receiver concentration in µM at the end of the incubation period; $C_d^{final}$ is the concentration of the donor in µM at the end of the incubation period. Efflux ratio (ER) is defined as $P_{app}$ (B-to-A)/$P_{app}$ (A-to-B).

Rat Pharmacokinetics

Intravenous dosing: Compounds are formulated at 0.5 mg/mL in a solution comprising 5% polyethylene glycol 400 and 95% (12% (w/v) sulfobutyl-β-cyclodextrin in water) (v/v). Formulated compounds are sterile filtered through a 0.22 micron filter before dosing. Compounds are administered to male, 7-11-week-old Sprague-Dawley rats by jugular vein cannula infusion over 30 minutes at a dose of 1 mg/kg.

Oral dosing: Compounds are formulated at 0.3 mg/mL or 0.6 mg/mL in a solution comprising 5% polyethylene glycol 400 and 95% (12% (w/v) sulfobutyl-β-cyclodextrin in water) (v/v). Formulated compounds are administered to male, 7-11 week old Sprague-Dawley rats by oral gavage at a dose of 10 mL/kg.

Sample collection: Blood collections of about 0.2 mL per time point are performed from jugular vein or other suitable site of each animal, into pre-chilled commercial EDTA-K2 tubes and placed on wet ice until centrifugation. Blood samples are processed for plasma by centrifugation at approximately 4° C., 3,200 g for 10 min. Plasma is collected and transferred into pre-labeled 96 well plate or polypropylene tubes, quick frozen over dry ice and kept at −60° C. or lower until LC-MS/MS analysis.

Data analysis: Plasma concentration versus time data are plotted in graph and analyzed by non-compartmental approaches using the Phoenix WinNonlin 6.3 software program. Related PK parameters are calculated according to dosing route, e.g., CL, $V_{dss}$ and $C_0$ for intravenous administration, $C_{max}$, $T_{max}$ or % F for extravascular administration, and $T_{1/2}$, $AUC_{(0-t)}$, $AUC_{(0-inf)}$, $MRT_{(0-t)}$, $MRT_{(0-inf)}$ for all routes.

EXAMPLES

For exemplary purposes, neutral compounds of Formula (0) and Formula (1) are synthesized and tested in the examples. It is understood that the neutral compounds of Formula (0) and Formula (1) may be converted to the corresponding pharmaceutically acceptable salts of the compounds using techniques in the art (e.g., by saponification of an ester to the carboxylic acid salt, or by hydrolyzing an amide to form a corresponding carboxylic acid and then converting the carboxylic acid to a carboxylic acid salt).

It is understood that the values described in the examples are approximate and subject to experimental and instrumental variations.

Abbreviations

ACN Acetonitrile
AIBN Azobisisobutyronitrile
BOC tert-butyl carbamate
BOP (benzotriazol-1-yloxy)tris(dimethylamino)phosphonium hexafluorophosphate
BTC bis(trichloromethyl) carbonate
CDI carbonyl diimidazole
DAD diode array detector
DCM Dichloromethane
DIEA/DIPEA N,N-diisopropylethylamine
DMF N,N-dimethylformamide
DMSO Dimethylsulfoxide
EA/EtOAc ethyl acetate
EDCI 1-ethyl-3-(3-dimethylaminopropyl) carbodiimide
ELSD evaporative light scattering detector
ES/ESI electrospray ionisation
HATU 1-[Bis(dimethylamino)methylene]-1H-1,2,3-triazolo[4,5-b]pyridinium 3-oxid hexafluorophosphate
HOAT 1-hydroxy-7-azabenzotriazole
HOBT hydroxy benzotriazole
HPLC high-performance liquid chromatography
IPA Isopropylalcohol
LC liquid chromatography LiHMDS lithium hexamethyl disilazide
MS mass spectrometry
NMR nuclear magnetic resonance
Py Pyridine
RT retention time
SFC supercritical fluid chromatography
TBAI tetrabutyl ammonium iodide
TEA Triethylamine
TFA trifluoroacetic acid
TFAA trifluoroacetic anhydride
THF Tetrahydrofuran
TLC thin layer chromatography
TMS tetramethyl silane
UV Ultraviolet Example 1 (Synthesis of Compound 1)

Compound 1 was prepared by the synthetic method shown in Scheme 1.

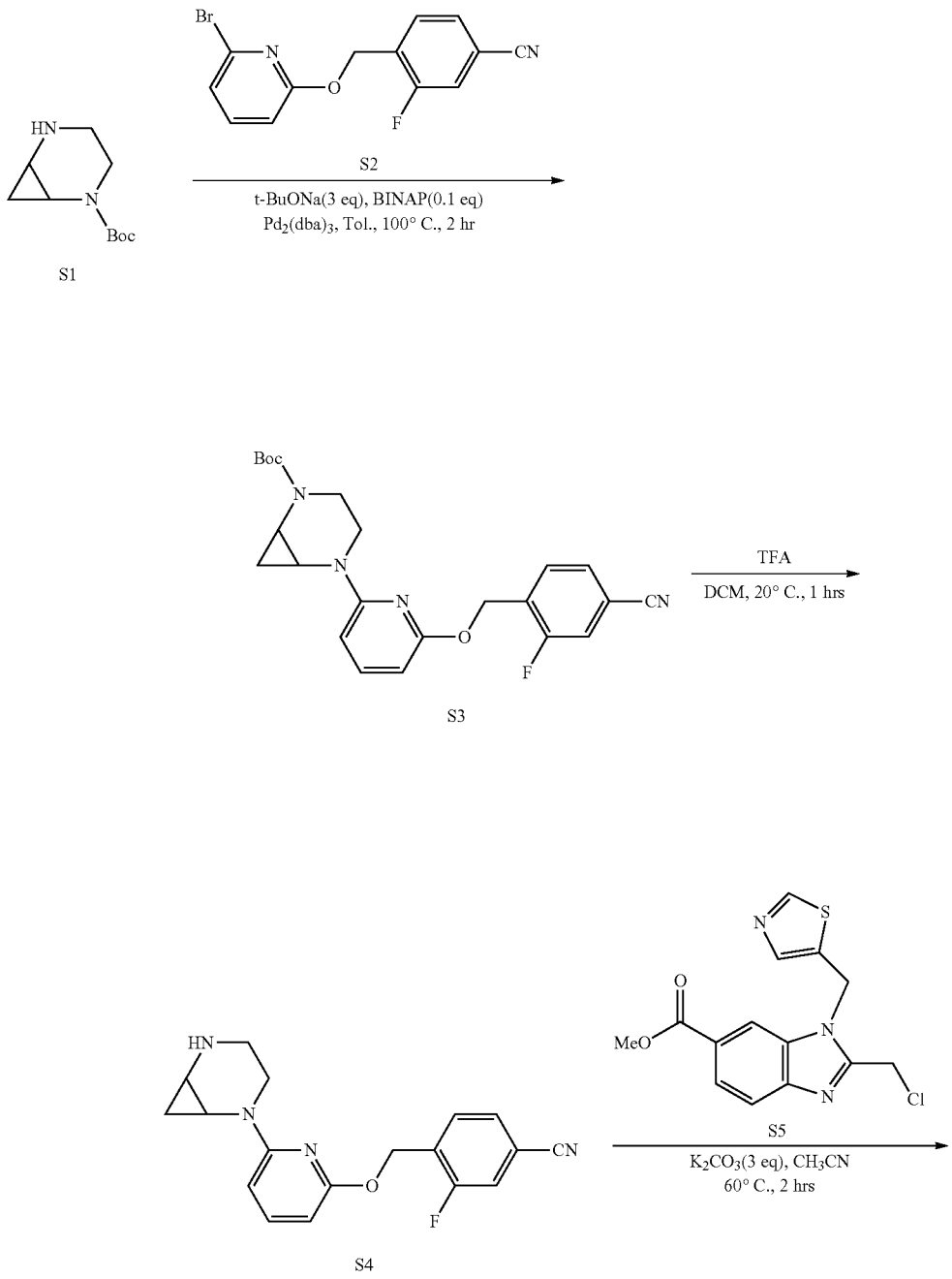

-continued
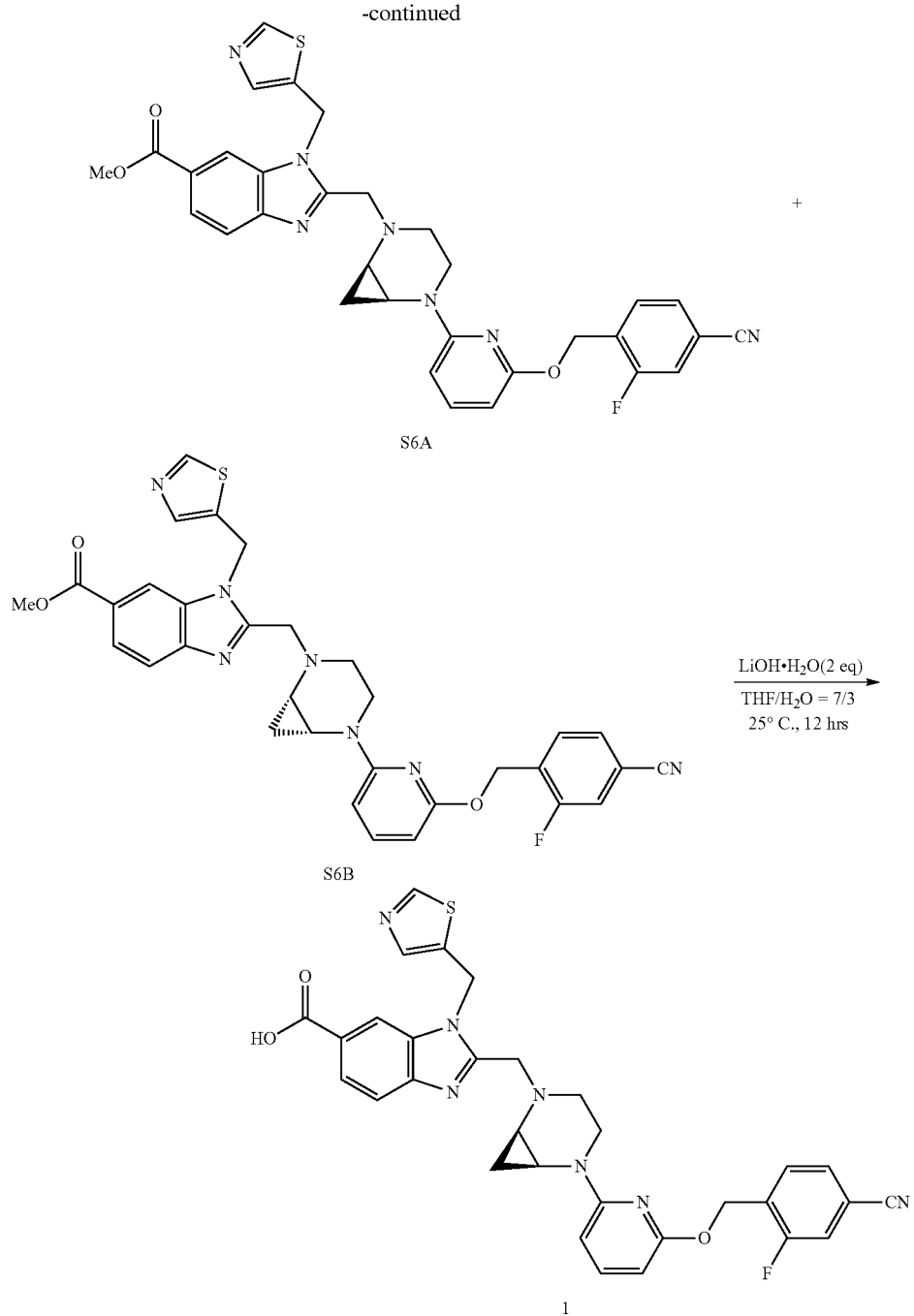
S6A
S6B
1
Procedure for the Preparation of Compound S3
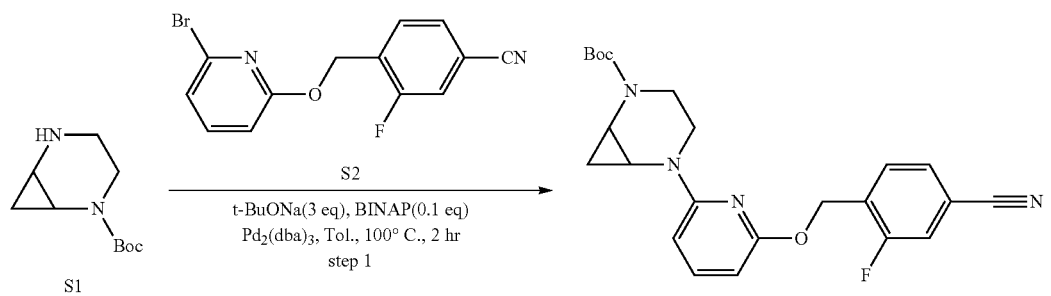

A mixture of compound S1 (500 mg, 2.52 mmol, 1.1 eq), compound S2 (704.12 mg, 2.29 mmol, 1 eq), Pd$_2$(dba)$_3$ (104.97 mg, 114.63 umol, 0.05 eq), rac-BINAP (142.76 mg, 229.27 umol, 0.1 eq), and t-BuONa (661.00 mg, 6.88 mmol, 3 eq) in Tol. (1 mL) was degassed and purged with N$_2$×3, and then the mixture was stirred at 100° C. for 2 hr under N$_2$ atmosphere. LC-MS showed compound S1 was consumed completely. The reaction mixture was cooled to 20° C., filtered, and concentrated under reduced pressure. The residue was purified by column chromatography (SiO$_2$, Petroleum ether/Ethyl acetate=100/1 to 10/1). Compound S3 (440 mg, 1.04 mmol, 45% yield) was obtained as a white solid.

LCMS: RT=2.142 min, MS cal.: 424.2, [M+H]$^+$=325.2

$^1$H NMR (400 MHz, CHLOROFORM-d) δ=0.39 (br s, 1H) 1.02-1.21 (m, 1H) 1.50 (s, 10H) 2.75-2.91 (m, 1H) 3.05-3.60 (m, 4H) 3.83-4.08 (m, 1H) 5.41-5.51 (m, 2H) 6.18 (d, J=7.82 Hz, 1H) 6.34 (br s, 1H) 7.37 (dd, J=9.29, 1.22 Hz, 1H) 7.43-7.51 (m, 2H) 7.59-7.66 (m, 1H).

General Procedure for Preparation of Compound S4

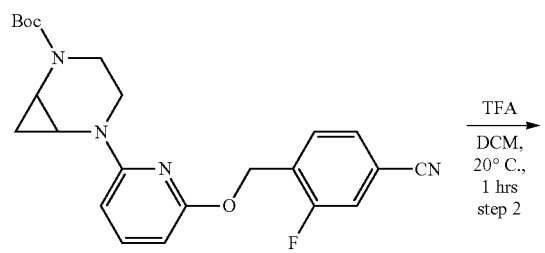

S3

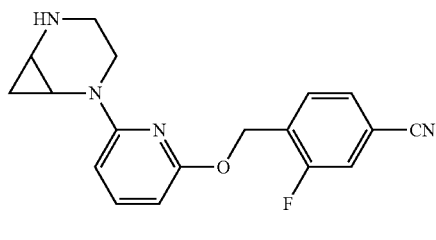

S4

A mixture of compound S3 (400 mg, 942.36 umol, 1 eq), TFA (1 mL) in DCM (3 mL) was degassed and purged with N$_2$×3 and then the mixture was stirred at 20° C. for 1 hr under an N2 atmosphere at which point the reaction mixture was concentrated under reduced pressure. Compound S4 was used directly as a yellow oil.

General Procedure for Preparation of Compound S6A and S6B

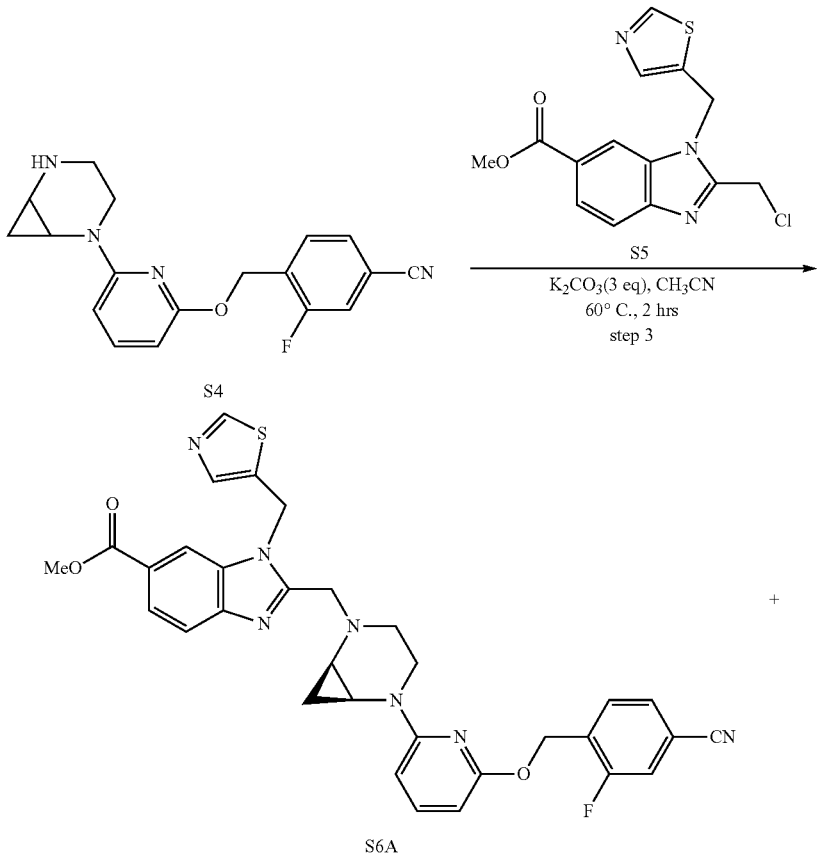

S6A

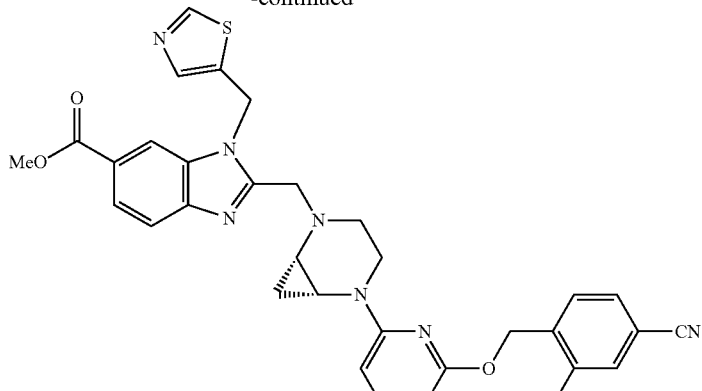

S6B

A mixture of compound S4, compound S5 (300 mg, 924.92 umol, 1 eq), K2CO₃ (383.49 mg, 2.77 mmol, 3 eq) in CH₃CN (5 mL) was degassed and purged with N₂×3, and then the mixture was stirred at 50° C. for 3 hr under N2 atmosphere. The reaction mixture was filtered and partitioned with 5 mL H₂O. The mixture was extracted with EtOAc (10 mL×3). The organic layers were combined and washed with 10 mL brine, concentrated under reduced pressure. The residue was purified by prep-HPLC (neutral condition column: Waters Xbridge Prep OBD C18 150*40 mm*10 um; mobile phase: [water(NH₄HCO₃)-ACN]; B %: 45%-80%, 8 min) to give desired compound (400 mg, yield 90%, purity 90%) as a white solid, which was further separated by SFC (condition: column: DAICEL CHIRALCEL OD (250 mm*30 mm, 10 um); mobile phase: [0.1% NH₃H₂O MEOH]; B %: 50%-50%, 15 min). Compound S6A (120 mg, 196.83 umol, 21.28% yield) was obtained as a white solid.

LCMS: RT=2.532 min, MS cal.: 617.2, [M+H]⁺=618.2

¹H NMR (400 MHz, CHLOROFORM-d) δ=0.46-0.61 (m, 1H) 0.79 (q, J=6.30 Hz, 1H) 1.22 (d, J=6.00 Hz, 1H) 1.25-1.31 (m, 1H) 2.37-2.45 (m, 1H) 2.58-2.66 (m, 1H) 2.72-2.83 (m, 2H) 3.00-3.09 (m, 1H) 3.96 (s, 3H) 4.01-4.08 (m, 1H) 4.10-4.21 (m, 3H) 5.37-5.52 (m, 2H) 5.86 (s, 2H) 6.16 (d, J=7.88 Hz, 1H) 6.31 (d, J=8.00 Hz, 1H) 7.34 (d, J=9.26 Hz, 1H) 7.41-7.51 (m, 2H) 7.61 (t, J=7.50 Hz, 1H) 7.79 (d, J=8.38 Hz, 1H) 7.90 (s, 1H) 8.02 (d, J=8.50 Hz, 1H) 8.15 (s, 1H) 8.74-8.77 (m, 1H).

Compound S6B (80 mg, 131.22 umol, 14.19% yield) was obtained as a white solid.

LCMS: RT=2.534 min, MS cal.: 617.2, [M+H]⁺=618.2

¹H NMR (400 MHz, CHLOROFORM-d) δ=0.50-0.60 (m, 1H) 0.79 (q, J=6.34 Hz, 1H) 1.20-1.29 (m, 1H) 2.39-2.47 (m, 1H) 2.59-2.67 (m, 1H) 2.72-2.84 (m, 3H) 3.05 (ddd, J=12.38, 9.76, 2.25 Hz, 1H) 3.96 (s, 4H) 4.03-4.21 (m, 4H) 5.37-5.50 (m, 2H) 5.86 (s, 2H) 6.16 (d, J=7.88 Hz, 1H) 6.31 (d, J=8.13 Hz, 1H) 7.34 (d, J=9.38 Hz, 1H) 7.41-7.50 (m, 3H) 7.61 (t, J=7.44 Hz, 1H) 7.79 (d, J=8.50 Hz, 1H) 7.90 (s, 1H) 8.02 (d, J=8.50 Hz, 1H) 8.15 (s, 1H) 8.74-8.77 (m, 1H).

General Procedure for Preparation of Compound 1

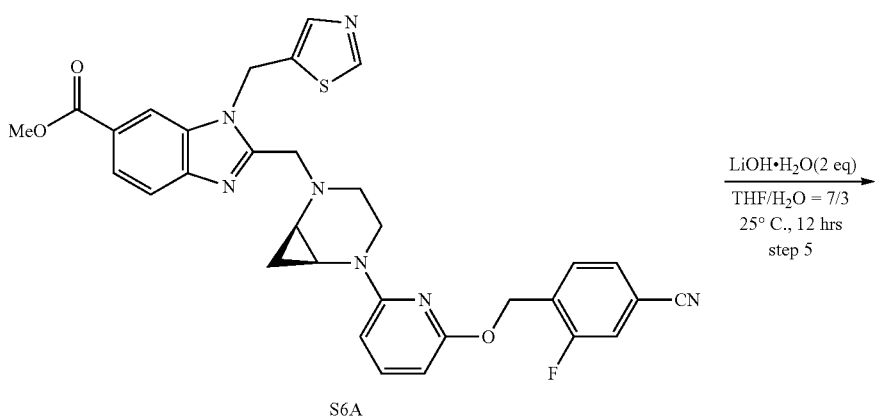

S6A

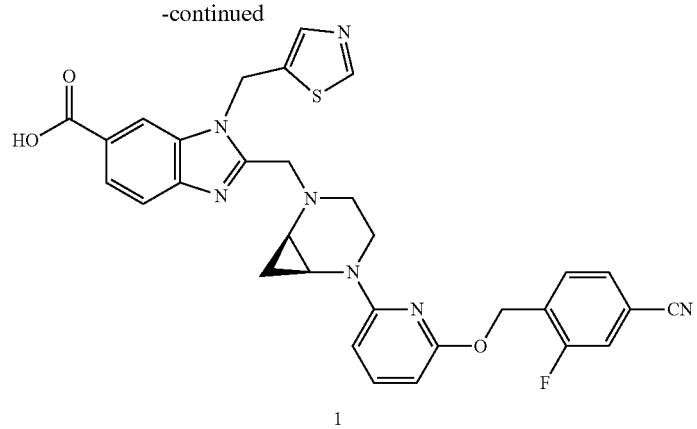

1

A mixture of compound S6A (90 mg, 147.62 umol, 1 eq), LiOH·H$_2$O (12.39 mg, 295.24 umol, 2 eq) in THF (0.7 mL) and H$_2$O (0.3 mL) was degassed and purged with N$_2$×3, and then the mixture was stirred at 25° C. for 16 hr under an N2 atmosphere. The reaction mixture was purified by prep-HPLC (neutral condition column: Waters Xbridge Prep OBD C18 150*40 mm*10 um; mobile phase: [water (NH$_4$HCO$_3$)-ACN]; B %: 20%-50%, 8 min). Compound 1 (29.88 mg, 50.16 umol, 33.98% yield) was obtained as a white solid.

LCMS: RT=2.508 min, MS cal.: 595.2, [M+H]$^+$=596.1

$^1$H NMR (400 MHz, METHANOL-d$_4$) δ ppm 0.49-0.55 (m, 1H) 0.75 (q, J=6.00 Hz, 1H) 2.37-2.45 (m, 1H) 2.67 (td, J=7.42, 5.42 Hz, 1H) 2.76-2.85 (m, 2H) 3.00 (ddd, J=12.84, 9.80, 2.62 Hz, 1H) 4.08-4.24 (m, 3H) 5.46 (s, 2H) 6.00 (s, 2H) 6.13 (d, J=7.75 Hz, 1H) 6.36 (d, J=8.11 Hz, 1H) 7.48 (t, J=7.93 Hz, 1H) 7.53-7.57 (m, 2H) 7.62-7.68 (m, 1H) 7.71 (d, J=8.46 Hz, 1H) 8.01 (dd, J=8.46, 1.43 Hz, 1H) 8.06 (s, 1H) 8.27 (d, J=0.83 Hz, 1H) 8.94 (d, J=0.72 Hz, 1H).

LCMS: RT=2.508 min, MS cal.: 595.2, [M+H]$^+$=596.1

HPLC: RT=11.351 min

Example 2 (Synthesis of Compound 2)

Compound 2 was prepared from Compound S6B. The preparation of Compound S6B was described in Example 1.

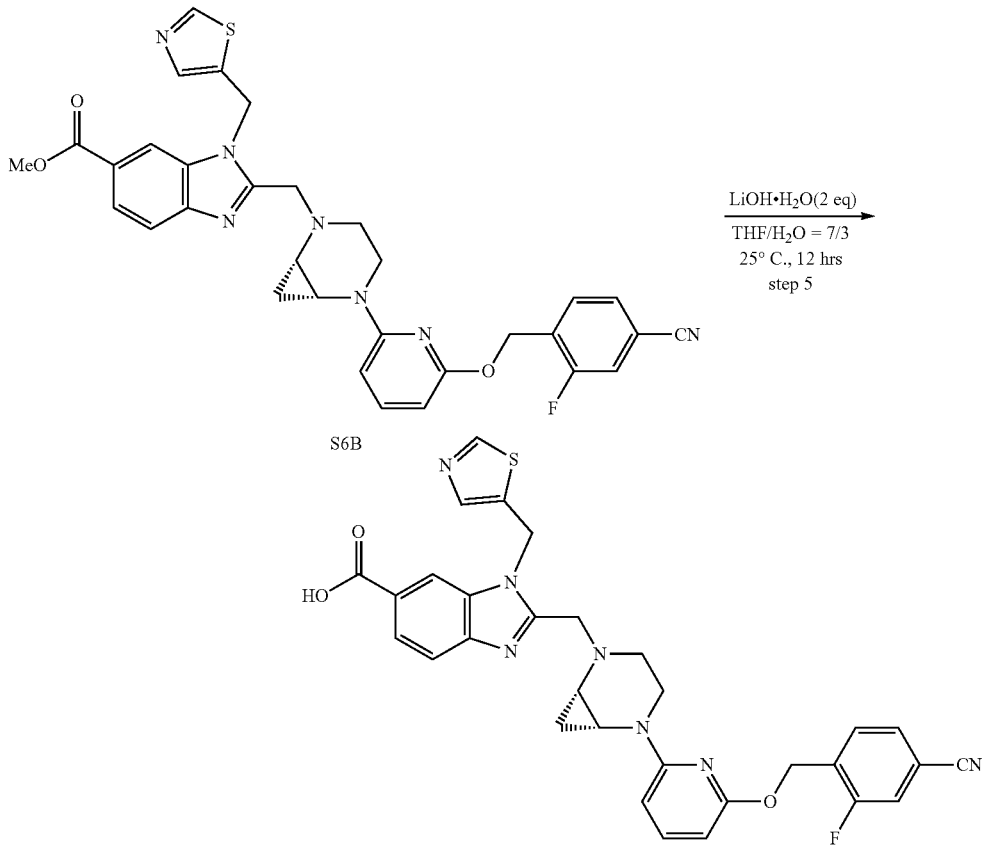

To a solution of compound S6B (70 mg, 114.82 umol, 1 eq) in THF (0.7 mL) was added LiOH·H$_2$O (9.64 mg, 229.63 umol, 2 eq) in H$_2$O (0.3 mL). The mixture was stirred at 25° C. for 12 hr. The mixture was purified directly. The residue was purified by prep-HPLC (neutral condition; column: Waters Xbridge BEH C18 100*30 mm*10 um; mobile phase: [water (NH$_4$HCO$_3$)-ACN]; B %: 30%-60%, 8 min). Compound 2 (35 mg, 58.76 umol, 51.18% yield) was obtained as a white solid.

LCMS: Rt=2.474 min, MS cal.: 595.65, [M+H]$^+$=596.6

HPLC: Rt=11.346 min $^1$H NMR (400 MHz, METHANOL-d4) δ=0.47-0.54 (m, 1H) 0.68-0.78 (m, 1H) 2.35-2.45 (m, 1H) 2.65 (td, J=7.43, 5.56 Hz, 1H) 2.73-2.85 (m, 2H) 2.93-3.02 (m, 1H) 4.06-4.25 (m, 3H) 5.44 (s, 2H) 5.98 (s, 2H) 6.11 (d, J=7.70 Hz, 1H) 6.34 (d, J=8.07 Hz, 1H) 7.46 (t, J=7.95 Hz, 1H) 7.51-7.58 (m, 2H) 7.60-7.66 (m, 1H) 7.71 (d, J=8.44 Hz, 1H) 7.99 (dd, J=8.56, 1.47 Hz, 1H) 8.05 (s, 1H) 8.27 (d, J=0.86 Hz, 1H) 8.92 (d, J=0.73 Hz, 1H)

Example 3 (Synthesis of Compound 16)

2-((5-(6-((4-Cyano-2-fluorobenzyl)oxy)pyridin-2-yl)-2-azabicyclo[4.1.0]heptan-2-yl)methyl)-1-(thiazol-5-ylmethyl)-1H-benzo[d]imidazole-6-carboxylic Acid, Mixture of 4 Diastereomers

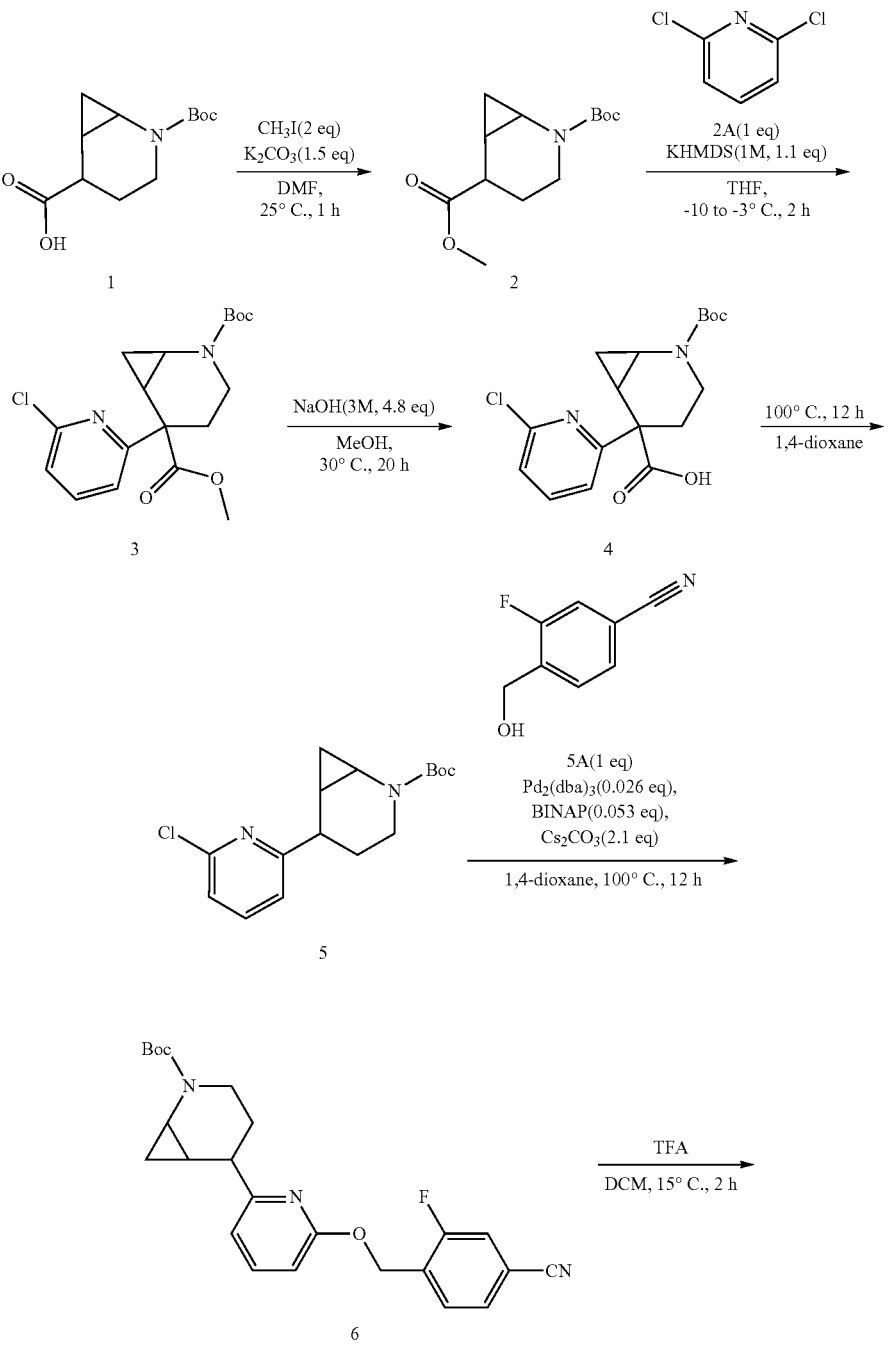

-continued
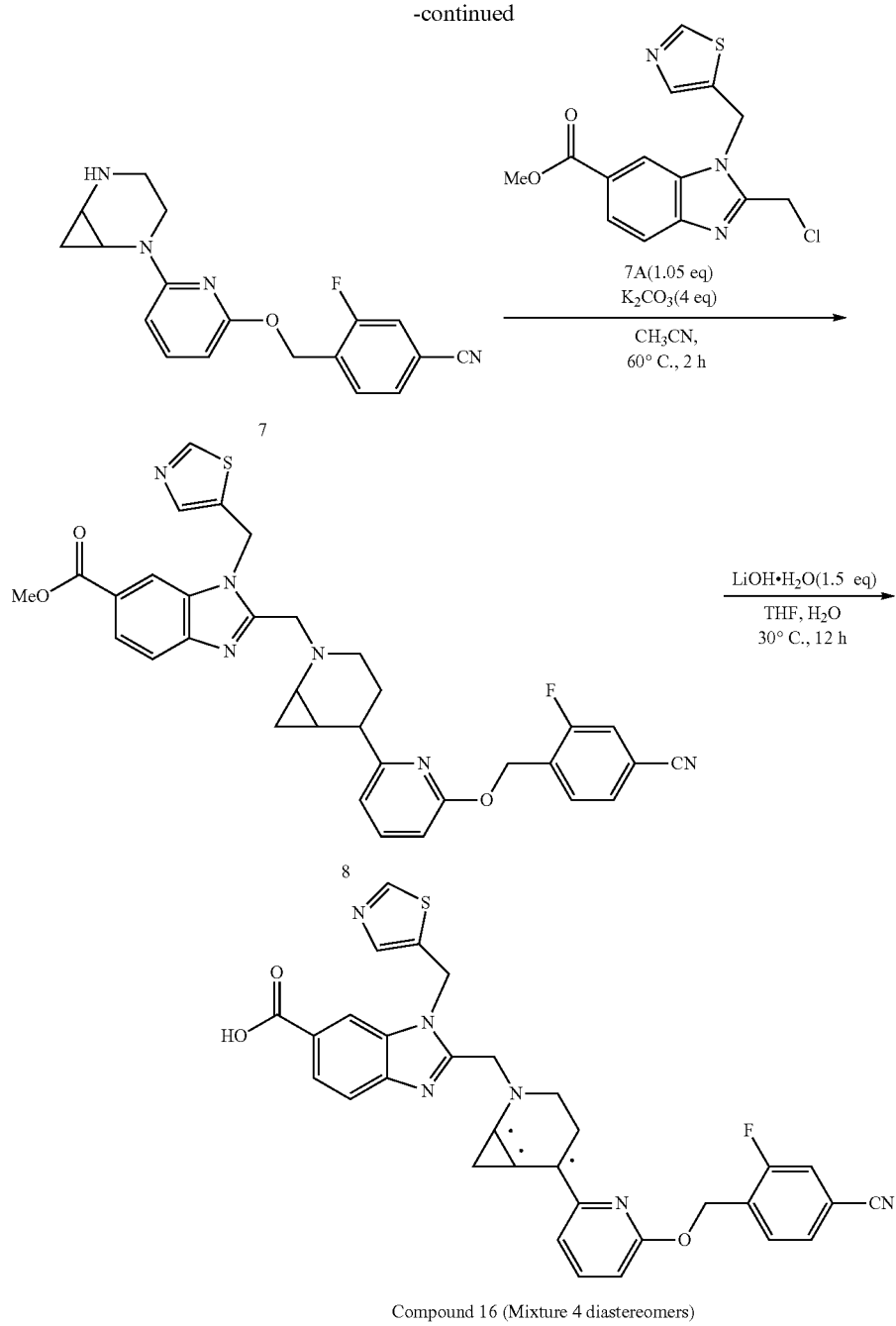
Compound 16 (Mixture 4 diastereomers)
Preparation of 2-(tert-Butyl) 5-methyl 2-azabicyclo[4.1.0]heptane-2,5-dicarboxylate (2)
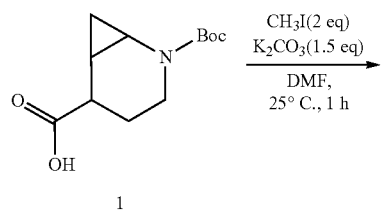
-continued
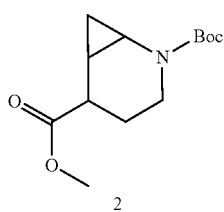
A mixture of 2-(tert-butoxycarbonyl)-2-azabicyclo[4.1.0]heptane-5-carboxylic acid (2.5 g, 10.4 mmol, 1 eq), CH₃I (2.94 g, 20.7 mmol, 1.29 mL, 2 eq), K2CO₃ (2.15 g, 15.5 mmol, 1.5 eq) in DMF (30 mL) was degassed and purged with N2 for 3 times, and then the mixture was stirred at 25° C. for 1 h under N2 atmosphere. TLC (Petroleum ether/Ethyl acetate=5/1 $R_f$=0.46) indicated starting material was consumed completely. The combined reaction mixture was poured into water (100 mL) and extracted with ethyl acetate (50 mL*2). The combined organic phase was concentrated in vacuo to give a residue. The residue was purified by column chromatography (SiO$_2$, Petroleum ether/Ethyl acetate=100/1 to 0/1) to provide product as an oil (2.4 g, 9.40 mmol, 90.7% yield); $^1$H NMR (400 MHz, DMSO-d$_6$) δ 3.67 (d, J=10.8 Hz, 3H), 3.45-3.38 (m, 0.5H), 3.04-2.90 (m, 0.5H), 2.89-2.61 (m, 2H), 1.86-1.71 (m, 1H), 1.70-1.55 (m, 1H), 1.45-1.40 (m, 9.5H), 1.33-1.19 (m, 0.5H), 0.88-0.73 (m, 1H), 0.34-0.26 (m, 1H).

Preparation of 2-(tert-Butyl) 5-methyl 5-(6-chloro-pyridin-2-yl)-2-azabicyclo[4.1.0]heptane-2,5-dicarboxylate (3)

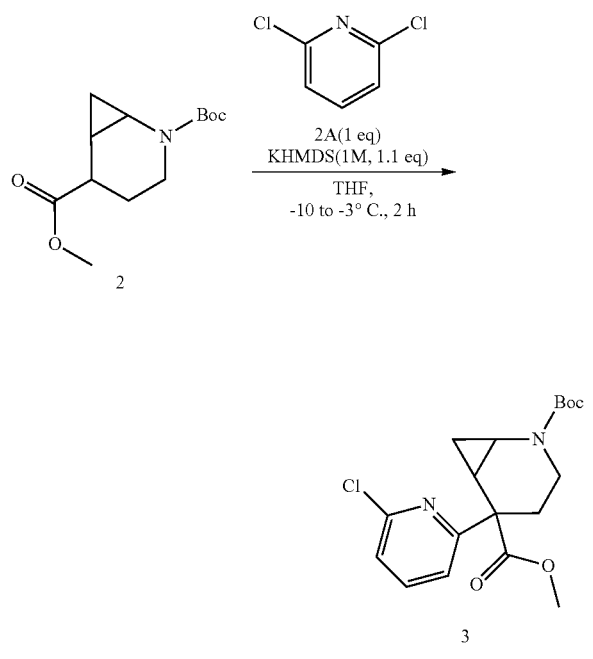

To a solution of 2-(tert-butyl) 5-methyl 2-azabicyclo[4.1.0]heptane-2,5-dicarboxylate (1.5 g, 5.88 mmol, 1 eq) and 2,6-dichloropyridine (869 mg, 5.88 mmol, 1 eq) in THF (15 mL) was added slowly a solution of KHMDS (1 M, 6.46 mL, 1.1 eq) to control the internal temperature within −10~−3° C. Then the reaction mixture was kept stirring at −10~−5° C. for 1.5~2 h. TLC indicated starting material was consumed completely. The reaction mixture was poured into water (50 mL) and extracted with ethyl acetate (50 mL*2). The combined organic phase was concentrated in vacuo to give a residue. The residue was purified by column chromatography (SiO$_2$, Petroleum ether/Ethyl acetate=100/1 to 0/1) to provide product as a white solid (1.5 g, 4.09 mmol, 69.6% yield).

Preparation of 2-(tert-Butoxycarbonyl)-5-(6-chloro-pyridin-2-yl)-2-azabicyclo[4.1.0]heptane-5-carboxylic Acid (4)

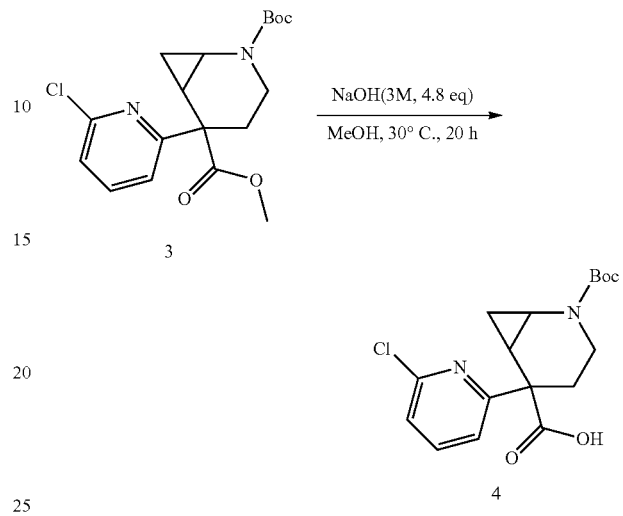

A mixture of 2-(tert-butyl) 5-methyl 5-(6-chloropyridin-2-yl)-2-azabicyclo[4.1.0]heptane-2,5-dicarboxylate (1.4 g, 3.82 mmol, 1 eq), NaOH (2 M, 5.72 mL, 3 eq) in MeOH (15 mL) was degassed and purged with N2 for 3 times, and then the mixture was stirred at 45° C. for 12 h under N2 atmosphere. LCMS showed the starting material was consumed completely. The solution was concentrated under vacuum at ~40° C. to remove ~1/2 solvents. The aqueous layer was neutralized by aq. HCl (2N, ~7 mL, 3.5 eq) at −5° C.~5° C. to pH around 3~5. A white suspension was formed during the neutralization. The reaction mixture was filtered and the filter cake was washed with H$_2$O (10 mL*3). The filter cake was dissolved in DCM (30 mL), washed with brine (30 mL) and concentrated under reduced pressure to provide product as a white solid (1.3 g, 3.68 mmol, 96.6% yield); LCMS: RT=1.262 min, MS cal.: 352.82, [M-55]$^+$=297.1.

Preparation of tert-Butyl 5-(6-chloropyridin-2-yl)-2-azabicyclo[4.1.0]heptane-2-carboxylate (5)

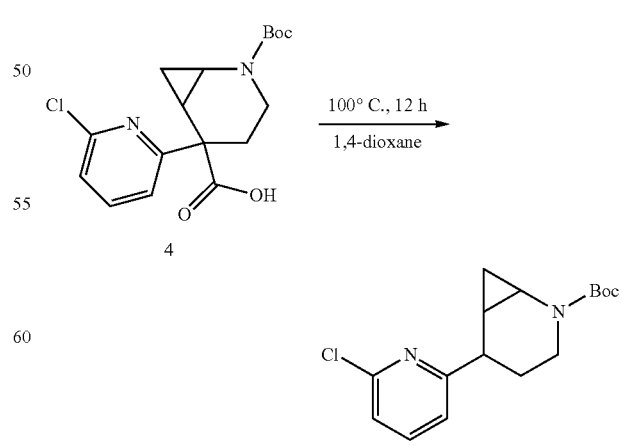

A mixture of 2-(tert-butoxycarbonyl)-5-(6-chloropyridin-2-yl)-2-azabicyclo[4.1.0]heptane-5-carboxylic acid (1.3 g, 3.68 mmol, 1 eq) in dioxane (13 mL) was degassed and purged with $N_2$ for 3 times, and then the mixture was stirred at 100° C. for 12 h under $N_2$ atmosphere. LCMS showed the starting material was consumed completely. The reaction mixture was concentrated to give crude product as a white solid (1.2 g, crude); LCMS: RT=2.127 min, MS cal.: 308.81, [M-55]$^+$=253.1.

Preparation of tert-butyl 5-(6-((4-Cyano-2-fluorobenzyl)oxy)pyridin-2-yl)-2-azabicyclo[4.1.0]heptane-2-carboxylate (6)

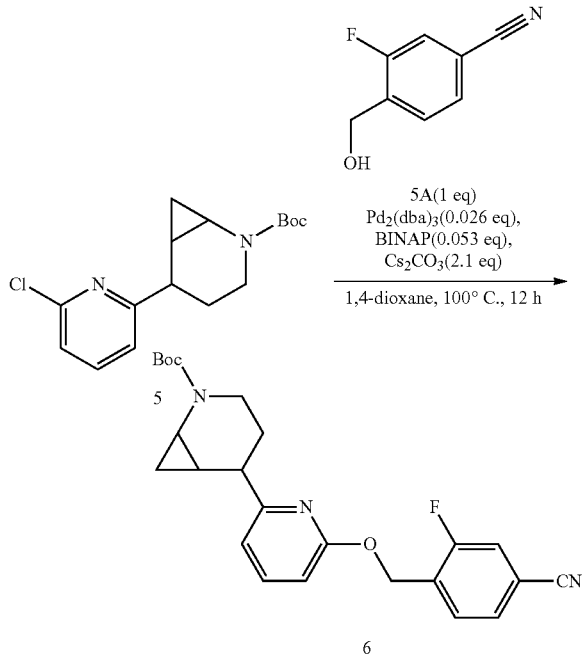

A mixture of tert-butyl 5-(6-chloropyridin-2-yl)-2-azabicyclo[4.1.0]heptane-2-carboxylate (0.8 g, 2.59 mmol, 1 eq), 3-fluoro-4-(hydroxymethyl)benzonitrile (392 mg, 2.59 mmol, 1 eq), $Cs_2CO_3$ (1.77 g, 5.44 mmol, 2.1 eq), $Pd_2(dba)_3$ (237 mg, 259 μmol, 0.1 eq) and BINAP (323 mg, 518 μmol, 0.2 eq) in dioxane (12 mL) was degassed and purged with $N_2$ for 3 times, and then the mixture was stirred at 100° C. for 12 h under $N_2$ atmosphere. LCMS showed the starting material was consumed completely. The combined reaction mixture was poured into water (50 mL) and extracted with ethyl acetate (50 mL*2). The combined organic phase was concentrated in vacuo to give a residue. The residue was purified by column chromatography ($SiO_2$, Petroleum ether/Ethyl acetate=100/1 to 0/1) to provide product as a white solid (0.8 g, 1.89 mmol, 72.9% yield); $^1$H NMR (400 MHz, DMSO-$d_6$) δ=7.94-7.83 (m, 1H), 7.75-7.63 (m, 3H), 7.09-6.99 (m, 1H), 6.82-6.72 (m, 1H), 5.53-5.43 (m, 2H), 3.87-3.66 (m, 1H), 3.27-3.15 (m, 1H), 2.93-2.81 (m, 1H), 2.66-2.57 (m, 1H), 1.84-1.74 (m, 1H), 1.46-1.41 (m, 10H), 0.91-0.79 (m, 1H), 0.72-0.60 (m, 1H), 0.44-0.31 (m, 1H).

Preparation of 4-(((6-(2-Azabicyclo[4.1.0]heptan-5-yl)pyridin-2-yl)oxy)methyl)-3-fluorobenzonitrile (7)

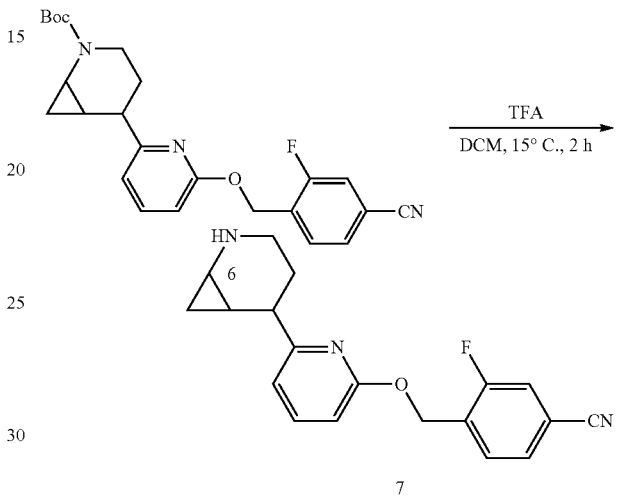

A mixture of tert-butyl 5-(6-((4-cyano-2-fluorobenzyl)oxy)pyridin-2-yl)-2-azabicyclo[4.1.0]heptane-2-carboxylate (0.7 g, 1.65 mmol, 1 eq) TFA (3.08 g, 27.0 mmol, 2 mL, 16.3 eq), in DCM (5 mL) was degassed and purged with $N_2$ for 3 times, and then the mixture was stirred at 25° C. for 1 h under $N_2$ atmosphere. LCMS showed the starting material was consumed completely. The reaction mixture was concentrated to provide crude product as a white solid (0.73 g, crude, TFA); LCMS: RT=0.899 min, MS cal.: 323.37, [M+H]$^+$=324.2.

Preparation of Methyl 2-((5-(6-((4-cyano-2-fluorobenzyl)oxy)pyridin-2-yl)-2-azabicyclo[4.1.0]heptan-2-yl)methyl)-1-(thiazol-5-ylmethyl)-1H-benzo[d]imidazole-6-carboxylate (8)

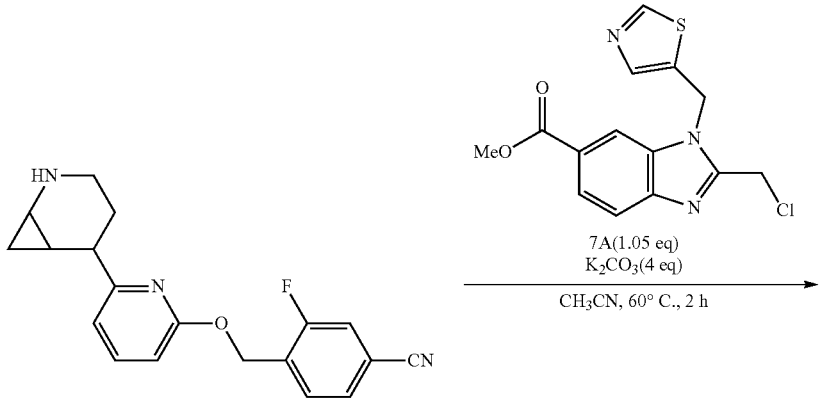

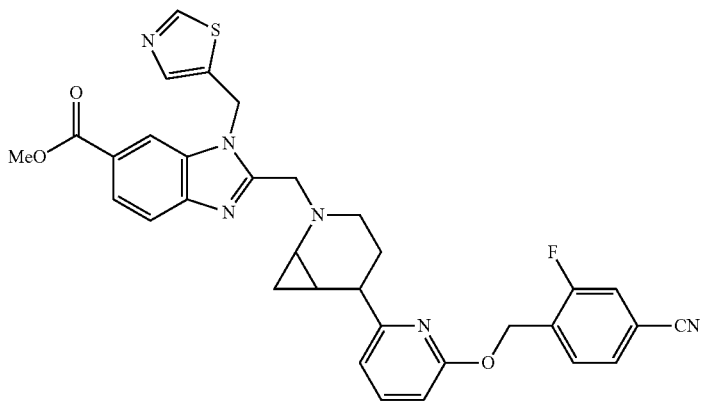

8

A mixture of 4-(((6-(2-azabicyclo[4.1.0]heptan-5-yl)pyridin-2-yl)oxy)methyl)-3-fluorobenzonitrile (483 mg, 1.50 mmol, 0.9 eq), methyl 2-(chloromethyl)-1-(thiazol-5-ylmethyl)-1H-benzo[d]imidazole-6-carboxylate (0.73 g, 1.67 mmol, 1 eq, TFA), $K_2CO_3$ (1.38 g, 10.0 mmol, 6 eq) in ACN (5 mL) was degassed and purged with $N_2$ for 3 times, and then the mixture was stirred at 60° C. for 2 h under $N_2$ atmosphere. LCMS showed the starting material was consumed completely. TLC (Petroleum ether/Ethyl acetate=0/1 $R_f$=0.45) indicated starting material was consumed completely. The combined reaction mixture was poured into water (50 mL) and extracted with ethyl acetate (50 mL*2). The combined organic phase was concentrated in vacuo to give a residue. The residue was purified by column chromatography ($SiO_2$, Petroleum ether/Ethyl acetate=100/1 to 0/1) to provide product as a white solid (0.6 g, 986 μmol, 59.1% yield); LCMS: RT=1.029 min, MS cal.: 608.89, $[M+H]^+$=609.3.

Preparation of 2-((5-(6-((4-Cyano-2-fluorobenzyl)oxy)pyridin-2-yl)-2-azabicyclo[4.1.0]heptan-2-yl)methyl)-1-(thiazol-5-ylmethyl)-1H-benzo[d]imidazole-6-carboxylic Acid (compound 16)

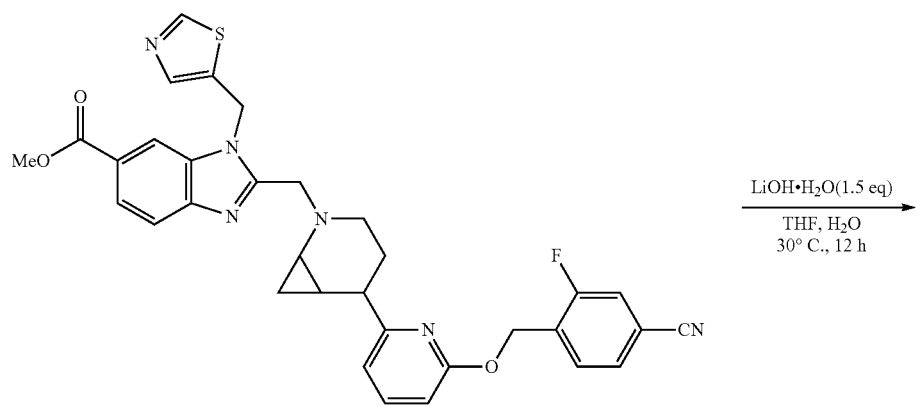

8

LiOH·H₂O (1.5 eq)
THF, H₂O
30° C., 12 h

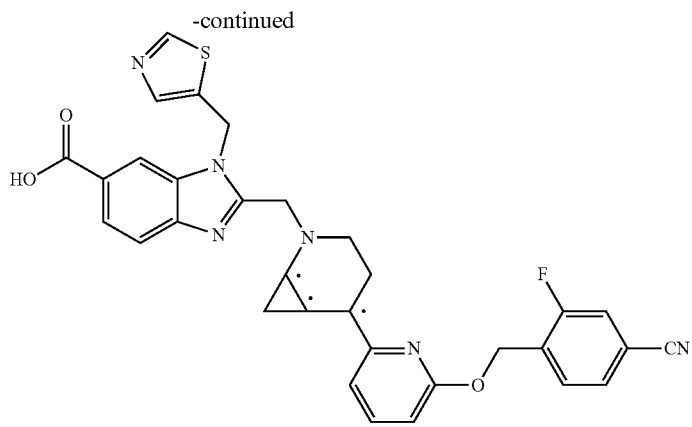

compound 16 (mixture 4 diastereomers)

A mixture of methyl 2-((5-(6-((4-cyano-2-fluorobenzyl)oxy)pyridin-2-yl)-2-azabicyclo[4.1.0]heptan-2-yl)methyl)-1-(thiazol-5-ylmethyl)-1H-benzo[d]imidazole-6-carboxylate (50 mg, 82.1 mol, 1 eq), LiOH·H$_2$O (5.17 mg, 123 μmol, 1.5 eq) in THF (0.7 mL) and H$_2$O (0.3 mL) was degassed and purged with N$_2$ for 3 times, and then the mixture was stirred at 30° C. for 12 h under N$_2$ atmosphere. LCMS showed the starting material was consumed completely. The reaction mixture was filtered and the filtrate was concentrated. The crude product was purified by reversed-phase HPLC (column: Phenomenex C18 75*30 mm*3 um; mobile phase: [water (NH$_4$HCO$_3$)-ACN]; B %: 25%-60%, 8 min) to provide product as a white solid (24.8 mg, 39.2 umol, 47.7% yield, 94% purity) was obtained as a white solid; LCMS: RT=1.654 min, MS cal.: 594.67, [M+H]$^+$=595.2; HPLC: RT=9.205 min, purity: 95.41%; $^1$H NMR (400 MHz, METHANOL-d$_4$) δ 8.92 (s, 1H), 8.23 (s, 1H), 8.04 (s, 1H), 8.01-7.94 (m, 1H), 7.72-7.49 (m, 5H), 7.00 (d, J=8.0 Hz, 1H), 6.72 (d, J=8.0 Hz, 1H), 6.03 (s, 2H), 5.57 (s, 2H), 4.23-4.08 (m, 2H), 3.28-3.20 (m, 1H), 2.74-2.60 (m, 2H), 2.55-2.45 (m, 1H), 1.75-1.62 (m, 2H), 1.49-1.38 (m, 1H), 0.67-0.60 (m, 1H), 0.44-0.32 (m, 1H).

Intermediates for Examples 4-6

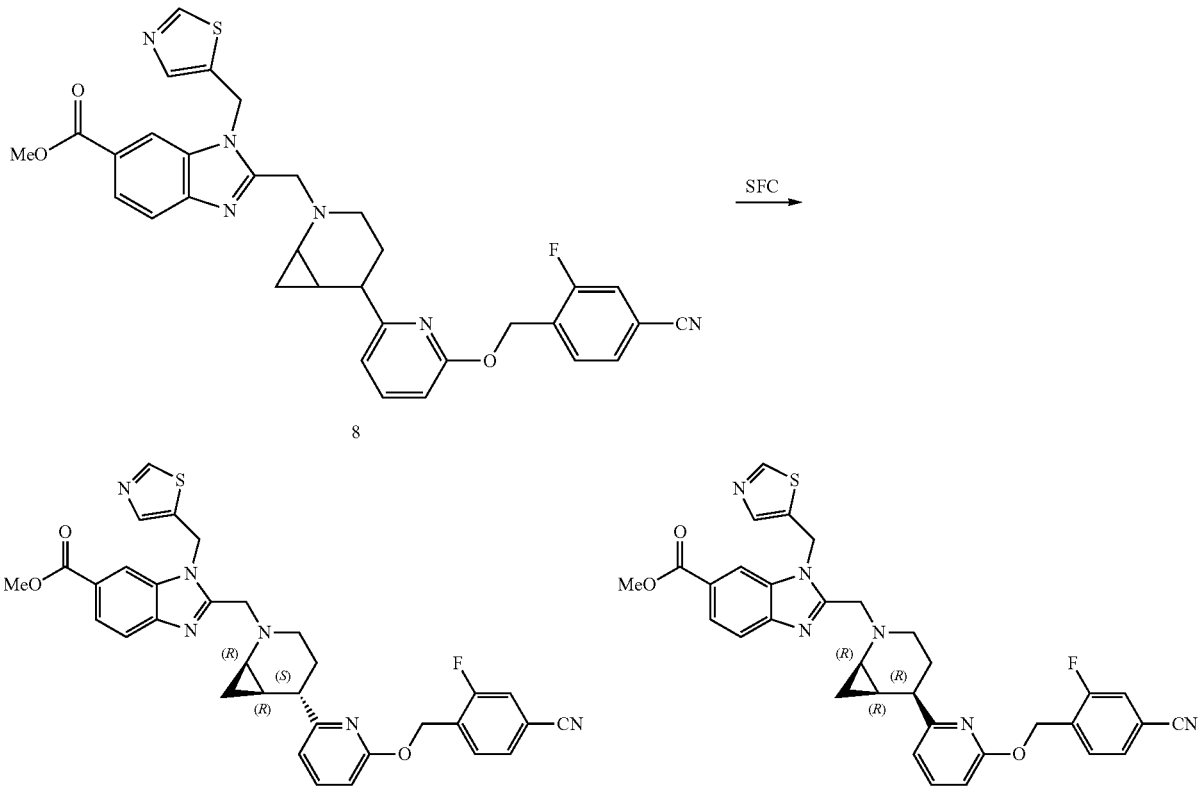

133

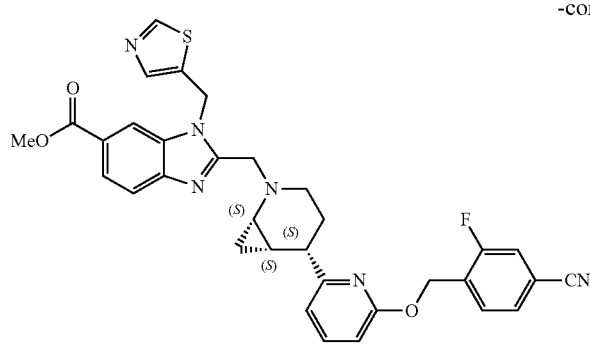

134

-continued

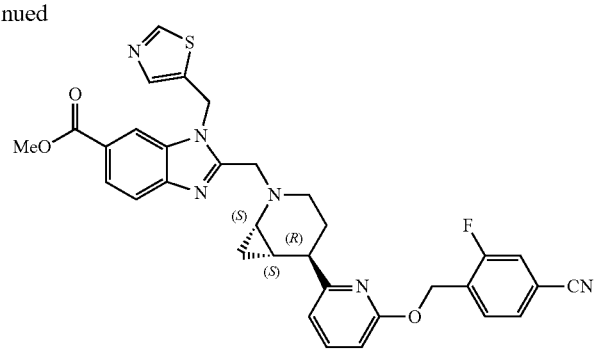

9A/9B/9C/9D

Methyl 2-((5-(6-((4-cyano-2-fluorobenzyl)oxy)pyridin-2-yl)-2-azabicyclo[4.1.0]heptan-2-yl)methyl)-1-(thiazol-5-ylmethyl)-1H-benzo[d]imidazole-6-carboxylate (0.58 g) was purified by SFC (column: DAICEL CHIRALPAK AD (250 mm*30 mm, 10 μm); mobile phase: [0.1% NH₃H₂O IPA]; B %: 40%-40%, 12 min) to provide intermediate 9A as a white solid (50 mg, 82.1 μmol, 8.62% yield), intermediate 9B as a white solid (50 mg, 82.1 μmol, 8.62% yield), intermediate 9C as a white solid (50 mg, 82.14 μmol, 8.62% yield) and intermediate 9D as a white solid (50 mg, 82.14 μmol, 8.62% yield).

Example 4 (Synthesis of Compound 4)

2-((5-(6-((4-Cyano-2-fluorobenzyl)oxy)pyridin-2-yl)-2-azabicyclo[4.1.0]heptan-2-yl)methyl)-1-(thiazol-5-ylmethyl)-1H-benzo[d]imidazole-6-carboxylic Acid, Diastereomer 1

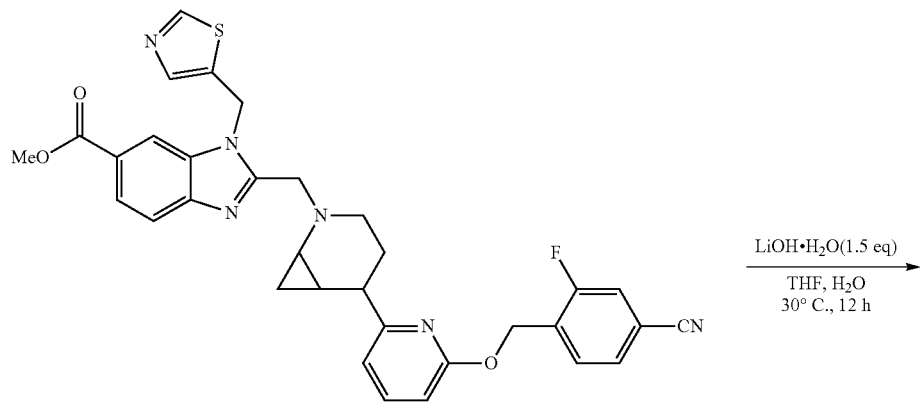

LiOH·H₂O(1.5 eq)
THF, H₂O
30° C., 12 h

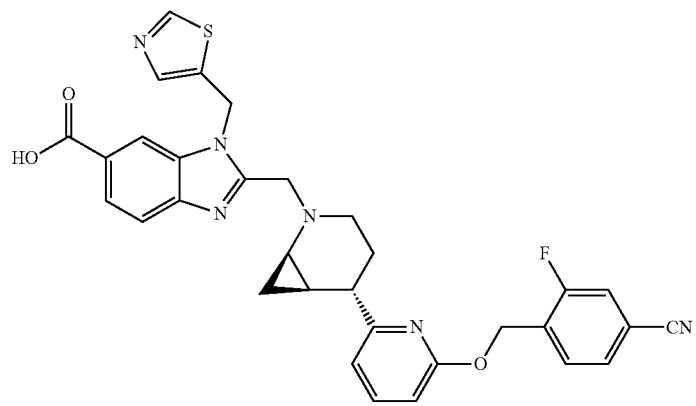

Compound 4

A mixture of methyl 2-((5-(6-((4-cyano-2-fluorobenzyl)oxy)pyridin-2-yl)-2-azabicyclo[4.1.0]heptan-2-yl)methyl)-1-(thiazol-5-ylmethyl)-1H-benzo[d]imidazole-6-carboxylate (Intermediate 9A, 50 mg, 82.1 μmol, 1 eq), LiOH·H$_2$O (5.17 mg, 123 umol, 1.5 eq) in THF (0.7 mL) H$_2$O (0.3 mL) was degassed and purged with N$_2$ for 3 times, and then the mixture was stirred at 30° C. for 12 h under N$_2$ atmosphere. LCMS showed starting material was consumed completely and one main peak with desired mass was detected. The reaction mixture was filtered and the filtrate was concentrated. The crude product was purified by reversed-phase HPLC (column: Waters Xbridge Prep OBD C18 150*40 mm*10 μm; mobile phase: [water (NH$_4$HCO$_3$)-ACN]; B %: 20%-50%, 8 min). The crude product was purified by reversed-phase HPLC (column: C18-1 150*30 mm*5 μm; mobile phase: [water (FA)-ACN]; B %: 15%-40%, 20 min) to provide product as a white solid (6.37 mg, 10.5 umol, 12.7% yield, 97.71% purity); LCMS: RT=2.274 min, MS cal.: 594.67, [M+H]$^+$=595.2; HPLC: RT=9.259 min, purity: 97.71%; SFC: RT=10.562 min, purity: 99.34%; $^1$H NMR (400 MHz, METHANOL-d$_4$) δ=8.93 (s, 1H), 8.25 (s, 1H), 8.05 (s, 1H), 7.98 (d, J=8.4 Hz, 1H), 7.71-7.67 (m, 2H), 7.62 (m, 1H), 7.56-7.50 (m, 2H), 6.91 (d, J=8.0 Hz, 1H), 6.69 (d, J=8.0 Hz, 1H), 6.02 (s, 2H), 5.58-5.47 (m, 2H), 4.22-4.15 (d, J=13.6 Hz, 1H), 4.09-4.03 (d, J=13.6 Hz, 1H), 2.84-2.79 (m, 1H), 2.71-2.66 (m, 1H), 2.42-2.33 (m, 2H), 1.78-1.66 (m, 2H), 1.30-1.24 (m, 1H), 0.56-0.49 (m, 2H).

Example 5 (Synthesis of Compound 5)

2-((5-(6-((4-Cyano-2-fluorobenzyl)oxy)pyridin-2-yl)-2-azabicyclo[4.1.0]heptan-2-yl)methyl)-1-(thiazol-5-ylmethyl)-1H-benzo[d]imidazole-6-carboxylic Acid, Diastereomer 2

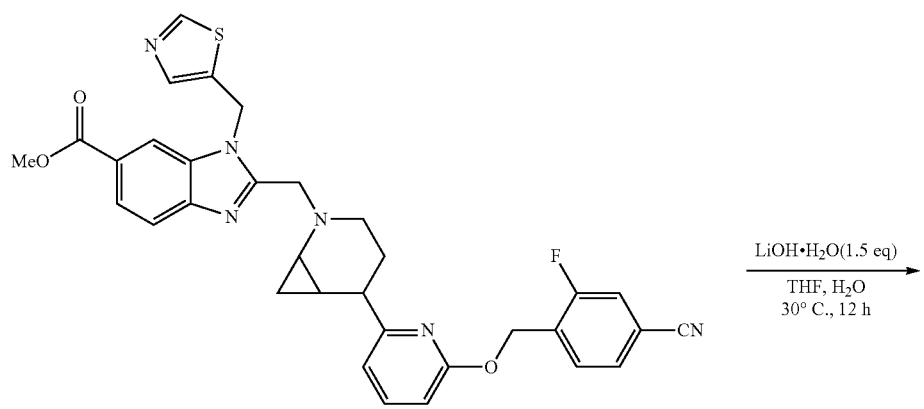

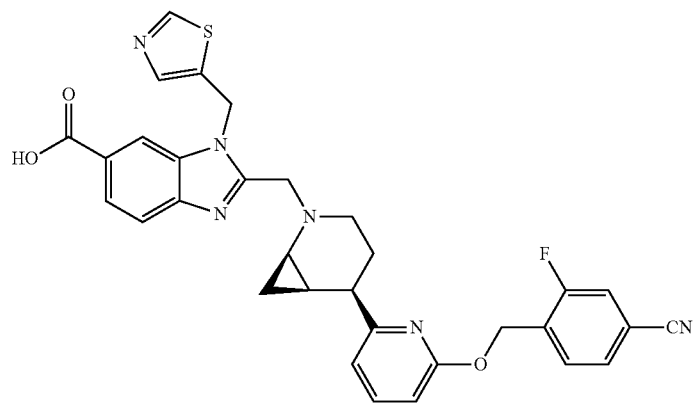

Compound 5

A mixture of methyl 2-((5-(6-((4-cyano-2-fluorobenzyl)oxy)pyridin-2-yl)-2-azabicyclo[4.1.0]heptan-2-yl)methyl)-1-(thiazol-5-ylmethyl)-1H-benzo[d]imidazole-6-carboxylate (Intermediate 9B, 100 mg, 164 μmol, 1 eq), LiOH·H$_2$O (10.34 mg, 246 μmol, 1.5 eq) in THF (0.7 mL) H$_2$O (0.3 mL) was degassed and purged with N$_2$ for 3 times, and then the mixture was stirred at 30° C. for 12 h under N$_2$ atmosphere. LCMS showed starting material was consumed completely and one main peak with desired mass was detected. The reaction mixture was filtered and the filtrate was concentrated. The crude product was purified by reversed-phase HPLC (column: Waters Xbridge Prep OBD C18 150*40 mm*10 μm; mobile phase: [water (NH$_4$HCO$_3$)-ACN]; B %: 20%-50%, 8 min) to provide product as a white solid (51.4 mg, 83.3 μmol, 50.7% yield, 96.4% purity); LCMS: RT=2.258 min, MS cal.: 594.67, [M+H]$^+$=595.2; HPLC: RT=9.326 min, purity: 96.40%; SFC: RT=9.504 min, purity: 98.74%; $^1$H NMR (400 MHz, DMSO-d6) δ=9.03 (s, 1H), 8.21 (s, 1H), 8.09 (s, 1H), 7.92 (d, J=10.1 Hz, 1H), 7.81 (d, J=8.4 Hz, 1H), 7.74-7.65 (m, 4H), 7.03 (d, J=8.0 Hz, 1H), 6.76 (d, J=8.0 Hz, 1H), 5.97 (s, 2H), 5.56-5.46 (m, 2H), 4.14-4.01 (m, 2H), 3.27-3.17 (m, 1H), 2.70-2.54 (m, 3H), 1.69-1.54 (m, 2H), 1.41-1.33 (m, 1H), 0.53 (m, 1H), 0.32-0.25 (m, 1H).

Example 6 (Synthesis of Compound 14)

2-((5-(6-((4-Cyano-2-fluorobenzyl)oxy)pyridin-2-yl)-2-azabicyclo[4.1.0]heptan-2-yl)methyl)-1-(thiazol-5-ylmethyl)-1H-benzo[d]imidazole-6-carboxylic Acid, Diastereomer 3

A mixture of methyl 2-((5-(6-((4-cyano-2-fluorobenzyl)oxy)pyridin-2-yl)-2-azabicyclo[4.1.0]heptan-2-yl)methyl)-1-(thiazol-5-ylmethyl)-1H-benzo[d]imidazole-6-carboxylate (Intermediate 9C, 100 mg, 164 μmol, 1 eq), LiOH·H$_2$O (10.3 mg, 246 μmol, 1.5 eq) in THF (0.7 mL) H$_2$O (0.3 mL) was degassed and purged with N$_2$ for 3 times, and then the mixture was stirred at 30° C. for 12 h under N$_2$ atmosphere. LCMS showed the starting material was consumed completely. The reaction mixture was filtered and the filtrate was concentrated. The crude product was purified by reversed-phase HPLC (column: Waters Xbridge Prep OBD C18 150*40 mm*10 μm; mobile phase: [water (NH$_4$HCO$_3$)-ACN]; B %: 30%-60%, 8 min) to provide product as a white solid (39.1 mg, 65.8 umol, 40.0% yield); LCMS: RT=1.646 min, MS cal.: 594.67, [M+H]$^+$=595.3; HPLC: RT=9.197 min, purity: 96.20%; SFC: RT=17.233 min, purity: 98.01%; $^1$H NMR (400 MHz, DMSO-d$_6$) δ=9.02 (s, 1H), 8.27-8.15 (m, 1H), 8.08 (m, 1H), 7.93-7.87 (m, 1H), 7.85-7.75 (m, 1H), 7.69 (m, 4H), 7.02 (d, J=8.0 Hz, 1H), 6.76-6.72 (d, J=8.0 Hz, 1H), 6.00-5.88 (s, 2H), 5.55-5.44 (m, 2H), 4.18-3.95 (s, 2H), 3.22 (m, 2H), 2.59-2.54 (m, 2H), 2.49-2.40 (m, 1H), 1.60 (m, 2H), 1.35 (m, 1H), 0.62-0.47 (m, 1H), 0.35-0.23 (m, 1H).

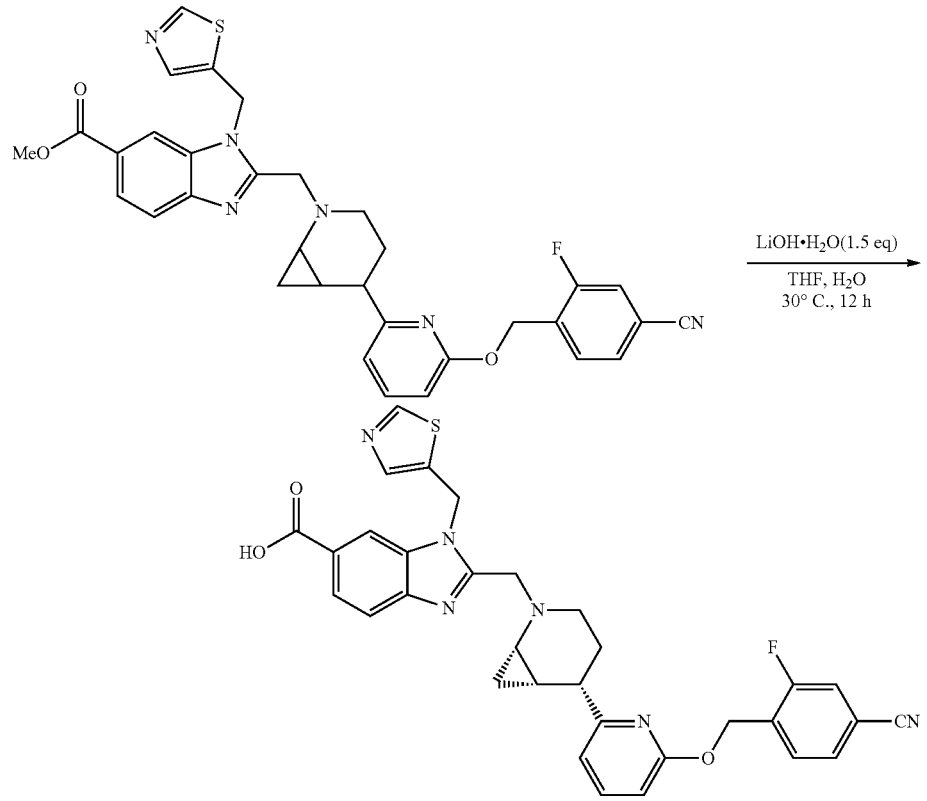

Compound 14

Example 7 (Synthesis of Compound 15)

2-((5-(6-((4-Cyano-2-fluorobenzyl)oxy)pyridin-2-yl)-2-azabicyclo[4.1.0]heptan-2-yl)methyl)-1-(thiazol-5-ylmethyl)-1H-benzo[d]imidazole-6-carboxylic Acid, Diastereomer 4

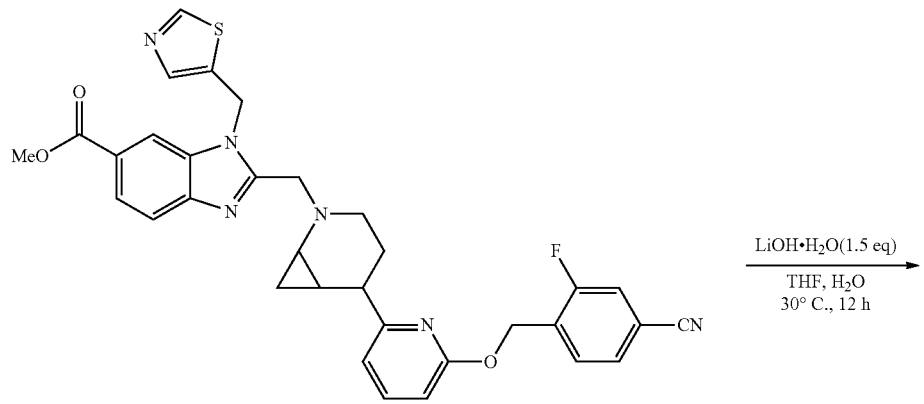

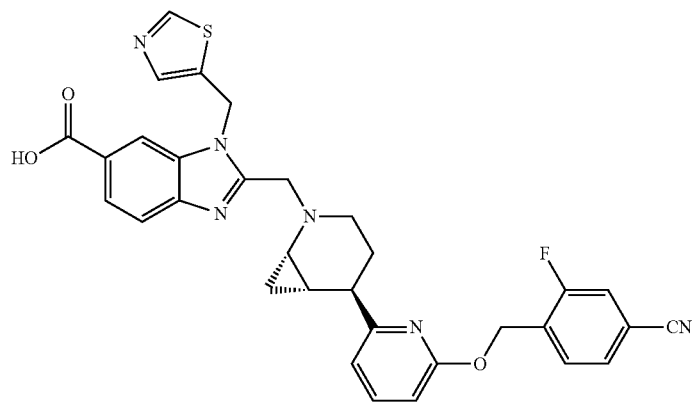

Compound 15

A mixture of methyl 2-((5-(6-((4-cyano-2-fluorobenzyl)oxy)pyridin-2-yl)-2-azabicyclo[4.1.0]heptan-2-yl)methyl)-1-(thiazol-5-ylmethyl)-1H-benzo[d]imidazole-6-carboxylate (Intermediate 9D, 30 mg, 49.3 μmol, 1 eq), LiOH·H$_2$O (3.10 mg, 73.9 μmol, 1.5 eq) in THF (0.7 mL) H$_2$O (0.3 mL) was degassed and purged with N$_2$ for 3 times, and then the mixture was stirred at 30° C. for 12 h under N$_2$ atmosphere. LCMS showed the starting material was consumed completely. The mixture was used directly, no work-up. The crude product was purified by reversed-phase HPLC (column: Waters Xbridge Prep OBD C18 150*40 mm*10 μm; mobile phase: [water (NH$_4$HCO$_3$)-ACN]; B %: 20%-50%, 8 min) to provide product as a white solid (12.7 mg, 21.4 μmol, 43.3% yield); LCMS: RT=1.628 min, MS cal.: 594.67, [M+H]$^+$=595.2; HPLC: RT=9.290 min, purity: 97.42%; SFC: RT=8.630 min, purity: 99.60%; $^1$H NMR (400 MHz, DMSO-d$_6$) δ=8.98 (s, 1H), 8.19 (s, 1H), 8.08 (s, 1H), 7.89-7.84 (m, 1H), 7.83-7.79 (m, 1H), 7.75-7.63 (m, 4H), 6.96-6.92 (d, J=8.0 Hz, 1H), 6.76-6.71 (d, J=8.0 Hz, 1H), 5.97 (s, 2H), 5.52-5.43 (m, 2H), 4.16-4.08 (d, J=13.6 Hz, 1H), 3.98 (d, J=13.6 Hz, 1H), 2.81-2.74 (m, 1H), 2.66-2.57 (m, 1H), 2.44-2.36 (m, 1H), 2.31-2.21 (m, 1H), 1.67-1.58 (m, 2H), 1.22-1.13 (m, 1H), 0.55-0.46 (m, 1H), 0.44-0.35 (m, 1H).

Example 8 (Synthesis of Compound 21)
2-((5-(6-((4-Cyano-2-fluorobenzyl)oxy)pyridin-2-yl)-2-azabicyclo[4.1.0]heptan-2-yl)methyl)-1-((R)-2-methoxypropyl)-1H-benzo[d]imidazole-6-carboxylic Acid, Mixture 4 Diastereomers
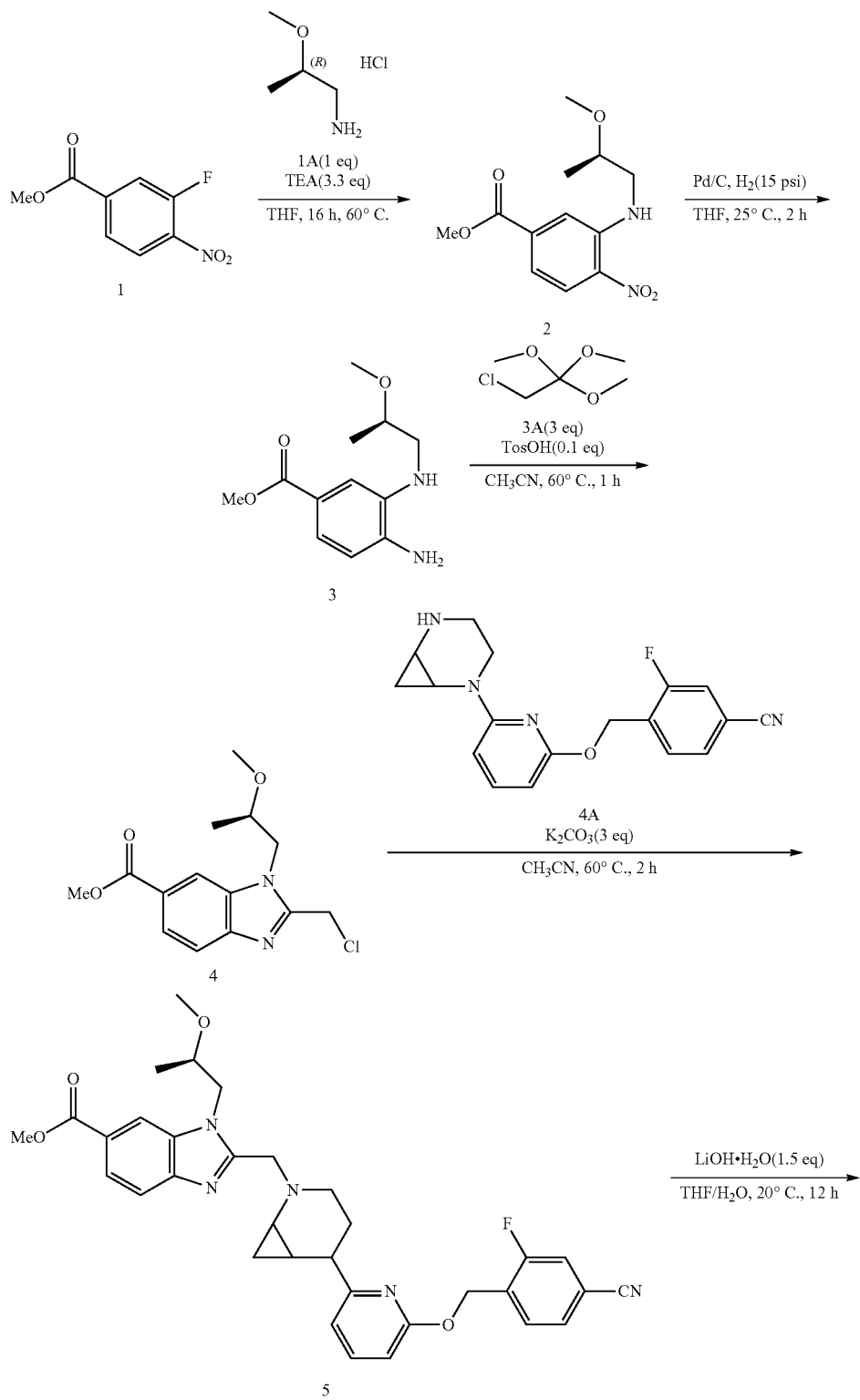

-continued

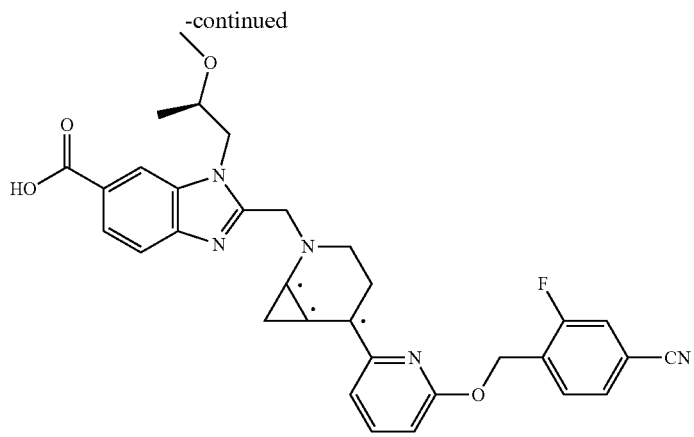

Compound 21 (mixture 4 diastereomers)

Preparation of Methyl (R)-3-((2-methoxypropyl)amino)-4-nitrobenzoate (2)

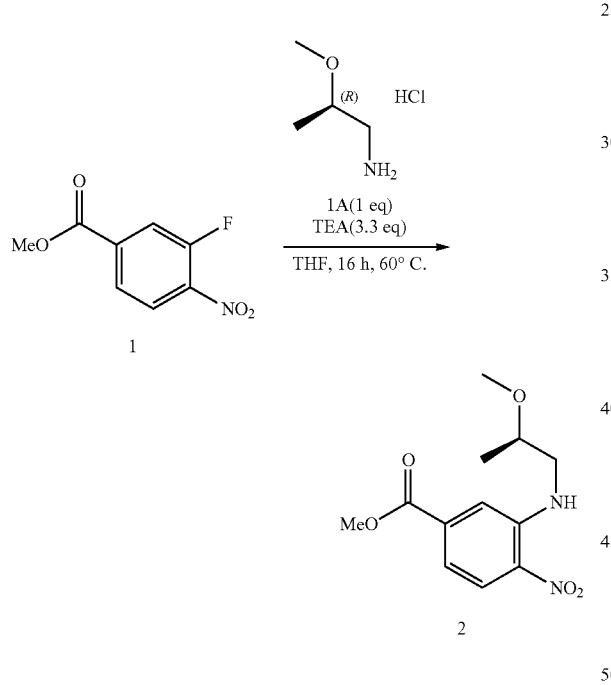

A mixture of methyl 3-fluoro-4-nitrobenzoate (2 g, 10.0 mmol, 1 eq), (R)-2-methoxypropan-1-amine (1.26 g, 10.0 mmol, 1 eq), TEA (3.35 g, 33.1 mmol, 4.61 mL, 3.3 eq) in THF (20 mL) was degassed and purged with $N_2$ for 3 times at 20° C., and then the mixture was stirred at 60° C. for 16 h under $N_2$ atmosphere. LC-MS showed starting material was consumed completely and one main peak with desired mass was detected. The residue was diluted with $H_2O$ 100 mL and extracted with EtOAc 150 mL (50 mL*3). The combined organic layers were washed with $H_2O$ 15 mL (5 mL*3), dried over $Na_2SO_4$, filtered and concentrated under reduced pressure to give a residue. The residue was purified by column chromatography ($SiO_2$, Petroleum ether/Ethyl acetate=100/1 to 10/1) to provide product as a yellow solid (2.6 g, 9.69 mmol, 96.50% yield); LCMS: RT=0.746 min, MS cal.: 268.2, [M+H]$^+$=269.0.

Preparation of methyl (R)-4-Amino-3-((2-methoxypropyl)amino)benzoate (3)

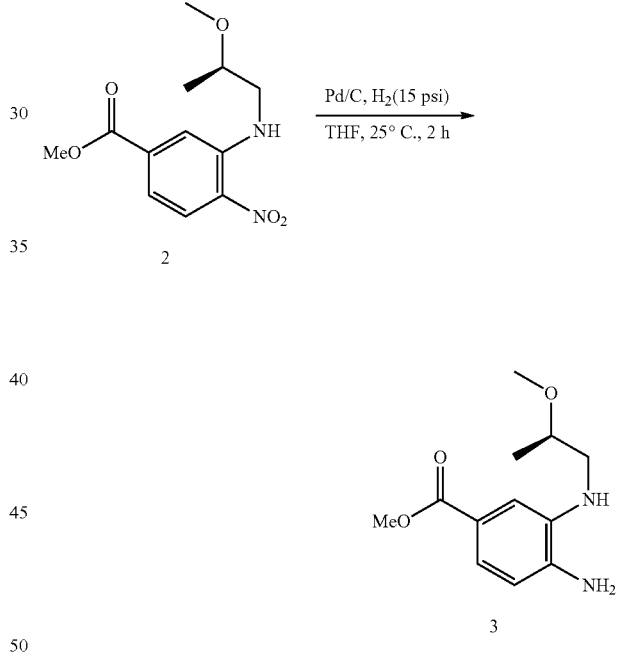

To a solution of methyl (R)-3-((2-methoxypropyl)amino)-4-nitrobenzoate (2.5 g, 9.32 mmol, 1 eq) in THF (30 mL) was added Pd/C (1 g, 10% purity) at 25° C. under $N_2$ atmosphere. The suspension was degassed and purged with $H_2$ for 3 times. The mixture was stirred under $H_2$ (15 psi) at 25° C. for 2 h. LC-MS showed starting material was consumed completely and one main peak with desired mass was detected. The reaction was filtered, the filter cake washed with ethyl acetate and concentrated under reduced pressure to provide product as a white solid (2.2 g, 9.23 mmol, 99.1% yield); LCMS: RT=0.494 min, MS cal.: 238.2, [M+H]$^+$=239.0; $^1$H NMR (400 MHz, CHLOROFORM-d) δ=7.46 (d, J=8.0 Hz, 1H), 7.35 (s, 1H), 6.69 (d, J=8.0 Hz, 1H), 3.91-3.85 (s, 3H), 3.80 (br s, 2H), 3.71-3.63 (m, 1H), 3.40 (s, 3H), 3.25 (m, 1H), 3.08 (m, 1H), 1.27 (d, J=6.0 Hz, 3H).

Preparation of Methyl (R)-2-(chloromethyl)-1-(2-methoxypropyl)-1H-benzo[d]imidazole-6-carboxylate (4)

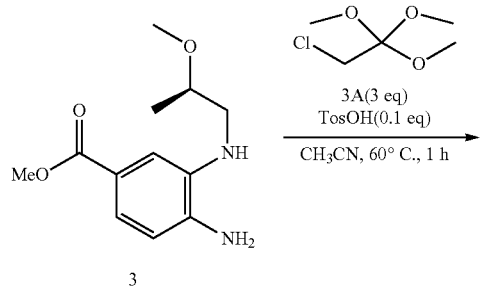

TosOH (72.3 mg, 420 umol, 0.1 eq) in CH₃CN (10 mL) was degassed and purged with N₂ for 3 times at 20° C., and then the mixture was stirred at 60° C. for 1 h under N₂ atmosphere. LC-MS showed starting material was consumed completely and one main peak desired mass was detected. The reaction mixture was concentrated under reduced pressure to remove solvent. The residue was purified by column chromatography (SiO₂, Petroleum ether/Ethyl acetate=100/1 to 10/1) to provide product as a white solid (1 g, 3.37 mmol, 80.3% yield); LCMS: RT=1.651 min, MS cal.: 296.7, [M+H]⁺=297.0.

Preparation of Methyl 2-((5-(6-((4-cyano-2-fluorobenzyl)oxy)pyridin-2-yl)-2-azabicyclo[4.1.0]heptan-2-yl)methyl)-1-((R)-2-methoxypropyl)-1H-benzo[d]imidazole-6-carboxylate (5)

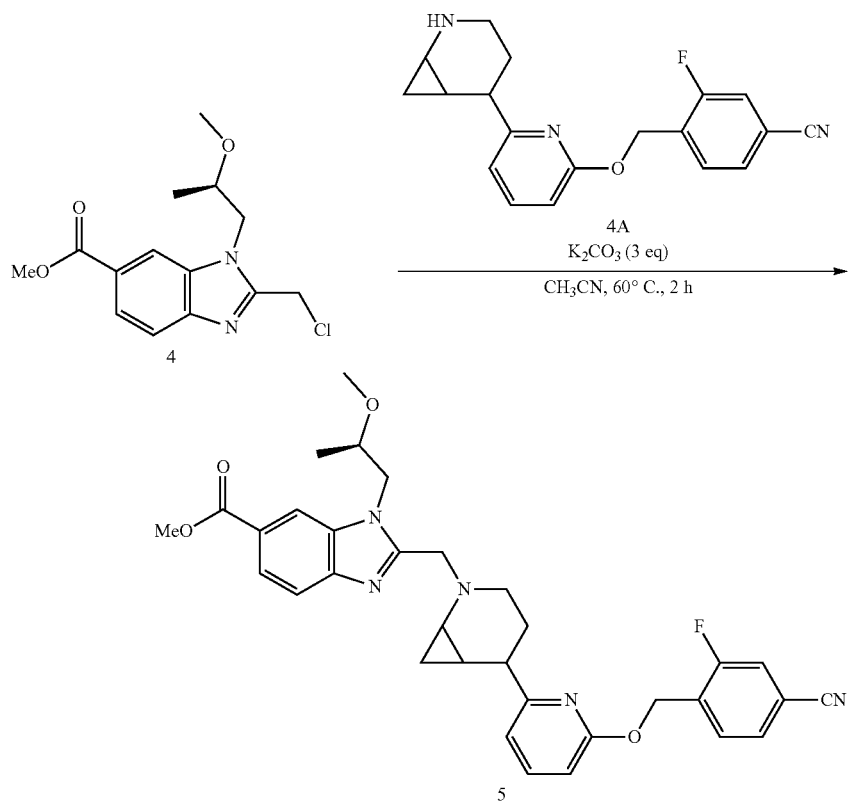

-continued

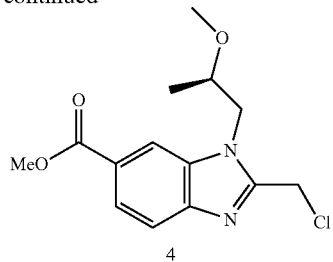

A mixture of methyl (R)-4-amino-3-((2-methoxypropyl)amino)benzoate (1 g, 4.20 mmol, 1 eq), 2-chloro-1,1,1-trimethoxyethane (1.95 g, 12.6 mmol, 1.69 mL, 3 eq), A mixture of methyl (R)-2-(chloromethyl)-1-(2-methoxypropyl)-1H-benzo[d]imidazole-6-carboxylate (91.8 mg, 309 μmol, 1 eq), 4-(((6-(2-azabicyclo[4.1.0]heptan-5-yl)pyridin-2-yl)oxy)methyl)-3-fluorobenzonitrile (100 mg, 309 μmol, 1 eq), K₂CO₃ (128 mg, 928 μmol, 3 eq) in CH₃CN (1 mL) was degassed and purged with N₂ for 3 times at 20° C., and then the mixture was stirred at 60° C. for 2 h under N₂ atmosphere. LC-MS showed starting material was consumed completely and one main peak with desired mass was detected. The residue was diluted with H₂O 1 mL, washed with EA (3 mL*3), dried over Na₂SO₄, filtered and concentrated under reduced pressure to give a residue. The residue was purified by column chromatography (SiO₂, Petroleum ether/Ethyl acetate=100/1 to 10/1) to provide product as a white solid (100 mg, 171 μmol, 55.4% yield); LCMS: RT=2.420 min, MS cal.: 583.6, [M+H]⁺=584.2.

Preparation of 2-((5-(6-((4-Cyano-2-fluorobenzyl)oxy)pyridin-2-yl)-2-azabicyclo[4.1.0]heptan-2-yl)methyl)-1-((R)-2-methoxypropyl)-1H-benzo[d]imidazole-6-carboxylic Acid, Mixture of 4 Diastereomers (Compound 21)

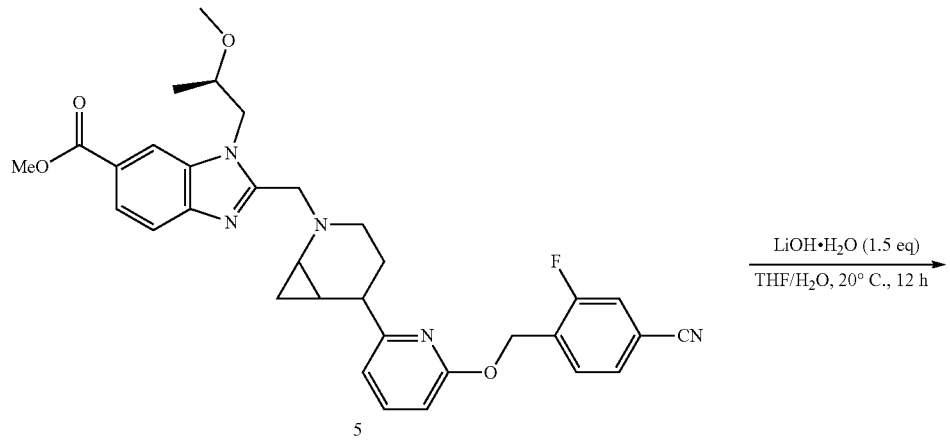

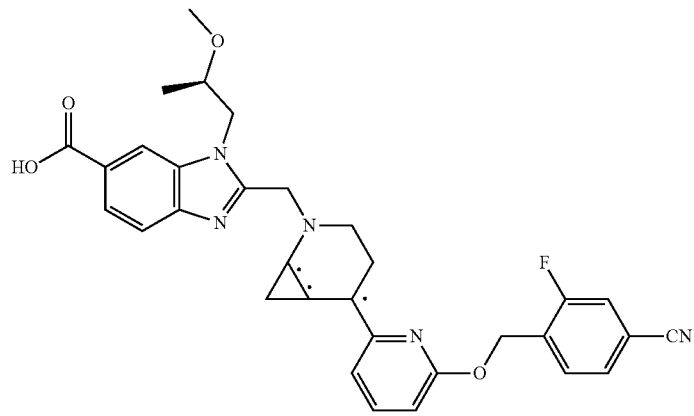

Compound 21 (mixture 4 diastereomers)

A mixture of methyl 2-((5-(6-((4-cyano-2-fluorobenzyl)oxy)pyridin-2-yl)-2-azabicyclo[4.1.0]heptan-2-yl)methyl)-1-((R)-2-methoxypropyl)-1H-benzo[d]imidazole-6-carboxylate (120 mg, 206 μmol, 1 eq), LiOH·H$_2$O (12.9 mg, 308 μmol, 1.5 eq) in THF (1.4 mL)/H$_2$O (0.6 mL) was degassed and purged with N$_2$ for 3 times at 20° C., and then the mixture was stirred at 20° C. for 12 h under N$_2$ atmosphere. LC-MS showed starting material was consumed completely and one main peak with desired mass was detected. The reaction mixture was filtered and the filtrate was concentrated. The crude product was purified by reversed-phase HPLC (column: Waters Xbridge BEH C18 100*25 mm*5 μm; mobile phase: [water (NH$_4$HCO$_3$)-ACN]; B %: 30%-65%, 8 min) to provide product as a white solid (36.8 mg, 61.3 μmol, 29.8% yield, 94.88% purity); LCMS: RT=2.660 min, MS cal.: 569.6, [M+H]$^+$=570.3; $^1$H NMR (400 MHz, CHLOROFORM-d) δ=8.24 (s, 1H) 8.06 (d, J=8.4 Hz, 1H) 7.82 (d, J=8.4 Hz, 1H) 7.67-7.52 (m, 2H) 7.48-7.34 (m, 2H) 6.99-6.85 (d, J=8.4 Hz, 1H) 6.68 (d, J=8.4 Hz, 1H) 5.51 (s, 2H) 4.61 (m, 1H) 4.45-4.05 (m, 3H) 3.89-3.75 (m, 1H) 3.32-3.14 (m, 4H) 2.74-2.60 (m, 2H) 2.43-2.57 (m, 1H) 1.84-1.57 (m, 2H) 1.47-1.38 (m, 1H) 1.34-1.26 (m, 3H) 0.66-0.57 (m, 1H) 0.53-0.39 (m, 1H).

Example 9 (Synthesis of Compound 46)
2-((2-(6-((4-Cyano-2-fluorobenzyl)oxy)pyridin-2-yl)-2-azabicyclo[4.1.0]heptan-5-yl)methyl)-1-(thiazol-5-ylmethyl)-1H-benzo[d]imidazole-6-carboxylic Acid, Mixture of 4 Diastereomers
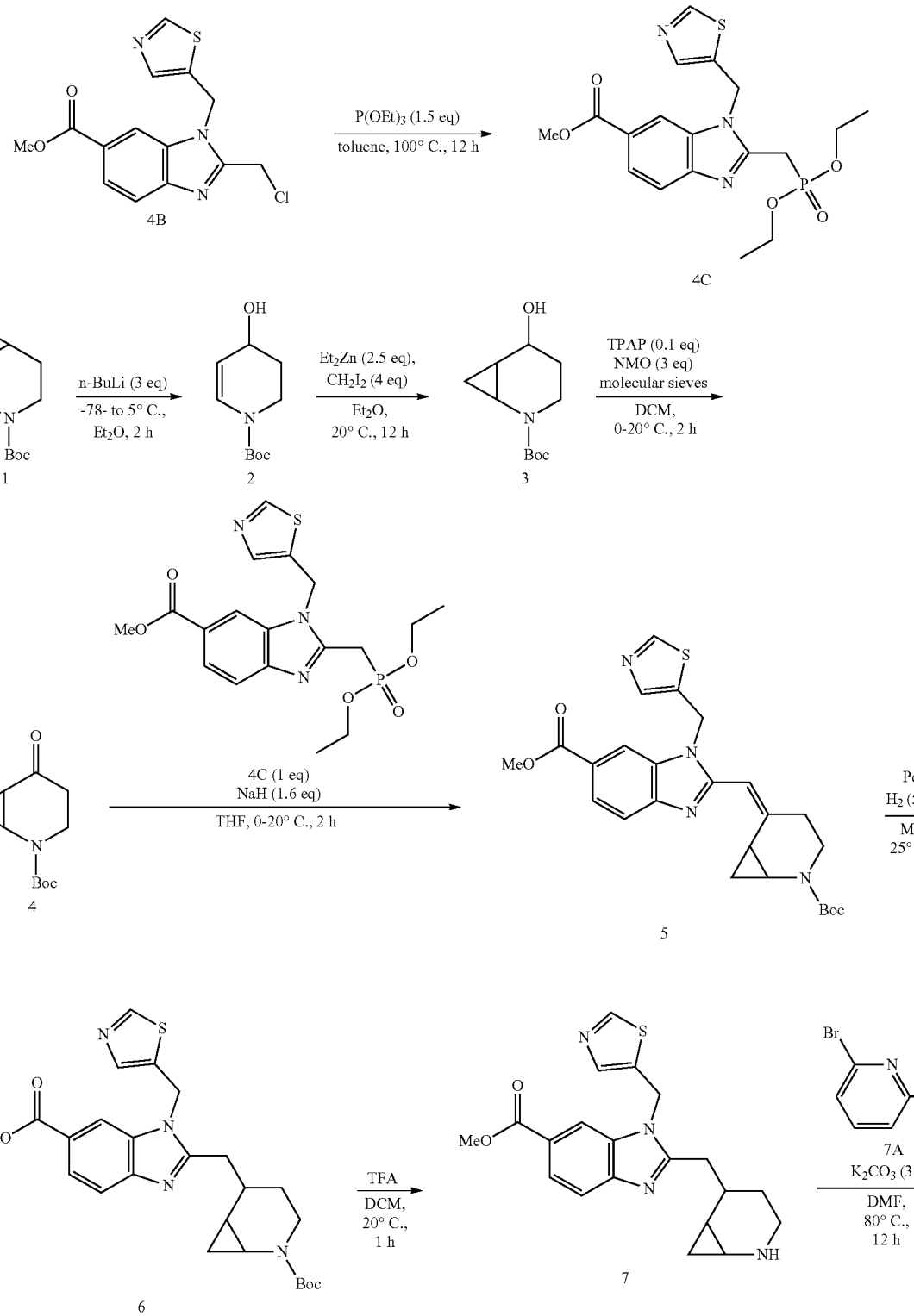

-continued
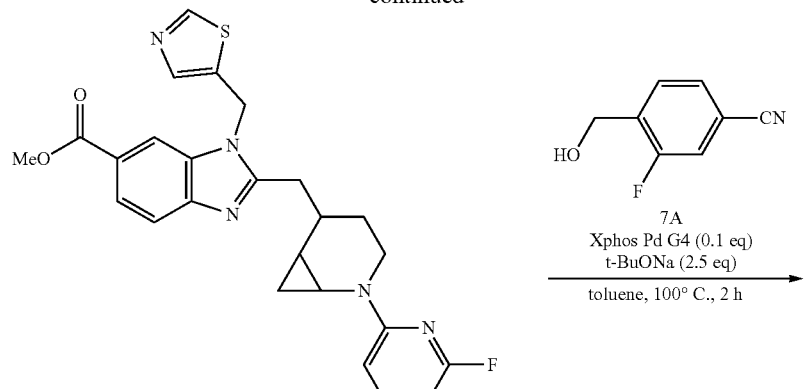
8
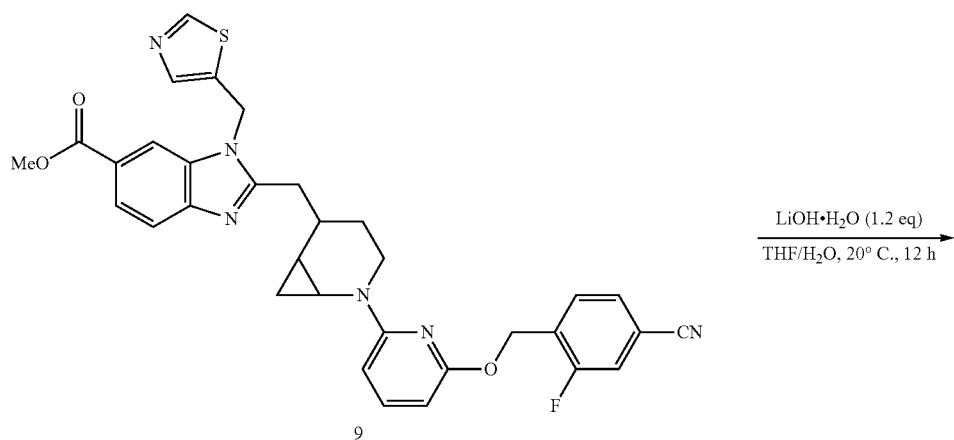
9
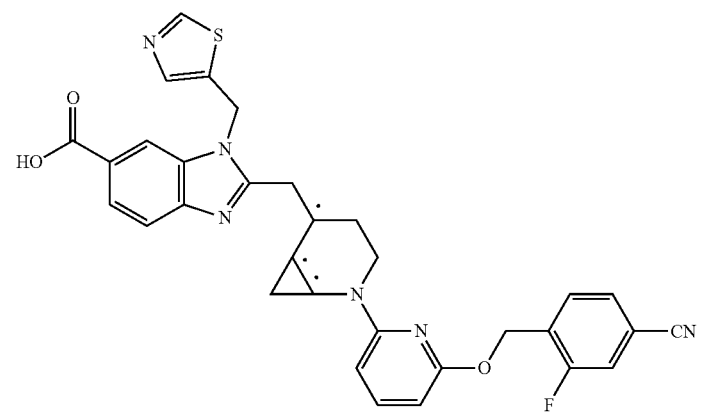
Compound 46 (mixture 4 diastereomers)

Preparation of Methyl 2-((diethoxyphosphoryl)methyl)-1-(thiazol-5-ylmethyl)-1H-benzo[d]imidazole-6-carboxylate (4c)

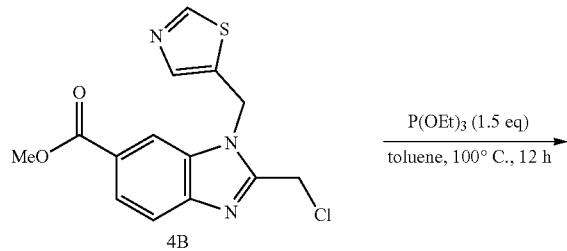

To a mixture of methyl 2-(chloromethyl)-1-(thiazol-5-ylmethyl)-1H-benzo[d]imidazole-6-carboxylate (5 g, 15.5 mmol, 1 eq) in toluene (50 mL) was added triethyl phosphite (3.87 g, 23.3 mmol, 4.00 mL, 1.5 eq) in one portion at 20° C. The mixture was stirred at 100° C. for 12 h. LC-MS showed ~58% of starting material remained. Several new peaks were shown on LC-MS and ~31% of desired compound was detected. The reaction mixture was concentrated under reduced pressure. The residue was purified by column chromatography (SiO$_2$, Petroleum ether/Ethyl acetate=10/1 to 0/1) to provide product as a yellow oil (1.9 g, 4.49 mmol, 28.9% yield); LCMS: RT=0.564 min, MS cal.: 423.10, [M+H]$^+$=424.1; LCMS: RT=1.395 min, MS cal.: 423.10, [M+H]$^+$=424.1; 1H NMR (400 MHz, CHLOROFORM-d) δ=8.75 (s, 1H), 8.12 (s, 1H), 8.03-7.97 (m, 1H), 7.81-7.70 (m, 2H), 5.89 (s, 2H), 4.13 (q, J=7.2 Hz, 4H), 3.94 (s, 3H), 3.59-3.51 (d, J=21.6 Hz, 2H), 1.30 (t, J=7.2 Hz, 6H)

Preparation of tert-Butyl 4-hydroxy-3,4-dihydropyridine-1(2H)-carboxylate (2)

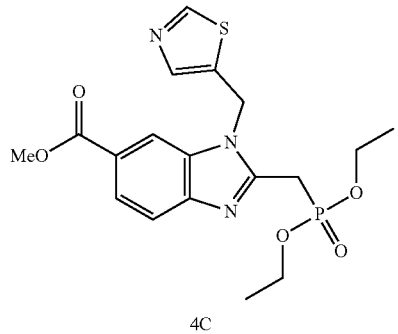

Et$_2$O (1000 mL) was charged to the 2 L three-necked round bottom flask, then tert-butyl 7-oxa-3-azabicyclo[4.1.0]heptane-3-carboxylate (25 g, 125 mmol, 1 eq) was added at 20° C. At −78° C., n-BuLi (2.5 M, 151 mL, 3 eq) was added dropwise to the reaction mixture at −78° C. within 1 h. After the addition, the mixture was stirred at −78° C. for 1 h. The resulting mixture was stirred at 25° C. for 1 h. TLC indicated starting material was consumed completely and many new spots formed. The reaction was messy according to TLC. The reaction mixture was quenched with sat. aq. NaHCO$_3$ (350 mL) at 0° C. within 30 min. The mixture was extracted by EtOAc (200 mL*3). Then organic phase was washed by aq. NaCl (300 mL). The organics were dried over Na$_2$SO$_4$, filtered and concentrated under reduced pressure at 30° C. to give a residue. The residue was purified by column chromatography (SiO$_2$, Petroleum ether/Ethyl acetate=15/1 to 6/1) to provide product as a yellow oil (17 g, 85.3 mmol, 34% yield); LCMS: Rt=1.368 min, MS cal.: 199.12, [M-tBu-OH]$^+$=126.1; 1H NMR (400 MHz, CHLOROFORM-d) δ=7.06-6.77 (m, 1H), 5.12-4.89 (m, 1H), 4.19 (m, 1H), 3.85 (m, 1H), 3.33 (m, 1H), 1.89-1.80 (m, 2H), 1.48 (s, 9H).

Preparation of tert-Butyl 5-hydroxy-2-azabicyclo[4.1.0]heptane-2-carboxylate (3)

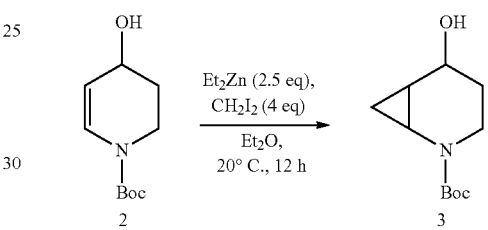

Et$_2$O (80 mL) was charged to the 500 mL three-necked round bottom flask, then material tert-butyl 4-hydroxy-3,4-dihydropyridine-1(2H)-carboxylate (8 g, 40.2 mmol, 1 eq) was added at 20° C. At 0° C., ZnEt$_2$ (1 M, 100 mL, 2.5 eq) was added dropwise to the reaction mixture at 0° C. within 1 h. CH$_2$I$_2$ (43 g, 161 mmol, 13 mL, 4 eq) was added dropwise to the reaction mixture at 0° C. within 0.5 h. After the addition, the mixture was stirred at 20° C. for 12 h. TLC indicated starting material was consumed completely and many new spots formed. The reaction mixture was added to H$_2$O (100 ml) at 0° C. within 0.5 h. The mixture was extracted by EtOAc (50 mL*3). Then organic phase was washed by NaCl (50 mL*1). The organics were dried (Na$_2$SO$_4$), filtered and concentrated. The residue was purified by column chromatography (SiO$_2$, Petroleum ether/Ethyl acetate=10/1 to 3/1)) to provide product as a yellow oil (3.5 g, 16.4 mmol, 20.4% yield); LCMS: RT=1.307 min, MS cal.: 213.14, [M-tBu+H]$^+$=158.1.

Preparation of tert-Butyl 5-oxo-2-azabicyclo[4.1.0]heptane-2-carboxylate (4)

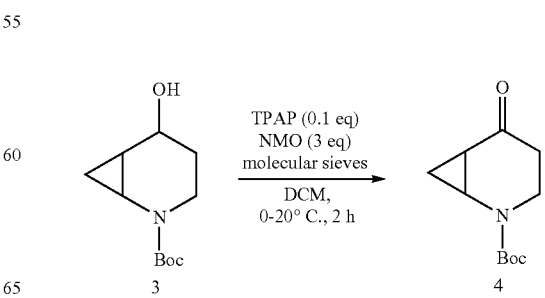

NMO (2.47 g, 21.1 mmol, 2.23 mL, 3 eq) was added at 0° C. to a solution of tert-butyl 5-hydroxy-2-azabicyclo[4.1.0]heptane-2-carboxylate (1.5 g, 7.03 mmol, 1 eq), molecular sieves 3A (2.5 g) and TPAP (247 mg, 703 μmol, 0.1 eq) in DCM (25 mL). The reaction mixture was allowed to warm to 20° C. and stirred for 2 h. TLC indicated starting material was consumed completely and one new spot formed. The reaction was clean according to TLC. The reaction mixture was diluted with DCM (5 mL) and filtered through silica gel. The organic layer was washed with sat. $Na_2S_2O_3$ (5 mL), water (2 mL), brine (2 mL), dried over $Na_2SO_4$ and concentrated in vacuum. The residue was purified by column chromatography ($SiO_2$, Petroleum ether/Ethyl acetate=15/1 to 8/1) to provide product as a yellow solid (1.05 g, 4.97 mmol, 70.7% yield); $^1$H NMR (400 MHz, CHLOROFORM-d) δ=4.21-3.89 (m, 1H), 3.58-3.21 (m, 2H), 2.46-2.21 (m, 2H), 1.87 (m, 1H), 1.49 (m, 10H), 1.23-1.06 (m, 1H).

Preparation of Methyl (Z)-2-((2-(tert-butoxycarbonyl)-2-azabicyclo[4.1.0]heptan-5-ylidene)methyl)-1-(thiazol-5-ylmethyl)-1H-benzo[d]imidazole-6-carboxylate (5)

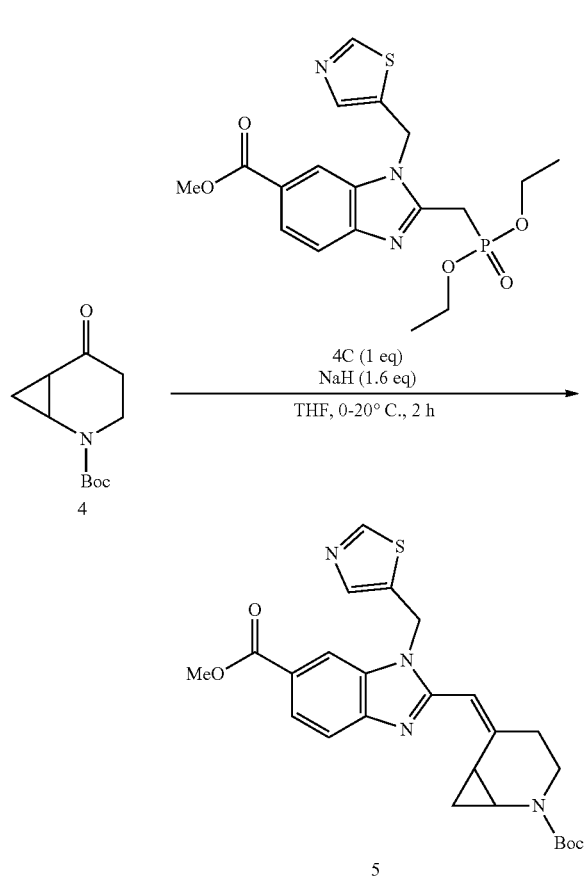

THF (10 mL) was charged to a 25 mL three-necked round bottom flask followed by methyl 2-((diethoxyphosphoryl)methyl)-1-(thiazol-5-ylmethyl)-1H-benzo[d]imidazole-6-carboxylate (1.82 g, 4.30 mmol, 1 eq). At 0° C., NaH (275 mg, 6.89 mmol, 60% purity, 1.6 eq) was added portionwise to the reaction mixture. After 30 min, tert-butyl 5-oxo-2-azabicyclo[4.1.0]heptane-2-carboxylate (1 g, 4.73 mmol, 1.1 eq) was added to the reaction mixture at 0° C. The mixture was stirred at 20° C. for 2 h. TLC showed starting material was consumed completely. The reaction mixture was added to $NaHCO_3$ at 0° C. The mixture was extracted by EtOAc (10 mL*2). Then organic phase was washed with brine 10 mL. The organics were dried $Na_2SO_4$, filtered and concentrated under reduced pressure at 30° C. to give a residue. The residue was purified by column chromatography ($SiO_2$, DCM: MeOH=100/1 to 50/1) to provide product as an oil (1.3 g, 2.71 mmol, 62.9% yield); LCMS: RT=0.633 min, MS cal.: 480.10, [M+H]$^+$=481.1; 1H NMR (400 MHz, CHLOROFORM-d) δ=8.75 (s, 1H), 8.09 (s, 1H), 8.00 (d, J=8.4 Hz, 1H), 7.83-7.73 (m, 2H), 6.56-6.34 (m, 1H), 5.63 (s, 2H), 4.16-3.97 (m, 0.5H), 3.95 (s, 3H), 3.93-3.81 (m, 1H), 3.53-3.44 (m, 0.5H), 3.35-3.18 (m, 1H), 3.01-2.74 (m, 1H), 2.48-2.36 (m, 1H), 2.34-2.18 (m, 0.5H), 2.10-1.96 (m, 0.5H), 1.71-1.57 (m, 0.5H), 1.53-1.48 (m, 9.5H), 0.96-0.82 (m, 1H).

Preparation of Methyl 2-((2-(tert-butoxycarbonyl)-2-azabicyclo[4.1.0]heptan-5-yl)methyl)-1-(thiazol-5-ylmethyl)-1H-benzo[d]imidazole-6-carboxylate (6)

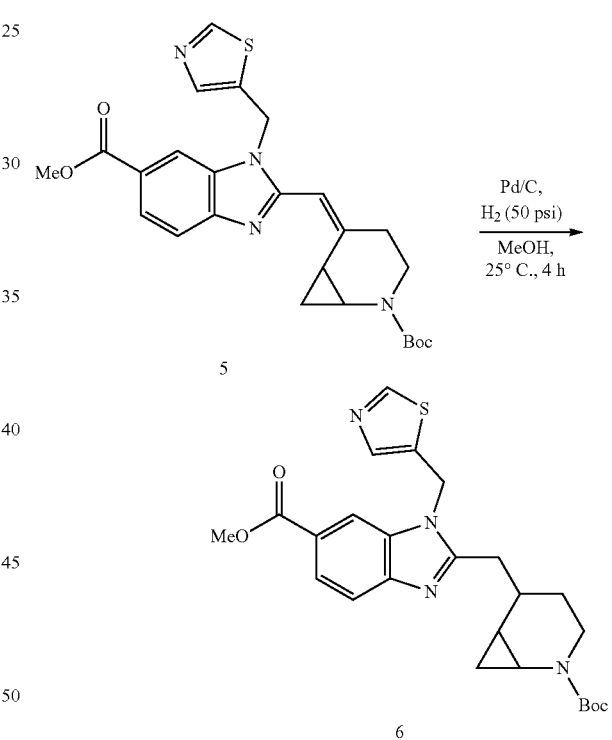

To a solution of methyl (Z)-2-((2-(tert-butoxycarbonyl)-2-azabicyclo[4.1.0]heptan-5-ylidene)methyl)-1-(thiazol-5-ylmethyl)-1H-benzo[d]imidazole-6-carboxylate (1 g, 2.08 mmol, 1 eq) in MeOH (100 mL) was added Pd/C (1 g, 10% purity) under $N_2$ atmosphere. The suspension was degassed and purged with $H_2$ for 3 times. The mixture was stirred under $H_2$ (50 psi) at 25° C. for 4 h. LC-MS showed starting material was consumed completely and desired mass was detected. The reaction mixture was filtered and concentrated under reduced pressure to give a residue. The residue was purified by column chromatography ($SiO_2$, Petroleum ether/Ethyl acetate=10/1 to 0/1) to provide product as a white solid (1 g, 2.07 mmol, 99.6% yield); LCMS: RT=1.306 min, MS cal.: 482.2, [M+H]$^+$=483.3.

Preparation of Methyl 2-((2-azabicyclo[4.1.0]heptan-5-yl)methyl)-1-(thiazol-5-ylmethyl)-1H-benzo[d]imidazole-6-carboxylate (7)

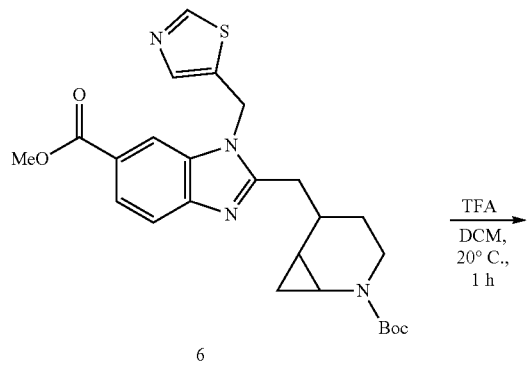

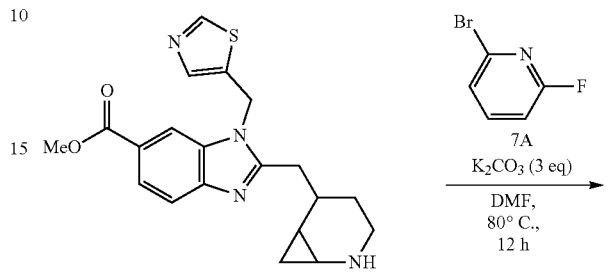

Preparation of Methyl 2-((2-(6-fluoropyridin-2-yl)-2-azabicyclo[4.1.0]heptan-5-yl)methyl)-1-(thiazol-5-ylmethyl)-1H-benzo[d]imidazole-6-carboxylate (8)

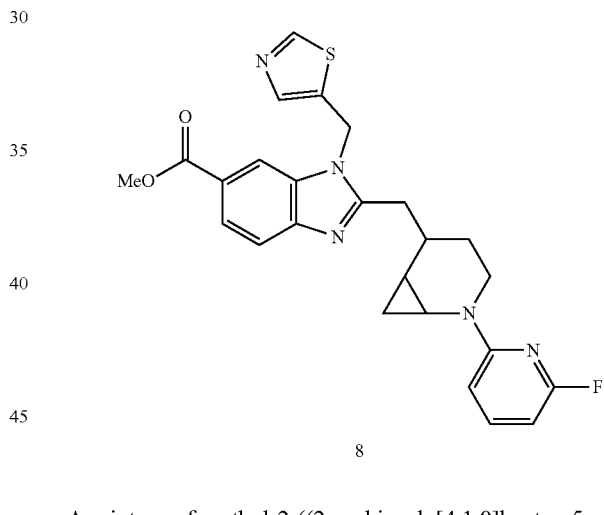

To a solution of methyl 2-((2-(tert-butoxycarbonyl)-2-azabicyclo[4.1.0]heptan-5-yl)methyl)-1-(thiazol-5-ylmethyl)-1H-benzo[d]imidazole-6-carboxylate (0.3 g, 622 µmol, 1 eq) in DCM (3 mL) was added TFA (924 mg, 8.10 mmol, 600.00 µL, 13.04 eq). The mixture was stirred at 20° C. for 1 h. TLC indicated starting material was consumed completely and one new spot was formed. The reaction mixture was diluted with Na$_2$CO$_3$ to pH=8-9 and extracted with DCM 30 mL (15 mL*2). The combined organic layers were dried over Na$_2$SO$_4$, filtered and concentrated under reduced pressure to provide product as a yellow solid (200 mg, 523 µmol, 84.1% yield); LCMS: RT=0.740 min, MS cal.: 382.15, [M+H]$^+$=383.1.

A mixture of methyl 2-((2-azabicyclo[4.1.0]heptan-5-yl)methyl)-1-(thiazol-5-ylmethyl)-1H-benzo[d]imidazole-6-carboxylate (143 mg, 375 µmol, 1.1 eq), 2-bromo-6-fluoropyridine (60 mg, 341 µmol, 1 eq), K$_2$CO$_3$ (141 mg, 1.02 mmol, 3 eq) in DMF (2 mL) was degassed and purged with N$_2$ for 3 times, and then the mixture was stirred at 80° C. for 12 h under N$_2$ atmosphere. LC-MS showed starting material was consumed completely and desired mass was detected. The residue was diluted with H$_2$O 20 mL and extracted with EtOAc 20 mL (10 mL*2). The combined organic layers were dried over Na$_2$SO$_4$, filtered and concentrated under reduced pressure to give a residue. The residue was purified by column chromatography (SiO$_2$, Petroleum ether/Ethyl acetate=10/1 to 0/1) to provide product as a white solid (100 mg, 186 umol, 54.5% yield); LCMS: RT=0.947 min, MS cal.: 477.17, [M+H]$^+$=478.2.

Preparation of Methyl 2-((2-(6-((4-cyano-2-fluorobenzyl)oxy)pyridin-2-yl)-2-azabicyclo[4.1.0]heptan-5-yl)methyl)-1-(thiazol-5-ylmethyl)-1H-benzo[d]imidazole-6-carboxylate (9)

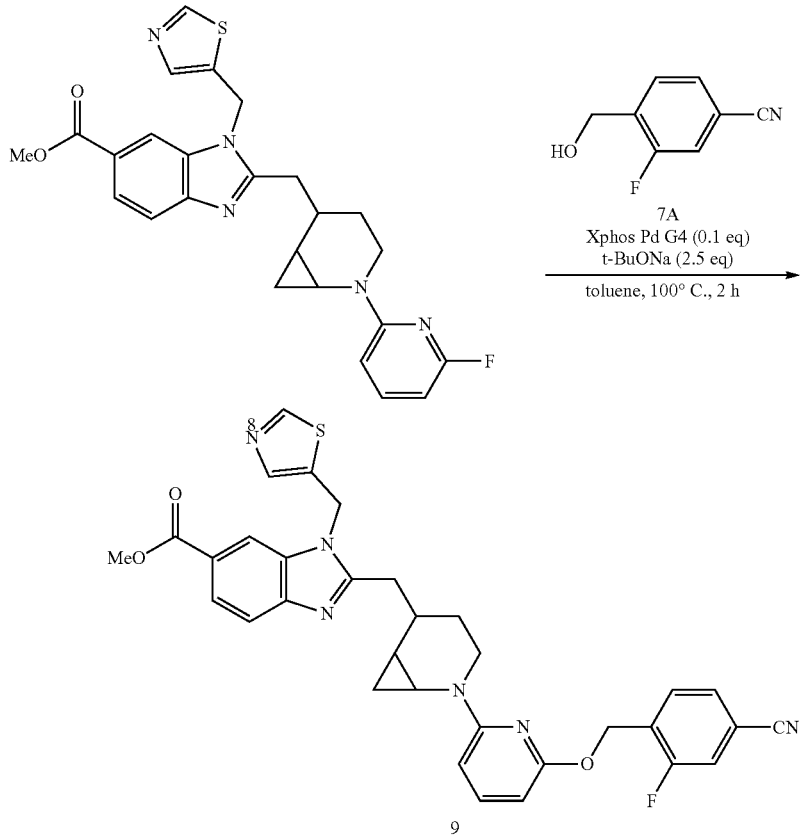

A mixture of methyl 2-((2-(6-fluoropyridin-2-yl)-2-azabicyclo[4.1.0]heptan-5-yl)methyl)-1-(thiazol-5-ylmethyl)-1H-benzo[d]imidazole-6-carboxylate (100 mg, 186 μmol, 1 eq), 3-fluoro-4-(hydroxymethyl)benzonitrile (28.07 mg, 186 μmol, 1 eq), Xphos Pd G4 (16 mg, 18.6 μmol, 0.1 eq), t-BuONa (44.6 mg, 464 μmol, 2.5 eq) in toluene (2 mL) was degassed and purged with $N_2$ for 3 times, and then the mixture was stirred at 100° C. for 2 h under $N_2$ atmosphere. LC-MS showed starting material was consumed completely and desired mass was detected. The residue was diluted with $H_2O$ 20 mL and extracted with EtOAc 20 mL (20 mL*3). The combined organic layers were dried over $Na_2SO_4$, filtered and concentrated under reduced pressure to give a residue. The residue was purified by column chromatography ($SiO_2$, Petroleum ether/Ethyl acetate=10/1 to 0/1) to provide product (70 mg, 115 μmol, 61.9% yield); LCMS: Rt=2.689 min, MS cal.: 608.2, [M+H]$^+$=609.2

Preparation of 2-((2-(6-((4-Cyano-2-fluorobenzyl)oxy)pyridin-2-yl)-2-azabicyclo[4.1.0]heptan-5-yl)methyl)-1-(thiazol-5-ylmethyl)-1H-benzo[d]imidazole-6-carboxylic Acid, Mixture of 4 Diastereomers (Compound 46)

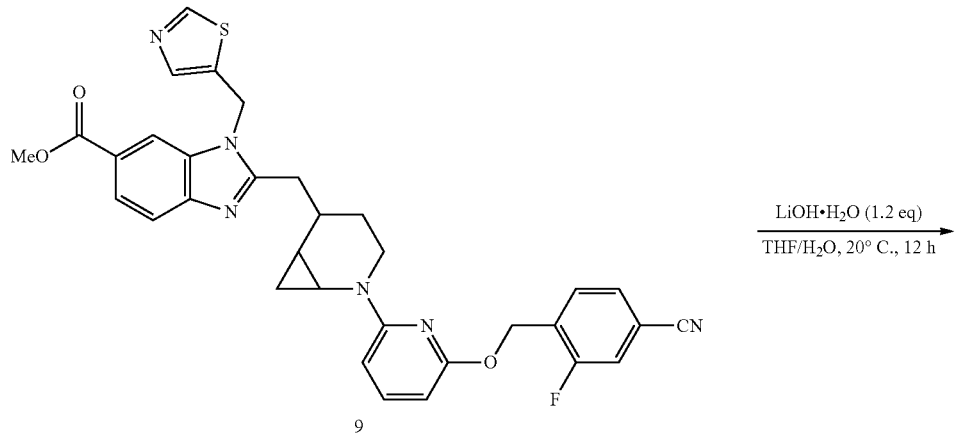

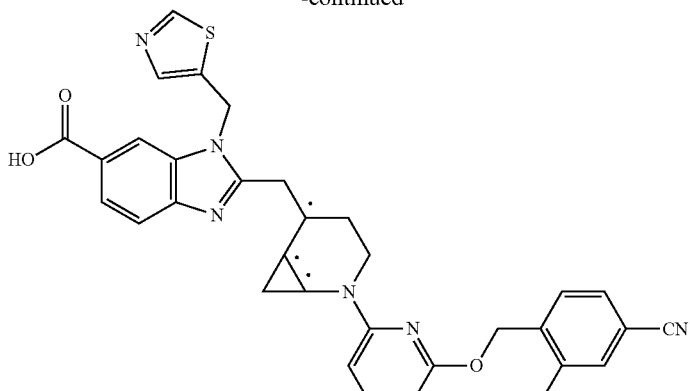

Compound 46 (mixture 4 diastereomers)

To a solution of methyl 2-((2-(6-(((4-cyano-2-fluorobenzyl)oxy)pyridin-2-yl)-2-azabicyclo[4.1.0]heptan-5-yl)methyl)-1-(thiazol-5-ylmethyl)-1H-benzo[d]imidazole-6-carboxylate (65 mg, 107 μmol, 1 eq) in THF (0.7 mL) was added LiOH·H$_2$O (5.38 mg, 128 μmol, 1.2 eq) in H$_2$O (0.3 mL). The mixture was stirred at 20° C. for 12 h. LC-MS showed starting material was consumed completely and desired mass was detected. The residue was purified by prep-HPLC (neutral condition; column: Waters Xbridge Prep OBD C18 150*40 mm*10 μm; mobile phase: [water (NH$_4$HCO$_3$)-ACN]; B %: 30%-70%, 8 min) to provide product as a white solid (28 mg, 47.1 μmol, 44.1% yield);

LCMS: RT=1.986 min, MS cal.: 594.18, [M+H]$^+$=595.2; HPLC: RT=3.096 min; $^1$H NMR (400 MHz, DMSO-d6) δ 9.00 (s, 1H) 8.27 (s, 1H) 7.99 (s, 1H) 7.90-7.85 (m, 1H) 7.81 (m, 1H) 7.72-7.62 (m, 3H) 7.51-7.42 (m, 1H) 6.35-6.28 (m, 1H) 6.10-6.03 (m, 1H) 5.96-5.88 (m, 2H) 5.44-5.36 (m, 2H) 4.40-4.31 (m, 1H) 3.12-3.02 (m, 1H) 3.00-2.90 (m, 1H) 2.84-2.68 (m, 2H) 2.61-2.55 (m, 1H) 1.76-1.68 (m, 1H) 1.54-1.43 (m, 1H) 1.00-0.82 (m, 1H) 0.79-0.69 (m, 1H), 0.25-0.21 (m, 1H).

Intermediates for Examples 10-11

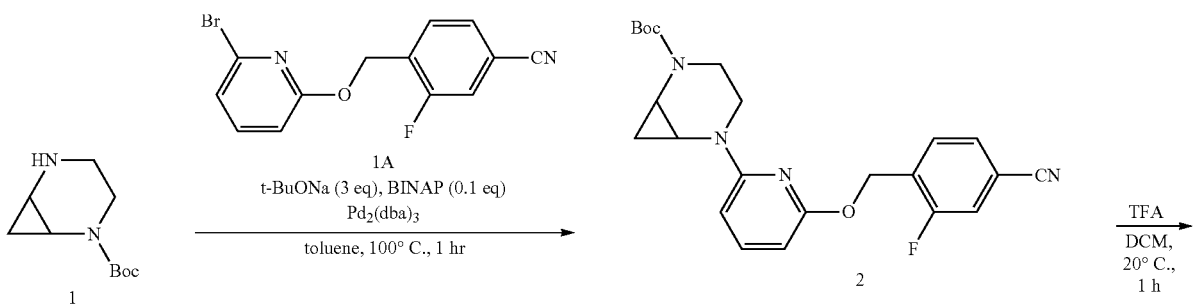

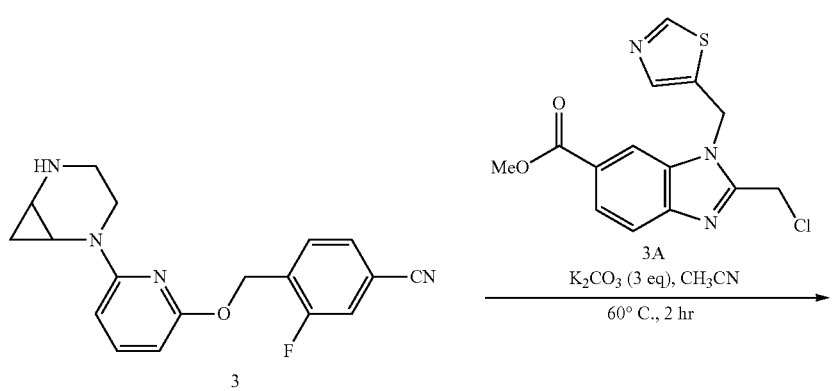

-continued

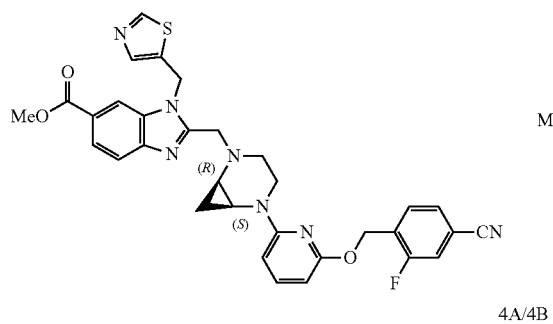

4A/4B

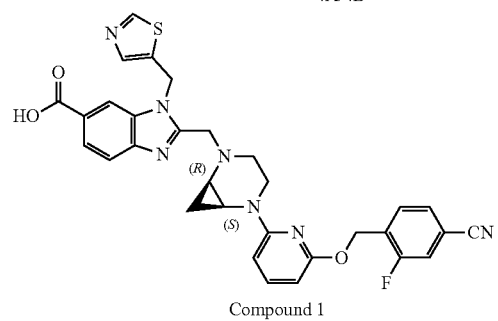

Compound 1

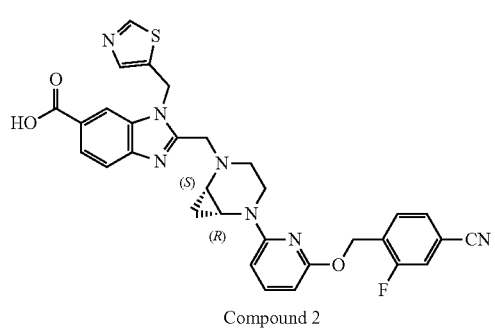

Compound 2

Preparation of tert-Butyl 5-(6-((4-cyano-2-fluorobenzyl)oxy)pyridin-2-yl)-2,5-diazabicyclo[4.1.0]heptane-2-carboxylate (2)

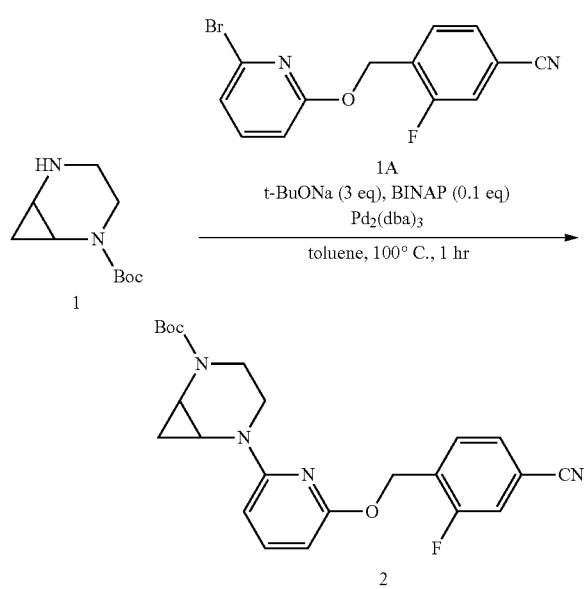

A mixture of tert-butyl 2,5-diazabicyclo[4.1.0]heptane-2-carboxylate (500 mg, 2.52 mmol, 1.1 eq), 4-(((6-bromopyridin-2-yl)oxy)methyl)-3-fluorobenzonitrile (704 mg, 2.29 mmol, 1 eq), Pd$_2$(dba)$_3$ (105 mg, 115 μmol, 0.05 eq), BINAP (143 mg, 229 μmol, 0.1 eq), and t-BuONa (661 mg, 6.88 mmol, 3 eq) in toluene (5 mL) was degassed and purged with N$_2$ for 3 times, and then the mixture was stirred at 100° C. for 1 h under N$_2$ atmosphere. LC-MS showed starting material was consumed completely and one main peak with desired mass was detected. The reaction mixture was diluted with H$_2$O (30 mL), extracted with EtOAc (50 mL). The organic layer was concentrated under reduced pressure to remove solvent. The residue was purified by column chromatography (SiO$_2$, Petroleum ether/Ethyl acetate=100/1 to 10/1) to provide product as a white solid (440 mg, 1.04 mmol, 45% yield); RT=2.142 min; MS cal.: 424.2, [M+H]$^+$=325.2; $^1$H NMR (400 MHz, CHLOROFORM-d) δ 7.66-7.59 (m, 1H), 7.51-7.43 (m, 2H), 7.37 (d, J=9.2 Hz, 1H), 6.34 (m, 1H), 6.18 (d, J=7.6 Hz, 1H), 5.51-5.41 (m, 2H), 4.08-3.83 (m, 1H), 3.60-3.05 (m, 4H), 2.91-2.75 (m, 1H), 1.50 (s, 9H), 1.21-1.02 (m, 1H), 0.39 (m, 1H).

Preparation of 4-(((6-(2,5-Diazabicyclo[4.1.0]heptan-2-yl)pyridin-2-yl)oxy)methyl)-3-fluorobenzonitrile (3)

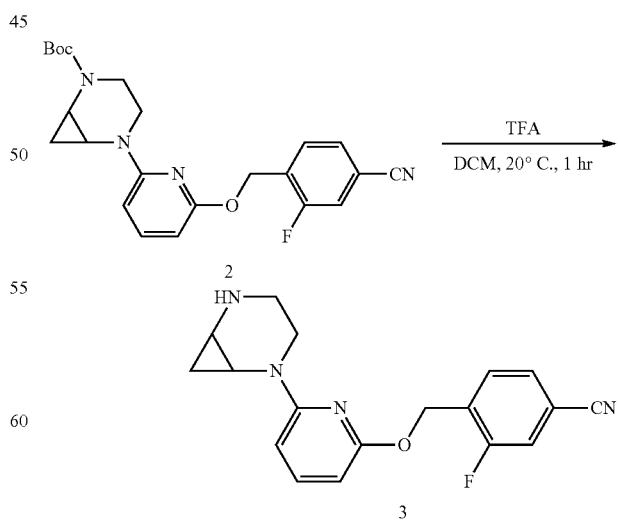

A mixture of tert-butyl 5-(6-((4-cyano-2-fluorobenzyl)oxy)pyridin-2-yl)-2,5-diazabicyclo[4.1.0]heptane-2-carboxylate (400 mg, 942 μmol, 1 eq), TFA (107 mg, 942 μmol, 69.8 μL, 1 eq) in DCM (4 mL) was degassed and purged with $N_2$ for 3 times, and then the mixture was stirred at 20° C. for 1 h under $N_2$ atmosphere. TLC indicated starting material was consumed completely and one new spot formed. The reaction was clean according to TLC. The reaction mixture was concentrated under reduced pressure to remove solvent. The residue was purified by prep-HPLC (neutral condition column: Waters Xbridge Prep OBD C18 150*40 mm*10 um; mobile phase: [water ($NH_4HCO_3$)-ACN]; gradient: 45%-80% B over 8 min) to provide desired compound as a white solid (300 mg, yield 45%, purity 95%).

Preparation of Methyl 2-((5-(6-((4-cyano-2-fluorobenzyl)oxy)pyridin-2-yl)-2,5-diazabicyclo[4.1.0]heptan-2-yl)methyl)-1-(thiazol-5-ylmethyl)-1H-benzo[d]imidazole-6-carboxylate (4A) and (4B)

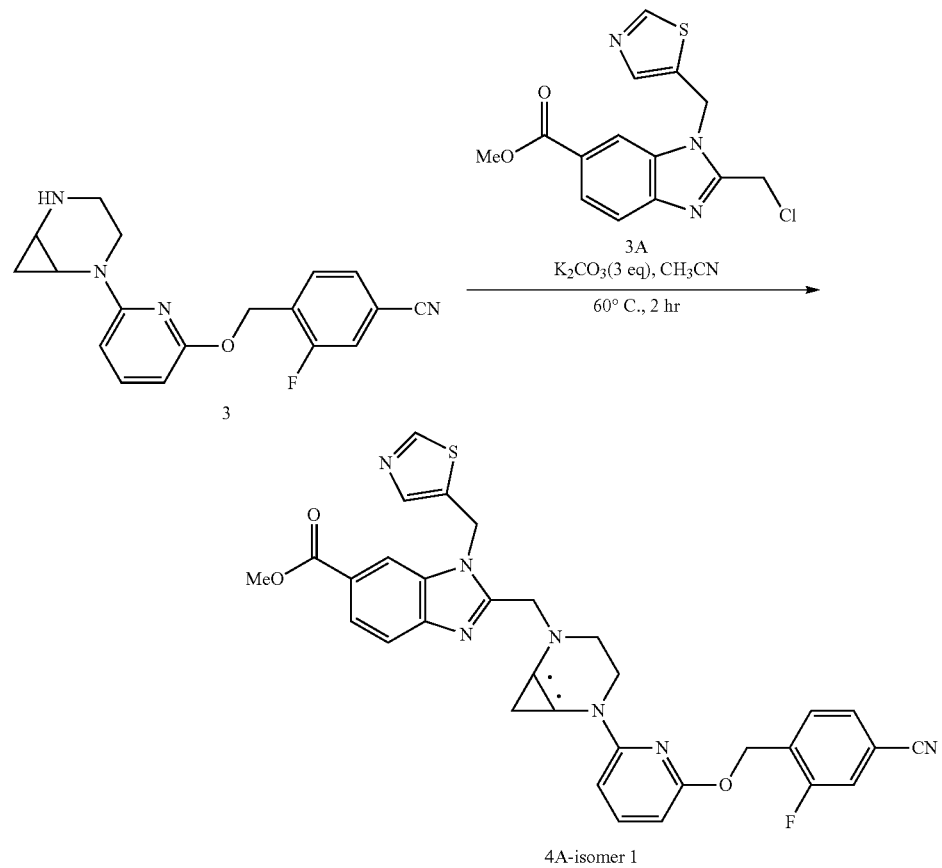

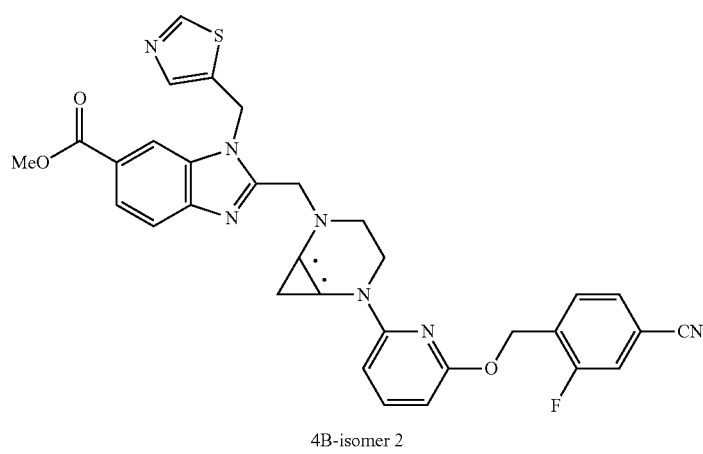

A mixture of 4-(((6-(2,5-diazabicyclo[4.1.0]heptan-2-yl)pyridin-2-yl)oxy)methyl)-3-fluorobenzonitrile (298 mg, 925 µmol, 1 eq), methyl 2-(chloromethyl)-1-(thiazol-5-ylmethyl)-1H-benzo[d]imidazole-6-carboxylate (300 mg, 925 µmol, 1 eq), K₂CO₃ (383 mg, 2.77 mmol, 3 eq) in CH₃CN (5 mL) was degassed and purged with N₂ for 3 times, and then the mixture was stirred at 60° C. for 3 h under N₂ atmosphere. LC-MS showed starting material was consumed completely and one main peak with desired mass was detected. The resulting product was dissolved in EtOAc (20 ml) and filtered to remove insoluble material. The filtrate was concentrated in vacuo. The residue was purified by prep-HPLC (neutral condition: column: Waters Xbridge Prep OBD C18 150*40 mm*10 µm; mobile phase: [water (NH₄HCO₃)-ACN]; B %: 45%-80%, 8 min) to give a mixture of intermediate 4A&4B (400 mg, yield 90%, purity 90%) as a white solid, which was further separated by SFC (condition: column: DAICEL CHIRALCEL OD nv (250 mm*30 mm, 10 µm); mobile phase: [0.1% NH₃H₂O MEOH]; B %: 50%-50%, 15 min). Intermediate 4A-isomer 1 was obtained as a white solid (120 mg, 197 µmol, 21.3% yield); RT=2.532 min, MS cal.: 617.2, [M+H]⁺=618.2; ¹H NMR (400 MHz, CHLOROFORM-d) δ 8.77 (s, 1H), 8.15 (s, 1H), 8.02 (d, J=8.4 Hz, 1H), 7.90 (s, 1H), 7.79 (d, J=8.4 Hz, 1H), 7.61 (t, J=7.6 Hz, 1H), 7.51-7.41 (m, 2H), 7.34 (d, J=9.2 Hz, 1H), 6.31 (d, J=8.0 Hz, 1H), 6.16 (d, J=8.0 Hz, 1H), 5.86 (s, 2H), 5.52-5.37 (m, 2H), 4.21-4.10 (m, 3H), 4.08-4.01 (m, 1H), 3.96 (s, 3H), 3.09-3.00 (m, 1H), 2.83-2.72 (m, 2H), 2.66-2.58 (m, 1H), 2.45-2.37 (m, 1H), 0.81-0.79 (m, 1H), 0.61-0.46 (m, 1H). Intermediate 4B-isomer 2 was obtained as a white solid (80 mg, 131 µmol, 14.2% yield); RT=2.534 min, MS cal.: 617.2, [M+H]⁺=618.2; ¹H NMR (400 MHz, CHLOROFORM-d) δ=8.77 (s, 1H), 8.15 (s, 1H), 8.02 (d, J=8.4 Hz, 1H), 7.90 (s, 1H), 7.79 (d, J=8.4 Hz, 1H), 7.61 (t, J=7.6 Hz, 1H), 7.50-7.41 (m, 2H), 7.34 (d, J=9.4 Hz, 1H), 6.31 (d, J=8.0 Hz, 1H), 6.16 (d, J=8.0 Hz, 1H), 5.86 (s, 2H), 5.50-5.37 (m, 2H), 4.21-4.03 (m, 4H), 3.96 (s, 3H), 3.05 (m, 1H), 2.84-2.72 (m, 2H), 2.67-2.59 (m, 1H), 2.47-2.39 (m, 1H), 0.81-0.79 (m, 1H), 0.60-0.50 (m, 1H).

Example 10 (Synthesis of Compound 2)

2-((5-(6-((4-Cyano-2-fluorobenzyl)oxy)pyridin-2-yl)-2,5-diazabicyclo[4.1.0]heptan-2-yl)methyl)-1-(thiazol-5-ylmethyl)-1H-benzo[d]imidazole-6-carboxylic Acid, Diastereomer 1

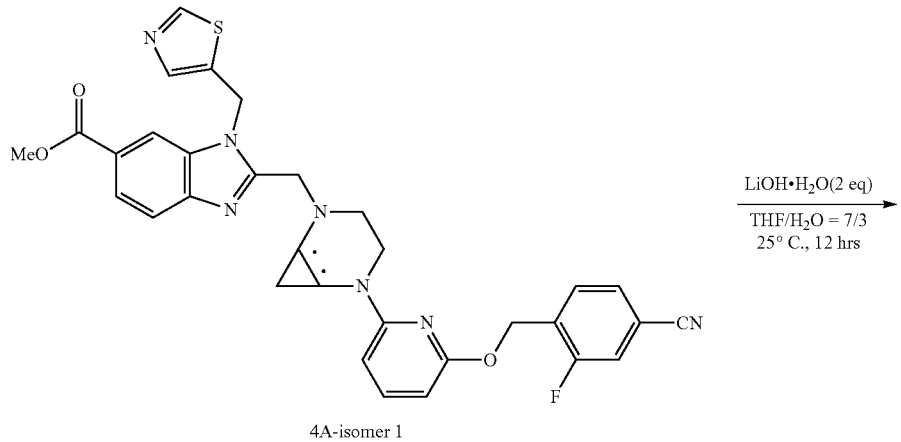

4A-isomer 1

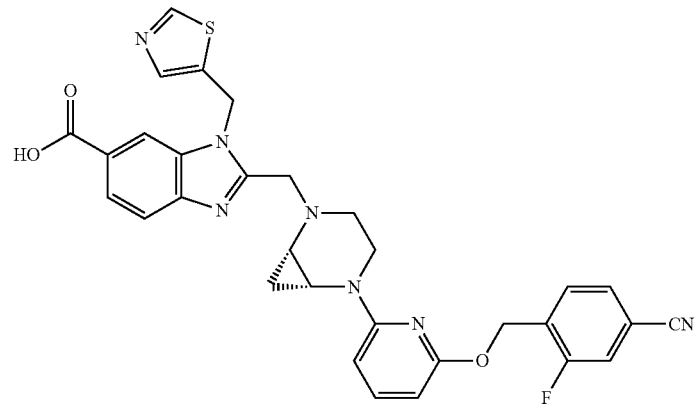

Compound 2

A mixture of methyl 2-((5-(6-((4-cyano-2-fluorobenzyl)oxy)pyridin-2-yl)-2,5-diazabicyclo[4.1.0]heptan-2-yl)methyl)-1-(thiazol-5-ylmethyl)-1H-benzo[d]imidazole-6-carboxylate (90 mg, 148 μmol, 1 eq) and LiOH·H$_2$O (12.4 mg, 295 μmol, 2 eq) in THF (0.7 mL) and H$_2$O (0.3 mL) was degassed and purged with N$_2$ for 3 times, and the mixture was stirred at 25° C. for 12 h under N$_2$ atmosphere. LC-MS showed starting material was consumed completely and one main peak with desired mass was detected. The reaction mixture was concentrated under reduced pressure to remove solvent. The residue was purified by prep-HPLC (neutral condition column: Waters Xbridge Prep OBD C18 150*40 mm*10 μm; mobile phase: [water (NH$_4$HCO$_3$)-ACN]; B %: 20%-50%, 8 min) to provide product as a white solid (29.9 mg, 50.2 μmol, 34% yield); RT=2.508 min, MS cal.: 595.2, [M+H]$^+$=596.1; $^1$H NMR (400 MHz, METHANOL-d4) δ=8.94 (s, 1H), 8.27 (s, 1H), 8.06 (s, 1H), 8.01 (d, J=8.4 Hz, 1H), 7.71 (d, J=8.4 Hz, 1H), 7.68-7.62 (m, 1H), 7.57-7.53 (m, 2H), 7.48 (t, J=8.0 Hz, 1H), 6.36 (d, J=8.0 Hz, 1H), 6.13 (d, J=8.0 Hz, 1H), 6.00 (s, 2H), 5.46 (s, 2H), 4.24-4.08 (m, 3H), 3.00 (m, 1H), 2.85-2.76 (m, 2H), 2.67 (m, 1H), 2.45-2.37 (m, 1H), 0.75 (m, 1H), 0.55-0.49 (m, 1H).

Example 11 (Synthesis of Compound 1)

2-((5-(6-((4-cyano-2-fluorobenzyl)oxy)pyridin-2-yl)-2,5-diazabicyclo[4.1.0]heptan-2-yl)methyl)-1-(thiazol-5-ylmethyl)-1H-benzo[d]imidazole-6-carboxylic Acid, Diastereomer 2

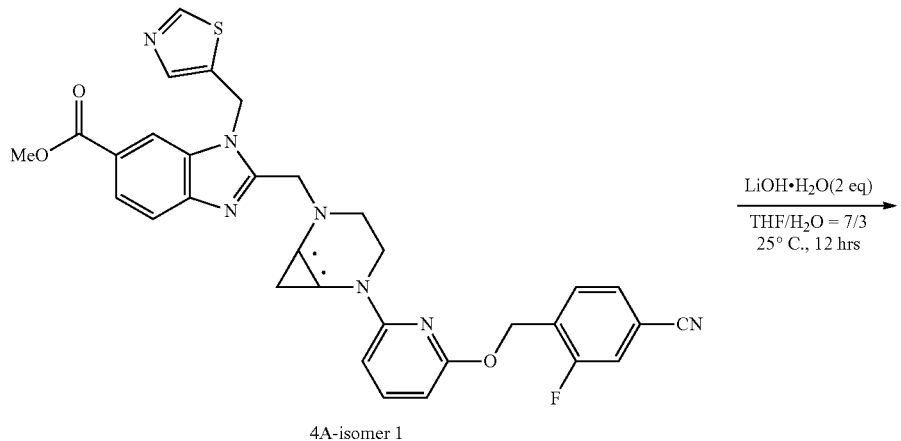

4A-isomer 1

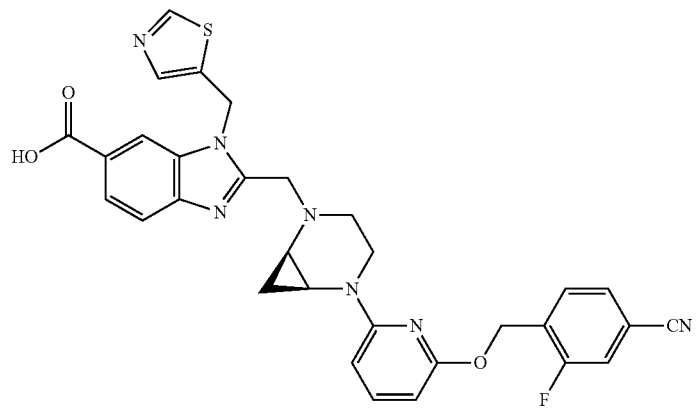

Compound 1

To a solution of methyl 2-((5-(6-((4-cyano-2-fluorobenzyl)oxy)pyridin-2-yl)-2,5-diazabicyclo[4.1.0]heptan-2-yl)methyl)-1-(thiazol-5-ylmethyl)-1H-benzo[d]imidazole-6-carboxylate (70 mg, 115 μmol, 1 eq) in THF (0.7 mL) was added LiOH·H$_2$O (9.64 mg, 230 μmol, 2 eq) in H$_2$O (0.3 mL). The mixture was stirred at 25° C. for 12 h. LC-MS showed starting material was consumed completely and desired mass was detected. The residue was purified by prep-HPLC (neutral condition: column: Waters Xbridge BEH C18 100*30 mm*10 um; mobile phase: [water (NH$_4$HCO$_3$)-ACN]; B %: 30%-60%, 8 min) to provide product as a white solid (35 mg, 58.76 μmol, 51.2% yield);

RT=1.843 min, MS cal.: 595.65, [M+H]$^+$=596; $^1$H NMR (400 MHz, METHANOL-d$_4$) δ 8.93 (s, 1H), 8.26 (s, 1H), 8.04 (s, 1H), 7.99 (d, J=8.4 Hz, 1H), 7.72 (d, J=8.4 Hz, 1H), 7.67-7.62 (m, 1H), 7.55-7.51 (m, 2H), 7.45 (t, J=8.0 Hz, 1H), 6.34 (d, J=8.0 Hz, 1H), 6.11 (d, J=8.0 Hz, 1H), 6.07 (s, 2H), 5.43 (s, 2H), 4.24-4.06 (m, 3H), 2.97 (m, 1H), 2.79-2.76 (m, 2H), 2.65 (m, 1H), 2.45-2.38 (m, 1H), 0.75 (m, 1H), 0.51-0.48 (m, 1H).

Intermediates for Examples 12-13

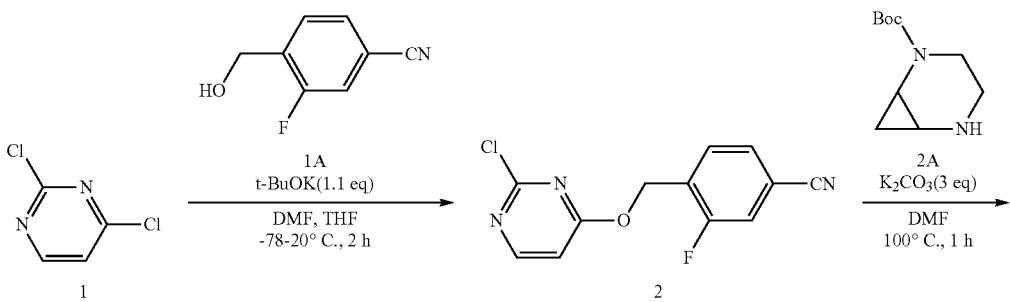

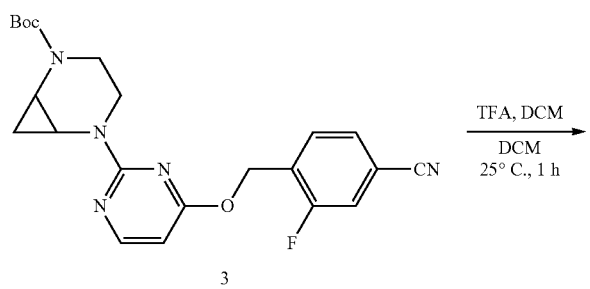

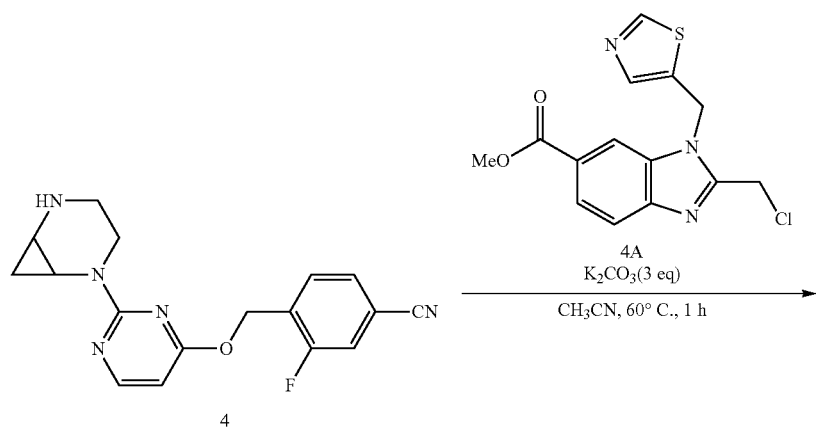

-continued

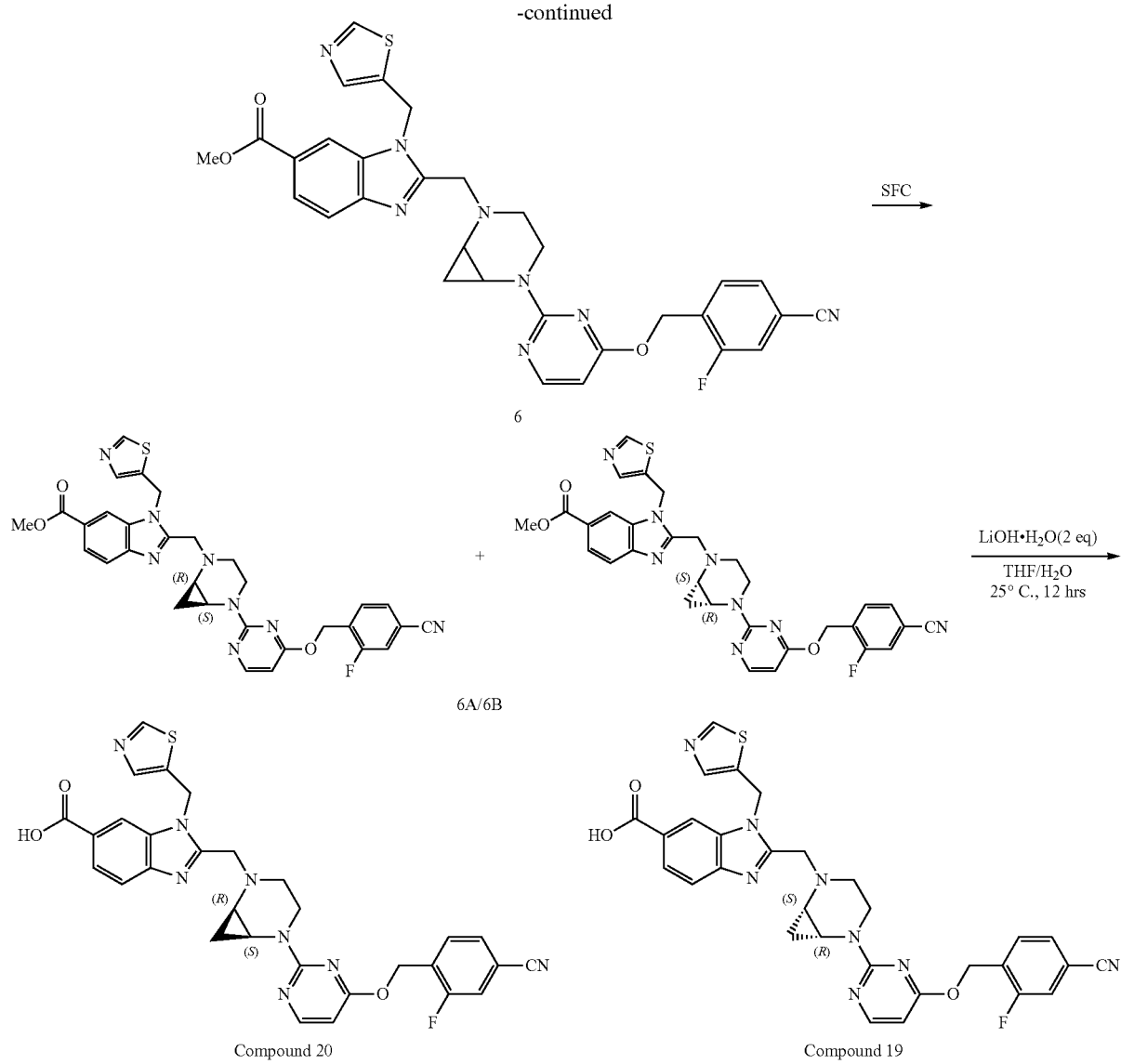

6

6A/6B

LiOH·H₂O (2 eq)
---
THF/H₂O
25° C., 12 hrs

Compound 20

Compound 19

Preparation of 4-(((2-Chloropyrimidin-4-yl)oxy)methyl)-3-fluorobenzonitrile (2)

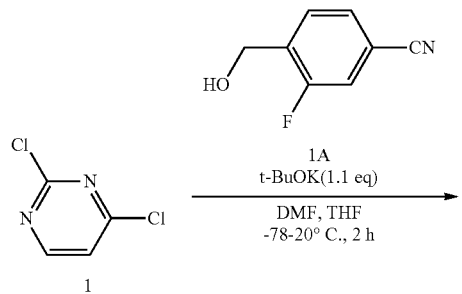

t-BuOK (4.14 g, 36.9 mmol, 1.1 eq) was added in portions to 3-fluoro-4-(hydroxymethyl)benzonitrile (5.33 g, 35.2 mmol, 1.05 eq) in THF (40 mL) at 20° C. and then stirred until completely dissolved. This solution was added dropwise to 2,4-dichloropyrimidine (5 g, 33.6 mmol, 1 eq) in DMF (60 mL) at <−65° C. over 1.5 hours under N₂ atmosphere. The reaction mixture was warmed to 10° C. slowly over 1.5 hours and stirred for 0.5 h. LCMS showed 0.3% starting material and 85.9% product. The reaction mixture was poured into H₂O (300 mL) slowly at 0° C. and a solid formed. The mixture was stirred for 15 mins and filtered. The solid was collected, dissolved in DCM (100 mL) and washed with brine (20 mL), dried over Na₂SO₄, filtered and concentrated under reduced pressure to give crude product (5 g). The crude product was stirred in MTBE (10 mL) and stirred for 5 mins, n-hexane (50 mL) was added to the mixture, stirred for 10 mins, filtered and the filter-cake collected. The cake was added into MTBE (5 mL) and stirred for 5 mins, n-hexane (25 mL) was added to the mixture, stirred for 5 mins, filtered and the cake was collected, dried under vacuum for 20 mins to afford the product as a yellow solid (4 g, 15.2 mmol, 45.2% yield); RT=2.056 min, MS cal.: 263.0, [M+H]$^+$=264.0; $^1$H NMR (400 MHz, CHLOROFORM-d) δ=8.40 (d, J=5.6 Hz, 1H) 7.64 (t, J=7.2 Hz, 1H) 7.55-7.39 (m, 2H) 6.80-6.71 (d, J=5.6 Hz, 1H, 1H) 5.55 (s, 2H).

Preparation of tert-Butyl 5-(4-((4-cyano-2-fluorobenzyl)oxy)pyrimidin-2-yl)-2,5-diazabicyclo[4.1.0]heptane-2-carboxylate (3)

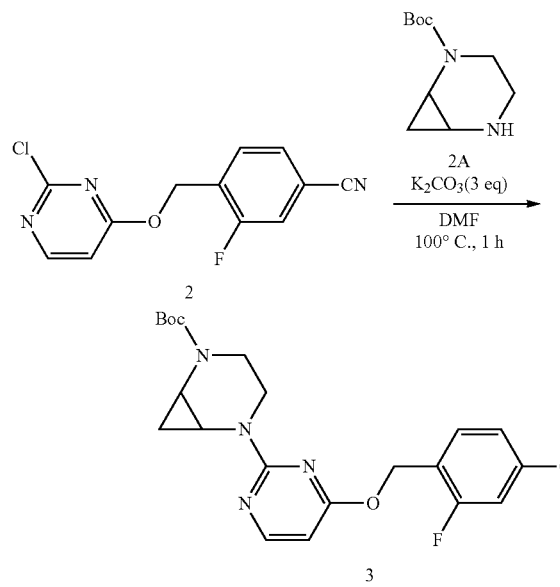

A mixture of 4-(((2-chloropyrimidin-4-yl)oxy)methyl)-3-fluorobenzonitrile (500 mg, 1.90 mmol, 1 eq), tert-butyl 2,5-diazabicyclo[4.1.0]heptane-2-carboxylate (490 mg, 2.09 mmol, 1.1 eq, HCl), K$_2$CO$_3$ (786 mg, 5.69 mmol, 3 eq), in DMF (5 mL) was degassed and purged with N$_2$ 3 times, and then the mixture was stirred at 100° C. for 1 h under N$_2$ atmosphere. LC-MS showed starting material was consumed completely and desired mass was detected. The residue was diluted with H$_2$O (30 mL) and extracted with EtOAc (30 mL*3). The combined organic layers were dried over Na$_2$SO$_4$, filtered and concentrated under reduced pressure to give a residue. The residue was purified by column chromatography (SiO$_2$, Petroleum ether/Ethyl acetate=20/1 to 0/1) to provide product as a white solid (500 mg, 1.18 mmol, 61.9% yield); RT=2.522 min, MS cal.: 425.19, [M+H]$^+$=426.2; $^1$H NMR (400 MHz, CHLOROFORM-d) δ=8.24 (s, 1H) 7.66-7.59 (m, 1H) 7.53 (d, J=9.6 Hz, 1H) 7.42 (d, J=9.6 Hz, 1H) 6.19 (d, J=5.6 Hz, 1H) 5.60 (s, 2H) 3.94-3.72 (m, 1H) 3.71-3.31 (m, 3H) 3.29-3.05 (m, 2H) 1.59-1.70 (m, 1H) 1.53 (s, 9H).

Preparation of 4-(((2-(2,5-Diazabicyclo[4.1.0]heptan-2-yl)pyrimidin-4-yl)oxy)methyl)-3-fluorobenzonitrile (4)

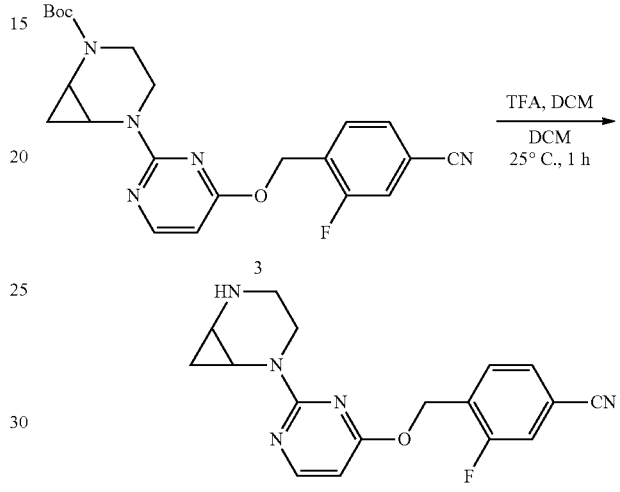

To a solution of tert-butyl 5-(4-((4-cyano-2-fluorobenzyl)oxy)pyrimidin-2-yl)-2,5-diazabicyclo[4.1.0]heptane-2-carboxylate (0.3 g, 705 μmol, 1 eq) in DCM (3 mL) was added TFA (1.54 g, 13.5 mmol, 1.00 mL, 19.2 eq). The mixture was stirred at 25° C. for 1 h. LC-MS showed starting material was consumed completely and desired mass was detected. The reaction mixture was concentrated under reduced pressure to provide product as a yellow oil (220 mg, 676 umol, 95.9% yield); RT=0.777 min, MS cal.: 325.13, [M+H]$^+$=326.3.

Preparation of Methyl 2-((5-(4-((4-cyano-2-fluorobenzyl)oxy)pyrimidin-2-yl)-2,5-diazabicyclo[4.1.0]heptan-2-yl)methyl)-1-(thiazol-5-ylmethyl)-1H-benzo[d]imidazole-6-carboxylate (6A and 6B)

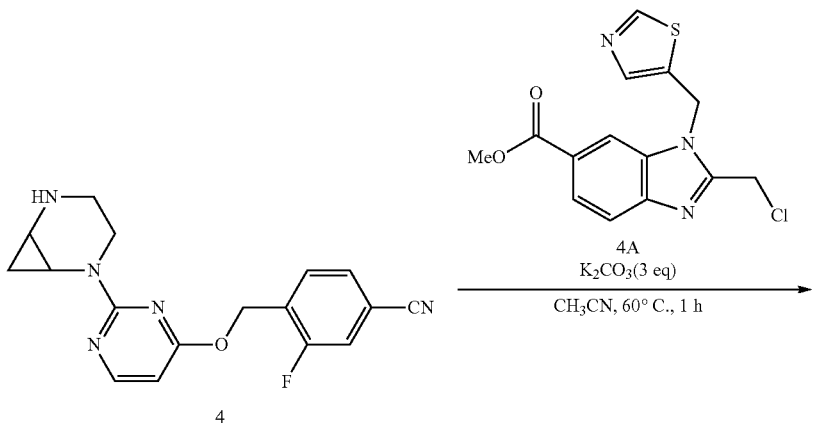

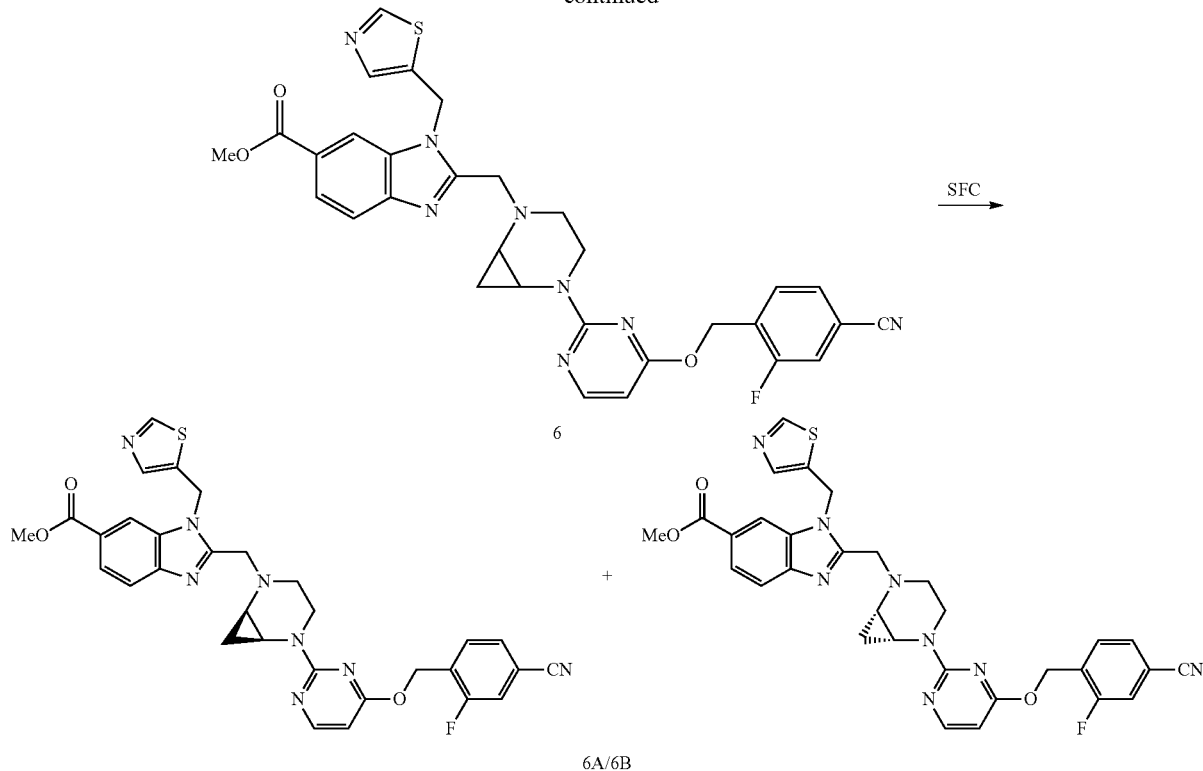

6

6A/6B

To a solution of 4-(((2-(2,5-diazabicyclo[4.1.0]heptan-2-yl)pyrimidin-4-yl)oxy)methyl)-3-fluorobenzonitrile (210 mg, 645 μmol, 1 eq) in CH₃CN (1 mL) was added K₂CO₃ (268 mg, 1.94 mmol, 3 eq) and methyl 2-(chloromethyl)-1-(thiazol-5-ylmethyl)-1H-benzo[d]imidazole-6-carboxylate (208 mg, 645 μmol, 1 eq). The mixture was stirred at 60° C. for 1 h. LC-MS showed starting material was consumed completely and desired mass was detected. The residue was diluted with H₂O (30 mL) and extracted with EtOAc (30 mL*3). The combined organic layers were dried over Na₂SO₄, filtered and concentrated under reduced pressure to give a residue. The residue was purified by column chromatography (SiO₂, Petroleum ether/Ethyl acetate=0/1 to Dichloromethane/Methanol=10/1). The residue was further separated by SFC (condition: column: DAICEL CHIRAL-PAK AD (250 mm*30 mm, 10 um); mobile phase: [0.1% NH₃H₂O MEOH]; B %: 60%-60%, 5 min) to provide intermediate 6A as a white solid (120 mg, 197 μmol, 30.4% yield); LCMS: RT=2.229 min, MS cal.: 610.19, [M+H]⁺=611.2; SFC: RT=1.174 min, ee %: 100.0% and intermediate 6B as a white solid (120 mg, 197 μmol, 30.4% yield); LCMS: RT=2.229 min, MS cal.: 610.19, [M+H]⁺=611.1; SFC: RT=1.685 min, ee %: 97.9%.

Example 12 (Synthesis of Compound 20)

2-((5-(4-((4-Cyano-2-fluorobenzyl)oxy)pyrimidin-2-yl)-2,5-diazabicyclo[4.1.0]heptan-2-yl)methyl)-1-(thiazol-5-ylmethyl)-1H-benzo[d]imidazole-6-carboxylic Acid

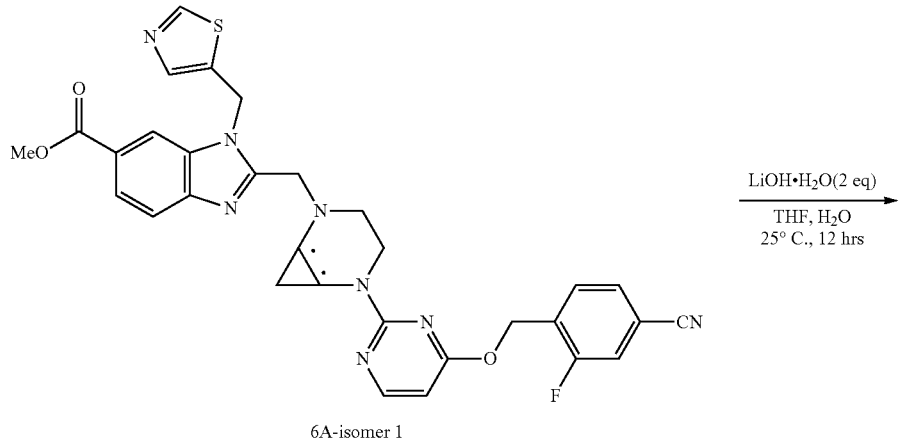

6A-isomer 1

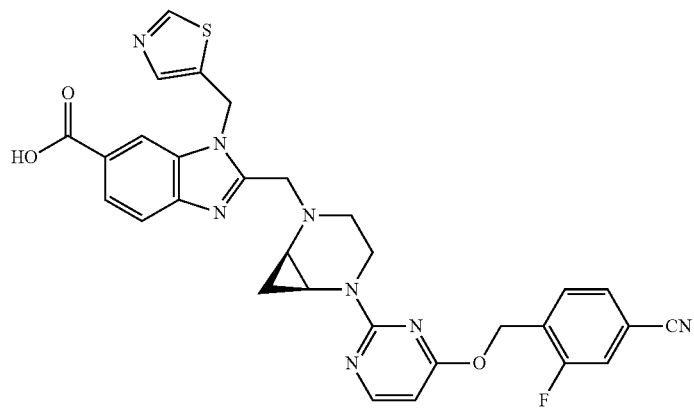

Compound 20

To a solution of methyl 2-((5-(4-((4-cyano-2-fluorobenzyl)oxy)pyrimidin-2-yl)-2,5-diazabicyclo[4.1.0]heptan-2-yl)methyl)-1-(thiazol-5-ylmethyl)-1H-benzo[d]imidazole-6-carboxylate (100 mg, 164 μmol, 1 eq) in THF (1.4 mL) was added LiOH·H$_2$O (13.7 mg, 328 μmol, 2 eq) in H$_2$O (0.6 mL). The mixture was stirred at 20° C. for 12 h. LC-MS showed starting material was consumed completely and desired mass was detected. The residue was purified by prep-HPLC (neutral condition: column: Waters Xbridge Prep OBD C18 150*40 mm*10 μm; mobile phase: [water (NH$_4$HCO$_3$)-ACN]; B %: 20%-60%, 8 min) to provide product as a white solid (29 mg, 48.6 umol, 29.7% yield); LCMS: RT=1.626 min, MS cal.: 596.18, [M+H]$^+$=597.2; SFC: RT=1.312 min, ee %: 99.64%; $^1$H NMR (400 MHz, METHANOL-d$_4$) δ=8.94 (s, 1H) 8.27 (s, 1H) 8.16-8.04 (m, 2H) 8.00 (d, J=8.4 Hz, 1H) 7.71 (d, J=8.4 Hz, 1H) 7.69-7.63 (m, 1H) 7.60-7.53 (m, 2H) 6.19 (d, J=5.6 Hz, 1H) 6.01 (s, 2H) 5.67 (s, 2H) 4.26-4.15 (m, 2H) 4.13-4.08 (m, 1H) 3.13-2.98 (m, 2H) 2.87-2.78 (m, 1H) 2.45-2.61 (m, 1H) 2.55-2.42 (m, 1H) 0.83-0.53 (m, 2H).

Example 13 (Synthesis of Compound 19)

2-((5-(4-((4-Cyano-2-fluorobenzyl)oxy)pyrimidin-2-yl)-2,5-diazabicyclo[4.1.0]heptan-2-yl)methyl)-1-(thiazol-5-ylmethyl)-1H-benzo[d]imidazole-6-carboxylic Acid

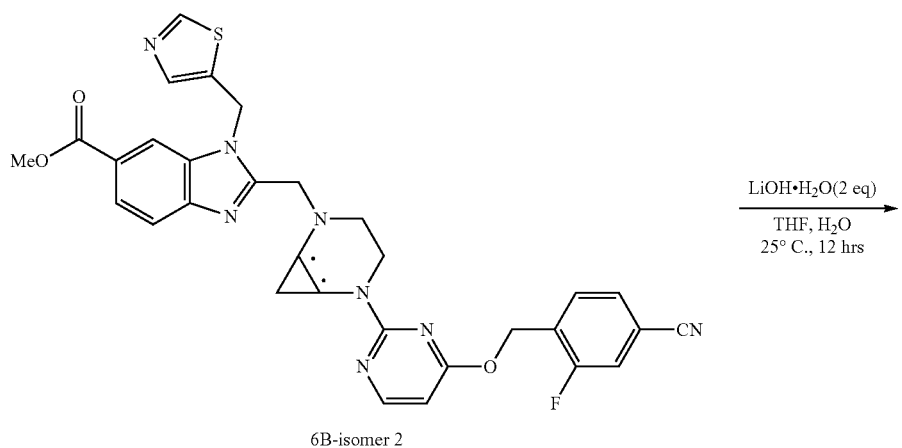

6B-isomer 2

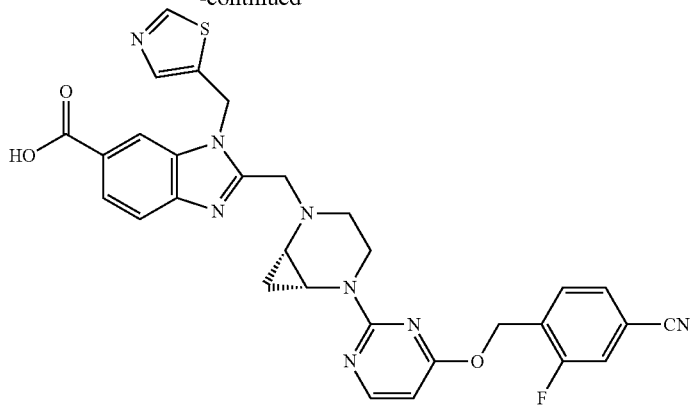

Compound 19

A mixture of methyl 2-((5-(4-((4-cyano-2-fluorobenzyl)oxy)pyrimidin-2-yl)-2,5-diazabicyclo[4.1.0]heptan-2-yl)methyl)-1-(thiazol-5-ylmethyl)-1H-benzo[d]imidazole-6-carboxylate (110 mg, 180 μmol, 1 eq), LiOH·H$_2$O (15.1 mg, 360 μmol, 2 eq) in THF (3 mL) and H$_2$O (1.2 mL) was degassed and purged with N$_2$ for 3 times, and then the mixture was stirred at 25° C. for 12 h under N$_2$ atmosphere. LC-MS showed starting material was consumed completely and one main peak with desired m/z. The reaction solution was adjusted with citric acid to pH=7. The residue was purified by prep-HPLC (neutral condition: column: Waters Xbridge Prep OBD C18 150*40 mm*10 μm; mobile phase: [water (NH$_4$HCO$_3$)-ACN]; B %: 10%-45%, 8 min) to provide product as a white solid (26.2 mg, 43.8 μmol, 24.3% yield); LCMS: RT=1.631 min, MS cal.: 596.18, [M+H]$^+$=597.2; SFC: RT=1.381 min, ee %: 99.70%; $^1$H NMR (400 MHz, METHANOL-d$_4$) δ=ppm 8.94 (s, 1H) 8.27 (s, 1H) 8.12-8.07 (m, 1H) 8.05 (s, 1H) 7.99 (d, J=8.6 Hz, 1H) 7.73-7.63 (m, 2H) 7.60-7.54 (m, 2H) 6.19 (d, J=5.6 Hz, 1H) 5.99 (s, 2H) 5.52 (s, 2H) 4.27-4.15 (m, 2H) 4.14-4.08 (m, 1H) 3.14-3.00 (m, 2H) 2.82 (m, 1H) 2.66 (m, 1H) 2.52-2.43 (m, 1H) 0.84-0.52 (m, 2H).

Intermediates for Examples 14-15

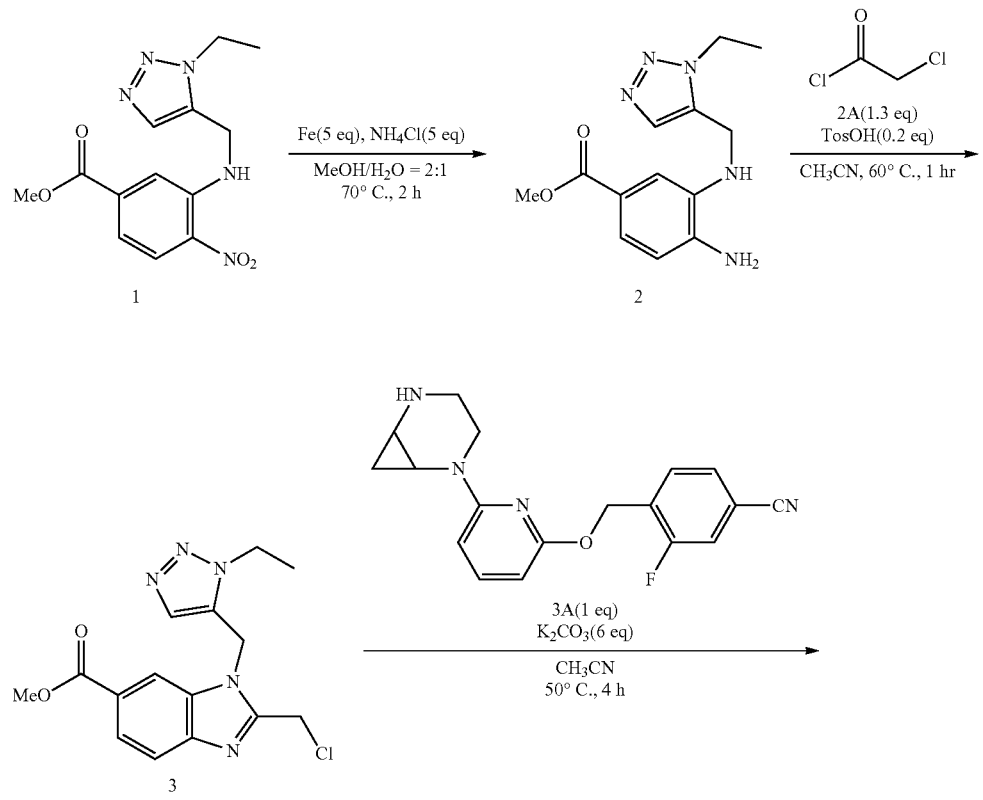

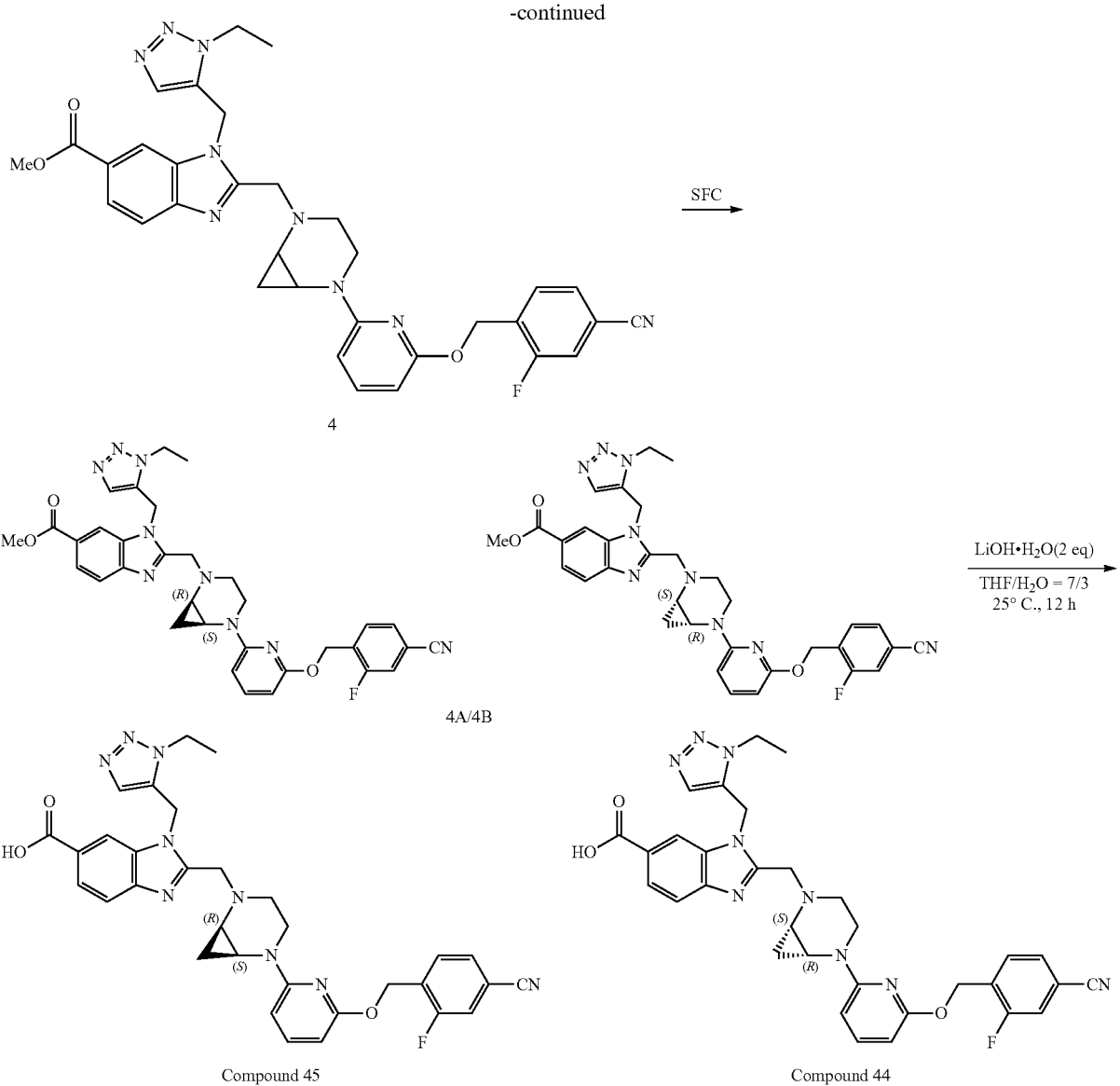

Preparation of Methyl 4-amino-3-(((1-ethyl-1H-1,2,3-triazol-5-yl)methyl)amino)benzoate (2)

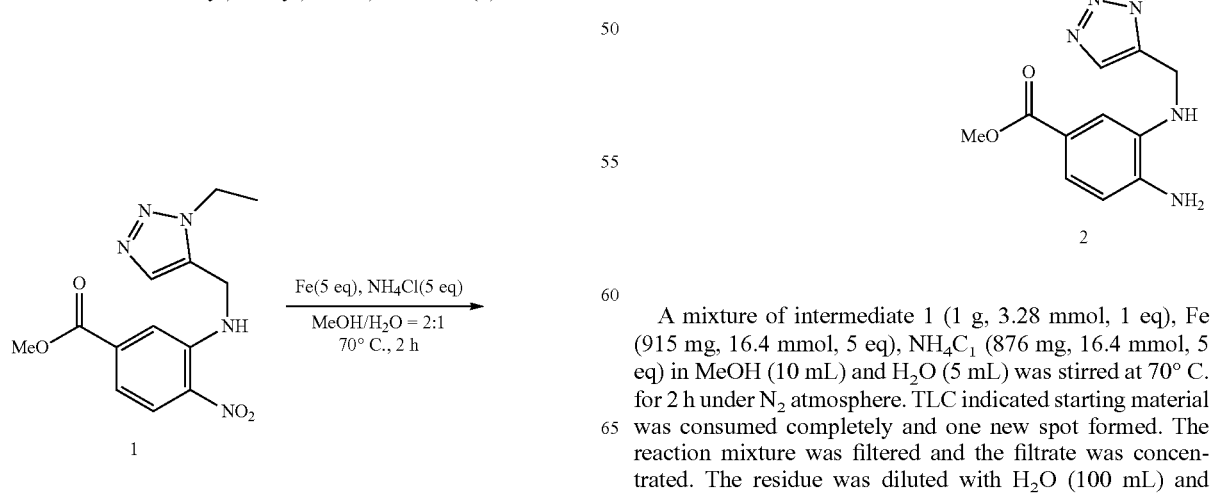

A mixture of intermediate 1 (1 g, 3.28 mmol, 1 eq), Fe (915 mg, 16.4 mmol, 5 eq), $NH_4Cl$ (876 mg, 16.4 mmol, 5 eq) in MeOH (10 mL) and $H_2O$ (5 mL) was stirred at 70° C. for 2 h under $N_2$ atmosphere. TLC indicated starting material was consumed completely and one new spot formed. The reaction mixture was filtered and the filtrate was concentrated. The residue was diluted with $H_2O$ (100 mL) and extracted with DCM (40 mL*3). The combined organic phase was dried over Na₂SO₄, filtered and concentrated under reduced pressure to give the product as a white solid (800 mg, 2.91 mmol, 88.7% yield), which was used directly for next step.

Preparation of Methyl 2-(chloromethyl)-1-((1-ethyl-1H-1,2,3-triazol-5-yl)methyl)-1H-benzo[d]imidazole-6-carboxylate (3)

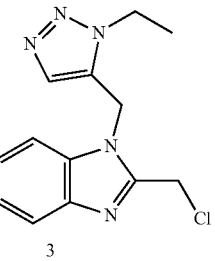

A mixture of methyl 4-amino-3-(((1-ethyl-1H-1,2,3-triazol-5-yl)methyl)amino)benzoate (300 mg, 1.09 mmol, 1 eq), 2-chloroacetyl chloride (110.77 mg, 980.73 μmol, 78.00 μL, 0.9 eq) and TosOH (37.53 mg, 217.94 μmol, 0.2 eq) in CH₃CN (5 mL) was stirred at 60° C. for 1 h under N₂ atmosphere. LCMS showed starting material was consumed completely and desired mass was detected. The reaction mixture was concentrated under reduced pressure to provide product as a brown solid (360 mg, 1.08 mmol, 99% yield), which was used directly in the next step; LCMS: RT=0.697 min, MS cal.: 333.8, [M+H]⁺=334.2

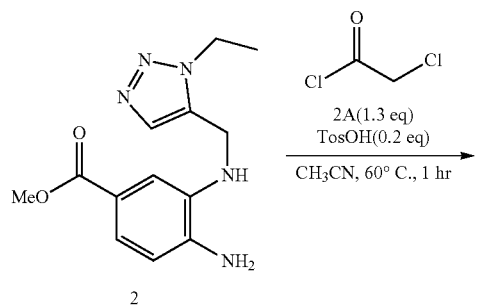

Preparation of Methyl 2-((5-(6-((4-cyano-2-fluorobenzyl)oxy)pyridin-2-yl)-2,5-diazabicyclo[4.1.0]heptan-2-yl)methyl)-1-((1-ethyl-1H-1,2,3-triazol-5-yl)methyl)-1H-benzo[d]imidazole-6-carboxylate (4A and 4B)

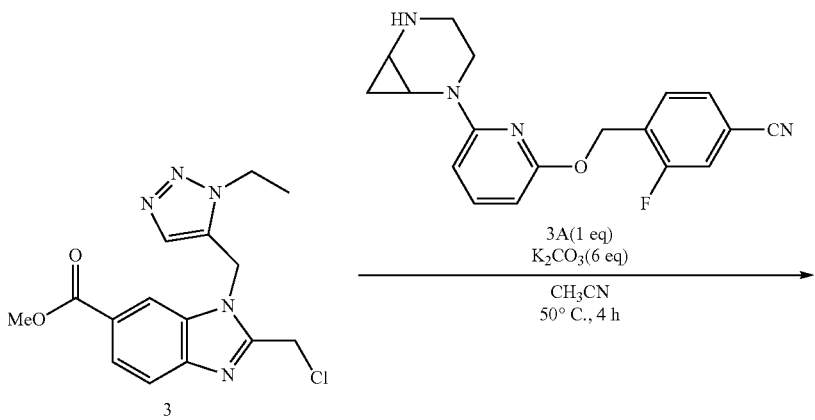

-continued

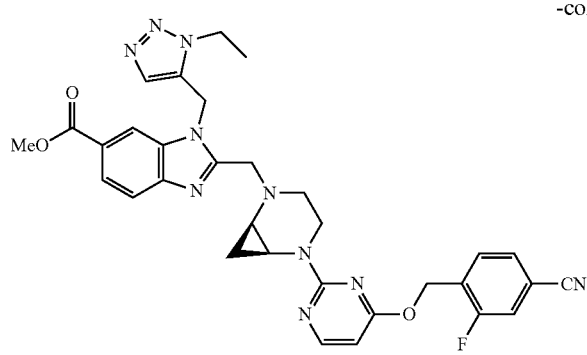 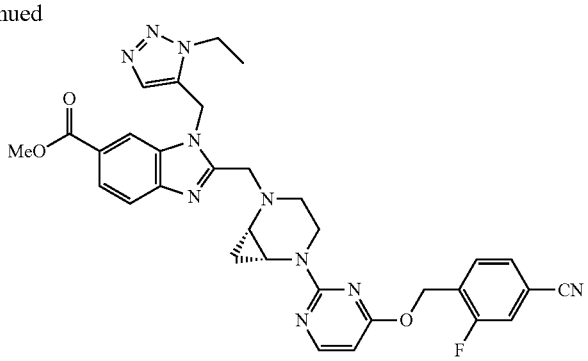

4A/4B

To a solution of methyl 2-(chloromethyl)-1-((1-ethyl-1H-1,2,3-triazol-5-yl)methyl)-1H-benzo[d]imidazole-6-carboxylate (320 mg, 958.74 μmol, 1 eq) and 4-(((6-(2,5-diazabicyclo[4.1.0]heptan-2-yl)pyridin-2-yl)oxy)methyl)-3-fluorobenzonitrile (311 mg, 959 μmol, 1 eq) in $CH_3CN$ (5 mL) was added $K_2CO_3$ (398 mg, 2.88 mmol, 3 eq). The mixture was stirred at 50° C. for 4 h. LCMS showed starting material was consumed completely and the desired mass was detected. The reaction mixture was diluted with $H_2O$ (20 mL) and extracted with EtOAc (20 mL*3). The combined organic layers were washed with brine (20 mL), dried over $Na_2SO_4$, filtered and concentrated under reduced pressure to give a residue, which was purified by column chromatography ($SiO_2$, Dichloromethane: Methanol=100/1 to 10/1) to provide product as a yellow solid (405 mg, 651 μmol, 68% yield); LCMS: RT=2.439 min, MS cal.: 621.7, $[M+H]^+$=622.3.

Product (400 mg) was further separated by SFC (condition, column: DAICEL CHIRALPAK AD (250 mm*30 mm, 10 um); mobile phase: [0.1% $NH_3H_2O$ MEOH]; B %: 60%-60%, 20 min) to provide intermediate 4A-isomer 1 as a yellow solid (150 mg, 241 μmol, 35% yield); LCMS: RT=2.448 min, MS cal.: 621.7, $[M+H]^+$=622.3; SFC: RT=1.678 min, ee %: 100%; $^1$H NMR (400 MHz, CHLOROFORM-d) δ=8.04 (d, J=8.0 Hz, 1H), 8.03 (s, 1H), 7.82 (d, J=9.2 Hz, 1H), 7.60 (t, J=7.6 Hz, 1H), 7.49-7.41 (m, 2H), 7.34 (d, J=9.2 Hz, 1H), 7.23 (s, 1H), 6.28 (d, J=8.0 Hz, 1H), 6.15 (d, J=8.0 Hz, 1H), 5.74 (s, 2H), 5.47 (d, J=14 Hz, 1H), 5.42 (d, J=14 Hz, 1H), 4.40 (q, J=7.2 Hz, 2H), 4.09-3.97 (m, 3H), 3.95 (s, 3H), 2.92-2.83 (m, 1H), 2.75-2.61 (m, 2H), 2.57-2.49 (m, 1H), 2.38-2.29 (m, 1H), 1.56-1.43 (t, J=7.2 Hz, 3H), 0.76-0.73 (m, 1H), 0.53-0.47 (m, 1H) and intermediate 4B-isomer 2 as a yellow solid (154 mg, 248 μmol, 36% yield); LCMS: RT=2.454 min, MS cal.: 621.7, $[M+H]^+$=622.3; SFC: RT=2.220 min, ee %: 100%; $^1$H NMR (400 MHz, CHLOROFORM-d) δ=8.07-8.02 (m, 2H), 7.83 (d, J=9.2 Hz, 1H), 7.61 (t, J=7.2 Hz, 1H), 7.49-7.41 (m, 2H), 7.34 (d, J=9.2 Hz, 1H), 7.24 (s, 1H), 6.28 (d, J=8.0 Hz, 1H), 6.16 (d, J=8.0 Hz, 1H), 5.74 (s, 2H), 5.46 (d, J=14 Hz, 1H), 5.38 (d, J=14 Hz, 1H), 4.40 (q, J=7.2 Hz, 2H), 4.11-4.01 (m, 2H), 4.00-3.95 (m, 1H), 3.95 (s, 3H), 2.93-2.83 (m, 1H), 2.76-2.61 (m, 2H), 2.53 (m, 1H), 2.35 (m, 1H), 1.50 (t, J=7.2 Hz, 3H), 0.76 (m, 1H), 0.51 (m, 1H).

Example 14 (Synthesis of Compound 45)

2-((5-(6-((4-Cyano-2-fluorobenzyl)oxy)pyridin-2-yl)-2,5-diazabicyclo[4.1.0]heptan-2-yl)methyl)-1-((1-ethyl-1H-1,2,3-triazol-5-yl)methyl)-1H-benzo[d]imidazole-6-carboxylic Acid

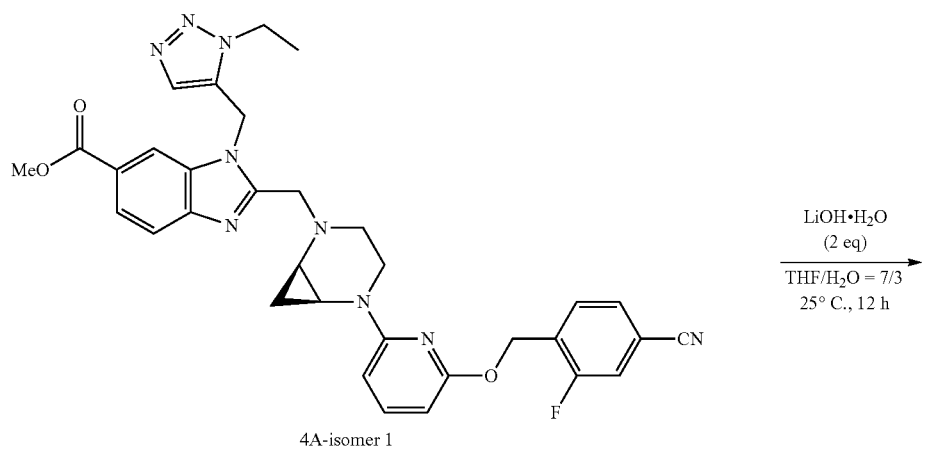

4A-isomer 1

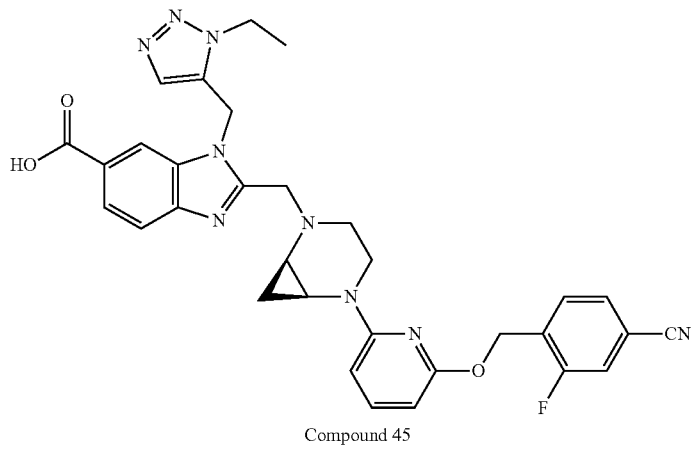

Compound 45

To a solution of methyl 2-((5-(6-((4-cyano-2-fluorobenzyl)oxy)pyridin-2-yl)-2,5-diazabicyclo[4.1.0]heptan-2-yl)methyl)-1-((1-ethyl-1H-1,2,3-triazol-5-yl)methyl)-1H-benzo[d]imidazole-6-carboxylate (80 mg, 129 μmol, 1 eq) in THF (0.7 mL) was added LiOH·H$_2$O (10.8 mg, 257 μmol, 2 eq) in H$_2$O (0.3 mL). The mixture was stirred at 25° C. for 12 h. LCMS showed starting material was consumed completely and one main peak with desired mass was detected. The reaction solution was adjusted with citric acid to pH 6-7. After concentration of the reagent, the residue was purified by prep-HPLC (neutral condition, column: Waters Xbridge Prep OBD C18 150*40 mm*10 μm; mobile phase: [water (NH$_4$HCO$_3$)-ACN]; B %: 20%-60%, 8 min) to provide product as a white solid (43.93 mg, 72.30 umol, 56.18% yield); LCMS: RT=2.491 min, MS cal.: 607.7, [M+H]$^+$=608.1; SFC: RT=1.476 min, ee %: 100%; HPLC: RT=11.507 min, purity: 98.57%; $^1$H NMR (400 MHz, METHANOL-d4) δ=8.17 (s, 1H), 8.03 (d, J=8.4 Hz, 1H), 7.75 (d, J=8.4 Hz, 1H), 7.62 (t, J=7.2 Hz, 1H), 7.56-7.50 (m, 2H), 7.44 (t, J=8 Hz, 1H), 7.20 (s, 1H), 6.30 (d, J=8.0 Hz, 1H), 6.09 (d, J=8.0 Hz, 1H), 5.94 (s, 2H), 5.41 (s, 2H), 4.52 (q, J=7.2 Hz, 2H), 4.20 (d, J=14.0 Hz, 1H), 4.01 (m, 2H), 2.71-2.54 (m, 4H), 2.29-2.22 (m, 1H), 1.50 (t, J=7.2 Hz, 3H), 0.69 (m, 1H), 0.46-0.41 (m, 1H).

Example 15 (Synthesis of Compound 44)

2-((5-(6-((4-Cyano-2-fluorobenzyl)oxy)pyridin-2-yl)-2,5-diazabicyclo[4.1.0]heptan-2-yl)methyl)-1-((1-ethyl-1H-1,2,3-triazol-5-yl)methyl)-1H-benzo[d]imidazole-6-carboxylic Acid

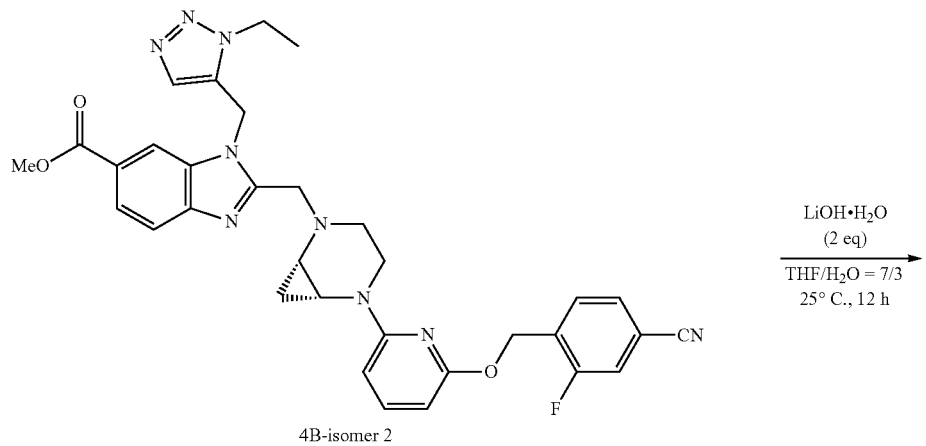

4B-isomer 2

LiOH·H$_2$O
(2 eq)
THF/H$_2$O = 7/3
25° C., 12 h

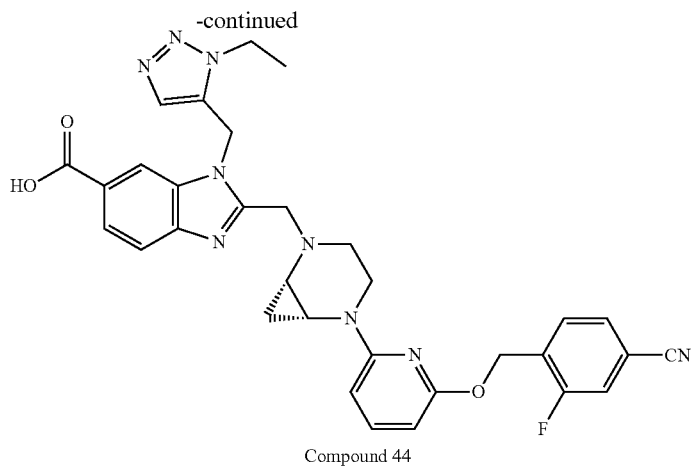

Compound 44

A mixture of methyl 2-((5-(6-(((4-cyano-2-fluorobenzyl)oxy)pyridin-2-yl)-2,5-diazabicyclo[4.1.0]heptan-2-yl)methyl)-1-((1-ethyl-1H-1,2,3-triazol-5-yl)methyl)-1H-benzo[d]imidazole-6-carboxylate (80 mg, 129 μmol, 1 eq) and LiOH·H$_2$O (10.8 mg, 257 μmol, 2 eq) in THF (0.7 mL) and H$_2$O (0.3 mL) was stirred at 25° C. for 12 h under N$_2$ atmosphere. LCMS showed starting material was consumed completely and one main peak with desired mass was detected. The reaction solution was adjusted with citric acid to pH 6-7. After concentration of the reagent, the residue was purified by prep-HPLC (neutral condition; column: Waters Xbridge Prep OBD C18 150*40 mm*10 μm; mobile phase: [water (NH$_4$HCO$_3$)-ACN]; B %: 25%-55%, 8 min) to provide product as a white solid (26.9 mg, 44.3 μmol, 34% yield); LCMS: RT=2.491 min, MS cal.: 607.7, [M+H]$^+$=608.1; SFC: RT=1.530 min, ee %: 100%; HPLC: RT=11.539 min, purity: 98.67%; $^1$H NMR (400 MHz, METHANOL-d$_4$) δ=8.15 (s, 1H) 8.03 (d, J=8.4 Hz, 1H) 7.76 (d, J=8.4 Hz, 1H) 7.59-7.65 (m, 1H) 7.51-7.55 (m, 2H) 7.44 (t, J=8.0 Hz, 1H) 7.20 (s, 1H) 6.30 (d, J=8.0 Hz, 1H) 6.10 (d, J=8.0 Hz, 1H) 5.93 (s, 2H) 5.41 (s, 2H) 4.52 (q, J=7.2 Hz, 2H) 4.20 (d, J=14 Hz, 1H) 3.95-4.05 (m, 2H) 2.66-2.73 (m, 1H) 2.54-2.65 (m, 3H) 2.26 (m, 1H) 1.50 (t, J=7.2 Hz, 3H) 0.69 (m, 1H) 0.44 (m, 1H).

Intermediates for Examples 16-17

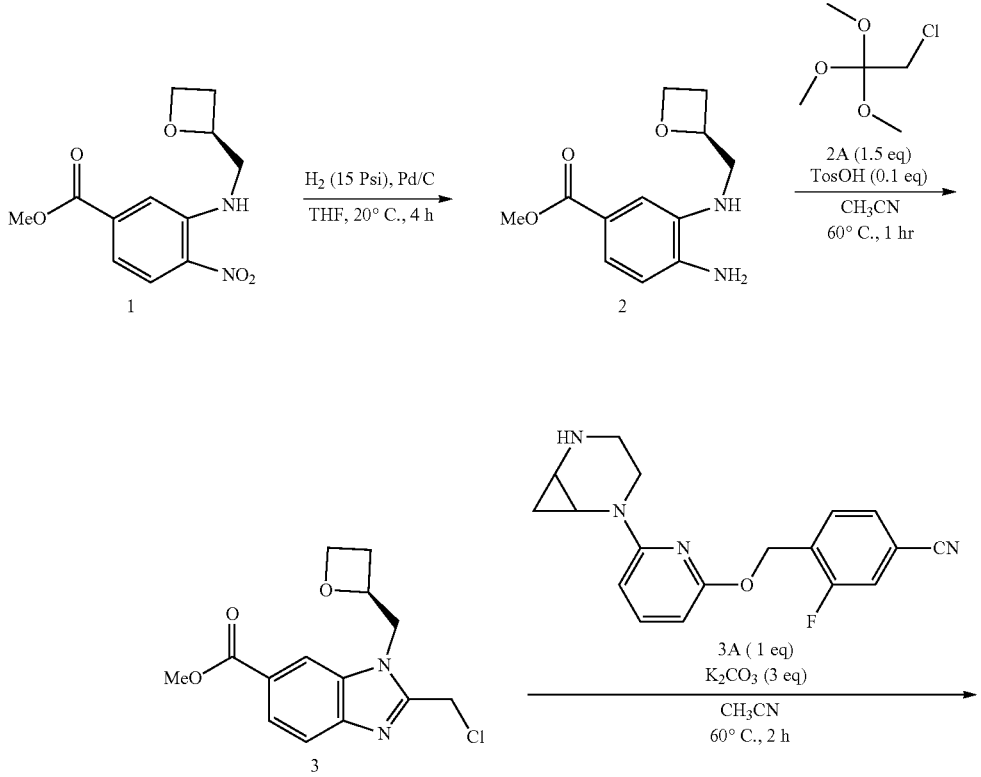

-continued

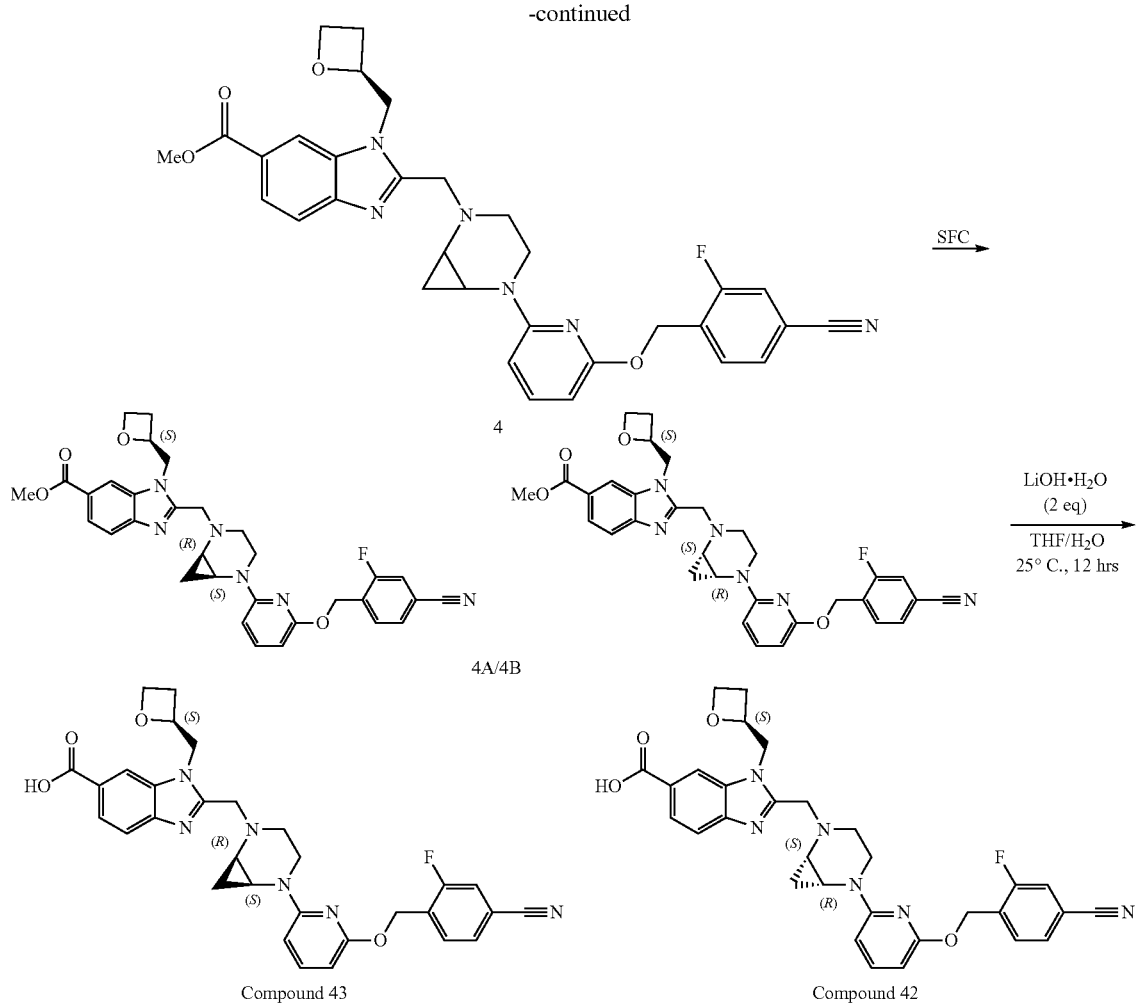

Compound 43

Compound 42

Preparation of Methyl (S)-4-amino-3-((oxetan-2-ylmethyl)amino)benzoate (2)

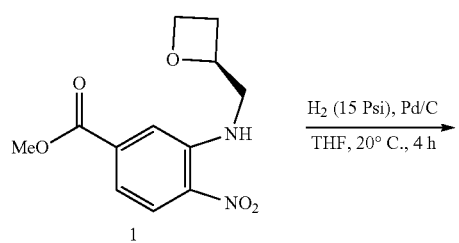

To a solution of methyl (S)-4-nitro-3-((oxetan-2-ylmethyl)amino)benzoate (0.5 g, 1.88 mmol, 1 eq) in THF (10 mL) was added Pd/C (0.1 g, 751 umol, 10% purity) under $N_2$ atmosphere. The suspension was degassed and purged with $H_2$ for 3 times. The mixture was stirred under $H_2$ (15 Psi) at 20° C. for 4 h. TLC indicated starting material was consumed completely and one new spot formed. The reaction mixture was filtered and the filtrate was concentrated under reduced pressure to provide product as a colorless oil (400 mg, 1.69 mmol, 90.2% yield).

Preparation of Methyl (S)-2-(chloromethyl)-1-(oxetan-2-ylmethyl)-1H-benzo[d]imidazole-6-carboxylate (3)

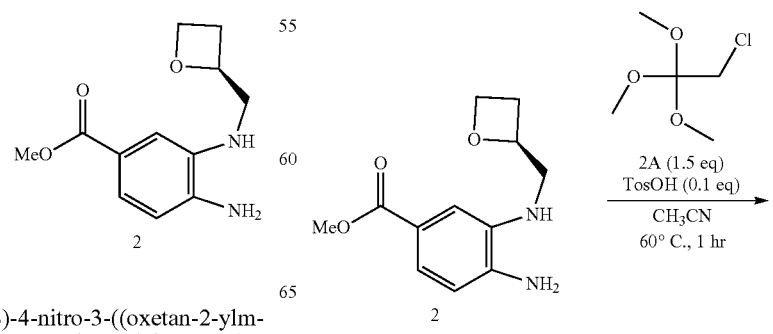

-continued

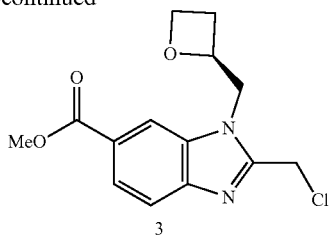

To a solution of methyl (S)-4-amino-3-((oxetan-2-ylmethyl)amino)benzoate (0.3 g, 1.27 mmol, 1 eq) in CH₃CN (3 mL) was added TosOH (21.9 mg, 127 μmol, 0.1 eq) and 2-chloro-1,1,1-trimethoxyethane (206 mg, 1.33 mmol, 179 μL, 1.05 eq). The mixture was stirred at 60° C. for 2 h. TLC showed starting material was consumed completely. The reaction mixture was concentrated under reduced pressure to provide product as a white solid (370 mg, 1.26 mmol, 99% yield); LCMS: RT=0.555 min, MS cal.: 294.74, [M+H]⁺=295.9; ¹H NMR (400 MHz, CHLOROFORM-d) δ=8.15 (s, 1H) 8.03 (d, J=8.4 Hz, 1H) 7.81-7.85 (d, J=8.4 Hz, 1H) 5.22 (m, 1H) 5.08 (s, 2H) 4.68-4.51 (m, 3H) 4.35 (m, Hz, 1H) 3.97 (s, 3H) 2.83-2.72 (m, 1H) 2.50-2.39 (m, 1H).

Preparation of Methyl 2-((5-(6-((4-cyano-2-fluorobenzyl)oxy)pyridin-2-yl)-2,5-diazabicyclo[4.1.0]heptan-2-yl)methyl)-1-(((S)-oxetan-2-yl)methyl)-1H-benzo[d]imidazole-6-carboxylate (4A and 4B)

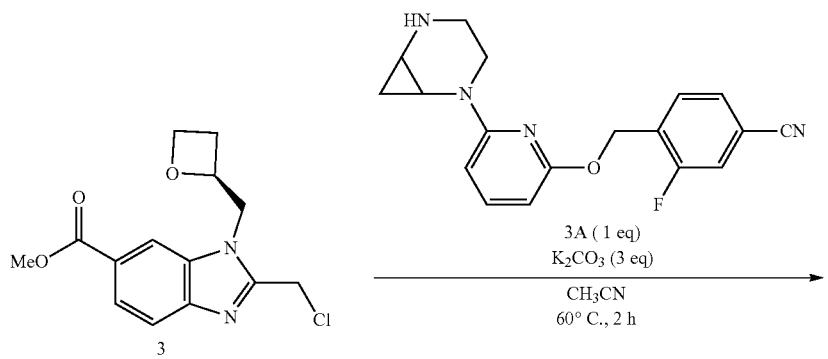

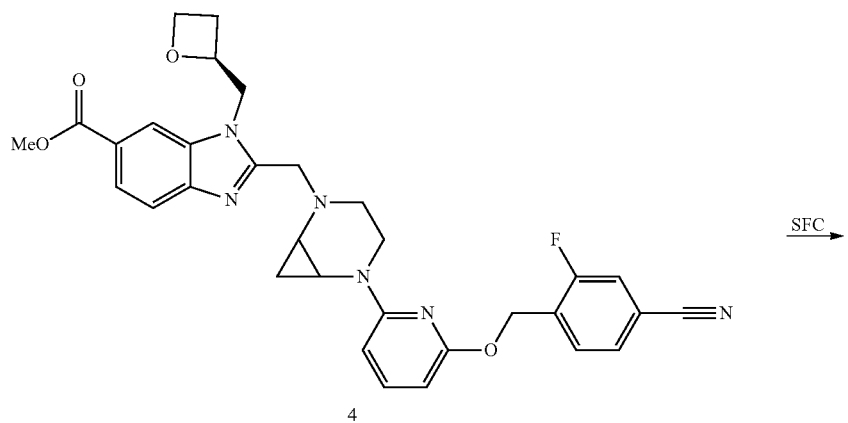

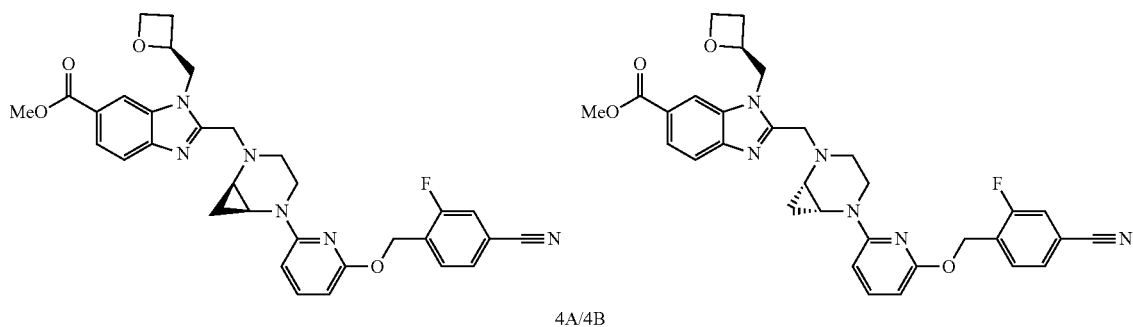

4A/4B

To a solution of methyl (S)-2-(chloromethyl)-1-(oxetan-2-ylmethyl)-1H-benzo[d]imidazole-6-carboxylate (0.37 g, 1.26 mmol, 1 eq) in ACN (10 mL) was added $K_2CO_3$ (522 mg, 3.78 mmol, 3 eq) and 4-(((6-(2,5-diazabicyclo[4.1.0]heptan-2-yl)pyridin-2-yl)oxy)methyl)-3-fluorobenzonitrile (409 mg, 1.26 mmol, 1 eq). The mixture was stirred at 60° C. for 2 h. LC-MS showed starting material was consumed completely and desired mass was detected. The residue was diluted with $H_2O$ 30 mL and extracted with EtOAc 30 mL (30 mL*3). The combined organic layers were dried over $Na_2SO_4$, filtered and concentrated under reduced pressure to give a residue. The residue was purified by column chromatography ($SiO_2$, Petroleum ether/Ethyl acetate=10/1 to 0/1) followed by SFC (column: DAICEL CHIRALPAK AD (250 mm*30 mm, 10 um); mobile phase: [0.1% $NH_3H_2O$ MEOH]; B %: 50%-50%, 40 min) to provide products 4A-isomer 1 as a white solid (180 mg, 309 μmol, 36% yield) and 4B-isomer 2 as a white solid (180 mg, 309 μmol, 36% yield); LCMS: RT=2.587 min, MS cal.: 582.64, $[M+H]^+$=583.2

Example 16 (Synthesis of Compound 43)

2-((5-(6-((4-Cyano-2-fluorobenzyl)oxy)pyridin-2-yl)-2,5-diazabicyclo[4.1.0]heptan-2-yl)methyl)-1-(((S)-oxetan-2-yl)methyl)-1H-benzo[d]imidazole-6-carboxylic Acid

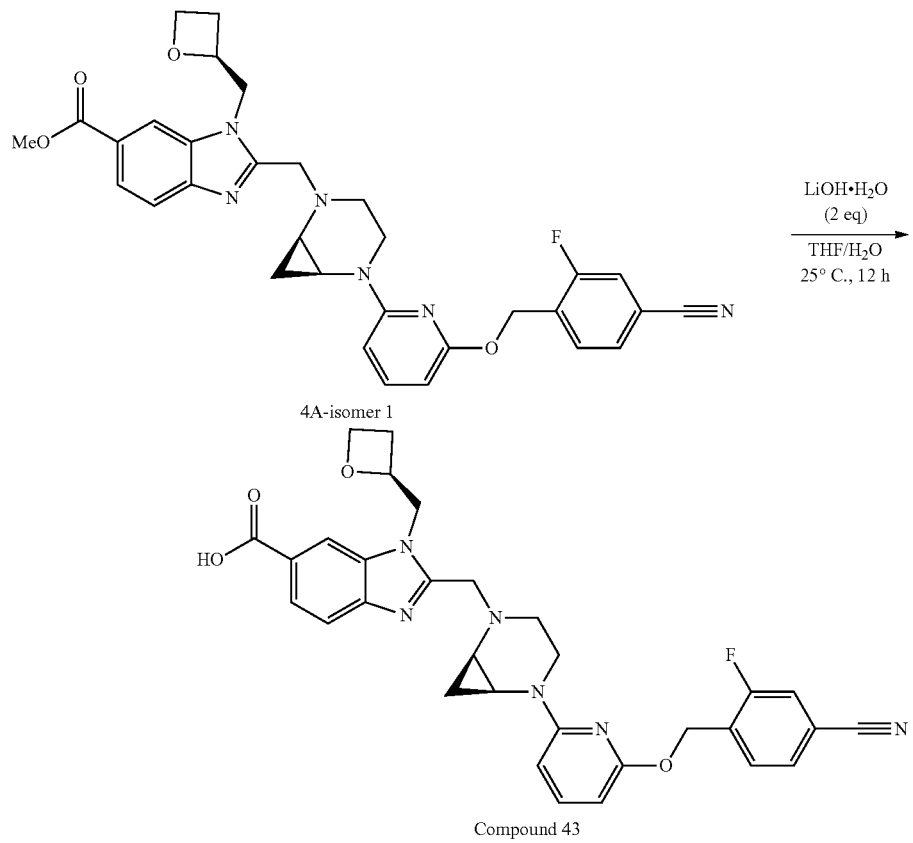

4A-isomer 1

Compound 43

To a solution of 4A-isomer 1 (100 mg, 172 umol, 1 eq) in THF (0.6 mL) was added $LiOH \cdot H_2O$ (14.4 mg, 343 umol, 2 eq) in $H_2O$ (0.2 mL). The mixture was stirred at 20° C. for 12 h. TLC indicated starting material was consumed completely and one new spot formed. The mixture was purified by prep-HPLC (neutral condition; column: Waters Xbridge Prep OBD C18 150*40 mm*10 μm; mobile phase: [water ($NH_4HCO_3$)-ACN]; B %: 20%-60%, 8 min) to provide product as a white solid (53 mg, 93.2 μmol, 54.3% yield); LCMS: RT=2.368 min, MS cal.: 568.61, $[M+H]^+$=569.2; HPLC: RT=10.178 min, purity: 99.30%; SFC: RT=1.443 min, ee %: 100%; $^1$H NMR (400 MHz, METHANOL-$d_4$) δ=8.32 (s, 1H) 7.97 (d, J=8.4 Hz, 1H) 7.67 (d, J=8.4 Hz, 1H) 7.65-7.55 (m, 3H) 7.45 (t, J=8.0 Hz, 1H) 6.34 (d, J=8.0 Hz, 1H) 6.10 (d, J=8.0 Hz, 1H) 5.43 (s, 2H) 5.24 (m, 1H) 4.71 (m, 1H) 4.66-4.59 (m, 1H) 4.46 (m, 1H) 4.29 (d, J=13.6 Hz, 1H) 4.15-4.09 (m, 1H) 4.06 (d, J=13.6 Hz, 1H) 3.07-2.97 (m, 1H) 2.84-2.64 (m, 4H) 2.56-2.46 (m, 1H) 2.42-2.33 (m, 1H) 0.74-0.65 (m, 1H) 0.48-0.40 (m, 1H).

Example 17 (Synthesis of Compound 42)

2-((5-(6-((4-cyano-2-fluorobenzyl)oxy)pyridin-2-yl)-2,5-diazabicyclo[4.1.0]heptan-2-yl)methyl)-1-(((S)-oxetan-2-yl)methyl)-1H-benzo[d]imidazole-6-carboxylic Acid

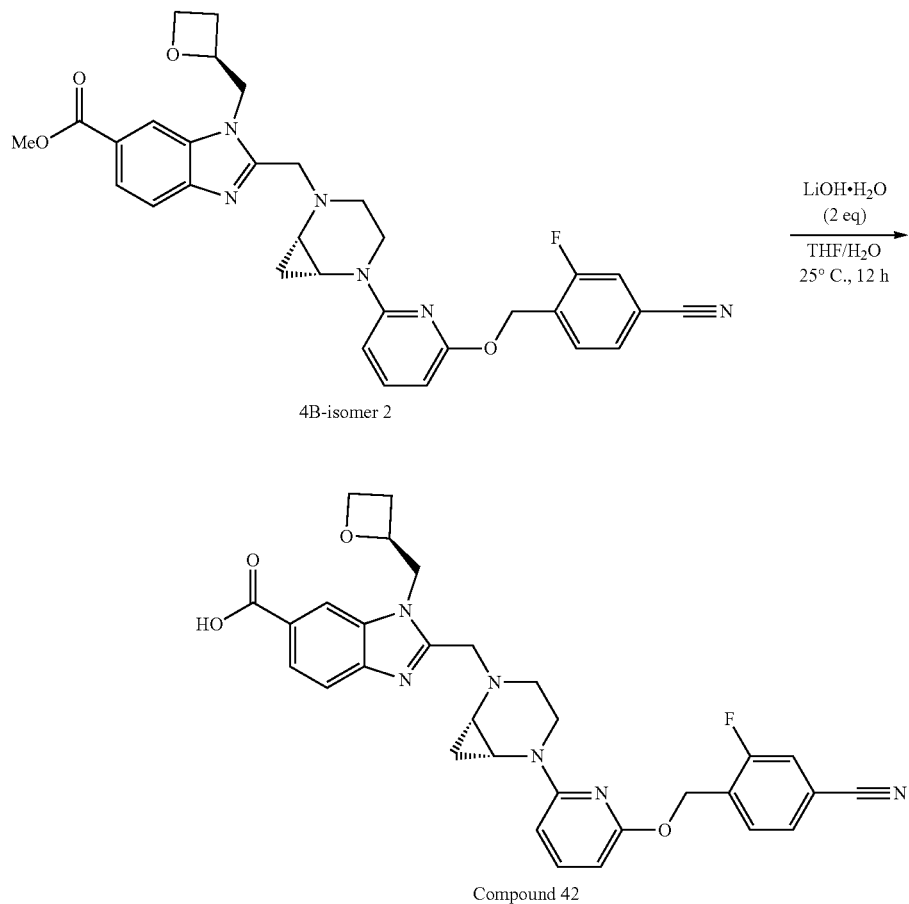

To a solution of 4B-isomer 2 (100 mg, 172 μmol, 1 eq) in THF (1.5 mL) was added LiOH·H$_2$O (14.41 mg, 343 μmol, 2 eq) in H$_2$O (0.3 mL). The mixture was stirred at 25° C. for 12 h. TLC indicated starting material was consumed completely. Adjust the solution to neutral with citric acid and concentrate solution. The residue was purified by prep-HPLC (neutral condition column: Waters Xbridge Prep OBD C18 150*40 mm*10 μm; mobile phase: [water (NH$_4$HCO$_3$)-ACN]; B %: 15%-45%, 8 min) to provide product as a white solid (31.9 mg, 56.0 μmol, 32.6% yield); LCMS: RT=1.824 min, MS cal.: 568.61, [M+H]$^+$=569.2; HPLC: RT=10.196 min, purity: 97.65%; SFC: RT=1.916 min, ee %: 99.14%; $^1$H NMR (400 MHz, METHANOL-d$_4$) δ=8.33 (s, 1H) 8.00 (d, J=8.4 Hz, 1H) 7.71 (d, J=8.4 Hz, 1H) 7.69-7.63 (m, 1H) 7.60-7.53 (m, 2H) 7.48-7.45 (m, 1H) 6.33 (d, J=7.2 Hz, 1H) 6.11 (d, J=7.2 Hz, 1H) 5.43 (s, 2H) 5.27-5.25 (m, 1H) 4.90-4.88 (m, 1H) 4.75-4.73 (m, 1H) 4.64-4.61 (m, 1H) 4.50-4.48 (m, 1H), 4.18 (s, 1H) 4.17-4.15 (m, 1H) 3.10-4.25 (m, 1H) 2.73-2.77 (m, 3H) 2.65-2.62 (m, 1H) 4.50-4.48 (m, 1H) 2.55-2.52 (m, 1H) 2.45-2.49 (m, 1H) 0.74-0.69 (m, 1H) 0.47-0.44 (m, 1H).

Example 18 (Synthesis of Compound 34)
2-((5-(2-(4-Cyano-2-fluorophenyl)-2-methylbenzo[d][1,3]dioxol-4-yl)-2,5-diazabicyclo[4.1.0]heptan-2-yl)methyl)-1-(thiazol-5-ylmethyl)-1H-benzo[d]imidazole-6-carboxylic Acid
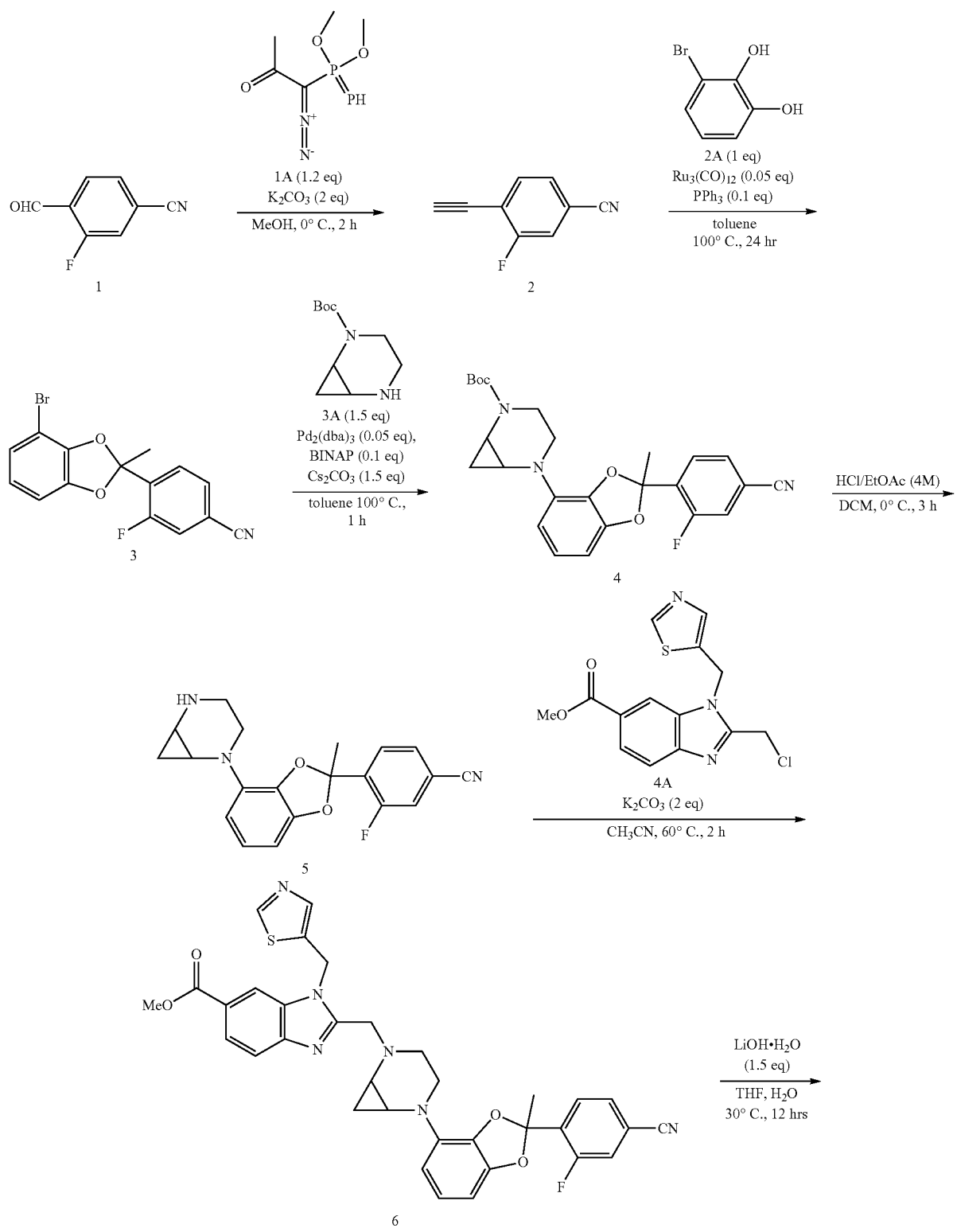

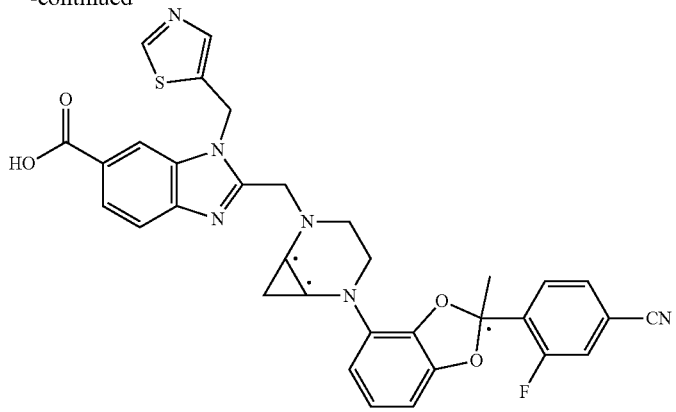

Compound 34 (mixture 4 diastereomers)

Preparation of 4-Ethynyl-3-fluorobenzonitrile (2)

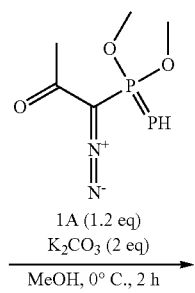

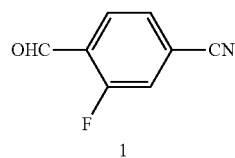

Preparation of 4-(4-Bromo-2-methylbenzo[d][1,3]dioxol-2-yl)-3-fluorobenzonitrile (3)

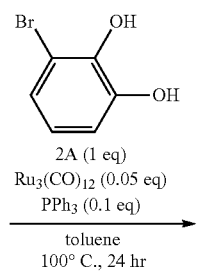

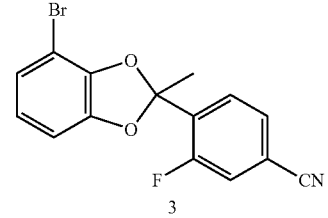

A mixture of 3-fluoro-4-formylbenzonitrile (20 g, 134 mmol, 1 eq), dimethyl (1-diazo-2-oxopropyl)phosphonate (38.6 g, 201 mmol, 1.5 eq) K$_2$CO$_3$ (27.8 g, 201 mmol, 1.5 eq) in MeOH (200 mL) was degassed and purged with N$_2$ for 3 times, and then the mixture was stirred at 0° C. for 2 h under N$_2$ atmosphere. TLC (Petroleum ether/Ethyl acetate=5/1 R$_f$=0.55) indicated starting material was consumed completely. The combined reaction mixture was poured into water (50 mL) and extracted with ethyl acetate (50 mL*2). The combined organic phase was concentrated in vacuo to give a residue. The residue was purified by column chromatography (SiO$_2$, Petroleum ether/Ethyl acetate=100/1 to 0/1) to provide product as a white solid (12 g, 82.7 mmol, 61.7% yield).

A mixture of 4-ethynyl-3-fluorobenzonitrile (15.6 g, 82.7 mmol, 1 eq), 3-bromobenzene-1,2-diol (12 g, 82.7 mmol, 1 eq), PPh$_3$ (2.17 g, 8.27 mmol, 0.1 eq), Ru$_3$ (CO)$_{12}$ (2.64 g, 4.13 mmol, 0.05 eq) in toluene (120 mL) was degassed and purged with N$_2$ for 3 times, and then the mixture was stirred at 100° C. for 24 h under N$_2$ atmosphere. HPLC showed the starting material was consumed completely. The combined reaction mixture was poured into water (100 mL) and extracted with ethyl acetate (50 mL*2). The combined organic phase was concentrated in vacuo to give a residue. The crude product was purified by reversed-phase HPLC (column: Welch Xtimate C18 250*100 mm #10 μm; mobile phase: [water (NH$_4$HCO$_3$)-ACN]; B %: 50%-85%, 20 min to provide product as a black oil (13 g, 38.9 mmol, 47% yield).

Preparation of tert-Butyl 5-(2-(4-cyano-2-fluorophenyl)-2-methylbenzo[d][1,3]dioxol-4-yl)-2,5-diazabicyclo[4.1.0]heptane-2-carboxylate (4)

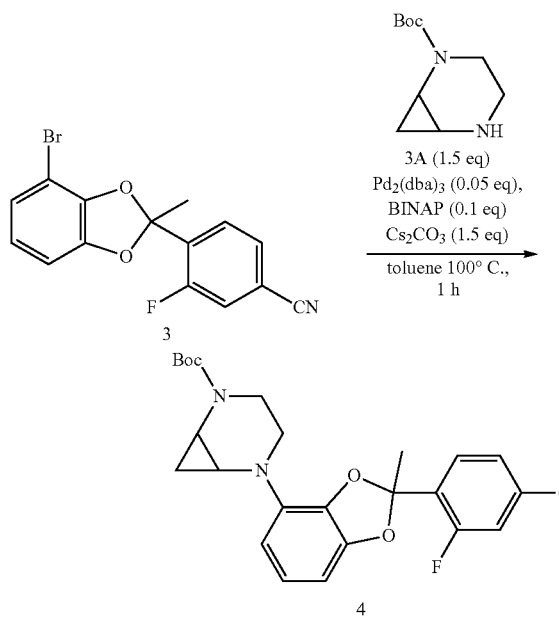

A mixture of tert-butyl 2,5-diazabicyclo[4.1.0]heptane-2-carboxylate (11.1 g, 56.1 mmol, 1.5 eq) 4-(4-bromo-2-methylbenzo[d][1,3]dioxol-2-yl)-3-fluorobenzonitrile (12.5 g, 37.4 mmol, 1 eq) $Cs_2CO_3$ (18.3 g, 56.1 mmol, 1.5 eq) BINAP (2.33 g, 3.74 mmol, 0.1 eq) $Pd_2(dba)_3$ (1.71 g, 1.87 mmol, 0.05 eq) in toluene (120 mL) was degassed and purged with $N_2$ for 3 times, and then the mixture was stirred at 100° C. for 1 h under $N_2$ atmosphere. LCMS showed the starting material was consumed completely. TLC (Petroleum ether/Ethyl acetate=3:1 $R_f$=0.4) showed the starting material was consumed completely. The combined reaction mixture was poured into water (100 mL) and extracted with ethyl acetate (50 mL*2). The combined organic phase was concentrated in vacuo to give a residue. The residue was purified by column chromatography ($SiO_2$, Petroleum ether/Ethyl acetate=100/1 to 0/1) to provide product as a yellow solid (5.6 g, 12.4 mmol, 33.2% yield); LCMS: RT=2.670 min, MS cal.: 451.5, [M-55]+=396.1.

Preparation of 4-(4-(2,5-Diazabicyclo[4.1.0]heptan-2-yl)-2-methylbenzo[d][1,3]dioxol-2-yl)-3-fluorobenzonitrile (5)

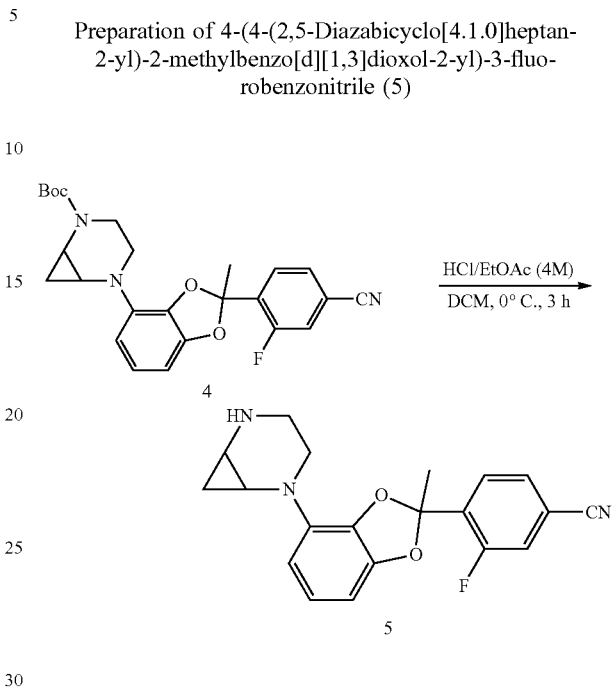

A mixture of tert-butyl 5-(2-(4-cyano-2-fluorophenyl)-2-methylbenzo[d][1,3]dioxol-4-yl)-2,5-diazabicyclo[4.1.0]heptane-2-carboxylate (334 mg, 740 μmol, 1 eq) and HCl/EtOAc (4 M, 1.67 mL, 9.03 eq), in DCM (2 mL) was degassed and purged with $N_2$ for 3 times, and then the mixture was stirred at 25° C. for 1 h under $N_2$ atmosphere. LCMS showed the starting material was consumed completely. The reaction mixture was concentrated to give the crude product as a white solid (260 mg, crude); LCMS: RT=0.579 min, MS cal.: 351.3, [M+H]+=352.1.

Preparation of Methyl 2-((5-(2-(4-cyano-2-fluorophenyl)-2-methylbenzo[d][1,3]dioxol-4-yl)-2,5-diazabicyclo[4.1.0]heptan-2-yl)methyl)-1-(thiazol-5-ylmethyl)-1H-benzo[d]imidazole-6-carboxylate (6)

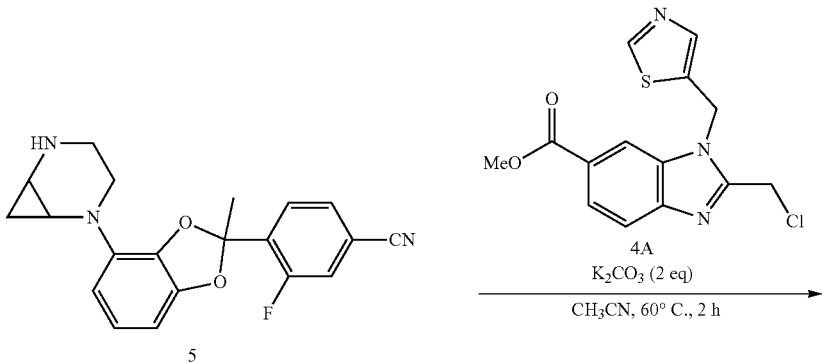

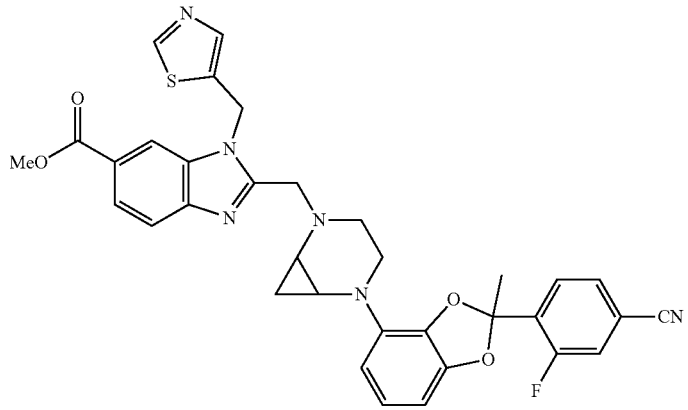

6

A mixture of 4-(4-(2,5-diazabicyclo[4.1.0]heptan-2-yl)-2-methylbenzo[d][1,3]dioxol-2-yl)-3-fluorobenzonitrile (238 mg, 740 μmol, 1 eq), methyl 2-(chloromethyl)-1-(thiazol-5-ylmethyl)-1H-benzo[d]imidazole-6-carboxylate (260 mg, 740 μmol, 1 eq), $K_2CO_3$ (307 mg, 2.22 mmol, 3 eq) in ACN (5 mL) was degassed and purged with $N_2$ for 3 times, and then the mixture was stirred at 60° C. for 2 h under $N_2$ atmosphere. LCMS showed the starting material was consumed completely. The combined reaction mixture was poured into water (20 mL) and extracted with ethyl acetate (50 mL*2). The combined organic phase was concentrated in vacuo to give a residue. The residue was purified by column chromatography ($SiO_2$, Petroleum ether/Ethyl acetate=100/1 to 0/1) to provide product as a white solid (330 mg, 518 μmol, 70% yield); LCMS: RT=0.754 min, MS cal.: 636.70, [M+H]$^+$=637.1; $^1$H NMR (400 MHz, CHLOROFORM-d) δ=8.76 (s, 1H) 8.15 (s, 1H) 8.15-8.05 (d, J=8.4 Hz, 1H) 7.91 (s, 1H) 7.81-7.66 (m, 2H) 7.47-7.42 (m, 1H) 7.41-7.34 (m, 1H) 6.77 (m, 1H) 6.49 (m, 1H) 6.40 (m, 1H) 5.95 (m, 2H) 4.19-4.08 (m, 1H) 4.06-4.00 (m, 1H) 3.99-3.92 (m, 3H) 3.86-3.66 (m, 1H) 3.44-3.30 (m, 1H) 2.96-2.83 (m, 2H) 2.65-2.42 (m, 2H) 2.01 (s, 3H) 0.59-0.78 (m, 2H).

Preparation of 2-((5-(2-(4-Cyano-2-fluorophenyl)-2-methylbenzo[d][1,3]dioxol-4-yl)-2,5-diazabicyclo[4.1.0]heptan-2-yl)methyl)-1-(thiazol-5-ylmethyl)-1H-benzo[d]imidazole-6-carboxylic Acid
(Compound 34)

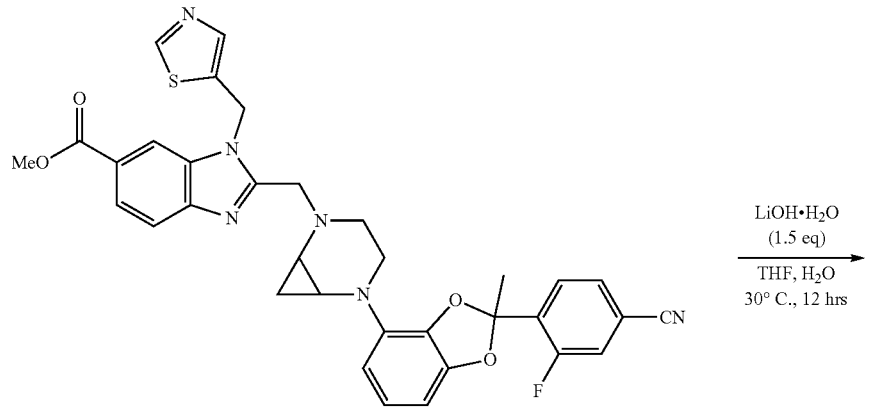

6

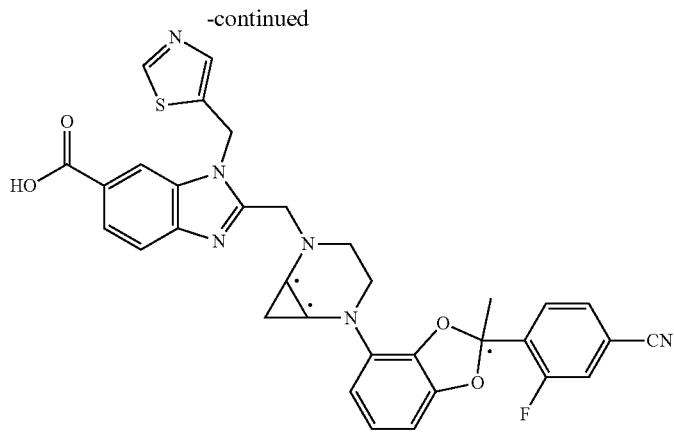

Compound 34 (mixture 4 diastereomers)

A mixture of methyl 2-((5-(2-(4-cyano-2-fluorophenyl)-2-methylbenzo[d][1,3]dioxol-4-yl)-2,5-diazabicyclo[4.1.0]heptan-2-yl)methyl)-1-(thiazol-5-ylmethyl)-1H-benzo[d]imidazole-6-carboxylate (330 mg, 518 μmol, 1 eq), LiOH·H$_2$O (30.5 mg, 726 μmol, 1.4 eq) in THF (2.8 mL) H$_2$O (1.2 mL) was degassed and purged with N$_2$ for 3 times, and then the mixture was stirred at 25° C. for 12 h under N$_2$ atmosphere. LCMS showed the starting material was consumed completely. The reaction mixture was filtered and the filter was concentrated. The crude product was purified by reversed-phase HPLC (column: Waters Xbridge Prep OBD C18 150*40 mm*10 um; mobile phase: [water (NH$_4$HCO$_3$)-ACN]; B %: 25%-55%, 8 min) to provide product as a white solid (25.3 mg, 37.3 μmol, 7.2% yield, 92% purity); LCMS: RT=1.882 min, MS cal.: 622.8, [M+H]$^+$=623.2; HPLC: RT=11.63 min, purity: 91.76%; $^1$H NMR (400 MHz, METHANOL-d$_4$) δ=8.94 (d, J=9.6 Hz, 1H) 8.26 (s, 1H) 8.06 (s, 1H) 8.01-7.97 (m, 1H) 7.80-7.67 (m, 2H) 7.64-7.53 (m, 2H) 6.69-6.77 (m, 1H) 6.50 (m, 1H) 6.31-6.36 (m, 1H) 5.99 (s, 2H) 4.24-4.14 (m, 1H) 4.13-4.03 (m, 1H) 3.80-3.71 (m, 1H) 3.29-3.23 (m, 1H) 2.95-2.74 (m, 2H) 2.67-2.43 (m, 2H) 2.05 (s, 3H) 0.74-0.50 (m, 2H).

Intermediates for Examples 19-22

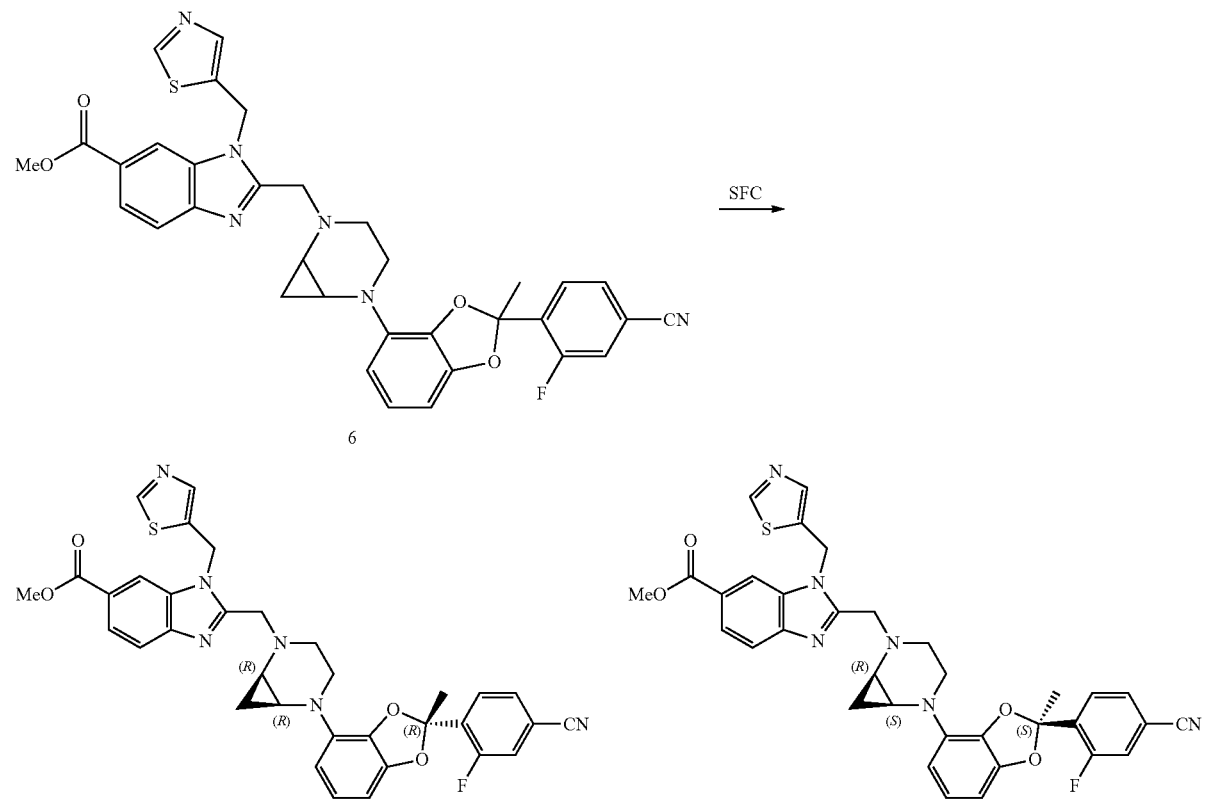

211

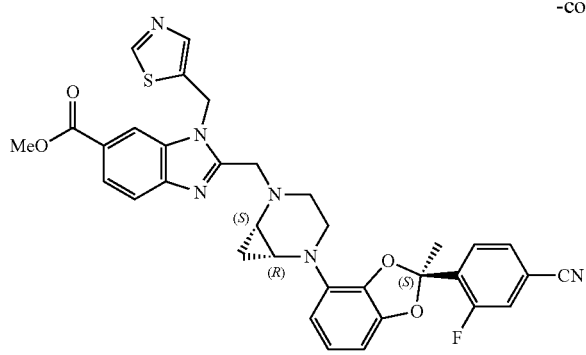

212

-continued

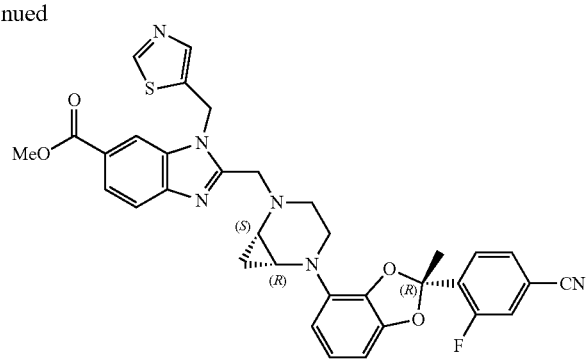

6A/6B/6C/6D

Example 19 (Synthesis of Compound 37)

2-((5-(2-(4-Cyano-2-fluorophenyl)-2-methylbenzo[d][1,3]dioxol-4-yl)-2,5-diazabicyclo[4.1.0]heptan-2-yl)methyl)-1-(thiazol-5-ylmethyl)-1H-benzo[d]imidazole-6-carboxylic Acid

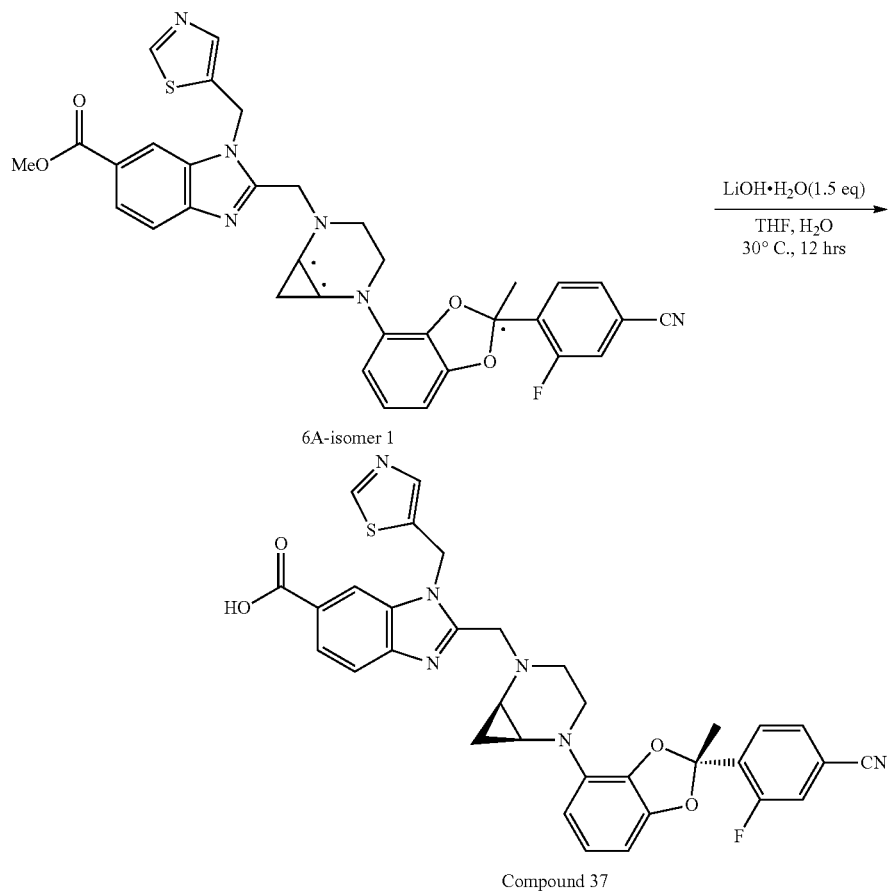

A mixture of methyl 2-((5-(2-(4-cyano-2-fluorophenyl)-2-methylbenzo[d][1,3]dioxol-4-yl)-2,5-diazabicyclo[4.1.0]heptan-2-yl)methyl)-1-(thiazol-5-ylmethyl)-1H-benzo[d]imidazole-6-carboxylate (90 mg, 141 μmol, 1 eq), LiOH·H$_2$O (8.90 mg, 212 μmol, 1.5 eq) in THF (0.7 mL) H$_2$O (0.3 mL) was degassed and purged with N$_2$ for 3 times, and then the mixture was stirred at 30° C. for 12 h under N$_2$ atmosphere. LCMS showed the starting material was consumed completely. The reaction mixture was filtered and the filter was concentrated. The crude product was purified by reversed-phase HPLC (column: Waters Xbridge Prep OBD C18 150*40 mm*10 um; mobile phase: [water (NH$_4$HCO$_3$)-ACN]; B %: 30%-60%, 8 min) to provide product as a white solid (21.2 mg, 34.1 μmol, 24.1% yield); LCMS: RT=1.733 min, MS cal.: 622.68, [M+H]$^+$=623.2; HPLC: RT=11.744 min, purity: 94.48%; SFC: RT=5.660 min, purity: 100.00%; $^1$H NMR (400 MHz, METHANOL-d4) δ=8.97 (s, 1H) 8.27 (s Hz, 1H) 8.06 (s, 1H) 7.99 (d, J=8.4 Hz, 1H) 7.78 (t, J=7.6 Hz, 1H) 7.70 (d, J=8.4 Hz, 1H) 7.66-7.54 (m, 2H) 6.69-6.78 (m, 1H) 6.52-6.48 (m, 1H) 6.36-6.33 (m, 1H) 5.99 (s, 2H) 4.22-4.16 (m, 1H) 4.12-4.07 (m, 1H) 3.80-3.73 (m, 1H) 3.29-3.24 (m, 1H) 2.91 (m, 1H) 2.80 (m, 1H) 2.64-2.50 (m, 2H) 2.03 (s, 3H) 0.63-0.55 (m, 2H).

Example 20 (Synthesis of Compound 38)

2-((5-(2-(4-Cyano-2-fluorophenyl)-2-methylbenzo[d][1,3]dioxol-4-yl)-2,5-diazabicyclo[4.1.0]heptan-2-yl)methyl)-1-(thiazol-5-ylmethyl)-1H-benzo[d]imidazole-6-carboxylic Acid

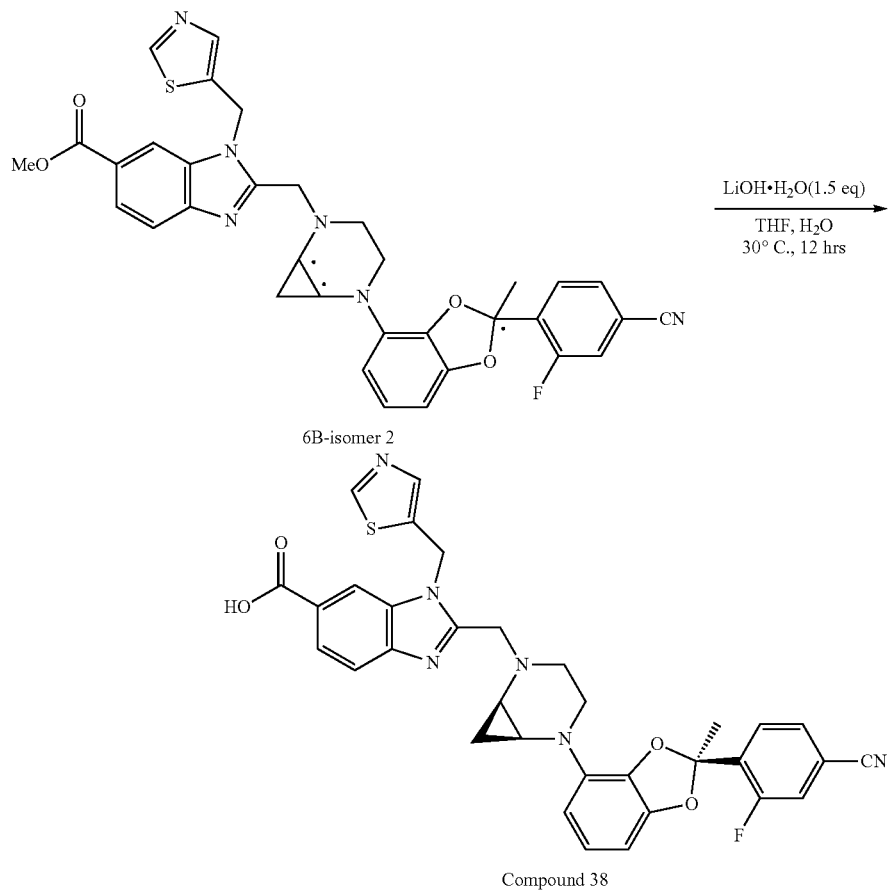

A mixture of methyl 2-((5-(2-(4-cyano-2-fluorophenyl)-2-methylbenzo[d][1,3]dioxol-4-yl)-2,5-diazabicyclo[4.1.0]heptan-2-yl)methyl)-1-(thiazol-5-ylmethyl)-1H-benzo[d]imidazole-6-carboxylate (50 mg, 78.5 μmol, 1 eq), LiOH·H$_2$O (4.94 mg, 118 μmol, 1.5 eq) in H2O (0.1 mL) THF (0.4 mL) was degassed and purged with N$_2$ for 3 times, and then the mixture was stirred at 30° C. for 12 h under N$_2$ atmosphere. 71% of desired compound was detected by LC-MS. Adjust the solution to neutral with citric acid and concentrate solution. The residue was purified by prep-HPLC (neutral condition column: Waters Xbridge Prep OBD C18 150*40 mm*10 um; mobile phase: [water (NH$_4$HCO$_3$)-ACN]; B %: 30%-60%, 8 min) to provide product as a white solid (17.5 mg, 28.1 umol, 35.7% yield); LCMS: RT=1.722 min, MS cal.: 622.68, [M+H]$^+$=623.2; HPLC: RT=11.691 min, purity: 91.87%; $^1$H NMR (400 MHz, METHANOL-d$_4$) δ=8.93 (s, 1H), 8.27 (s, 1H), 8.06 (s, 1H), 7.99 (d, J=8.4 Hz, 1H), 7.78-7.68 (m, 2H), 7.63-7.54 (m, 2H), 6.77-6.71 (m, 1H), 6.52 (m, 1H), 6.37-6.32 (m, 1H), 5.99 (s, 2H), 4.24-4.16 (d, J=13.6 Hz, 1H), 4.11-4.04 (d, J=13.6 Hz, 1H), 3.79-3.71 (m, 1H), 2.87-2.75 (m, 2H), 2.67-2.60 (m, 1H), 2.48 (m, 1H), 2.02 (s, 3H), 0.72-0.60 (m, 2H).

Example 21 (Synthesis of Compound 36)

2-((5-(2-(4-Cyano-2-fluorophenyl)-2-methylbenzo[d][1,3]dioxol-4-yl)-2,5-diazabicyclo[4.1.0]heptan-2-yl)methyl)-1-(thiazol-5-ylmethyl)-1H-benzo[d]imidazole-6-carboxylic Acid

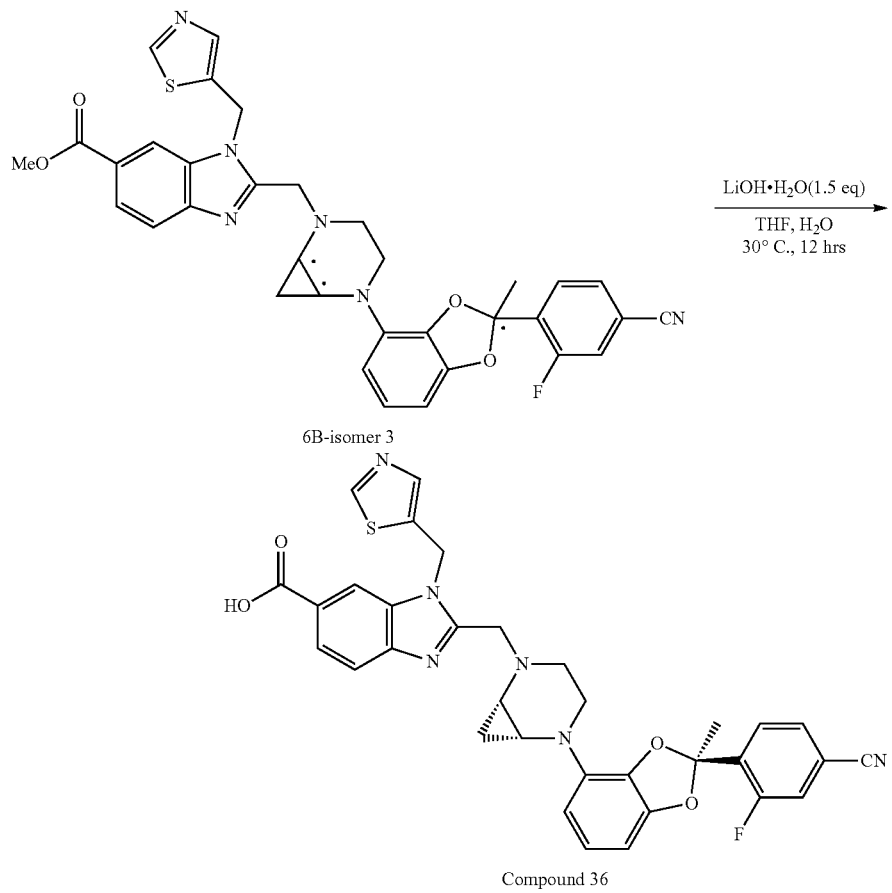

A mixture of methyl 2-((5-(2-(4-cyano-2-fluorophenyl)-2-methylbenzo[d][1,3]dioxol-4-yl)-2,5-diazabicyclo[4.1.0]heptan-2-yl)methyl)-1-(thiazol-5-ylmethyl)-1H-benzo[d]imidazole-6-carboxylate (110 mg, 173 μmol, 1 eq), LiOH·H$_2$O (10.9 mg, 259 μmol, 1.5 eq) in THF (0.7 mL) H$_2$O (0.3 mL) was degassed and purged with N$_2$ for 3 times, and then the mixture was stirred at 30° C. for 12 h under N$_2$ atmosphere. TLC showed the starting material was consumed completely. The reaction mixture was filtered and the filter was concentrated. The crude product was purified by reversed-phase HPLC (column: Waters Xbridge Prep OBD C18 150*40 mm*10 um; mobile phase: [water (NH$_4$HCO$_3$)-ACN]; B %: 35%-65%, 8 min) to provide product as a white solid (15.2 mg, 24.4 μmol, 14.1% yield); LCMS: RT=1.733 min, MS cal.: 622.68, [M+H]$^+$=623.2; HPLC: RT=11.770 min, purity: 93.95%; SFC: RT=5.825 min, purity: 100.00%; $^1$H NMR (400 MHz, METHANOL-d$_4$) δ=8.92 (s, 1H) 8.26 (s, 1H) 8.06 (s, 1H) 7.99 (d, J=8.4 Hz, 1H) 7.77-7.68 (m, 2H) 7.61-7.454 (m, 2H) 6.76-6.71 (m, 1H) 6.51 (m, 1H) 6.34 (m, 1H) 5.98 (s, 2H) 4.22-4.16 (m, 1H) 4.10-4.04 (m, 1H) 3.79-3.71 (m, 1H) 3.29-3.23 (m, 1H) 2.85-2.76 (m, 2H) 2.66-2.60 (m, 1H) 2.50-2.44 (m, 1H) 2.02 (s, 3H) 0.71-0.60 (m, 2H).

Example 22 (Synthesis of Compound 35)

2-((5-(2-(4-Cyano-2-fluorophenyl)-2-methylbenzo[d][1,3]dioxol-4-yl)-2,5-diazabicyclo[4.1.0]heptan-2-yl)methyl)-1-(thiazol-5-ylmethyl)-1H-benzo[d]imidazole-6-carboxylic Acid

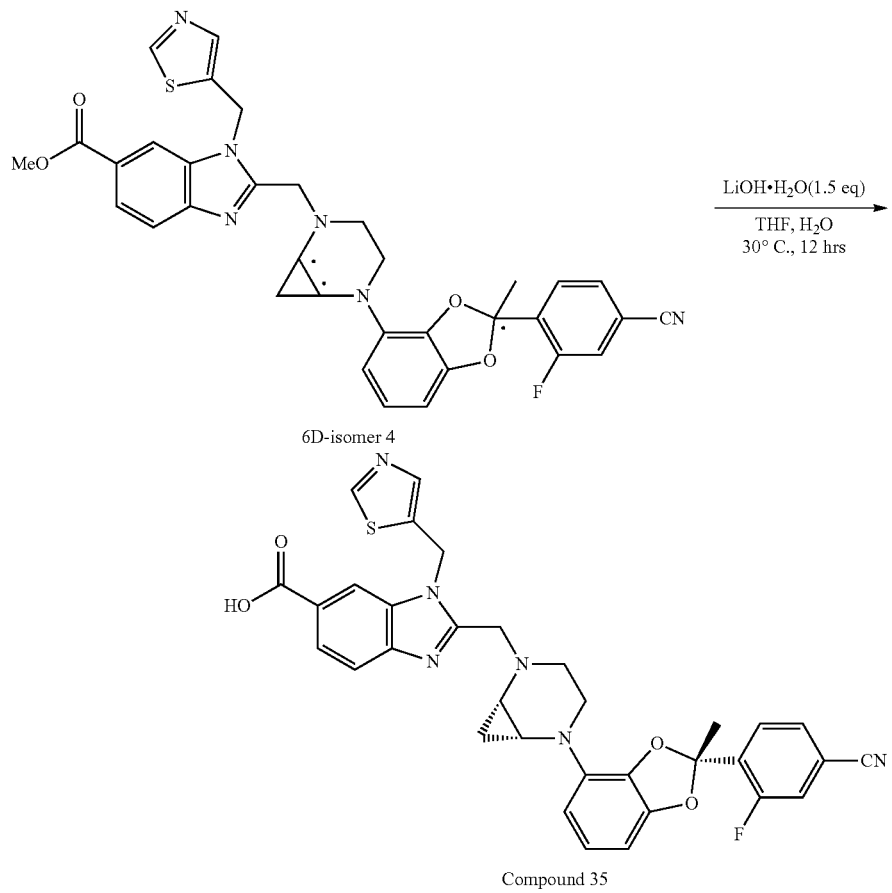

Compound 35

To a solution of methyl 2-((5-(2-(4-cyano-2-fluorophenyl)-2-methylbenzo[d][1,3]dioxol-4-yl)-2,5-diazabicyclo[4.1.0]heptan-2-yl)methyl)-1-(thiazol-5-ylmethyl)-1H-benzo[d]imidazole-6-carboxylate (100 mg, 157 μmol, 1 eq) in THF (0.7 mL) was added LiOH·H$_2$O (9.89 mg, 236 μmol, 1.5 eq) in H$_2$O (0.3 mL). The mixture was stirred at 20° C. for 12 h. LC-MS showed starting material was consumed completely and desired mass was detected. The residue was purified by prep-HPLC (column: Waters Xbridge Prep OBD C18 150*40 mm*10 um; mobile phase: [water (NH$_4$HCO$_3$)-ACN]; gradient: 30%-60% B over 8 min) to provide product as a white solid (34.6 mg, 55.5 μmol, 35.3% yield); LCMS: RT=2.118 min, MS cal.: 622.68, [M+H]$^+$=623.2; HPLC: RT=11.544 min, purity: 93.04%; SFC: RT=1.914 min, purity: 100.00%; $^1$H NMR (400 MHz, METHANOL-d$_4$) δ=8.96 (s, 1H) 8.27 (s, 1H) 8.14 (, 1H) 8.00 (dd, J=8.4 Hz, 1H) 7.78 (t, J=7.6 Hz, 1H) 7.70 (d, J=8.4 Hz, 1H) 7.66-7.53 (m, 2H) 6.78-6.67 (m, 1H) 6.50 (m, 1H) 6.41-6.30 (m, 1H) 6.00 (s, 2H) 4.30-4.04 (m, 2H) 3.81-3.70 (m, 1H) 3.29-3.24 (m, 1H) 2.98-2.88 (m, 1H) 2.85-2.73 (m, 1H) 2.65-2.43 (m, 2H) 2.04 (s, 3H) 0.67-0.53 (m, 2H).

Example 23 (Synthesis of Compound 41). 2-((5-(2-(4-cyano-2-fluorophenyl)-2-methylbenzo[d][1,3]dioxol-4-yl)-2,5-diazabicyclo[4.1.0]heptan-2-yl)methyl)-1-(((S)-oxetan-2-yl)methyl)-1H-benzo[d]imidazole-6-carboxylic Acid, Mixture of 4 Diastereomers
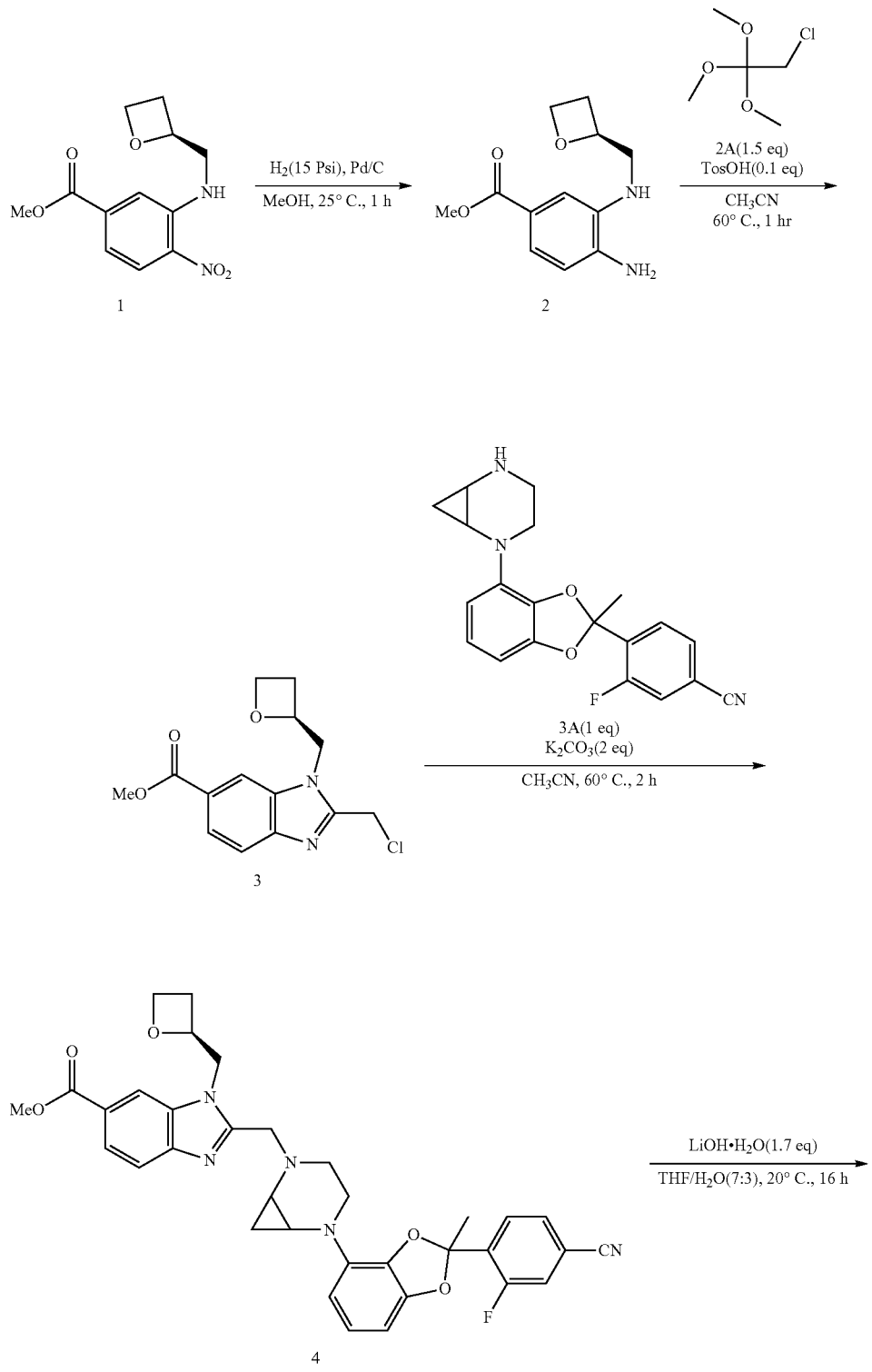

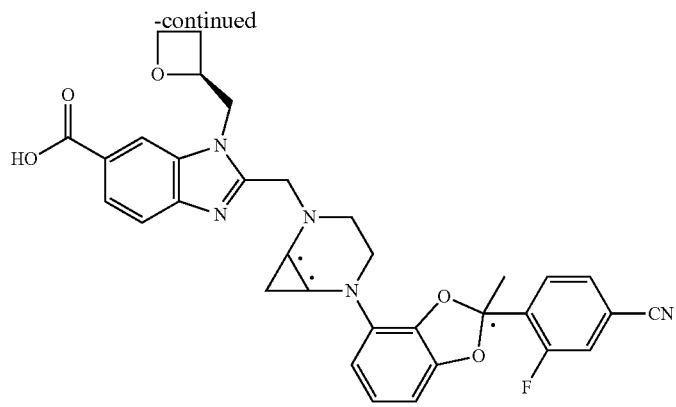

Compound 41 (mixture 4 diastereomers)

Preparation of Methyl (S)-4-amino-3-((oxetan-2-ylmethyl)amino)benzoate (2)

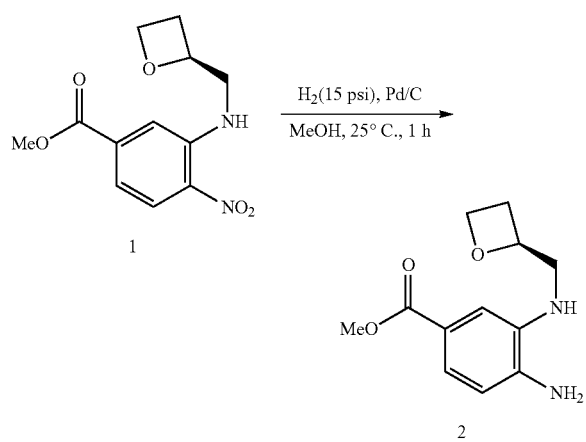

To a solution of methyl (S)-4-nitro-3-((oxetan-2-ylmethyl)amino)benzoate (500 mg, 1.88 mmol, 1 eq) in MeOH (5 mL) was added Pd/C (10%, 200 mg) under N₂ atmosphere. The suspension was degassed and purged with H₂ for 3 times. The mixture was stirred under H₂ (15 Psi.) at 25° C. for 1 h. TLC indicated starting material was consumed completely and one new spot formed. The reaction was clean according to TLC. The reaction solution was filtered and the filtrate was concentrated to provide product (400 mg, 1.69 mmol, 90.2% yield) as a white solid.

Preparation of Methyl (S)-2-(chloromethyl)-1-(oxetan-2-ylmethyl)-1H-benzo[d]imidazole-6-carboxylate (3)

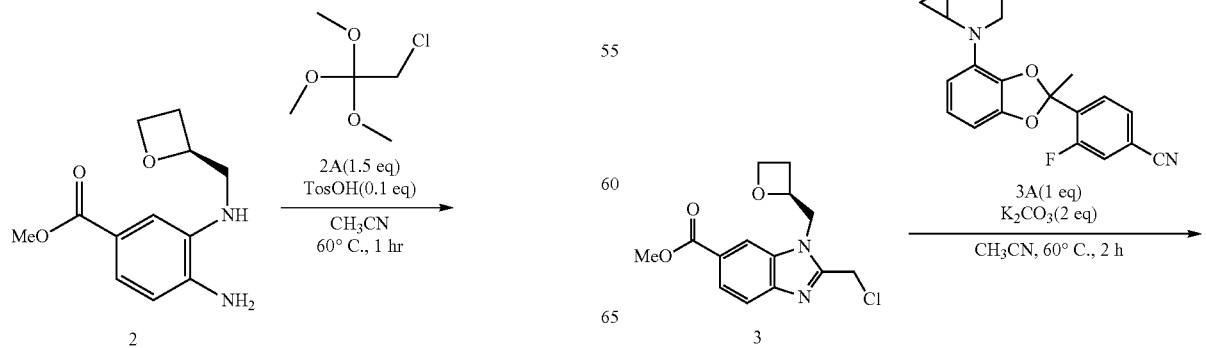

A mixture of methyl (S)-4-amino-3-((oxetan-2-ylmethyl)amino)benzoate (300 mg, 1.27 mmol, 1 eq), 2-chloro-1,1,1-trimethoxyethane (393 mg, 2.54 mmol, 341 μL, 2 eq), TosOH (43.7 mg, 254 μmol, 0.2 eq) in CH₃CN (3 mL) was degassed and purged with N₂ for 3 times, and then the mixture was stirred at 60° C. for 1 h under N₂ atmosphere. TLC indicated starting material was consumed completely and one new spot formed. The reaction was clean according to TLC. The reaction mixture was concentrated under reduced pressure to give product as a white solid (350 mg, 1.19 mmol, 93.5% yield); LCMS: RT=1.590 min, MS cal.: 294.74, [M+H]⁺=295.0.

Preparation of Methyl 2-((5-(2-(4-cyano-2-fluorophenyl)-2-methylbenzo[d][1,3]dioxol-4-yl)-2,5-diazabicyclo[4.1.0]heptan-2-yl)methyl)-1-(((S)-oxetan-2-yl)methyl)-1H-benzo[d]imidazole-6-carboxylate (4)

-continued

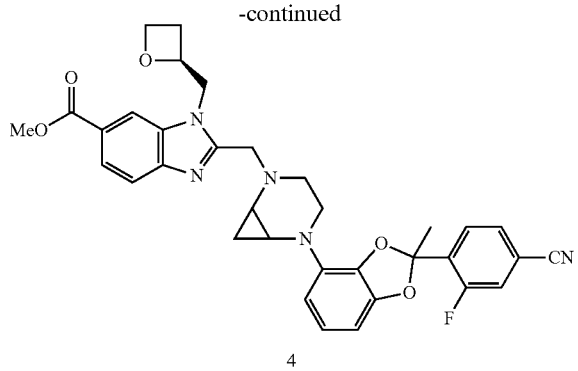

4

A mixture of methyl (S)-2-(chloromethyl)-1-(oxetan-2-ylmethyl)-1H-benzo[d]imidazole-6-carboxylate (247 mg, 840 μmol, 1 eq), 4-(4-(2,5-diazabicyclo[4.1.0]heptan-2-yl)-2-methylbenzo[d][1,3]dioxol-2-yl)-3-fluorobenzonitrile (295 mg, 840 μmol, 1 eq), K$_2$CO$_3$ (232 mg, 1.68 mmol, 2 eq) in ACN (5 mL) was degassed and purged with N$_2$ for 3 times, and then the mixture was stirred at 60° C. for 2 h under N$_2$ atmosphere. LC-MS showed starting material was consumed completely and one main peak with desired mass was detected. The reaction mixture was diluted with H$_2$O 50 mL and extracted with EtOAc 150 mL (50 mL*3), dried over Na$_2$SO$_4$, filtered and concentrated under reduced pressure to give a residue. The residue was purified by column chromatography (SiO$_2$, Petroleum ether/Ethyl acetate=100/1 to 0/1) to provide product as a white solid (250 mg, 410 μmol, 49% yield); LCMS: RT=2.624 min, MS cal.: 609.66, [M+H]$^+$=610.2.

Preparation of 2-((5-(2-(4-Cyano-2-fluorophenyl)-2-methylbenzo[d][1,3]dioxol-4-yl)-2,5-diazabicyclo[4.1.0]heptan-2-yl)methyl)-1-(((S)-oxetan-2-yl)methyl)-1H-benzo[d]imidazole-6-carboxylic Acid, Mixture of 4 Diastereomers (Compound 41)

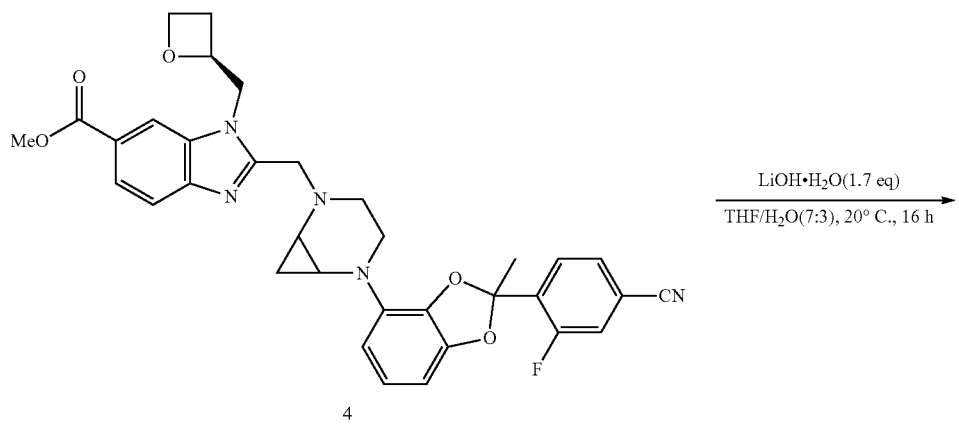

4

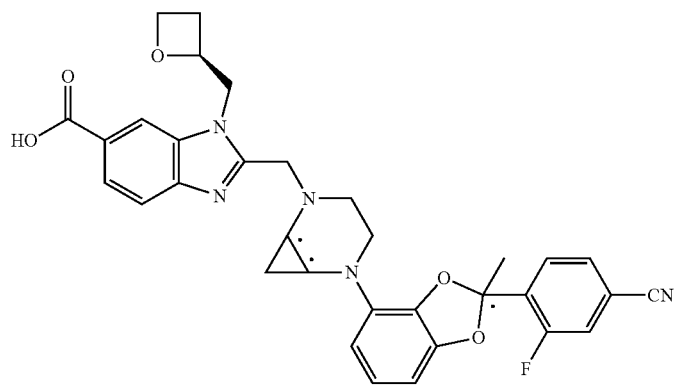

Compound 41 (mixture 4 diastereomers)

A mixture of methyl 2-((5-(2-(4-cyano-2-fluorophenyl)-2-methylbenzo[d][1,3]dioxol-4-yl)-2,5-diazabicyclo[4.1.0]heptan-2-yl)methyl)-1-(((S)-oxetan-2-yl)methyl)-1H-benzo[d]imidazole-6-carboxylate (150 mg, 246 μmol, 1 eq), LiOH·H$_2$O (17.6 mg, 418 μmol, 1.7 eq) in THF (1.2 mL) and H$_2$O (0.3 mL) was degassed and purged with N$_2$ for 3 times, and then the mixture was stirred at 20° C. for 16 h under N$_2$ atmosphere. LC-MS showed 22% of starting material remained. Several new peaks were shown on LC-MS and 62% of desired compound was detected. Adjust the solution to neutral with citric acid and concentrated. The residue was purified by prep-HPLC (neutral condition column: Waters Xbridge Prep OBD C18 150*40 mm*10 um; mobile phase: [water (NH$_4$HCO$_3$)-ACN]; B %: 20%-60%, 8 min) to provide product as a white solid (30 mg, 50.4 μmol, 20.5% yield) was obtained; LCMS: RT=1.865 min, MS cal.: 595.63, [M+H]$^+$=596.3; HPLC: RT=10.534 min, purity: 96.05%; $^1$H NMR (400 MHz, METHANOL-d4) δ=8.33 (s, 1H) 7.97 (d, J=8.4 Hz, 1H) 7.77-7.70 (m, 1H) 7.68 (d, J=8.4 Hz, 1H) 7.66-7.60 (m, 1H) 7.55 (d, J=8.0 Hz, 1H) 6.73-6.72 (m, 1H) 6.53-6.49 (m, 1H) 6.35-6.32 (m, 1H) 5.26-5.24 (m, 1H) 4.90-4.89 (m, 1H) 4.74-4.70 (m, 1H) 4.64-4.62 (m, 1H) 4.47-4.46 (m, 1H) 4.28-4.26 (m, 0.5H) 4.17-4.18 (m, 1H) 4.10-4.05 (m, 0.5H) 3.706-3.7 (m, 1H) 3.33-3.31 (m, 1H) 2.80-2.78 (m, 4H) 2.55-2.51 (m, 2H) 2.03-2.01 (d, J=4.8 Hz, 3H) 0.69-0.52 (m, 2H).

Example 24 (Synthesis of Compound 40)

2-((5-(2-(4-Cyano-2-fluorophenyl)-2-methylbenzo[d][1,3]dioxol-4-yl)-2,5-diazabicyclo[4.1.0]heptan-2-yl)methyl)-1-((1-cyanocyclopropyl)methyl)-1H-benzo[d]imidazole-6-carboxylic Acid, Mixture of 4 Diastereomers

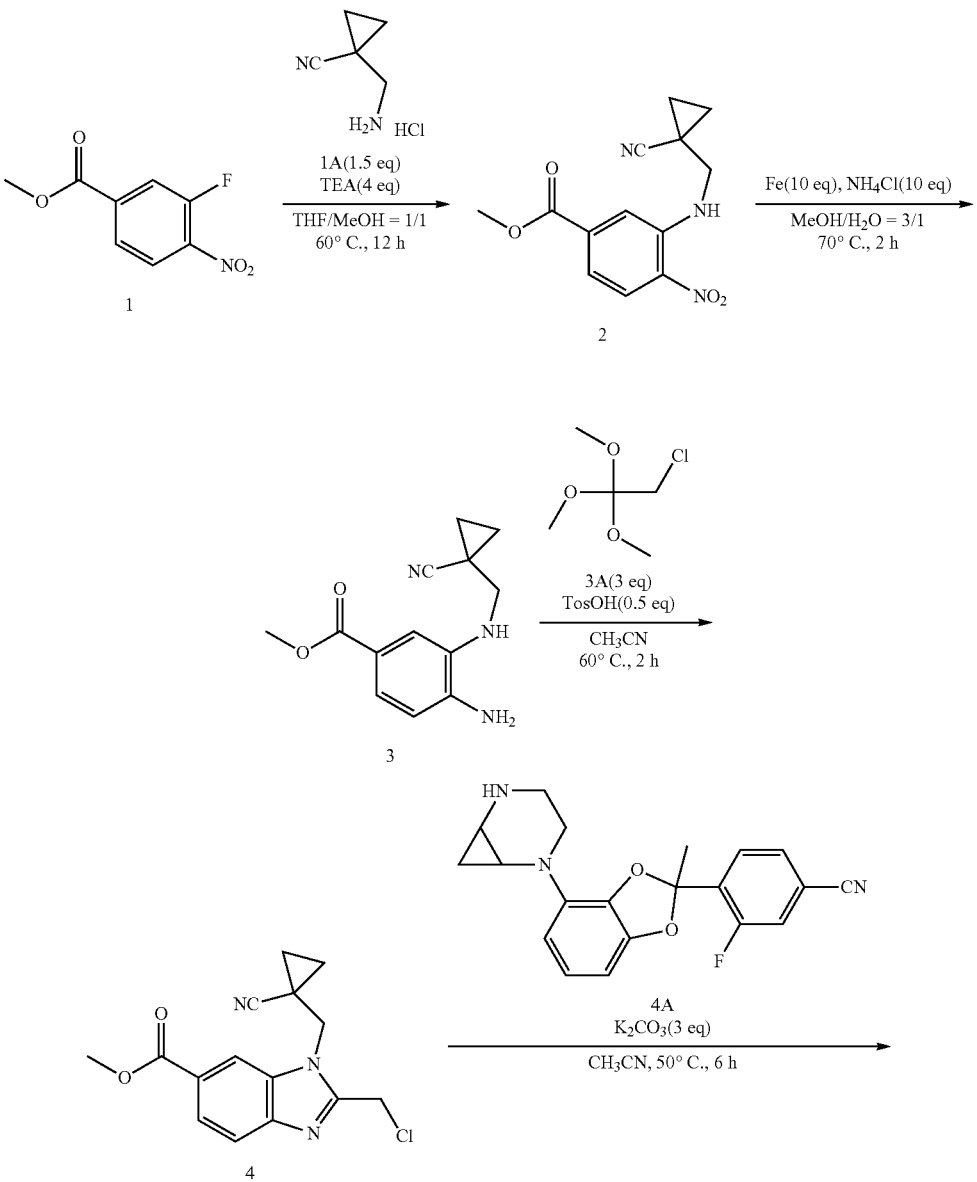

-continued

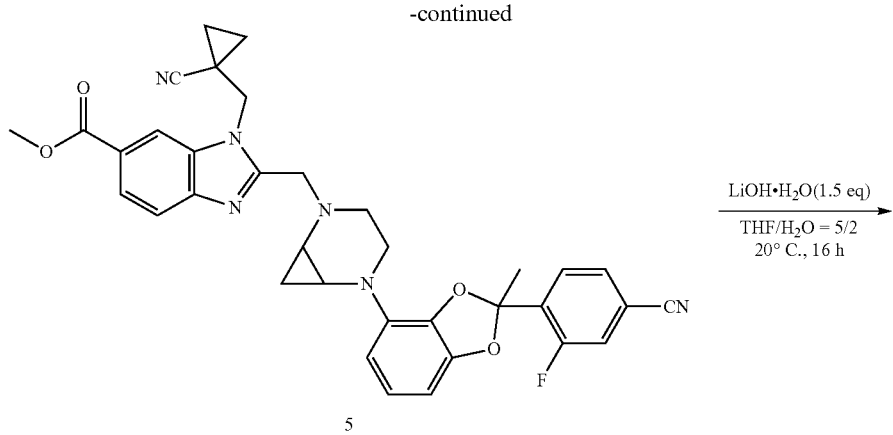

Compound 40 (mixture 4 diastereomers)

Preparation of Methyl 3-(((1-cyanocyclopropyl)methyl)amino)-4-nitrobenzoate (2)

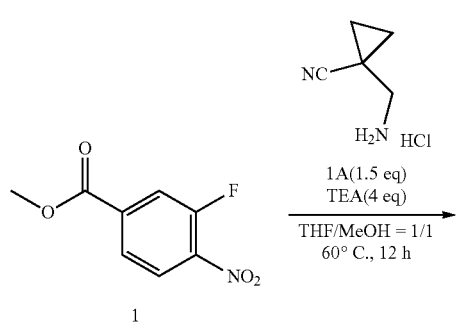

A mixture of methyl 3-fluoro-4-nitrobenzoate (1.90 g, 9.55 mmol, 1 eq), 1-(aminomethyl)cyclopropane-1-carbonitrile (1.9 g, 14.3 mmol, 1.5 eq), TEA (3.87 g, 38.2 mmol, 5.32 mL, 4 eq) in THF (10 mL) and MeOH (10 mL) was degassed and purged with $N_2$ for 3 times, and then the mixture was stirred at 60° C. for 12 h under $N_2$ atmosphere. TLC (Petroleum ether/Ethyl acetate=3/1, $R_f$=0.46) indicated starting material was consumed completely and one new spot formed. The reaction was clean according to TLC. The residue was diluted with H2O (100 ml) and extracted with ethyl acetate (100 mL*3). The combined organic phase was washed with brine (100 mL), dried with anhydrous $Na_2SO_4$, filtered and concentrated in vacuum. The residue was purified by column chromatography ($SiO_2$, Petroleum ether/Ethyl acetate=100/1 to 0/1) to provide product as a yellow solid (2.5 g, 9.08 mmol, 95.07% yield); LCMS: RT=1.948 min, MS cal.: 275.26, [M+H]$^+$=276.2; $^1$H NMR (400 MHz, CHLOROFORM-d) δ=8.25 (d, J=8.8 Hz, 1H), 8.15 (br s, 1H), 7.58 (s, 1H), 7.35 (d, J=8.8 Hz, 1H), 4.01 (s, 3H), 3.57 (d, J=5.6 Hz, 2H), 1.48-1.42 (m, 2H), 1.14-1.08 (m, 2H).

Preparation of Methyl 4-amino-3-(((1-cyanocyclopropyl)methyl)amino)benzoate (3)

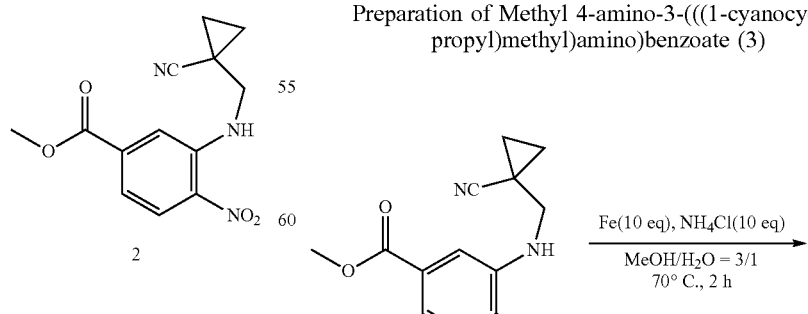

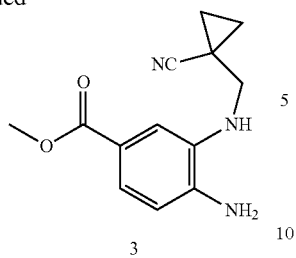

3

A mixture of methyl 3-(((1-cyanocyclopropyl)methyl)amino)-4-nitrobenzoate (2.5 g, 9.08 mmol, 1 eq), Fe (5.07 g, 90.8 mmol, 10 eq), NH$_4$Cl (4.86 g, 90.8 mmol, 10 eq) in H$_2$O (8 mL) and MeOH (24 mL) was degassed and purged with N$_2$ for 3 times, and then the mixture was stirred at 70° C. for 2 h under N$_2$ atmosphere. TLC (Petroleum ether/Ethyl acetate=3/1, R$_f$=0.35) indicated starting material was consumed completely and one new spot formed. The resulting product was dissolved in MeOH and filtered to remove the insoluble. The filtrate was concentrated in vacuo. The residue was purified by column chromatography (SiO$_2$, Petroleum ether/Ethyl acetate=100/1 to 0/1) to provide product as a yellow solid (1.94 g, 7.91 mmol, 87% yield); LCMS: RT=1.529 min, MS cal.: 245.28, [M+H]$^+$=246.1; $^1$H NMR (400 MHz, DMSO-d$_6$) δ=7.22 (d, J=8.0 Hz, 1H), 7.04 (s, 1H), 6.56 (d, J=8.0 Hz, 1H), 5.55 (br s, 2H), 4.94 (br t, J=5.6 Hz, 1H), 3.72 (s, 3H), 3.23 (d, J=5.6 Hz, 2H), 1.30-1.21 (m, 2H), 1.10-1.01 (m, 2H).

Preparation of Methyl 2-(chloromethyl)-1-((1-cyanocyclopropyl)methyl)-1H-benzo[d]imidazole-6-carboxylate (4)

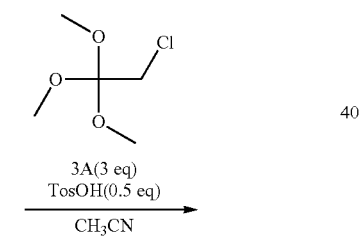

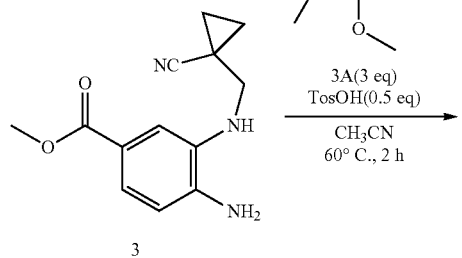

A mixture of methyl 4-amino-3-(((1-cyanocyclopropyl)methyl)amino)benzoate (300 mg, 1.22 mmol, 1 eq), 2-chloro-1,1,1-trimethoxyethane (567 mg, 3.67 mmol, 493 μL, 3 eq), TosOH (105 mg, 612 μmol, 0.5 eq) in ACN (5 mL) was degassed and purged with N$_2$ for 3 times, and then the mixture was stirred at 60° C. for 2 h under N$_2$ atmosphere. LC-MS showed the starting material was consumed completely. The reaction mixture was concentrated under reduced pressure to provide product as a white solid (372 g, crude); LCMS: RT=1.588 min, MS cal.: 303.72, [M+H]$^+$=304.1.

Preparation of Methyl 2-((5-(2-(4-cyano-2-fluorophenyl)-2-methylbenzo[d][1,3]dioxol-4-yl)-2,5-diazabicyclo[4.1.0]heptan-2-yl)methyl)-1-((1-cyanocyclopropyl)methyl)-1H-benzo[d]imidazole-6-carboxylate (5)

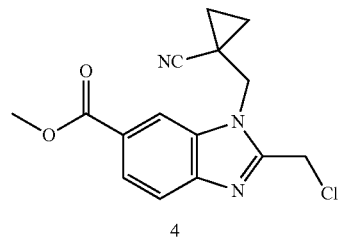

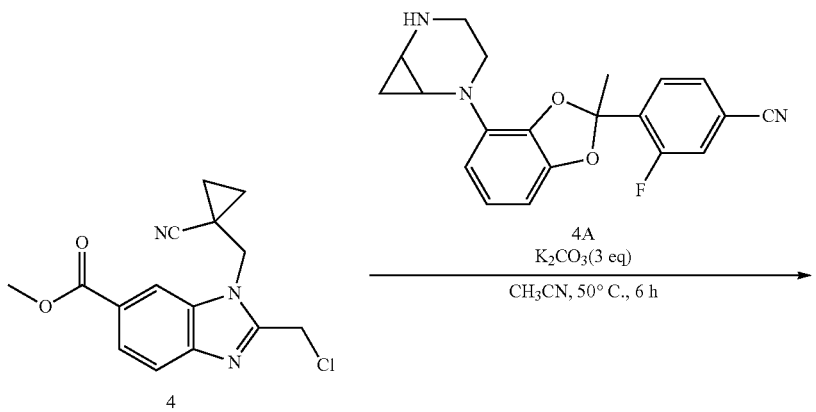

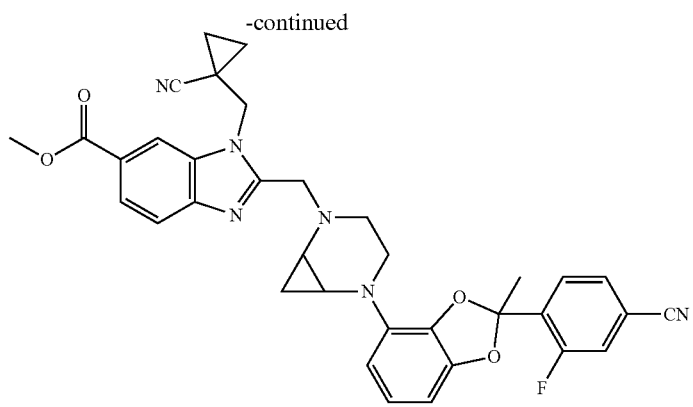

A mixture of methyl 2-(chloromethyl)-1-((1-cyanocyclopropyl)methyl)-1H-benzo[d]imidazole-6-carboxylate (216 mg, 711 μmol, 1 eq), 4-(4-(2,5-diazabicyclo[4.1.0]heptan-2-yl)-2-methylbenzo[d][1,3]dioxol-2-yl)-3-fluorobenzonitrile (250 mg, 711 μmol, 1 eq), K₂CO₃ (295 mg, 2.13 mmol, 3 eq) in ACN (5 mL) was degassed and purged with N₂ for 3 times, and then the mixture was stirred at 50° C. for 6 h under N₂ atmosphere. LC-MS showed the starting material was consumed completely. TLC (Petroleum ether/Ethyl acetate=0/1, R$_f$=0.47) indicated starting material was consumed completely. The residue was diluted with H₂O (30 ml) and extracted with ethyl acetate (30 mL*3). The combined organic phase was washed with brine (20 mL), dried with anhydrous Na₂SO₄, filtered and concentrated in vacuum. The residue was purified by column chromatography (SiO₂, Petroleum ether/Ethyl acetate=100/1 to 0/1) to give product as a yellow solid (240 mg, 388 μmol, 54.5% yield); LCMS: RT=2.630 min, MS cal.: 618.66, [M+H]⁺=619.3.

Preparation of 2-((5-(2-(4-Cyano-2-fluorophenyl)-2-methylbenzo[d][1,3]dioxol-4-yl)-2,5-diazabicyclo[4.1.0]heptan-2-yl)methyl)-1-((1-cyanocyclopropyl)methyl)-1H-benzo[d]imidazole-6-carboxylic Acid (Compound 40)

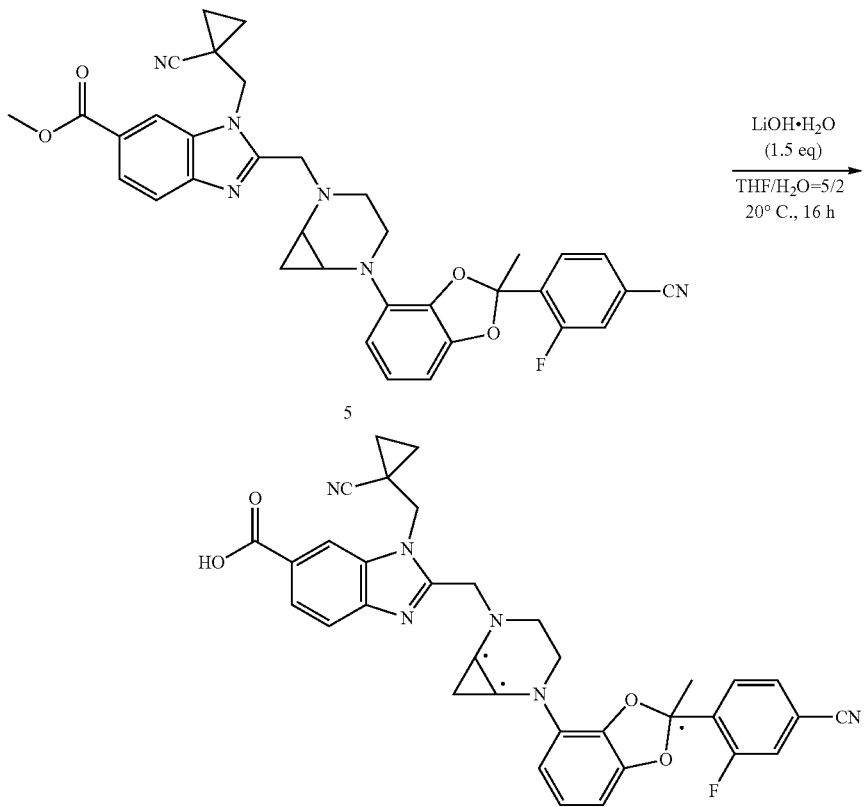

Compound 40 (mixture 4 diastereomers)

A mixture of methyl 2-((5-(2-(4-cyano-2-fluorophenyl)-2-methylbenzo[d][1,3]dioxol-4-yl)-2,5-diazabicyclo[4.1.0]heptan-2-yl)methyl)-1-((1-cyanocyclopropyl)methyl)-1H-benzo[d]imidazole-6-carboxylate (100 mg, 162 μmol, 1 eq), LiOH·H₂O (10.17 mg, 242.46 μmol, 1.5 eq) in THF (1.5 mL) and H₂O (0.6 mL) was degassed and purged with N₂ for 3 times, and then the mixture was stirred at 20° C. for 16 h under N₂ atmosphere. LCMS showed the starting material was consumed completely. The crude product was purified by reversed-phase HPLC (column: Waters Xbridge Prep OBD C18 150*40 mm*10 um; mobile phase: [water (NH₄HCO₃)-ACN]; B %: 20%-50%, 8 min) to provide product as a white solid (18 mg, 29.8 umol, 18.4% yield); LCMS: RT=2.510 min, MS cal.: 604.63, [M+H]⁺=605.3; HPLC: purity=93.9%; ¹H NMR (400 MHz, METHANOL-d₄) δ=8.35 (s, 1H), 8.02 (d, J=8.4 Hz, 1H), 7.80-7.74 (m, 1H), 7.73-7.69 (m, 1H), 7.65-7.59 (m, 1H), 7.58-7.54 (m, 1H), 6.73 (m, 1H), 6.51 (m, 1H), 6.37-6.31 (m, 1H), 4.81-4.77 (m, 2H), 4.36-4.26 (m, 1H), 4.20-4.13 (m, 1H), 3.83-3.71 (m, 1H), 3.40-3.33 (m, 1H), 2.90-2.84 (m, 2H), 2.68-2.60 (m, 1H), 2.58-2.45 (m, 1H), 2.02 (d, J=4.6 Hz, 3H), 1.52-1.43 (m, 4H), 0.72-0.49 (m, 2H).

Example 25 (Synthesis of Compound 13)

3-Fluoro-4-(2-methyl-4-(5-((1-(thiazol-5-ylmethyl)-6-(5-(trifluoromethyl)-4H-1,2,4-triazol-3-yl)-1H-benzo[d]imidazol-2-yl)methyl)-2,5-diazabicyclo[4.1.0]heptan-2-yl)benzo[d][1,3]dioxol-2-yl)benzonitrile, Mixture of 4 Diastereomers

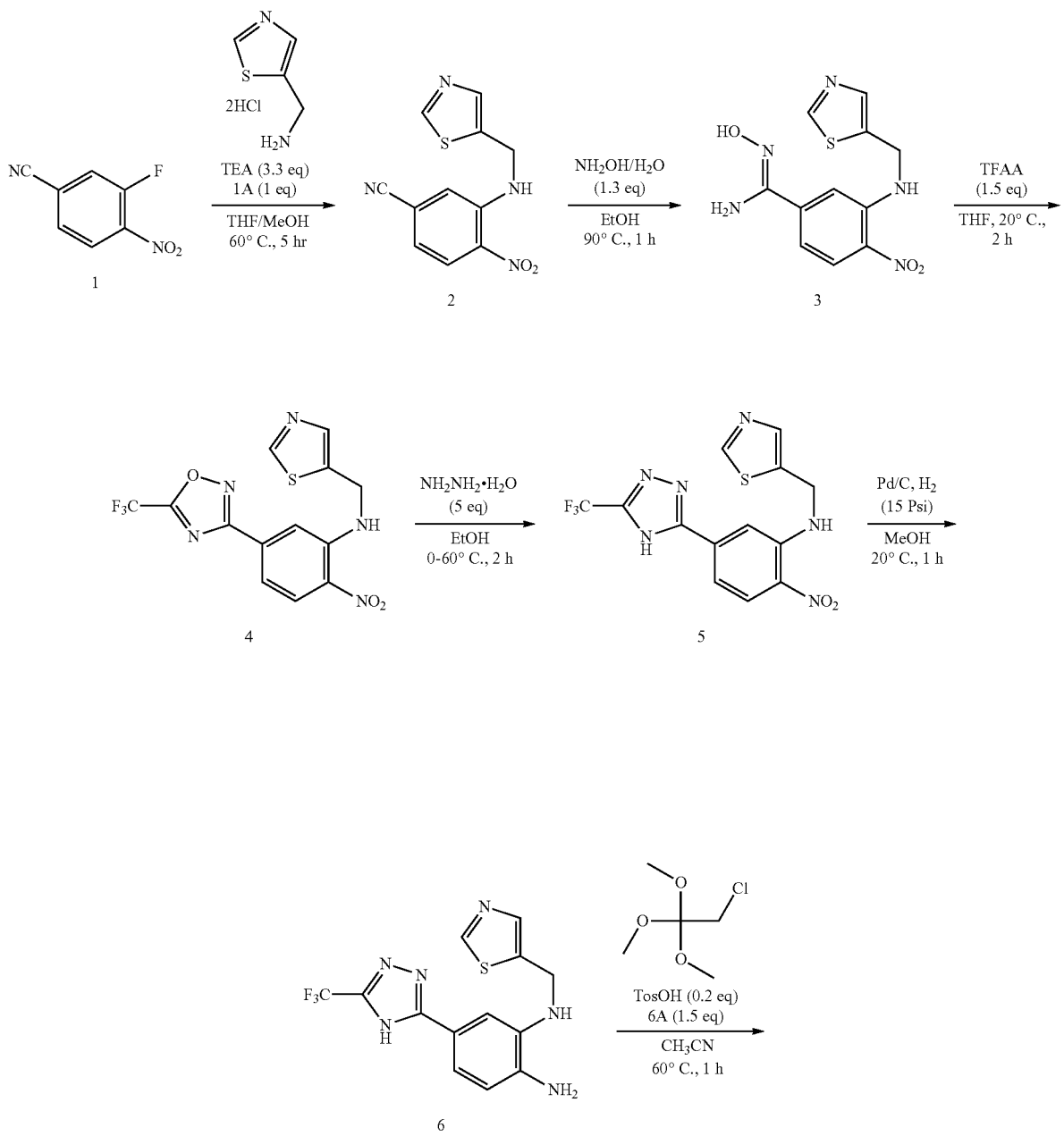

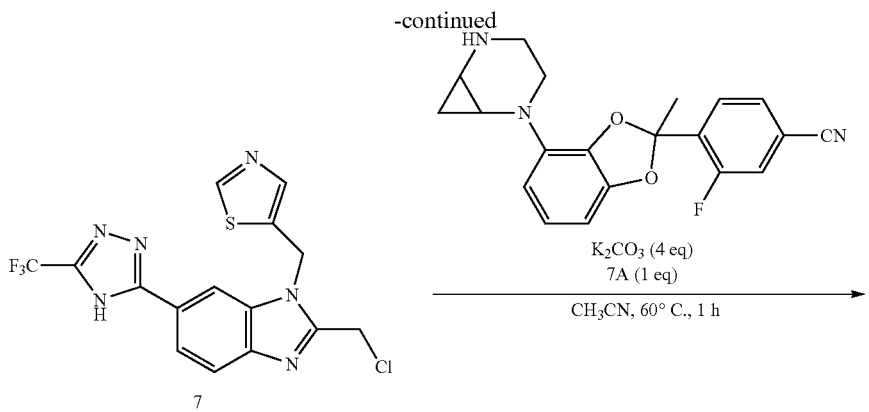

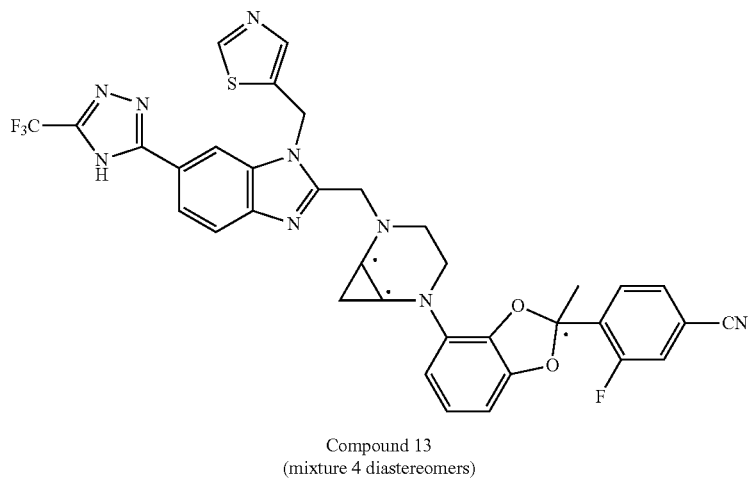

Compound 13
(mixture 4 diastereomers)

Preparation of 4-Nitro-3-((thiazol-5-ylmethyl)amino)benzonitrile (2)

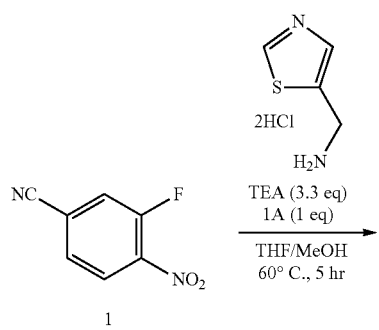

To a solution of 3-fluoro-4-nitrobenzonitrile (2 g, 12.0 mmol, 1 eq) and thiazol-5-ylmethanamine (2.25 g, 12.0 mmol, 1 eq, 2HCl) in THF (10 mL) and MeOH (10 mL) was added TEA (4.02 g, 39.7 mmol, 5.53 mL, 3.3 eq). The mixture was stirred at 60° C. for 5 hours. TLC indicated starting material was consumed completely and one new spot formed. The reaction mixture was poured into H$_2$O (60 mL) slowly at 0° C. and the solid formed. The mixture was stirred for 15 mins and filtered. The solid was collected and under reduced pressure to give product as a yellow solid (3 g, 11.5 mmol, 95.7% yield); LCMS: RT=0.774 min, MS cal.: 260.3, [M+H]$^+$=261.1; $^1$H NMR (400 MHz, DMSO-d$_6$) δ 8.99 (s, 1H) 8.72 (br t, J=6.0 Hz, 1H) 8.19 (d, J=8.8 Hz, 1H) 7.96 (s, 1H) 7.67 (s, 1H) 7.06 (d, J=8.8 Hz, 1H) 4.93 (d, J=6.0 Hz, 2H).

Preparation of N'-hydroxy-4-nitro-3-((thiazol-5-ylmethyl)amino)benzimidamide (3)

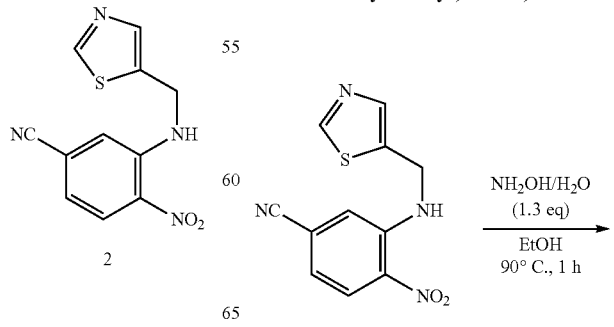

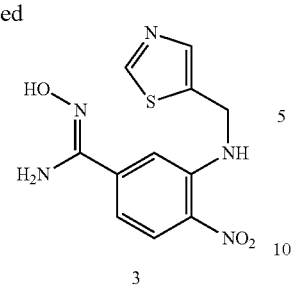

3

To a solution of 4-nitro-3-((thiazol-5-ylmethyl)amino)benzonitrile (1.3 g, 4.99 mmol, 1 eq) in EtOH (15 mL) was added hydroxylamine (429 mg, 6.49 mmol, 50% purity, 1.3 eq). The mixture was stirred at 90° C. for 1 hour. LC-MS showed starting material was consumed completely and desired mass was detected. The reaction mixture was concentrated under reduced pressure to remove solvent. The crude product was obtained as a yellow solid (1.46 g); LCMS: RT=1.290 min, MS cal.: 293.3, [M+H]+=294.0; $^1$H NMR (400 MHz, DMSO-$d_6$) δ=10.10 (br s, 1H) 8.98 (s, 1H) 8.71 (br t, J=6.0 Hz, 1H) 8.03 (d, J=9.2 Hz, 1H) 7.90 (s, 1H) 7.34 (s, 1H) 7.05 (d, J=9.2 Hz, 1H) 6.02 (br s, 2H) 4.96 (d, J=6.0 Hz, 2H).

Preparation of 2-Nitro-N-(thiazol-5-ylmethyl)-5-(5-(trifluoromethyl)-1,2,4-oxadiazol-3-yl)aniline (4)

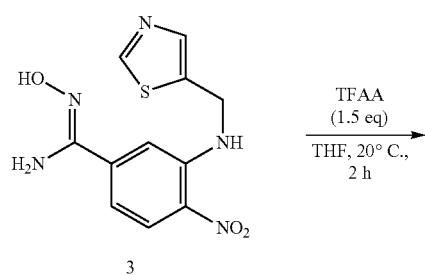

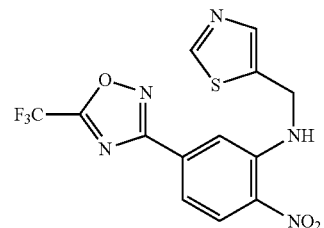

4

To a solution of N'-hydroxy-4-nitro-3-((thiazol-5-ylmethyl)amino)benzimidamide (1.3 g, 4.43 mmol, 1 eq) in THF (8 mL) was added TFAA (1.40 g, 6.65 mmol, 924.76 μL, 1.5 eq). The mixture was stirred at 20° C. for 2 hours. LC-MS showed starting material was consumed completely and desired mass was detected. The residue was diluted with NaHCO$_3$ (30 mL) and extracted with EtOAc (30 mL*2). The combined organic layers were dried over Na$_2$SO$_4$, filtered and concentrated under reduced pressure to give a residue. The residue was purified by column chromatography (SiO$_2$, Petroleum ether/Ethyl acetate=30/1 to 1/1) to provide product as a yellow solid (1.5 g, 4.04 mmol, 91% yield); LCMS: RT=2.324 min, MS cal.: 371.3, [M+H]+=372.0; $^1$H NMR (400 MHz, CHLOROFORM-d) δ=8.81 (s, 1H) 8.45 (br s, 1H) 8.40 (d, J=8.8 Hz, 1H) 7.95 (s, 1H) 7.72 (s, 1H) 7.48 (d, J=8.8 Hz, 1H) 4.90 (d, J=5.6 Hz, 2H).

Preparation of 2-Nitro-N-(thiazol-5-ylmethyl)-5-(5-(trifluoromethyl)-4H-1,2,4-triazol-3-yl)aniline (5)

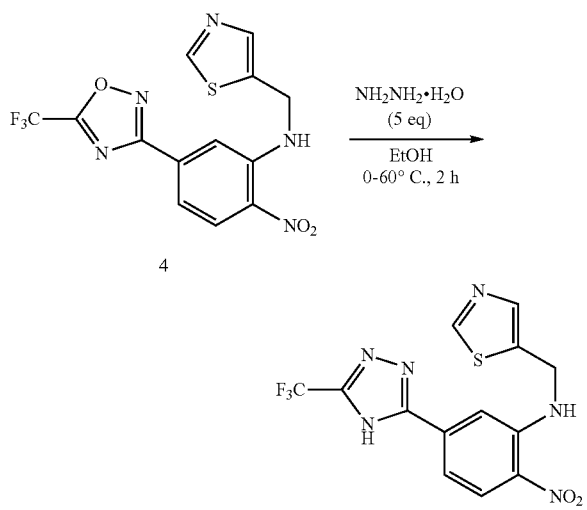

To a solution of 2-nitro-N-(thiazol-5-ylmethyl)-5-(5-(trifluoromethyl)-1,2,4-oxadiazol-3-yl)aniline (0.8 g, 2.15 mmol, 1 eq) in EtOH (10 mL) was added NH$_2$NH$_2$·H$_2$O (539 mg, 10.8 mmol, 524 μL, 5 eq) dropwise at 0-5° C. The mixture was stirred at 60° C. for 2 hours. LC-MS showed starting material was consumed completely and desired mass was detected. The reaction mixture was concentrated under reduced pressure at 30° C. to give a residue. The residue was diluted with H$_2$O (20 mL) and extracted with EtOAc/i-PrOH=2/1 (20 mL*3). The combined organic layers were washed with brine (20 mL), dried over Na$_2$SO$_4$, filtered and concentrated under reduced pressure to give a residue. The residue was purified by prep-HPLC (neutral condition; column: Phenomenex luna C18 250*50 mm*10 um; mobile phase: [water (TFA)-ACN]; B %: 25%-55%, 10 min) to provide product as a yellow solid (500 mg, 1.35 mmol, 62.7% yield); LCMS: RT=1.815 min, MS cal.: 370.3, [M+H]+=371.1; $^1$H NMR (400 MHz, METHANOL-$d_4$) δ=9.03 (s, 1H) 8.36 (d, J=8.8 Hz, 1H) 8.01 (s, 1H) 7.78 (s, 1H) 7.35 (d, J=8.8 Hz, 1H) 5.02 (s, 2H).

Preparation of N1-(Thiazol-5-ylmethyl)-5-(5-(trifluoromethyl)-4H-1,2,4-triazol-3-yl)benzene-1,2-diamine (6)

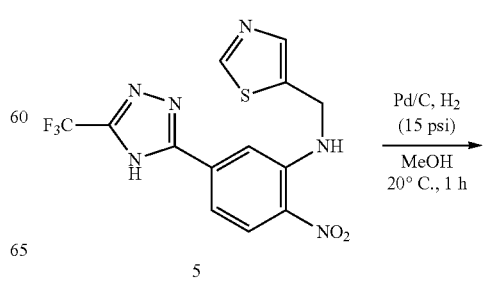

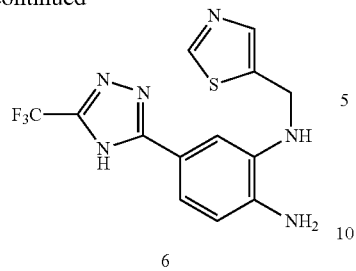

6

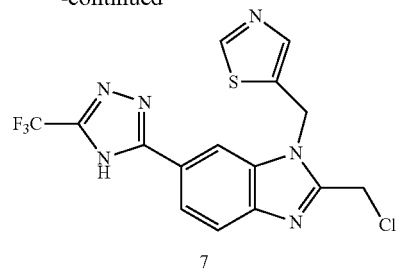

7

To a solution of 2-nitro-N-(thiazol-5-ylmethyl)-5-(5-(trifluoromethyl)-4H-1,2,4-triazol-3-yl)aniline (130 mg, 351 µmol, 1 eq) in MeOH (5 mL) was added Pd/C under N₂ atmosphere. The suspension was degassed and purged with H₂ for 3 times. The mixture was stirred under H₂ (15 psi) at 20° C. for 1 hour. LC-MS showed starting material was consumed completely and desired mass was detected. The reaction mixture was filtered and concentrated under reduced pressure to provide product as a yellow solid (119 mg, 350 umol, 99.6% yield); LCMS: Rt=1.327 min, MS cal.: 340.3, [M+H]+=341.0.

Preparation of 5-((2-(Chloromethyl)-6-(5-(trifluoromethyl)-4H-1,2,4-triazol-3-yl)-1H-benzo[d]imidazol-1-yl)methyl)thiazole (7)

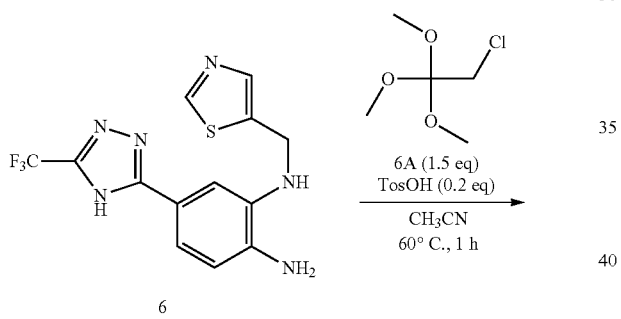

To a solution of N1-(thiazol-5-ylmethyl)-5-(5-(trifluoromethyl)-4H-1,2,4-triazol-3-yl)benzene-1,2-diamine (0.11 g, 323 µmol, 1 eq) in CH₃CN (1 mL) was added TosOH (11.1 mg, 64.6 µmol, 0.2 eq) and 2-chloro-1,1,1-trimethoxyethane (75 mg, 485 µmol, 65.2 µL, 1.5 eq). The mixture was stirred at 60° C. for 1 hour. LC-MS showed starting material was consumed completely and desired mass was detected. The reaction mixture was concentrated under reduced pressure to provide product as a yellow solid (120 mg, 301 µmol, 93.1% yield); LCMS: RT=1.284 min, MS cal.: 398.8, [M+H]⁺=399.0.

Preparation of 3-Fluoro-4-(2-methyl-4-(5-((1-(thiazol-5-ylmethyl)-6-(5-(trifluoromethyl)-4H-1,2,4-triazol-3-yl)-1H-benzo[d]imidazol-2-yl)methyl)-2,5-diazabicyclo[4.1.0]heptan-2-yl)benzo[d][1,3]dioxol-2-yl)benzonitrile, Mixture of 4 Diastereomers (Compound 13)

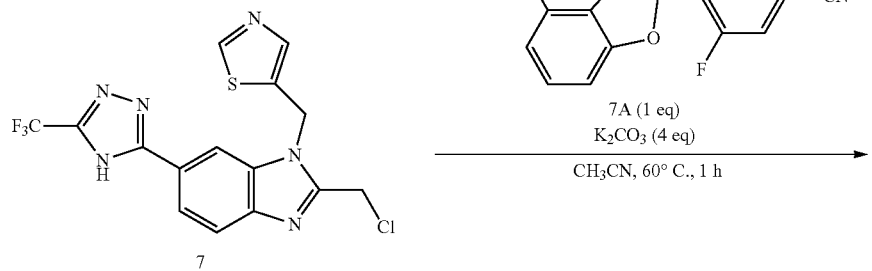

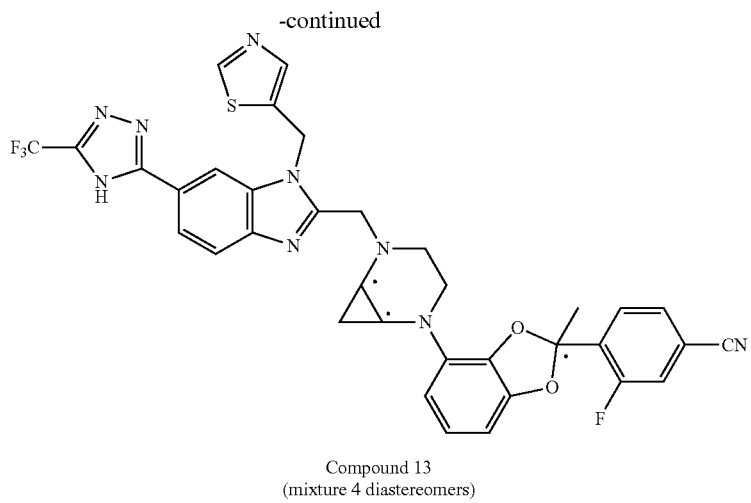

Compound 13
(mixture 4 diastereomers)

To a solution of 5-((2-(chloromethyl)-6-(5-(trifluoromethyl)-4H-1,2,4-triazol-3-yl)-1H-benzo[d]imidazol-1-yl)methyl)thiazole (110 mg, 166 μmol, 60% purity, 1 eq) in CH$_3$CN (2 mL) was added K$_2$CO$_3$ (91.5 mg, 662 μmol, 4 eq) and 4-(4-(2,5-diazabicyclo[4.1.0]heptan-2-yl)-2-methyl-benzo[d][1,3]dioxol-2-yl)-3-fluorobenzonitrile (64 mg, 166 μmol, 1 eq, HCl). The mixture was stirred at 60° C. for 1 hour. LC-MS showed starting material was consumed completely and desired mass was detected. The reaction mixture was filtered and concentrated under reduced pressure to give a residue. The residue was purified by prep-HPLC (neutral condition; column: Phenomenex C18 75*30 mm*3 um; mobile phase: [water (NH$_3$H$_2$O+NH$_4$HCO$_3$)-ACN]; B %: 40%-65%, 8 min) to provide product as a white solid (8.88 mg, 12.4 μmol, 7.5% yield); LCMS: RT=2.201 min, MS cal.: 713.7, [M+H]$^+$=714.2; HPLC: RT=4.071 min, purity: 87.6%; $^1$H NMR (400 MHz, METHANOL-d$_4$) δ=8.94 (d, J=11.4 Hz, 1H), 8.27 (s, 1H), 8.10 (s, 1H), 7.96-7.91 (m, 1H), 7.83-7.79 (m, 1H), 7.79-7.73 (m, 1H), 7.65-7.54 (m, 2H), 6.74 (dt, J=2.8, 8.1 Hz, 1H), 6.54-6.48 (m, 1H), 6.35 (dd, J=1.3, 7.8 Hz, 1H), 6.00 (s, 2H), 4.24-4.17 (m, 1H), 4.13-4.05 (m, 1H), 3.80-3.72 (m, 1H), 3.30-3.25 (m, 1H), 2.95-2.77 (m, 2H), 2.69-2.59 (m, 1H), 2.59-2.45 (m, 1H), 2.03 (d, J=4.8 Hz, 3H), 0.73-0.55 (m, 2H).

Example 26 (Synthesis of Compound 12)

3-Fluoro-4-(((6-(5-((1-(thiazol-5-ylmethyl)-6-(5-(trifluoromethyl)-4H-1,2,4-triazol-3-yl)-1H-benzo[d]imidazol-2-yl)methyl)-2,5-diazabicyclo[4.1.0]heptan-2-yl)pyridin-2-yl)oxy)methyl)benzonitrile, Mixture of 2 Diastereomers

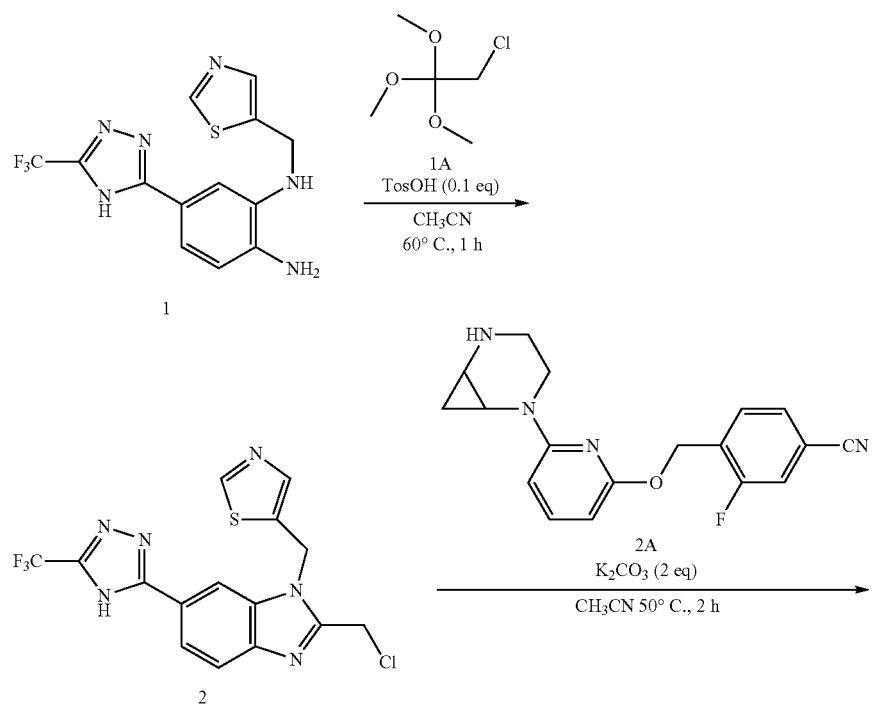

-continued

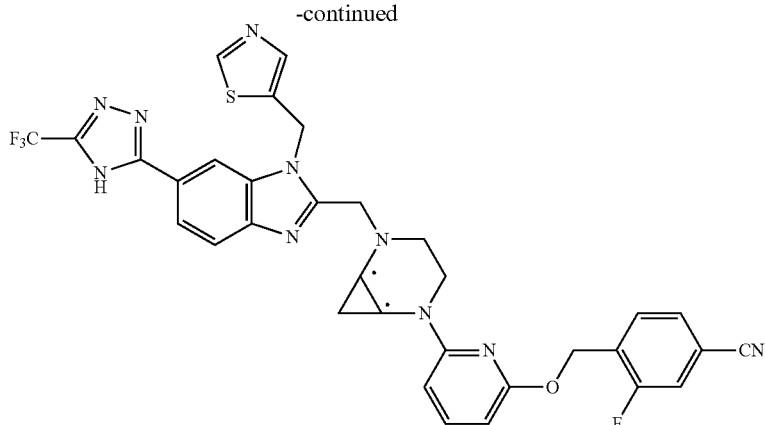

Compound 12
(mixture 2 diastereomers)

Preparation of 5-((2-(Chloromethyl)-6-(5-(trifluoromethyl)-4H-1,2,4-triazol-3-yl)-1H-benzo[d]imidazol-1-yl)methyl)thiazole (2)

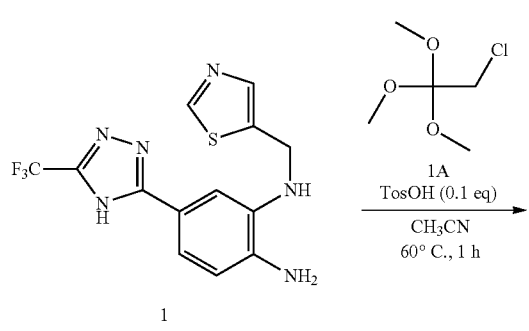

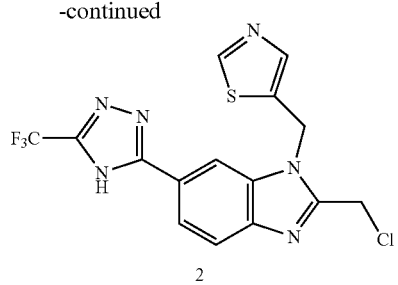

A mixture of N1-(thiazol-5-ylmethyl)-5-(5-(trifluoromethyl)-4H-1,2,4-triazol-3-yl)benzene-1,2-diamine (100 mg, 294 μmol, 1 eq), 2-chloro-1,1,1-trimethoxyethane (114 mg, 735 mol, 98.8 μL, 2.5 eq), TosOH (5.06 mg, 294 μmol, 0.1 eq) in CH$_3$CN (2 mL) was degassed and purged with N$_2$ for 3 times, and then the mixture was stirred at 60° C. for 1 h under N$_2$ atmosphere. LC-MS showed starting material was consumed completely and one main peak desired mass was detected. The reaction solution was concentrated to provide product as a white solid (80 mg, 201 μmol, 68.3% yield); LCMS: RT=1.140 min, MS cal.: 398.1, [M+H]$^+$=399.0.

Preparation of 3-Fluoro-4-((((6-(5-((1-(thiazol-5-ylmethyl)-6-(5-(trifluoromethyl)-4H-1,2,4-triazol-3-yl)-1H-benzo[d]imidazol-2-yl)methyl)-2,5-diazabicyclo[4.1.0]heptan-2-yl)pyridin-2-yl)oxy)methyl)benzonitrile (Compound 12)

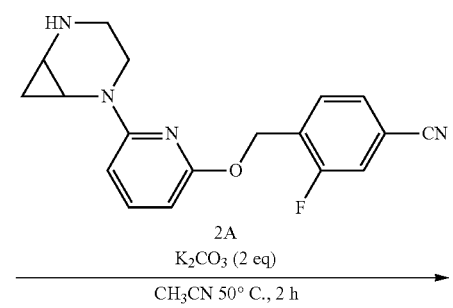

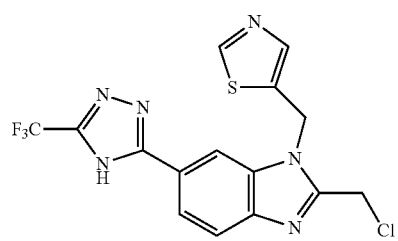

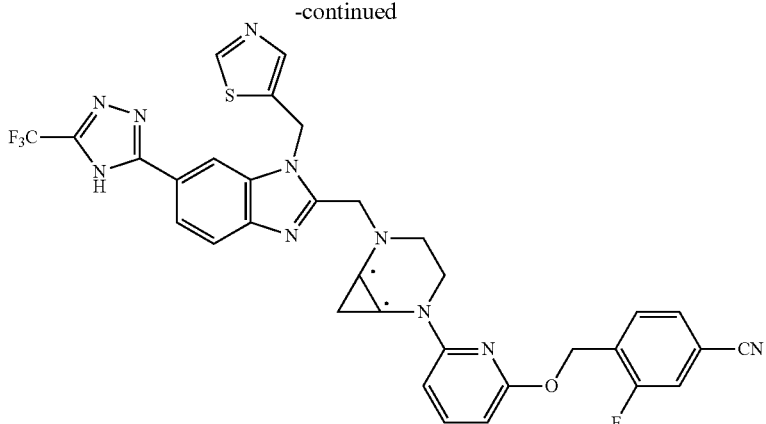

Compound 12
(mixture 2 diastereomers)

A mixture of 5-((2-(chloromethyl)-6-(5-(trifluoromethyl)-4H-1,2,4-triazol-3-yl)-1H-benzo[d]imidazol-1-yl)methyl)thiazole (80 mg, 201 μmol, 1 eq), 4-(((6-(2,5-diazabicyclo[4.1.0]heptan-2-yl)pyridin-2-yl)oxy)methyl)-3-fluorobenzonitrile (65.1 mg, 201 mol, 1 eq), $K_2CO_3$ (55 mg, 401 μmol, 2 eq) in ACN (3 mL) was degassed and purged with $N_2$ for 3 times, and then the mixture was stirred at 50° C. for 2 h under $N_2$ atmosphere. LCMS showed starting material was consumed completely and one main desired mass was detected. The reaction mixture was diluted with $H_2O$ (30 mL) and extracted with EtOAc 60 mL (20 mL*3), dried over $Na_2SO_4$, filtered and concentrated under reduced pressure to give a residue. The residue was purified by prep-HPLC (neutral condition; column: Waters Xbridge Prep OBD C18 150*40 mm*10 um; mobile phase: [water ($NH_4HCO_3$)-ACN]; B %: 30%-70%, 8 min) to provide product as a white solid (2.73 mg, 3.98 umol, 1.98% yield); LCMS: RT=2.673 min, MS cal.: 686.1, [M+H]$^+$=687.2; HPLC: RT=3.232 min, purity: 91.2%; $^1$H NMR (400 MHz, METHANOL-$d_4$) δ=8.91 (s, 1H) 8.27 (s, 1H) 8.08 (s, 1H) 7.94 (d, J=8.4 Hz, 1H) 7.84-7.79 (m, 1H) 7.64 (t, J=7.6 Hz, 1H) 7.56-7.51 (m, 2H) 7.49-7.44 (m, 1H) 6.37 (d, J=8.4 Hz, 1H) 6.14 (d, J=8.4 Hz, 1H) 5.99 (s, 2H) 5.44 (s, 2H) 4.24-4.08 (m, 3H) 2.98 (m, 1H) 2.84-2.74 (m, 2H) 2.71-2.63 (m, 1H) 2.44-2.36 (m, 1H) 0.75-0.71 (m, 1H) 0.54-0.47 (m, 1H).

Example 27 (Synthesis of Compound 39)

2-((5-(2-(4-Cyano-2-fluorophenyl)-2-methylbenzo[d][1,3]dioxol-4-yl)-2,5-diazabicyclo[4.1.0]heptan-2-yl)methyl)-1-((R)-2-methoxypropyl)-1H-benzo[d]imidazole-6-carboxylic Acid

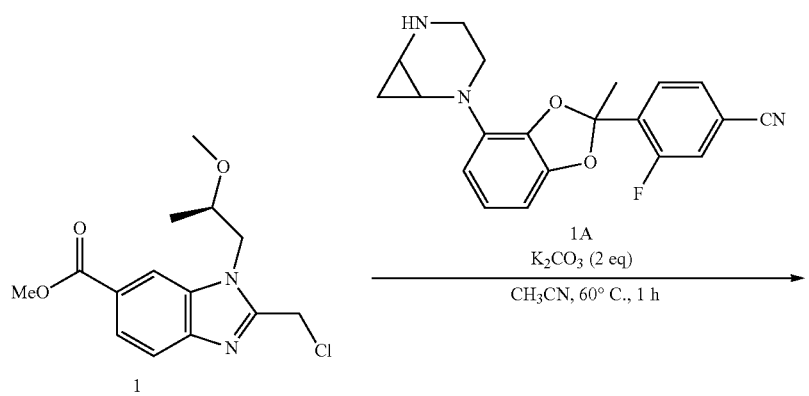

-continued
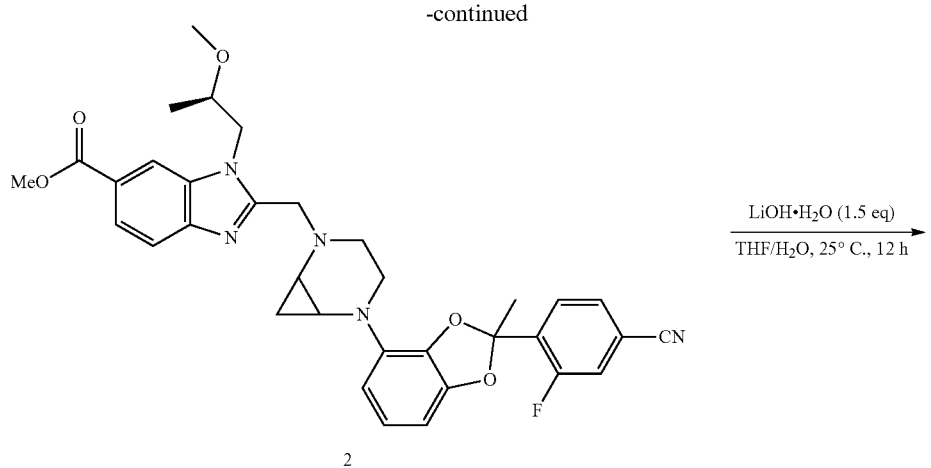
2
LiOH·H₂O (1.5 eq)
———————————→
THF/H₂O, 25° C., 12 h
Compound 39
(mixture 4 diastereomers)
Preparation of Methyl 2-((5-(2-(4-cyano-2-fluorophenyl)-2-methylbenzo[d][1,3]dioxol-4-yl)-2,5-diazabicyclo[4.1.0]heptan-2-yl)methyl)-1-((R)-2-methoxypropyl)-1H-benzo[d]imidazole-6-carboxylate (2)
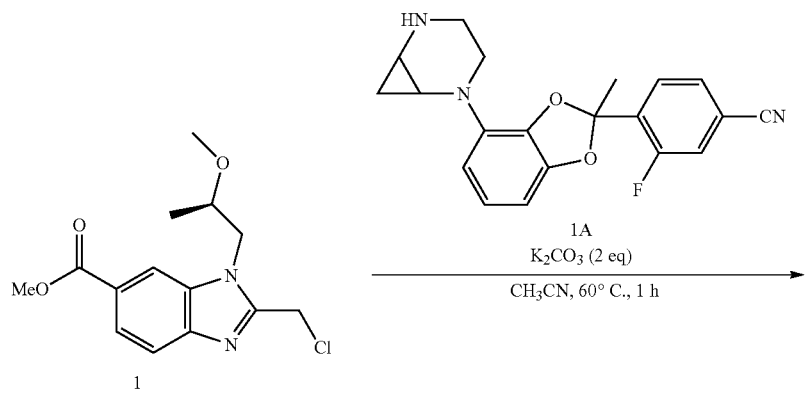
1
1A
K₂CO₃ (2 eq)
———————————→
CH₃CN, 60° C., 1 h

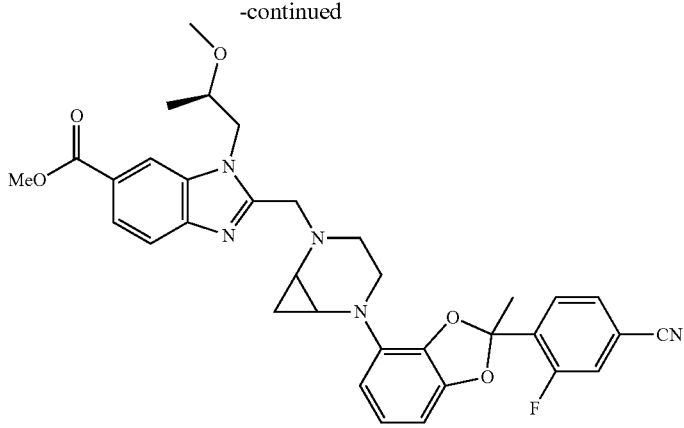

A mixture of methyl (R)-2-(chloromethyl)-1-(2-methoxypropyl)-1H-benzo[d]imidazole-6-carboxylate (250 mg, 842 umol, 1.29 eq), 4-(4-(2,5-diazabicyclo[4.1.0]heptan-2-yl)-2-methylbenzo[d][1,3]dioxol-2-yl)-3-fluorobenzonitrile (230 mg, 655 umol, 1 eq), K$_2$CO$_3$ (271 mg, 1.96 mmol, 3 eq), in CH$_3$CN (3 mL) was degassed and purged with N$_2$ for 3 times at 25° C., and then the mixture was stirred at 60° C. for 1 h under N$_2$ atmosphere. LC-MS showed starting material was consumed completely and one main peak with desired mass was detected. The reaction mixture was concentrated under reduced pressure to remove solvent. The residue was diluted with H$_2$O 25 mL and extracted with DCM 45 mL (15 mL*3). The combined organic layers were washed with H$_2$O 35 mL, dried over Na$_2$SO$_4$, filtered and concentrated under reduced pressure to product as a white solid (200 mg, 327 umol, 50% yield); LCMS: RT=2.437 min, MS cal.: 611.6, [M+H]$^+$=612.2.

Preparation of 2-((5-(2-(4-Cyano-2-fluorophenyl)-2-methylbenzo[d][1,3]dioxol-4-yl)-2,5-diazabicyclo[4.1.0]heptan-2-yl)methyl)-1-((R)-2-methoxypropyl)-1H-benzo[d]imidazole-6-carboxylic Acid, Mixture of 4 Diastereomers (Compound 39)

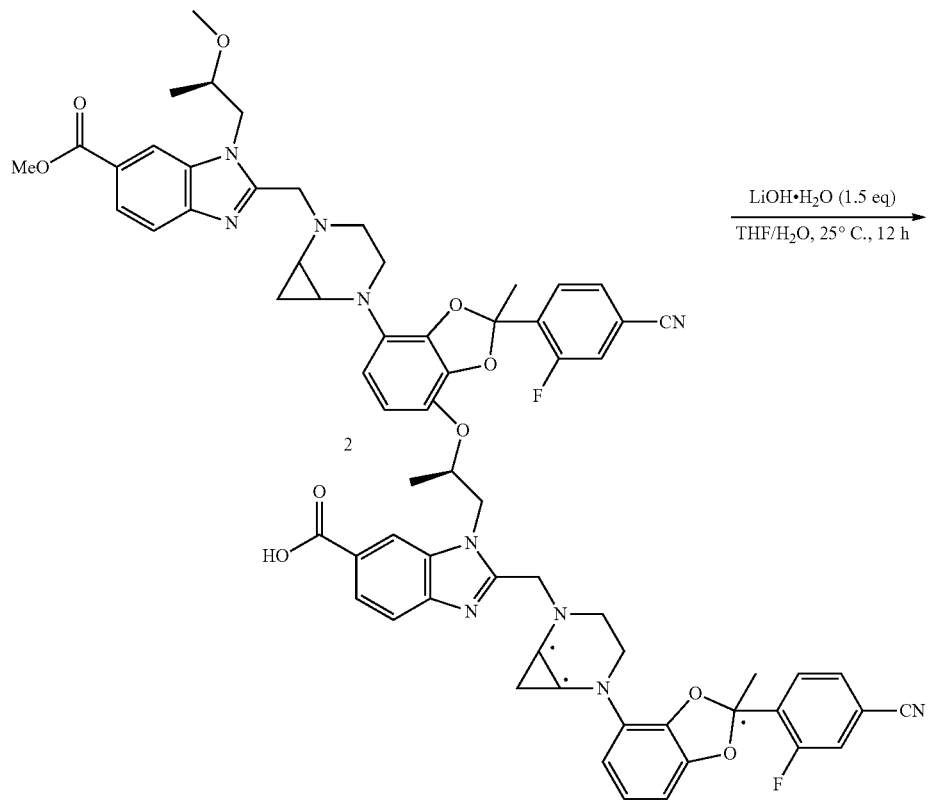

Compound 39
(mixture 4 diastereomers)

A mixture of methyl 2-((5-(2-(4-cyano-2-fluorophenyl)-2-methylbenzo[d][1,3]dioxol-4-yl)-2,5-diazabicyclo[4.1.0]heptan-2-yl)methyl)-1-((R)-2-methoxypropyl)-1H-benzo[d]imidazole-6-carboxylate (120 mg, 196 μmol, 1 eq), LiOH·H$_2$O (12.4 mg, 294 μmol, 1.5 eq), in H$_2$O (0.6 mL)/THF (1.4 mL) was degassed and purged with N$_2$ for 3 times at 25° C., and then the mixture was stirred at 25° C. for 12 h under N$_2$ atmosphere. LC-MS showed starting material was consumed completely and one main peak with desired mass was detected. The reaction mixture was concentrated under reduced pressure to remove solvent. The residue was purified by prep-HPLC (column: Phenomenex C18 75*30 mm*3 um; mobile phase: [water (NH$_4$HCO$_3$)-ACN]; B %: 30%-65%, 8 min) to provide product as a white solid (26 mg, 43.5 umol, 22.2% yield); LCMS: RT=2.427 min, MS cal.: 597.6, [M+H]$^+$=598.3; $^1$H NMR (400 MHz, DMSO-d$_6$) δ=8.19 (s, 1H) 7.99-7.93 (m, 1H) 7.80 (d, J=8.4 Hz, 1H) 7.76-7.69 (m, 2H) 7.64 (d, J=8.4 Hz, 1H) 6.74 (m, 1H) 6.45-6.53 (m, 1H) 6.39 (m, 1H) 4.52-4.37 (m, 2H) 4.23-4.13 (m, 1H) 3.99-3.84 (m, 1H) 3.82-3.74 (m, 1H) 3.58-3.73 (m, 1H) 3.21 (m, 1H) 3.13 (s, 3H) 2.89-2.60 (m, 3H) 2.47-2.29 (m, 1H) 2.06 (s, 3H) 1.27-1.17 (m, 3H) 0.66-0.41 (m, 2H).

Biological Assays

Example B1: GLP-1R Cell Assay

Stable cell lines expressing high and low GLP-1R surface expression were generated in CHO-K1 cells transfected (Fugene 6) with a puromycin selectable DNA plasmid encoding human GLP-1R receptor (accession number: NM_002062.5) under control of an EF1A promoter. Transfected cells were seeded into 24-well plates (9,000 cells/well) containing complete medium and incubated in a humidified incubator at 37° C. with 5% carbon dioxide. After overnight incubation, medium was replaced with complete medium supplemented with puromycin (6 μg/mL) and refreshed every 2-3 days to select for stably transfected cells. Individual pools of selected cells were expanded prior to analysis for responsiveness to GLP-1 control peptide using a TR-FRET assay to detect cAMP (LANCE Ultra cAMP Assay, Perkin Elmer). Briefly, cells were collected in Versene solution, plated in 384-well plates (1,000 cells/well) and combined with serially diluted GLP-1R control peptide (10 nL) using an acoustic dispenser (ECHO). Plates were incubated for 30 minutes at 25° C. prior to the addition of EU-cAMP tracer (5 μL) and Ulight-anti-cAMP (5 μL) reagents to each well, followed by 15 minutes incubation at 25° C. TR-FRET signal was detected using an EnVision Multimode Plate Reader (excitation=320 nm; emission=615 and 655 nm). Dose-response curves were used to generate EC$_{50}$ values as a measure of responsiveness to the GLP-1R control peptide. Selected cell lines were monitored for responsiveness over multiple passages to ensure stability. CHO-K1_hGLP-1Rhigh_clone16 and CHO-K1_hGLP-1Rlow_clone10 showed consistently high and low responsiveness to GLP-1R control peptide, respectively, and were chosen for further analysis to determine relative levels of GLP-1R surface expression. Briefly, GLP-1R expression was analyzed by flow cytometry using a fluorescein-labeled Exendin-4 peptide fluorescent probe (FLEX). Cells were harvested in Versene solution and washed 3-times with PBS+0.5% BSA before incubation with FLEX reagent (10 μM) for 2 hours at room temperature. After incubation, cells were washed 3-times in PBS+0.5% BSA before final resuspension in PBS prior to analysis by flow cytometry to measure FLEX mean fluorescence intensity (MFI) as a measure of GLP-1R expression on the cell surface. Both cell lines showed higher MFI values relative to control CHO-K1 cells, confirming GLP-1R surface expression; CHO-K1_hGLP-1Rhigh_clone16 cells showed significantly higher MFI levels relative to CHO-K1-hGLP-1low_clone10 cells.

For compound testing in the CHO-K1_hGLP-1Rlow_clone10 cell lines, cells were seeded in 384-well plates (1,000 cells/well). Test compounds were serially diluted in DMSO (10-point, 3-fold dilution), added to wells using an ECHO dispenser (10 nL/well) and plates were centrifuged for 1 min and agitated for 2 min at room temperature prior to 30-minute incubation at 25° C. After incubation, Eu-cAMP (5 μL) and Ulight-anti-cAMP (5 μL) reagents were added to each well, followed by centrifugation for 1 minute, agitation for 2 minutes at room temperature, and final incubation of the plates at 25° C. for 15 minutes. Plates were read using an EnVision microplate reader (excitation=320 nm; emission=615 and 655 nm). Dose-response curves were generated from duplicate wells based on percent activation calculated relative to a control GLP-1 peptide agonist that was run in parallel. EC$_{50}$ values were determined by fitting percent activation as a function of compound concentration using the Hill equation (XLfit).

The EC50 values of exemplary compounds in the low expression assay are shown in the table below. The EC50 values are compared to Reference Compound A and Reference Compound B. The compounds tested were compound samples prepared according to the General Procedures described in the Examples section.

| Compound No. | GLP-1R Low Expression Cell Assay EC50 |
|---|---|
| | D |

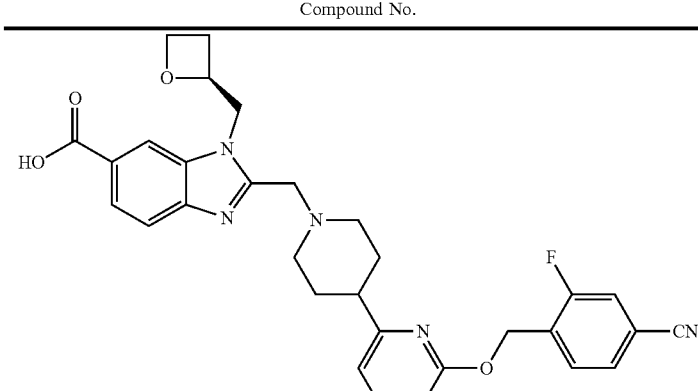

Reference Compound A

-continued

| Compound No. | GLP-1R Low Expression Cell Assay EC50 |
|---|---|
| 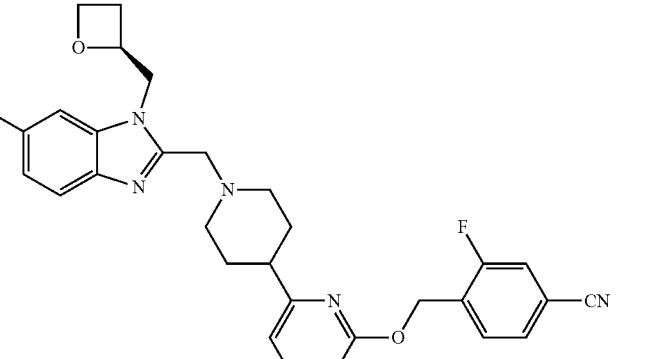<br>Reference Compound B | D |
| 1 | D |
| 2 | B |
| 4 | D |
| 5 | C |
| 12 | A |
| 13 | A |
| 14 | C |
| 15 | C |
| 16 | C |
| 18 | D |
| 19 | A |
| 20 | C |
| 21 | C |
| 34 | D |
| 35 | A |
| 36 | C |
| 37 | D |
| 38 | A |
| 39 | B |
| 40 | D |
| 41 | D |
| 42 | B |
| 43 | D |
| 44 | A |
| 45 | D |
| 46 | B |

A: >100 nM; B: 50-100 nM; C: 5.0-50 nM; D: <5.0 nM

Example B2: Metabolic Stability in Hepatocytes

Test compounds were incubated in human hepatocytes and stability was assessed from the substrate depilation approach. Test compounds were dissolved in dimethyl sulfoxide (DMSO) to create a 10 mM Stock, and then further diluted to create a 1000× Working Stock of 1 mM with DMSO in 96-well plates for test compounds and the positive control (midazolam). Vials containing cryopreserved hepatocytes were removed from the liquid nitrogen tank and immediately immersed in a 37° C. water bath. The vials were shaken gently until the contents had thawed and were then immediately emptied into 48 mL of pre-warmed HT Medium in a 50 mL conical tube. Cells remaining in the vial were resuspended with 1.0 mL of pre-warmed HT Medium and added to the conical tube. The tube was capped and then gently inverted several times to resuspend the hepatocytes. The cell suspension was centrifuged at 50×g at room temperature for 5 minutes and the supernatant discarded. The cell pellet was loosened by gently swirling the centrifuge tube and was re-suspended in 4 mL of warm Dulbecco's Modified Eagle medium (DMEM). Cell density was determined by a cell counter by Nexcelom, and DMEM medium was added to obtain a target density of 1×106 cells/mL. The assay was carried out in 96-well microtiter plates. Test Compounds were incubated at 1 µM with 1×10$^6$ cells/mL hepatocytes in DMEM for 0, 30, 60, 120 and 240 minutes. The incubation was carried out with gentle shaking at 37° C. under a humid atmosphere of 95% air/5% $CO_2$. The volume of the incubation mixture was 37 µL with a final 0.1% DMSO. At each of the time points, the incubation was stopped by adding 150 µL quenching solution (100% acetonitrile, 0.1% formic acid containing bucetin as an internal standard for positive ESI mode). Subsequently, the mixtures were vortexed for 20 min and centrifuged at 4,000 RPM at 10° C. The supernatant (80 µL) was transferred to a clean 96-well plate and analyzed by LC-MS/MS. Midazolam at 1 µM with a final 0.1% DMSO was included as a positive control to verify assay performance. The percent parent remaining, intrinsic and predicted hepatic clearance and $t_{1/2}$ were calculated. All samples were analyzed by LC-MS/MS using an AB Sciex API 4000 instrument, coupled to a Shimadzu LC-20AD LC Pump system. Separation was achieved using a Waters Atlantis T3 dC18 reverse phase HPLC column (20 mm×2.1 mm) at a flow rate of 0.5 mL/min. The mobile phase consisted of 0.1% formic acid in water (solvent A) and 0.1% formic acid in 100% acetonitrile (solvent B). Elution conditions are detailed below.

| Time (min) | Flow (μL/min) | % A | % B |
|---|---|---|---|
| 0 | 500 | 98 | 2 |
| 0.30 | 500 | 98 | 2 |
| 1.40 | 500 | 2 | 98 |
| 2.20 | 500 | 2 | 98 |
| 2.21 | 500 | 98 | 2 |
| 3.00 | 500 | 98 | 2 |

The ion optics of each test compound were optimized for their declustering potential (DP), collection energy (CE), collision-cell exit potential (CXP) and used in a selected ion monitoring experiment in the positive ion mode. The peak area ratio of each test compound to internal standard was then evaluated for stability. The extent of metabolism was calculated based on the disappearance of the test compound, compared to its initial concentration. The initial rates of clearance of the test compound were calculated using the linear regression plot of semi-log % remaining of the compound versus time. The elimination rate constant (k) of the linear regression plot was then used to determine $t_{1/2}$ and the intrinsic clearance ($CL_{int}$) using the following formula, where $C_{hepatocyte}$ (million cells/mL) is the cell density of the incubation:

$k = -\text{slope}$ $t_{1/2} = 0.693/k$ $CL_{int} = k/C_{hepatocyte}$

This method of intrinsic clearance determination assumes that the test compound concentration is far below the Michaelis-Menten constant of the compound to its metabolizing enzymes.

The predicted hepatic clearance ($CL_{hep}$) was calculated using the well stirred method with the following formula with $CL_{int(in\ vivo)}$ normalized based on liver weight:

$CL_{int(in\ vivo)} = CL_{int} \times \text{Hepatocellularity} \times \text{liver weight}$ $CL_{hep\ predicted} = (CL_{int(in\ vivo)} \times Q_{liver})/(CL_{int}(\text{in vivo}) + Q_{liver})$ Where $Q_{liver}$ ((ml/min/kg) is Liver Blood Flow The relevant physiological parameters of liver weight, blood flow, and hepatocellularity for humans are listed below:

| Liver Weight (g liver/kg body weight) | Hepatocellularity (106 cells/g liver) | Liver BloodFlow ($Q_{liver}$, mL/min/kg) |
|---|---|---|
| 25.7 | 135 | 20.7 |

Results are presented in the Table below for the intrinsic clearance (mL/min/kg) and half-life ($t_{1/2}$).

TABLE 2

| Cmpd No. | hHep $CL_{int}$ (mL/min/kg) | hHep $t_{1/2}$ (min) |
|---|---|---|
| Reference Compound B | 15.5 | 156 |
| 1 | 11.9 | 201.8 |
| 2 | 5.01 | 480 |

TABLE 2-continued

| Cmpd No. | hHep $CL_{int}$ (mL/min/kg) | hHep $t_{1/2}$ (min) |
|---|---|---|
| 4 | 14 | 172 |
| 5 | 7.46 | 322 |
| 14 | 7.86 | 306 |
| 15 | 9.24 | 260 |
| 18 | 17.5 | 13.8 |
| 19 | 5.01 | 480 |
| 20 | 6.4 | 376 |
| 40 | 5.86 | 411 |
| 42 | 5.01 | 480 |
| 43 | 7.09 | 339 |
| 44 | 5.01 | 480 |
| 45 | 6.46 | 372 |

Example B3. Passive Permeability and Efflux Ratio

Caco-2 cells (clone C2BBe1) were obtained from American Type Culture Collection (Manassas, VA). Cell monolayers were grown to confluence on collagen-coated, microporous membranes in 12-well assay plates. Details of the plates and their certification are shown below. The permeability assay buffer was Hanks' balanced salt solution containing 10 mM HEPES and 15 mM glucose at a pH of 7.4. The buffer in the receiver chamber also contained 1% bovine serum albumin. The dosing solution concentration was 5 μM of test article in the assay buffer. Cell monolayers were dosed on the apical side (A-to-B) or basolateral side (B-to-A) and incubated at 37° C. with 5% $CO_2$ in a humidified incubator. Samples were taken from the donor and receiver chambers at 120 minutes. Each determination was performed in duplicate. The flux of lucifer yellow was also measured post-experimentally for each monolayer to ensure no damage was inflicted to the cell monolayers during the flux period. All samples were assayed by LC-MS/MS using electrospray ionization. The apparent permeability ($P_{app}$) and percent recovery were calculated as follows:

$$P_{app} = (dC_r/dt) \times V_r/(A \times C_A) \quad (1)$$

$$\text{Percent Recovery} = 100 \times ((V_r \times C_r^{final}) + (V_d \times C_d^{final}))/(V_d \times C_N) \quad (2),$$

where, $dC_r/dt$ is the slope of the cumulative receiver concentration versus time in μM s$^{-1}$; $V_r$ is the volume of the receiver compartment in cm$^3$; $V_d$ is the volume of the donor compartment in cm$^3$; A is the area of the insert (1.13 cm$^2$ for 12-well); $C_A$ is the average of the nominal dosing concentration and the measured 120-minute donor concentration in μM; $C_N$ is the nominal concentration of the dosing solution in μM; $C_r^{final}$ is the cumulative receiver concentration in μM at the end of the incubation period; $C_d^{final}$ is the concentration of the donor in μM at the end of the incubation period. Efflux ratio (ER) is defined as $P_{app}$ (B-to-A)/$P_{app}$ (A-to-B).

TABLE 3

| Compound # | $P_{app}$ (A-to-B) | ER |
|---|---|---|
| 1 | 15 | 2.51 |
| 5 | 27.9 | 1.71 |
| 18 | 16.8 | 1.31 |

TABLE 3-continued

| Compound # | $P_{app}$ (A-to-B) | ER |
|---|---|---|
| 34 | 19.9 | 1.82 |
| 40 | 17.5 | 2.27 |

Example B4: Rat Pharmacokinetics

Intravenous dosing: Compounds were formulated at 0.5 mg/mL in a solution comprising 5% polyethylene glycol 400 and 95% (12% (w/v) sulfobutyl-β-cyclodextrin in water) (v/v). Formulated compounds were sterile filtered through a 0.22 micron filter before dosing. Compounds were administered to male, 7-11-week-old Sprague-Dawley rats by jugular vein cannula infusion over 30 minutes at a dose of 1 mg/kg.

Oral dosing: Compounds were formulated at 0.3 mg/mL or 0.6 mg/mL in a solution comprising 5% polyethylene glycol 400 and 95% (12% (w/v) sulfobutyl-β-cyclodextrin in water) (v/v). Formulated compounds were administered to male, 7-11 week old Sprague-Dawley rats by oral gavage at a dose of 10 mL/kg.

Sample collection: Blood collections of about 0.2 mL per time point were performed from jugular vein or other suitable site of each animal, into pre-chilled commercial EDTA-K2 tubes and placed on wet ice until centrifugation. Blood samples were processed for plasma by centrifugation at approximately 4° C., 3,200 g for 10 min. Plasma was collected and transferred into pre-labeled 96 well plate or polypropylene tubes, quick frozen over dry ice and kept at −60° C. or lower until LC-MS/MS analysis.

Data analysis: Plasma concentration versus time data was plotted in graph and analyzed by non-compartmental approaches using the Phoenix WinNonlin 6.3 software program. Related PK parameters were calculated according to dosing route, e.g., CL, $V_{dss}$ and $C_0$ for intravenous administration, $C_{max}$, $T_{max}$ or % F for extravascular administration, and $T_{1/2}$, $AUC_{(0-t)}$, $AUC_{(0-inf)}$, $MRT_{(0-t)}$, $MRT_{(0-inf)}$ for all routes.

TABLE 4

| Compound No. | Rat Cmax (ng/mL) | Rat $T_{1/2}$ (h) | Rat AUC (ng · h/mL) |
|---|---|---|---|
| 1 | 34.7 ± 13.7 | 4.58 | 71.8 ± 90.3 |
| 2 | 44.1 ± 6.5 | 2.41 | 63.5 ± 11.1 |
| 4 | 70 ± 31.99 | 0.92 | 86.3 ± 27.2 |
| 5 | 282 ± 4.04 | 1.31 | 418 ± 49.6 |
| 14 | 59.3 ± 5.68 | 0.645 | 66.8 ± 7.06 |
| 15 | 77.4 ± 16.2 | 0.597 | 71.7 ± 16.1 |
| 18 | 89.5 ± 23.6 | 0.89 | 84.9 ± 32.2 |
| 20 | 15.5 ± 7.15 | 0.578 | 22.9 ± 30 |
| 36 | 19.3 ± 2.70 | 1.8 | 20.7 ± 12.6 |
| 37 | 20 ± 7.7 | ND | 15.8 ± 7.6 |
| 38 | 58.3 ± 9.74 | 1.6 | 109 ± 21.5 |
| 40 | 28.3 ± 6.42 | 2.78 | 44.2 ± 8.62 |
| 43 | 64.5 ± 17.8 | 1.19 | 118 ± 10.0 |
| 45 | 9.62 | ND | 9.48 |

EXEMPLARY EMBODIMENTS

Exemplary Embodiment No. 1. A compound of Formula (0):

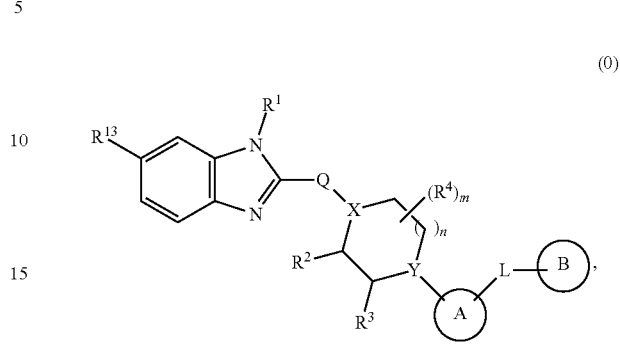

(0)

or a pharmaceutically acceptable salt, wherein:
$R^{13}$ is —C(O)OH or

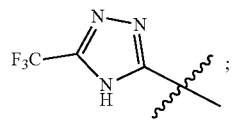

;

X is N or $CR^x$, wherein $R^x$ is hydrogen, OH or $C_1$-$C_6$ alkyl;

Y is N or $CR^y$, wherein $R^y$ is hydrogen, OH or $C_1$-$C_6$ alkyl;

n is 0 or 1;

Q is selected from the group consisting of —C($R^7$)($R^8$)—, —O—, —N($R^9$)—, and —S—, wherein
  $R^7$ and $R^8$ are independently hydrogen, halogen, or $C_1$-$C_6$ alkyl; and
  $R^9$ is hydrogen or $C_1$-$C_6$ alkyl;

$R^1$ is optionally substituted —$C_1$-$C_6$ alkylene or —$C_1$-$C_6$ alkylene-$R^5$, wherein $R^5$ is $C_3$-$C_6$ cycloalkyl, 3- to 6-membered heterocyclyl, or 5- to 6-membered heteroaryl, each of which is independently optionally substituted by one to three substituents independently selected from the group consisting of halo, oxo, CN, $C_1$-$C_6$ alkyl, $C_3$-$C_6$ cycloalkyl, and —O$C_1$-$C_6$ alkyl, wherein each $C_1$-$C_6$ alkyl, $C_3$-$C_6$ cycloalkyl, and —O$C_1$-$C_6$ alkyl substituent is independently optionally substituted by halo or CN;

$R^2$ and $R^3$ are taken together with the carbon atoms to which they are attached to form an optionally substituted $C_3$-$C_4$ cycloalkyl ring; or $R^2$ and $R^x$, when present, are taken together with the carbon atoms to which they are attached to form an optionally substituted $C_3$-$C_5$ cycloalkyl ring, and $R^3$ is hydrogen, oxo, or $C_1$-$C_6$ alkyl;

m is 0, 1, 2, or 3;

$R^4$ is oxo or $C_1$-$C_6$ alkyl;

Ring A is $C_6$-$C_{14}$ aryl, 5- to 12-membered heterocyclyl or 5- to 12-membered heteroaryl, each of which is independently optionally substituted by halo, OH, CN, $C_3$-$C_6$ cycloalkyl, or $C_1$-$C_6$ alkyl optionally substituted by halo or OH;

L is a bond, —O—, $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-**, wherein * represents the point of attachment to ring A and ** represents the point of attachment to ring B, and wherein:

when L is $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-**, L is optionally substituted by one to three $R^L$ substituents, wherein each $R^L$ is independently halo, OH, or $C_1$-$C_6$ alkyl; or two $R^L$ are taken together with the carbon atom or atoms to which they are attached to form $C_3$-$C_6$ cycloalkyl or 3- to 6-membered heterocyclyl;

$R^6$, when present, is hydrogen or $C_1$-$C_6$ alkyl; and

Ring B is $C_3$-$C_{10}$ cycloalkyl, $C_6$-$C_{14}$ aryl, 4- to 12-membered heterocyclyl, or 5- to 12-membered heteroaryl, each of which is independently optionally substituted by one to three substituents independently selected from the group consisting of halo, CN, oxo, $C_1$-$C_6$ alkyl optionally substituted by halo or CN, —$OC_1$-$C_6$ alkyl optionally substituted by halo or CN, —$COCH_3$, —$CONH_2$, —$S(O)_2CH_3$, and phenyl optionally substituted by halo or CN.

Exemplary Embodiment No. 2. A compound of Formula (1):

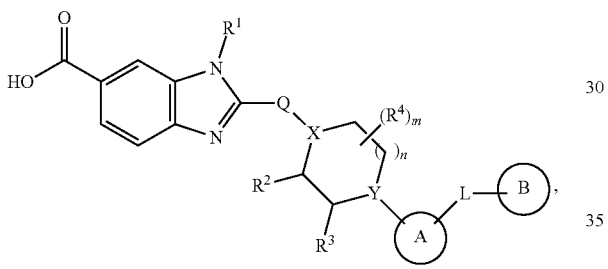

(1)

or a pharmaceutically acceptable salt thereof, wherein:

X is N or $CR^x$, wherein $R^x$ is hydrogen, OH or $C_1$-$C_6$ alkyl, and

Y is N or $CR^y$, wherein $R^y$ is hydrogen, OH or $C_1$-$C_6$ alkyl;

n is 0 or 1;

Q is selected from the group consisting of —$C(R^7)(R^8)$—, —O—, —$N(R^9)$—, and —S—, wherein $R^7$ and $R^8$ are independently hydrogen, halogen, or $C_1$-$C_6$ alkyl, and $R^9$ is hydrogen or $C_1$-$C_6$ alkyl;

$R^1$ is —$C_1$-$C_6$ alkylene-$R^5$, wherein $R^5$ is 3- to 6-membered heterocyclyl or 5- to 6-membered heteroaryl, each of which is independently optionally substituted by one to three substituents independently selected from the group consisting of halo, oxo, CN, $C_1$-$C_6$ alkyl, $C_3$-$C_6$ cycloalkyl, and —$OC_1$-$C_6$ alkyl, wherein each $C_1$-$C_6$ alkyl, $C_3$-$C_6$ cycloalkyl, and —$OC_1$-$C_6$ alkyl substituent is independently optionally substituted by halo or CN;

$R^2$ and $R^3$ are taken together with the carbon atoms to which they are attached to form an optionally substituted $C_3$-$C_4$ cycloalkyl ring; or $R^2$ and $R^x$, when present, are taken together with the carbon atoms to which they are attached to form an optionally substituted $C_3$-$C_5$ cycloalkyl ring, and $R^3$ is hydrogen, oxo, or $C_1$-$C_6$ alkyl;

m is 0, 1, 2, or 3;

$R^4$ is oxo or $C_1$-$C_6$ alkyl;

Ring A is $C_6$-$C_{14}$ aryl, 5- to 12-membered heterocyclyl or 5- to 12-membered heteroaryl, each of which is independently optionally substituted by halo, OH, CN, $C_3$-$C_6$ cycloalkyl, or $C_1$-$C_6$ alkyl optionally substituted by halo or OH;

L is a bond, —O—, $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-**, wherein * represents the point of attachment to ring A and ** represents the point of attachment to ring B, and wherein:

when L is $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-**, L is optionally substituted by one to three $R^L$ substituents, wherein each $R^L$ is independently halo, OH, or $C_1$-$C_6$ alkyl; or two $R^L$ are taken together with the carbon atom or atoms to which they are attached to form $C_3$-$C_6$ cycloalkyl or 3- to 6-membered heterocyclyl; and $R^6$, when present, is hydrogen or $C_1$-$C_6$ alkyl; and Ring B is $C_3$-$C_{10}$ cycloalkyl, $C_6$-$C_{14}$ aryl, 4- to 12-membered heterocyclyl, or 5- to 12-membered heteroaryl, each of which is independently optionally substituted by one to three substituents independently selected from the group consisting of halo, CN, oxo, $C_1$-$C_6$ alkyl optionally substituted by halo or CN, —$OC_1$-$C_6$ alkyl optionally substituted by halo or CN, —$COCH_3$, —$CONH_2$, —$S(O)_2CH_3$, and phenyl optionally substituted by halo or CN.

Exemplary Embodiment No. 3. The compound of Exemplary Embodiments No. 1 or 2, or a pharmaceutically acceptable salt thereof, wherein the compound is of Formula (0'):

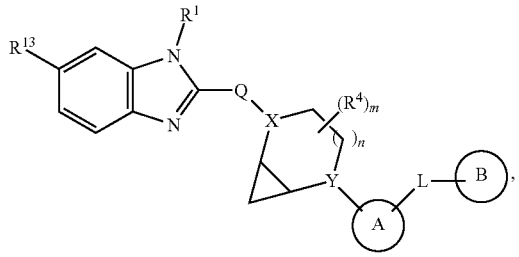

(0')

or a pharmaceutically acceptable salt thereof.

Exemplary Embodiment No. 4. The compound of Exemplary Embodiments No. 1-3, or a pharmaceutically acceptable salt thereof, wherein $R^{13}$ is —C(O)OH.

Exemplary Embodiment No. 5. The compound of Exemplary Embodiments No. 1-3, or a pharmaceutically acceptable salt thereof, wherein $R^{13}$ is H

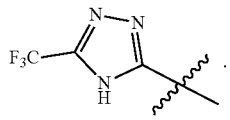

Exemplary Embodiment No. 6. The compound of Exemplary Embodiments No. 1-5, or a pharmaceutically acceptable salt thereof, wherein X is N and Y is $CR^y$.

Exemplary Embodiment No. 7. The compound of Exemplary Embodiments No. 1-5, or a pharmaceutically acceptable salt thereof, wherein X is $CR^x$ and Y is N.

Exemplary Embodiment No. 8. The compound of Exemplary Embodiments No. 1-5, or a pharmaceutically acceptable salt thereof, wherein X is N and Y is N.

Exemplary Embodiment No. 9. The compound of Exemplary Embodiments No. 1-8, wherein n is 0.

Exemplary Embodiment No. 10. The compound of Exemplary Embodiments No. 1-8, or a pharmaceutically acceptable salt thereof, wherein n is 1.

Exemplary Embodiment No. 11. The compound of Exemplary Embodiments No. 1-10, or a pharmaceutically acceptable salt thereof, wherein Q is —C($R^7$)($R^8$)—.

Exemplary Embodiment No. 12. The compound of Exemplary Embodiments No. 1-10, or a pharmaceutically acceptable salt thereof, wherein Q is —$CH_2$—.

Exemplary Embodiment No. 13. The compound of Exemplary Embodiments No. 1-10, or a pharmaceutically acceptable salt thereof, wherein Q is —O—.

Exemplary Embodiment No. 14. The compound of Exemplary Embodiments No. 1-10, or a pharmaceutically acceptable salt thereof, wherein Q is —N($R^9$)—.

Exemplary Embodiment No. 15. The compound of Exemplary Embodiments No. 1-14, or a pharmaceutically acceptable salt thereof, wherein $R^1$ is —$CH_2$—$R^5$.

Exemplary Embodiment No. 16. The compound of Exemplary Embodiments No. 1-15, or a pharmaceutically acceptable salt thereof, wherein $R^5$ is $C_3$-$C_6$ cycloalkyl optionally substituted by halo, oxo, $C_1$-$C_6$ alkyl, $C_{1-6}$ alkenyl, or $C_1$-$C_6$ haloalkyl.

Exemplary Embodiment No. 17. The compound of Exemplary Embodiment No. 16, or a pharmaceutically acceptable salt thereof, wherein $R^5$ is cyclopropyl optionally substituted by halo, oxo, $C_1$-$C_6$ alkyl, $C_{1-6}$ alkenyl, or $C_1$-$C_6$ haloalkyl.

Exemplary Embodiment No. 18. The compound of Exemplary Embodiments No. 1-15, or a pharmaceutically acceptable salt thereof, wherein $R^5$ is 4- to 5-membered heterocyclyl optionally substituted by halo, oxo, $C_1$-$C_6$ alkyl, $C_{1-6}$ alkenyl, or $C_1$-$C_6$ haloalkyl.

Exemplary Embodiment No. 19. The compound of Exemplary Embodiment No. 18, or a pharmaceutically acceptable salt thereof, wherein $R^5$ is 4-membered heterocyclyl optionally substituted by halo, oxo, $C_1$-$C_6$ alkyl, $C_{1-6}$ alkenyl, or $C_1$-$C_6$ haloalkyl.

Exemplary Embodiment No. 20. The compound of Exemplary Embodiment No. 19, or a pharmaceutically acceptable salt thereof, wherein $R^5$ is oxetanyl optionally substituted by halo, oxo, $C_1$-$C_6$ alkyl, $C_{1-6}$ alkenyl, or $C_1$-$C_6$ haloalkyl.

Exemplary Embodiment No. 21. The compound of Exemplary Embodiments No. 1-15, or a pharmaceutically acceptable salt thereof, wherein $R^5$ is 5-membered heteroaryl optionally substituted by halo, —O—$C_{1-6}$ alkyl, $C_{1-6}$ alkyl, $C_{1-6}$ alkenyl, or $C_1$-$C_6$ haloalkyl.

Exemplary Embodiment No. 22. The compound of Exemplary Embodiment No. 21, or a pharmaceutically acceptable salt thereof, wherein $R^5$ is oxazolyl, triazolyl, thiazolyl or isothiazolyl, each of which is optionally substituted by halo, —O—$C_{1-6}$ alkyl, $C_1$-$C_6$ alkyl, $C_{1-6}$ alkenyl, or $C_1$-$C_6$ haloalkyl.

Exemplary Embodiment No. 23. The compound of Exemplary Embodiment No. 22, or a pharmaceutically acceptable salt thereof, wherein $R^5$ is triazolyl or thiazolyl, each of which is optionally substituted by halo, —O—$C_{1-6}$ alkyl, $C_1$-$C_6$ alkyl, $C_{1-6}$ alkenyl, or $C_1$-$C_6$ haloalkyl.

Exemplary Embodiment No. 24. The compound of Exemplary Embodiment No. 23, or a pharmaceutically acceptable salt thereof, wherein $R^5$ is

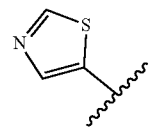

optionally substituted by halo, —O—$C_{1-6}$ alkyl, $C_1$-$C_6$ alkyl, $C_{1-6}$ alkenyl, or $C_1$-$C_6$ haloalkyl.

Exemplary Embodiment No. 25. The compound of Exemplary Embodiment No. 23, or a pharmaceutically acceptable salt thereof, wherein $R^5$ is

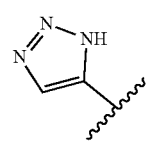

optionally substituted by halo, —O—$C_{1-6}$ alkyl, $C_1$-$C_6$ alkyl, $C_{1-6}$ alkenyl, or $C_1$-$C_6$ haloalkyl.

Exemplary Embodiment No. 26. The compound of Exemplary Embodiment No. 23, or a pharmaceutically acceptable salt thereof wherein $R^5$ is

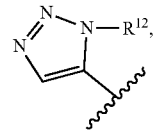

wherein $R^{12}$ is $C_1$-$C_6$ alkyl.

Exemplary Embodiment No. 27. The compound of Exemplary Embodiment No. 26, or a pharmaceutically acceptable salt thereof, wherein $R^{12}$ is methyl.

Exemplary Embodiment No. 28. The compound of Exemplary Embodiment No. 26, or a pharmaceutically acceptable salt thereof, wherein $R^{12}$ is ethyl.

Exemplary Embodiment No. 29. The compound of Exemplary Embodiments No. 1-28, or a pharmaceutically acceptable salt thereof, wherein Ring A is 5- to 6-membered heteroaryl optionally substituted by halo, CN, $C_3$-$C_6$ cycloalkyl, or $C_1$-$C_6$ alkyl optionally substituted by halo or OH.

Exemplary Embodiment No. 30. The compound of Exemplary Embodiment No. 29, or a pharmaceutically acceptable salt thereof, wherein Ring A is 6-membered heteroaryl optionally substituted by halo, CN, $C_3$-$C_6$ cycloalkyl, or $C_1$-$C_6$ alkyl optionally substituted by halo or OH.

Exemplary Embodiment No. 31. The compound of Exemplary Embodiment No. 30, or a pharmaceutically acceptable salt thereof, wherein Ring A is pyridyl, pyrimidinyl, or pyrazinyl, each of which is optionally substituted by halo, CN, $C_3$-$C_6$ cycloalkyl, or $C_1$-$C_6$ alkyl optionally substituted by halo or OH.

Exemplary Embodiment No. 32. The compound of Exemplary Embodiment No. 31, or a pharmaceutically acceptable salt thereof, wherein Ring A is

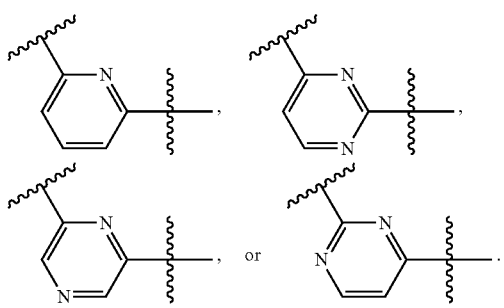

Exemplary Embodiment No. 33. The compound of Exemplary Embodiment No. 32, or a pharmaceutically acceptable salt thereof, wherein Ring A is

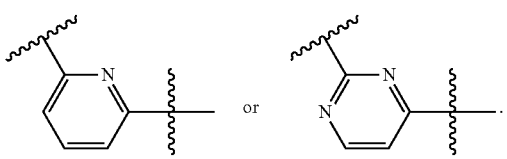 [SMILES: *c1cccc(*)n1 ; *c1ccnc(*)n1]

Exemplary Embodiment No. 34. The compound of Exemplary Embodiment No. 33, or a pharmaceutically acceptable salt thereof, wherein Ring A is

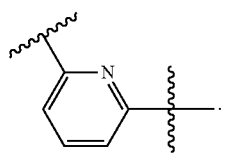 [SMILES: *c1cccc(*)n1]

Exemplary Embodiment No. 35. The compound of Exemplary Embodiments No. 1-28, or a pharmaceutically acceptable salt thereof, wherein Ring A is 10- to 12-membered heterocyclyl or 10- to 12-membered heteroaryl optionally substituted by halo, CN, $C_3$-$C_6$ cycloalkyl, or $C_1$-$C_6$ alkyl optionally substituted by halo or OH.

Exemplary Embodiment No. 36. The compound of Exemplary Embodiment No. 35, or a pharmaceutically acceptable salt thereof, wherein Ring A is an optionally substituted benzodioxole.

Exemplary Embodiment No. 37. The compound of Exemplary Embodiment No. 36, or a pharmaceutically acceptable salt thereof, wherein Ring A is

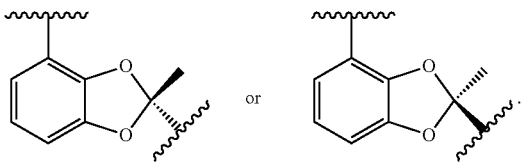 [SMILES: *c1cccc2c1O[C@@](*)(C)O2 ; *c1cccc2c1O[C@](*)(C)O2]

Exemplary Embodiment No. 38. The compound of Exemplary Embodiments No. 1-37, or a pharmaceutically acceptable salt thereof, wherein L is *—O—$C_1$-$C_6$ alkylene-** optionally substituted by $R^L$.

Exemplary Embodiment No. 39. The compound of Exemplary Embodiment No. 38, or a pharmaceutically acceptable salt thereof, wherein L is *—O—$CH_2$—**.

Exemplary Embodiment No. 40. The compound of Exemplary Embodiments No. 1-37, or a pharmaceutically acceptable salt thereof, wherein L is —O—.

Exemplary Embodiment No. 41. The compound of Exemplary Embodiments No. 1-37, or a pharmaceutically acceptable salt thereof, wherein L is a bond.

Exemplary Embodiment No. 42. The compound of Exemplary Embodiments No. 1-41, or a pharmaceutically acceptable salt thereof, wherein Ring B is $C_6$-$C_{14}$ aryl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl.

Exemplary Embodiment No. 43. The compound of Exemplary Embodiment No. 42, or a pharmaceutically acceptable salt thereof, wherein Ring B is phenyl optionally substituted by one to three substituents each independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl.

Exemplary Embodiment No. 44. The compound of Exemplary Embodiment No. 43, or a pharmaceutically acceptable salt thereof, wherein Ring B is

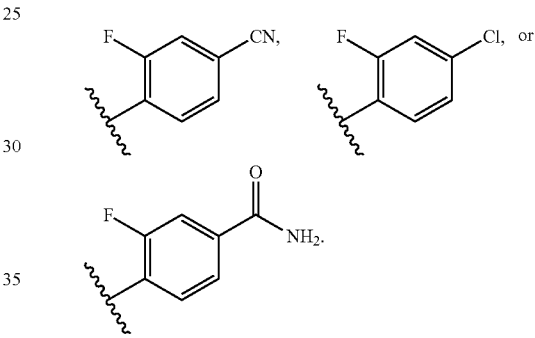

Exemplary Embodiment No. 45. The compound of Exemplary Embodiment No. 44, or a pharmaceutically acceptable salt thereof, wherein Ring B is

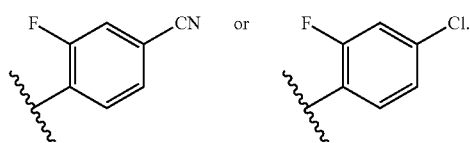 [SMILES: *c1ccc(C#N)cc1F ; *c1ccc(Cl)cc1F]

Exemplary Embodiment No. 46. The compound of Exemplary Embodiments No. 1-41, or a pharmaceutically acceptable salt thereof, wherein Ring B is 4- to 12-membered heterocyclyl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl.

Exemplary Embodiment No. 47. The compound of Exemplary Embodiment No. 46, or a pharmaceutically acceptable salt thereof, wherein Ring B is tetrahydroisoquinolinyl optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl.

Exemplary Embodiment No. 48. The compound of Exemplary Embodiment No. 47, or a pharmaceutically acceptable salt thereof, wherein Ring B is

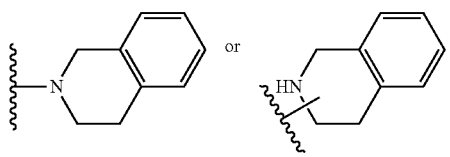

optionally substituted by one to three substituents independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$ and phenyl.

Exemplary Embodiment No. 49. The compound of Exemplary Embodiment No. 48, or a pharmaceutically acceptable salt thereof, wherein Ring B is

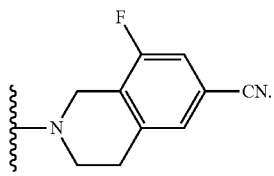 [SMILES: *N1CCc2cc(C#N)cc(F)c2C1]

Exemplary Embodiment No. 50. The compound of Exemplary Embodiments No. 1-41, or a pharmaceutically acceptable salt thereof, wherein Ring B is 5- to 12-membered heteroaryl, which is optionally substituted by one to three substituents independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$ and phenyl.

Exemplary Embodiment No. 51. The compound of Exemplary Embodiment No. 50, or a pharmaceutically acceptable salt thereof, wherein Ring B is 9-membered heteroaryl, which is optionally substituted by one to three substituents independently selected from the group consisting of halo, CN, oxo, $C_1$-$C_6$ alkyl, $C_1$-$C_6$ haloalkyl, —COCH$_3$, —CONH$_2$, —S(O)$_2$CH$_3$ and phenyl.

Exemplary Embodiment No. 52. The compound of Exemplary Embodiment No. 1, wherein the compound is of Formula (8):

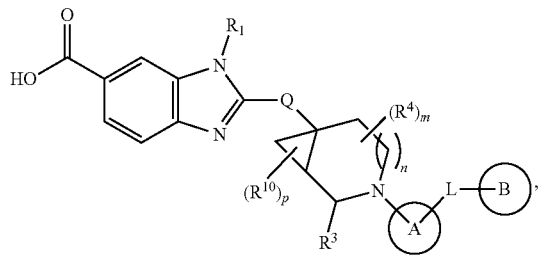

or a pharmaceutically acceptable salt thereof.

Exemplary Embodiment No. 53. A compound, or pharmaceutically acceptable salt thereof, wherein the compound is selected from any one of the compounds in Table 1.

Exemplary Embodiment No. 54. A pharmaceutical composition comprising the compound of Exemplary Embodiments No. 1-53, or a pharmaceutically acceptable salt thereof, and a pharmaceutical acceptable excipient.

Exemplary Embodiment No. 55. A method of treating a disease mediated by glucagon-like peptide-1 receptor (GLP-1R) in an individual in need thereof, comprising administering to the individual a therapeutically effective amount of the compound of Exemplary Embodiments No. 1-53, or a pharmaceutically acceptable salt thereof, or the pharmaceutical composition of Exemplary Embodiment No. 54.

Exemplary Embodiment No. 56. The method of Exemplary Embodiment No. 55, wherein the disease is a liver disease.

Exemplary Embodiment No. 57. The method of Exemplary Embodiment No. 56, wherein the liver disease is primary biliary cirrhosis (PBC), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, viral hepatitis, alcoholic liver disease, nonalcoholic fatty liver disease (NAFLD), nonalcoholic steatohepatitis (NASH), graft versus host disease, transplant liver regeneration, congenital hepatic fibrosis, choledocholithiasis, granulomatous liver disease, intra- or extrahepatic malignancy, Sjogren's syndrome, sarcoidosis, Wilson's disease, Gaucher's disease, hemochromatosis, or oti-antitrypsin deficiency.

Exemplary Embodiment No. 58. The method of Exemplary Embodiment No. 55, wherein the disease is diabetes.

Exemplary Embodiment No. 59. The method of Exemplary Embodiment No. 55, wherein the disease is a cardiometabolic disease.

Exemplary Embodiment No. 60. The method of Exemplary Embodiment No. 55, wherein the disease is obesity.

Exemplary Embodiment No. 61. Use of the compound of Exemplary Embodiments No. 1-53, or a pharmaceutically acceptable salt thereof, in the manufacture of a medicament for treating a disease mediated by GLP-1R.

EQUIVALENTS

It is understood that the invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

The invention claimed is:

1. A compound of Formula (0'):

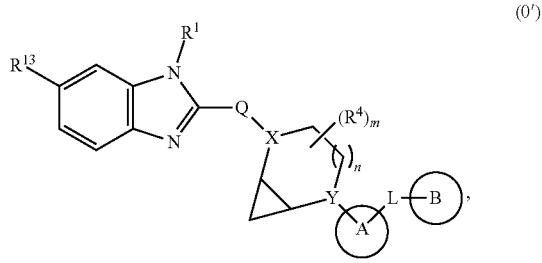

or a pharmaceutically acceptable salt, wherein:
$R^{13}$ is —C(O)OH or

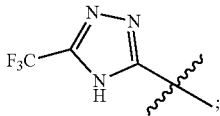 [SMILES: *c1nnc(C(F)(F)F)[nH]1]

X is N or $CR^x$, wherein $R^x$ is hydrogen, OH or $C_1$-$C_6$ alkyl;
Y is N or $CR^y$, wherein $R^y$ is hydrogen, OH or $C_1$-$C_6$ alkyl;
n is 0 or 1;
Q is selected from the group consisting of —C($R^7$)($R^8$)—, —O—, —N($R^9$)—, and —S—, wherein:
  $R^7$ and $R^8$ are independently hydrogen, halogen, or $C_1$-$C_6$ alkyl; and
  $R^9$ is hydrogen or $C_1$-$C_6$ alkyl;
$R^1$ is optionally substituted —$C_1$-$C_6$ alkylene or —$C_1$-$C_6$ alkylene-$R^5$, wherein $R^5$ is $C_3$-$C_6$ cycloalkyl, 3- to 6-membered heterocyclyl, or 5- to 6-membered heteroaryl, each of which is independently optionally substituted by one to three substituents independently selected from the group consisting of halo, oxo, CN, $C_1$-$C_6$ alkyl, $C_3$-$C_6$ cycloalkyl, and —O$C_1$-$C_6$ alkyl, wherein each $C_1$-$C_6$ alkyl, $C_3$-$C_6$ cycloalkyl, and —O$C_1$-$C_6$ alkyl substituent is independently optionally substituted by halo or CN;
m is 0, 1, 2, or 3;
$R^4$ is oxo or $C_1$-$C_6$ alkyl;
Ring A is $C_6$-$C_{14}$ aryl, 5- to 12-membered heterocyclyl or 5- to 12-membered heteroaryl, each of which is independently optionally substituted by halo, OH, CN, $C_3$-$C_6$ cycloalkyl, or $C_1$-$C_6$ alkyl optionally substituted by halo or OH;
L is a bond, —O—, $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-**, wherein * represents the point of attachment to ring A and ** represents the point of attachment to ring B, and wherein:
  when L is $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-**, L is optionally substituted by one to three $R^L$ substituents, wherein each $R^L$ is independently halo, OH, or $C_1$-$C_6$ alkyl; or two $R^L$ are taken together with the carbon atom or atoms to which they are attached to form $C_3$-$C_6$ cycloalkyl or 3- to 6-membered heterocyclyl;
$R^6$, when present, is hydrogen or $C_1$-$C_6$ alkyl; and
Ring B is $C_3$-$C_{10}$ cycloalkyl, $C_6$-$C_{14}$ aryl, 4- to 12-membered heterocyclyl, or 5- to 12-membered heteroaryl, each of which is independently optionally substituted by one to three substituents independently selected from the group consisting of halo, CN, oxo, $C_1$-$C_6$ alkyl optionally substituted by halo or CN, —O$C_1$-$C_6$ alkyl optionally substituted by halo or CN, —COCH$_3$, —CONH$_2$, —S(O)$_2$CH$_3$, and phenyl optionally substituted by halo or CN.

2. The compound of claim 1, or a pharmaceutically acceptable salt thereof, wherein $R^{13}$ is —C(O)OH.

3. The compound of claim 1, or a pharmaceutically acceptable salt thereof, wherein:
  (i) X is N and Y is $CR^y$;
  (ii) X is $CR^x$ and Y is N; or
  (iii) X is N and Y is N.

4. The compound of claim 1, or a pharmaceutically acceptable salt thereof, wherein:
  (i) n is 0 or 1;
  (ii) Q is —C($R^7$)($R^8$)—, —CH$_2$—, —O—, or —N($R^9$)—; and/or
  (iii) $R^1$ is —CH$_2$—$R^5$.

5. The compound of claim 1, or a pharmaceutically acceptable salt thereof, wherein $R^5$ is:
  (i) $C_3$-$C_6$ cycloalkyl optionally substituted by halo, oxo, $C_1$-$C_6$ alkyl, $C_{1-6}$ alkenyl, or $C_1$-$C_6$ haloalkyl;
  (ii) 4- to 5-membered heterocyclyl optionally substituted by halo, oxo, $C_1$-$C_6$ alkyl, $C_{1-6}$ alkenyl, or $C_1$-$C_6$ haloalkyl; or
  (iii) 5-membered heteroaryl optionally substituted by halo, —O—$C_{1-6}$ alkyl, $C_{1-6}$ alkyl, $C_{1-6}$ alkenyl, or $C_1$-$C_6$ haloalkyl.

6. The compound of claim 5, or a pharmaceutically acceptable salt thereof, wherein $R^5$ is:
  (i) cyclopropyl optionally substituted by halo, oxo, $C_1$-$C_6$ alkyl, $C_{1-6}$ alkenyl, or $C_1$-$C_6$ haloalkyl;
  (ii) oxetanyl optionally substituted by halo, oxo, $C_1$-$C_6$ alkyl, $C_{1-6}$ alkenyl, or $C_1$-$C_6$ haloalkyl; or
  (iii) oxazolyl, triazolyl, thiazolyl or isothiazolyl, each of which is optionally substituted by halo, —O—$C_{1-6}$ alkyl, $C_1$-$C_6$ alkyl, $C_{1-6}$ alkenyl, or $C_1$-$C_6$ haloalkyl.

7. The compound of claim 6, or a pharmaceutically acceptable salt thereof, wherein $R^5$ is:

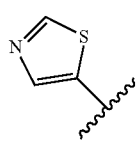

(i)

optionally substituted by halo, —O—$C_{1-6}$ alkyl, $C_1$-$C_6$ alkyl, $C_{1-6}$ alkenyl, or $C_1$-$C_6$ haloalkyl;

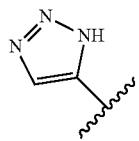

(ii)

optionally substituted by halo, —O—$C_{1-6}$ alkyl, $C_1$-$C_6$ alkyl, $C_{1-6}$ alkenyl, or $C_1$-$C_6$ haloalkyl; or

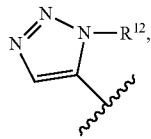

(iii)

wherein $R^{12}$ is $C_1$-$C_6$ alkyl.

8. The compound of claim 7, or a pharmaceutically acceptable salt thereof, wherein $R^{12}$ is methyl or ethyl.

9. The compound of claim 1, or a pharmaceutically acceptable salt thereof, wherein Ring A is:
  (i) 5- to 6-membered heteroaryl optionally substituted by halo, CN, $C_3$-$C_6$ cycloalkyl, or $C_1$-$C_6$ alkyl optionally substituted by halo or OH; or (ii) 10- to 12-membered heterocyclyl or 10- to 12-membered heteroaryl optionally substituted by halo, CN, $C_3$-$C_6$ cycloalkyl, or $C_1$-$C_6$ alkyl optionally substituted by halo or OH.

10. The compound of claim 9, or a pharmaceutically acceptable salt thereof, wherein Ring A is:
(i) pyridyl, pyrimidinyl, or pyrazinyl, each of which is optionally substituted by halo, CN, $C_3$-$C_6$ cycloalkyl, or $C_1$-$C_6$ alkyl optionally substituted by halo or OH; or
(ii) optionally substituted benzodioxole.

11. The compound of claim 10, or a pharmaceutically acceptable salt thereof, wherein Ring A is

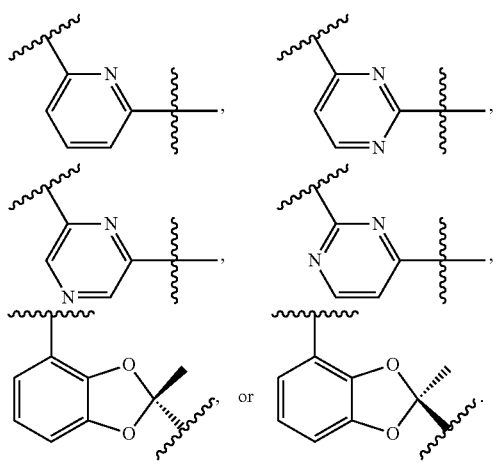

12. The compound of claim 1, or a pharmaceutically acceptable salt thereof, wherein L is:
(i) *—O—$C_1$-$C_6$ alkylene-** optionally substituted by $R^L$;
(ii) —O—; or
(iii) a bond.

13. The compound of claim 12, or a pharmaceutically acceptable salt thereof, wherein L is *—O—$CH_2$—**.

14. The compound of claim 1, or a pharmaceutically acceptable salt thereof, wherein Ring B is:
(i) $C_6$-$C_{14}$ aryl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl;
(ii) 4- to 12-membered heterocyclyl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl; or
(iii) 5- to 12-membered heteroaryl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl.

15. The compound of claim 14, or a pharmaceutically acceptable salt thereof, wherein Ring B is:
(i) phenyl optionally substituted by one to three substituents each independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl;
(ii) tetrahydroisoquinolinyl optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl; and/or
(iii) 9-membered heteroaryl, which is optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl.

16. The compound of claim 15, or a pharmaceutically acceptable salt thereof, wherein Ring B is

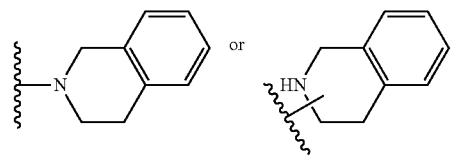

optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$ and phenyl.

17. The compound of claim 15, or a pharmaceutically acceptable salt thereof, wherein Ring B is

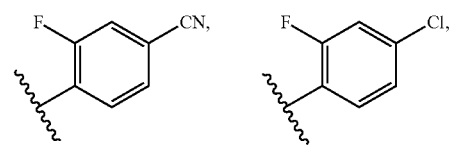

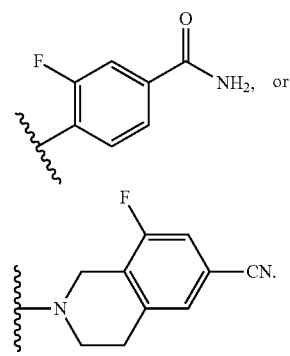

18. A compound, or pharmaceutically acceptable salt thereof, wherein the compound is selected from any one of the following compounds:

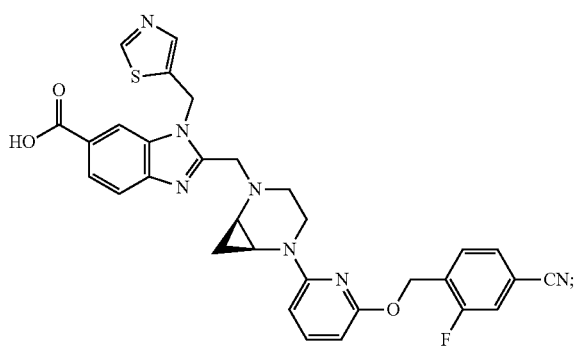

271
-continued
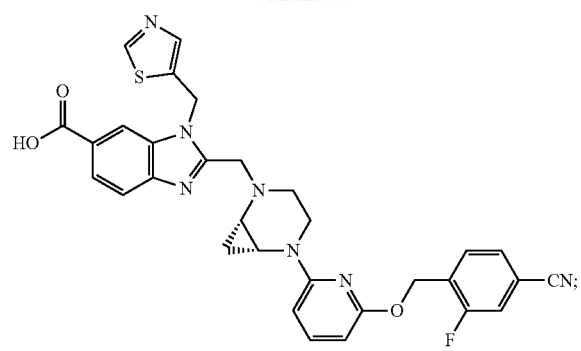
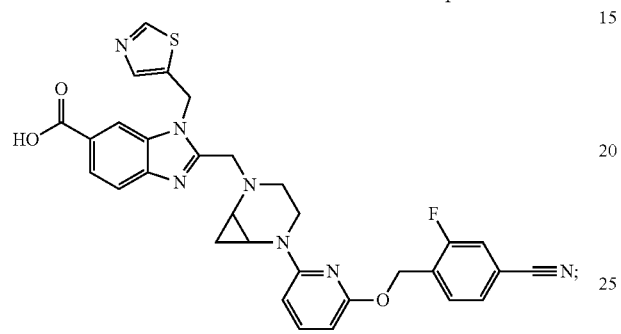
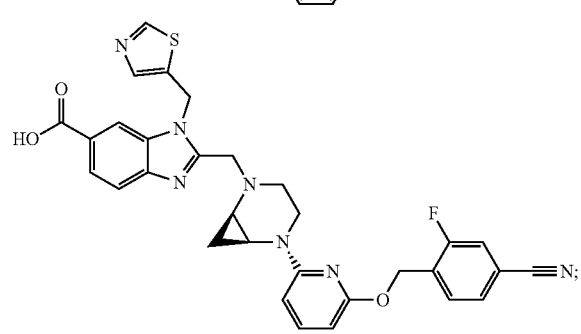
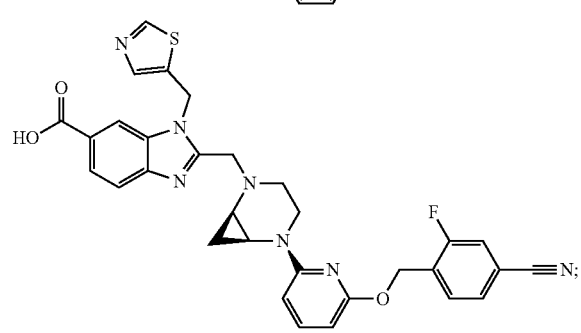
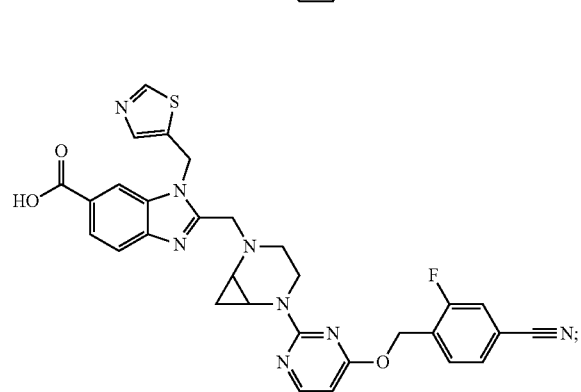
272
-continued
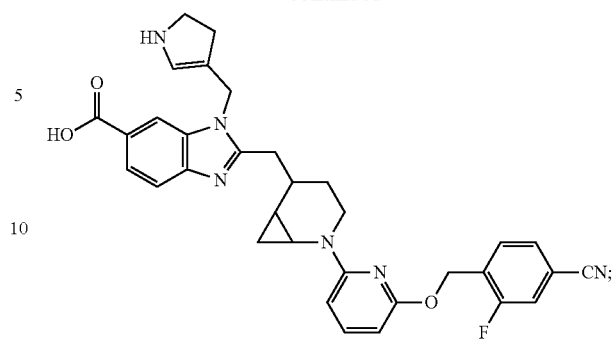
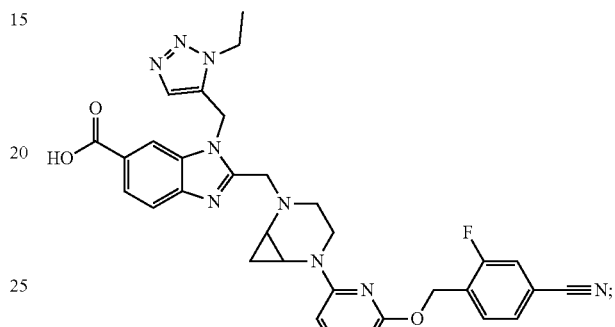
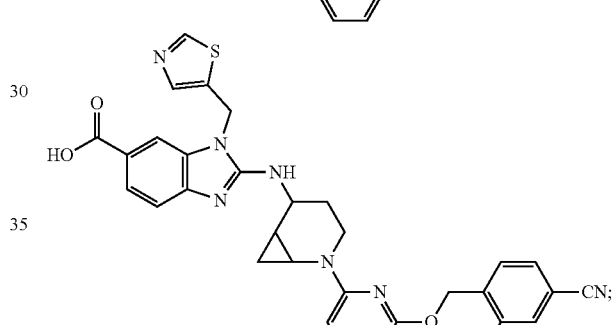
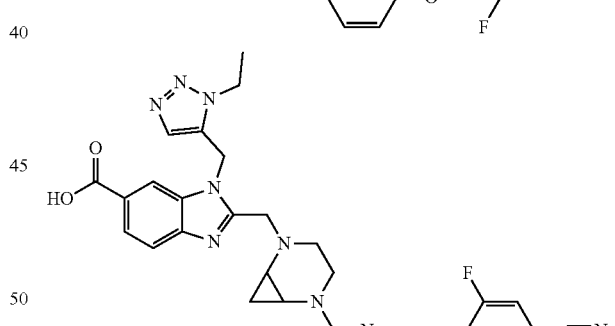
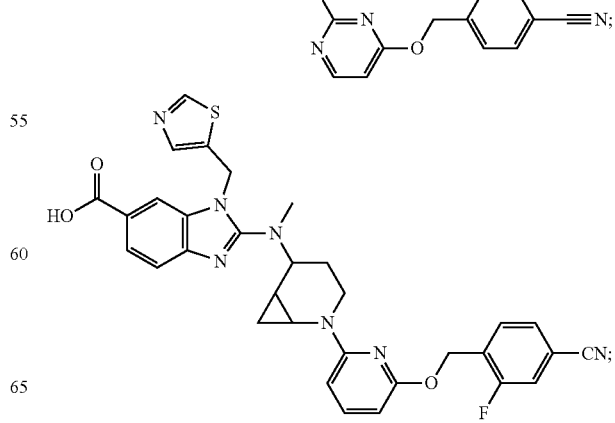

273
-continued
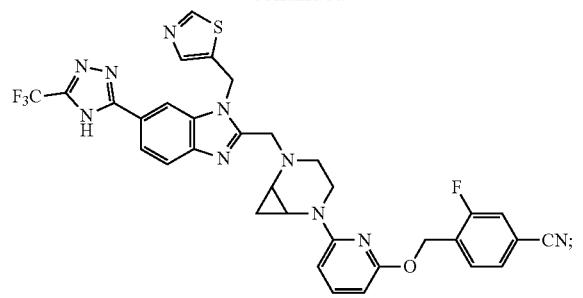
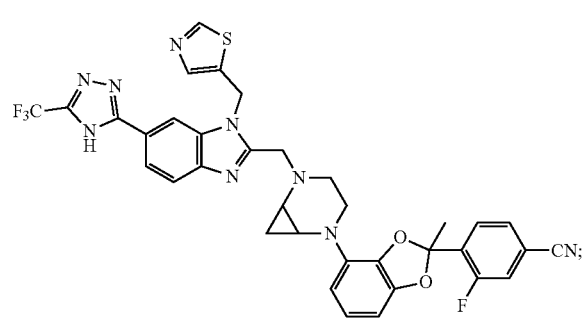
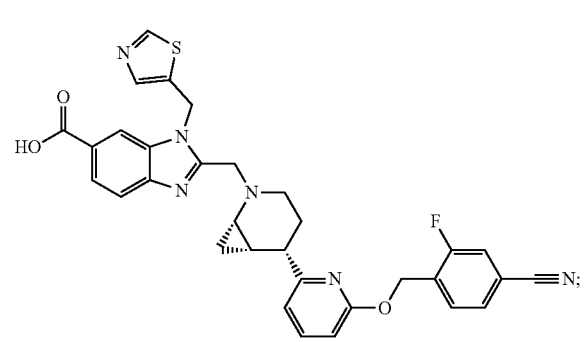
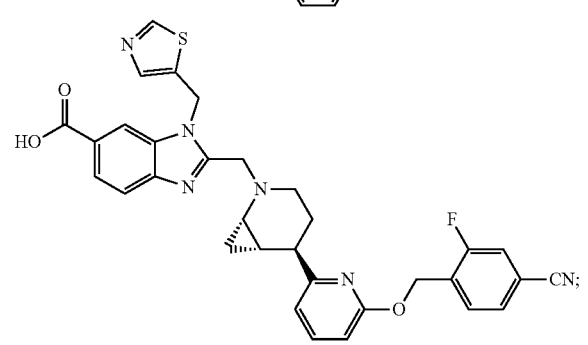
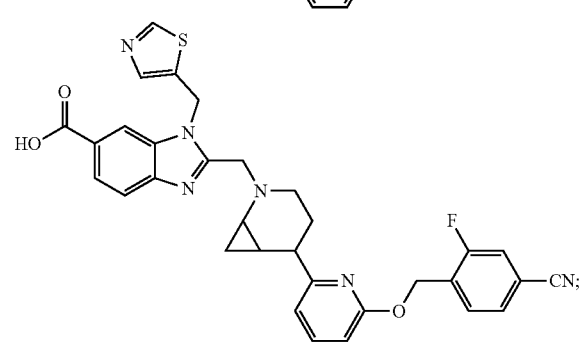
274
-continued
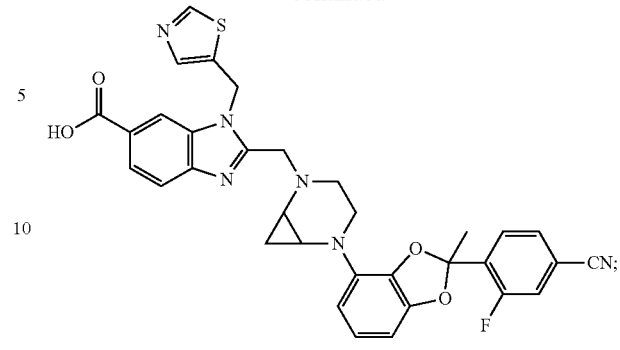
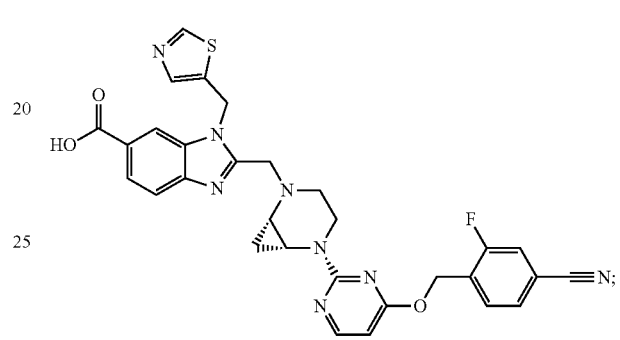
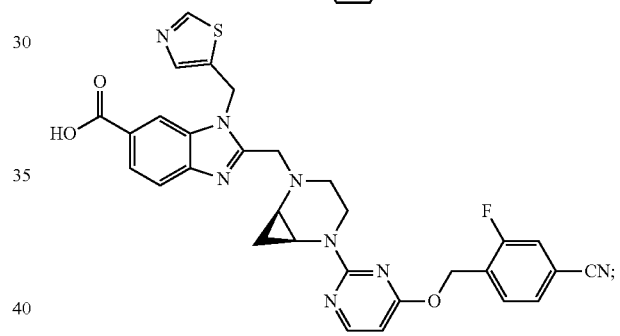
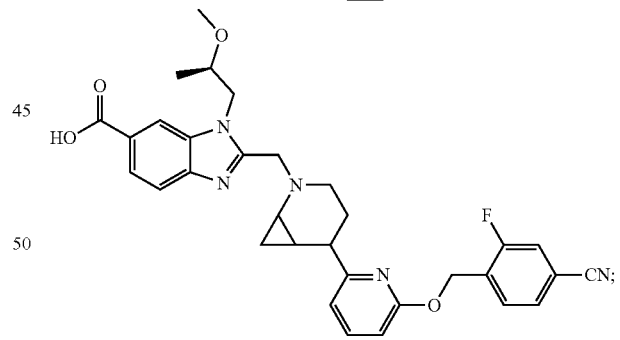
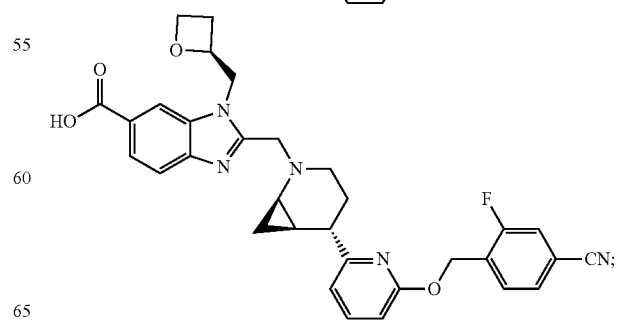

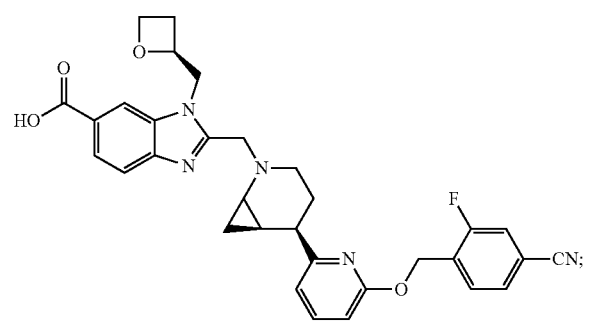
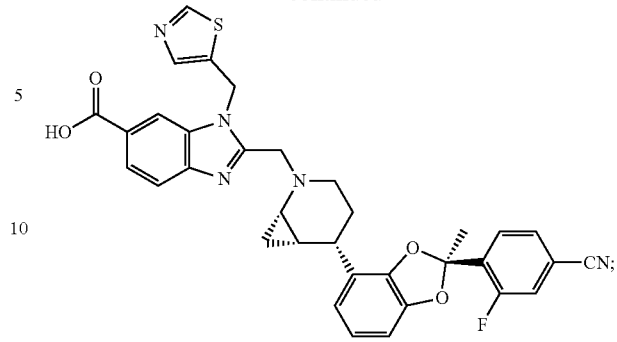
-continued
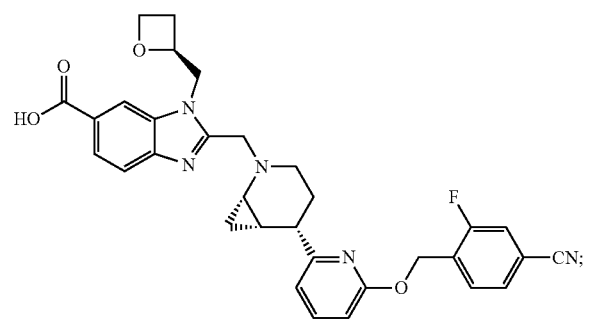
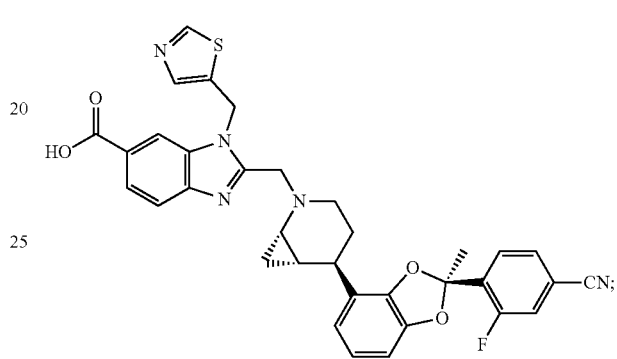
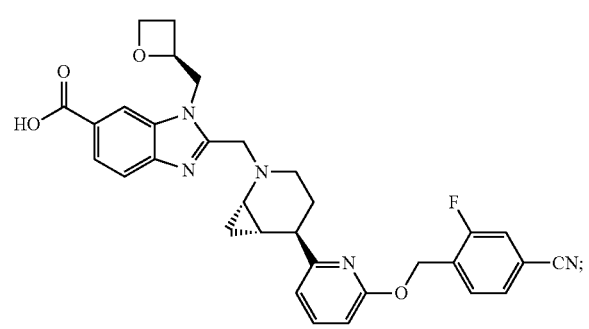
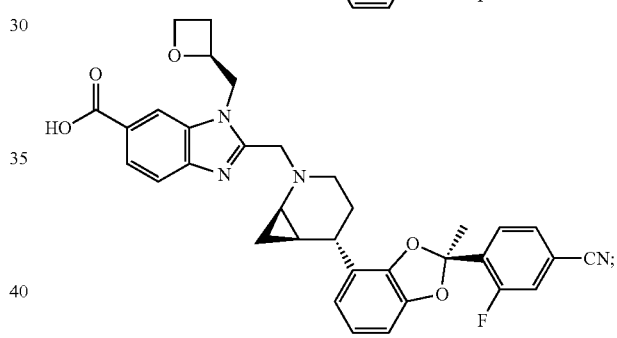
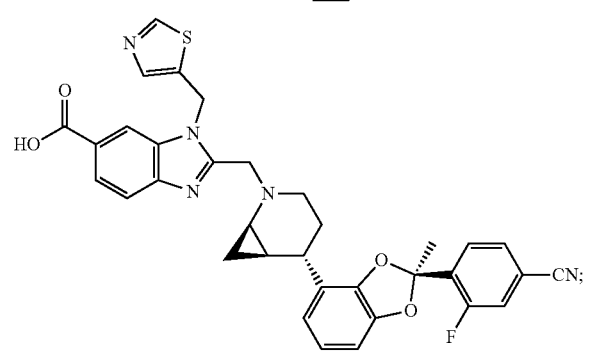
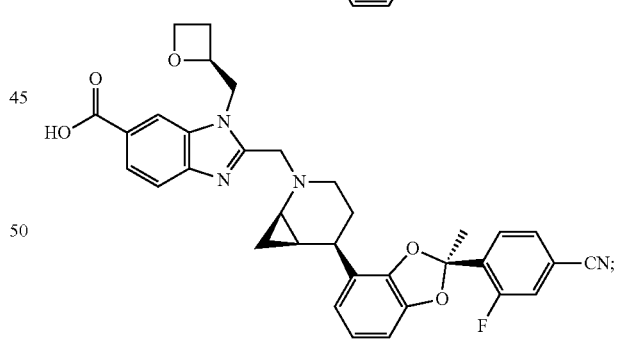
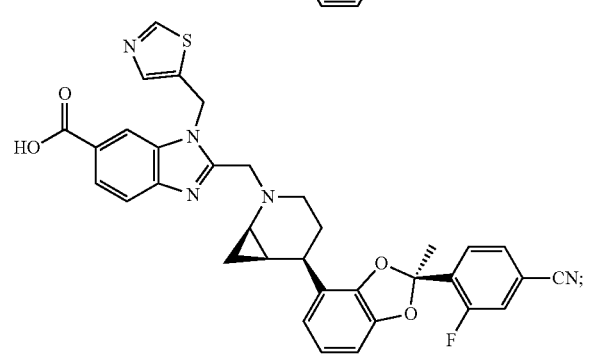
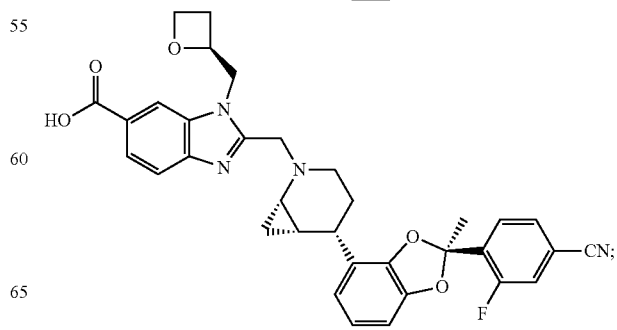

-continued
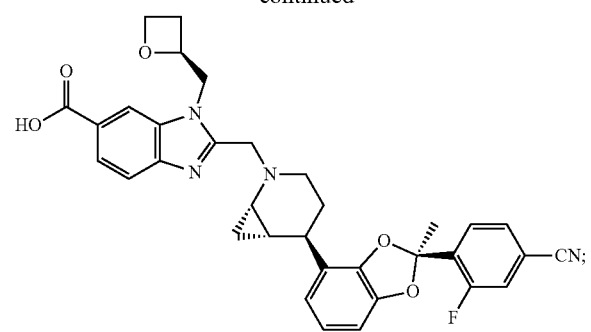
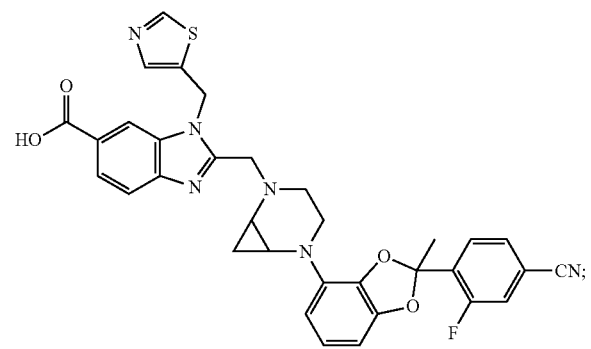
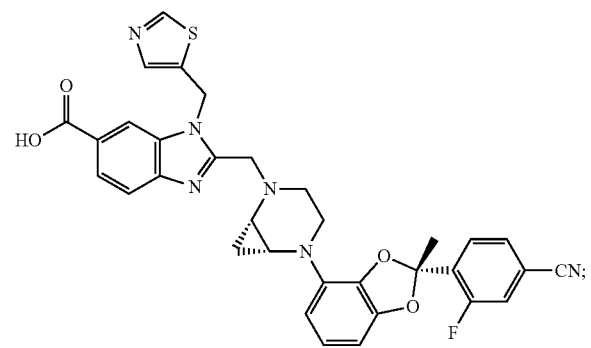
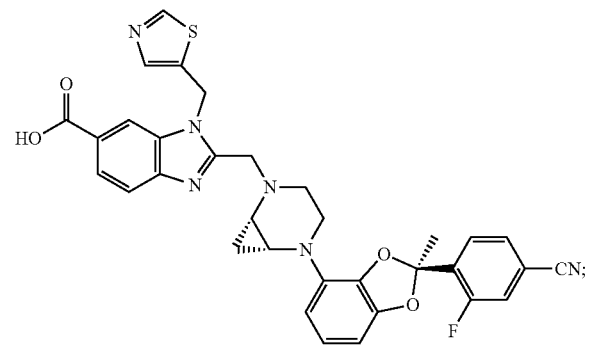
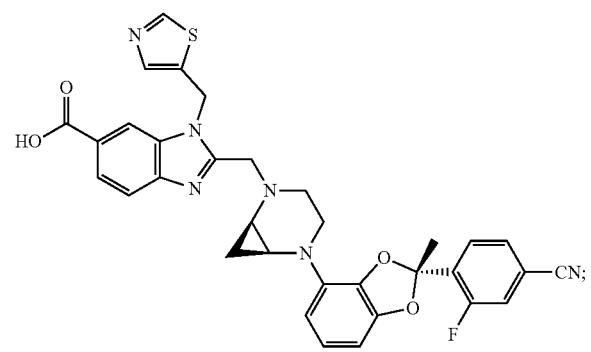
-continued
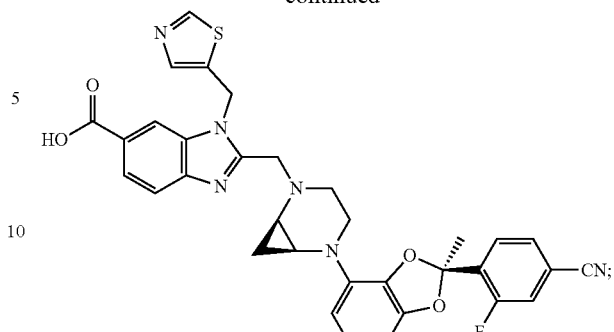
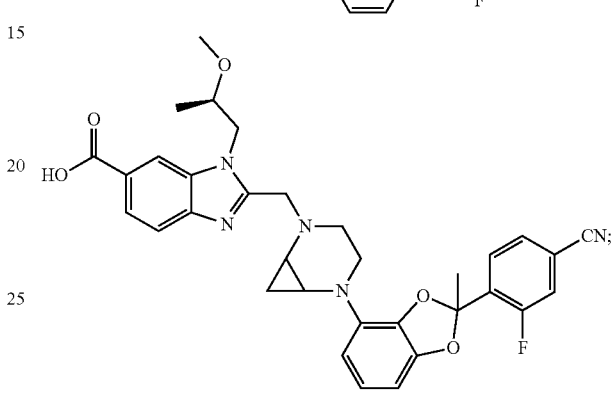
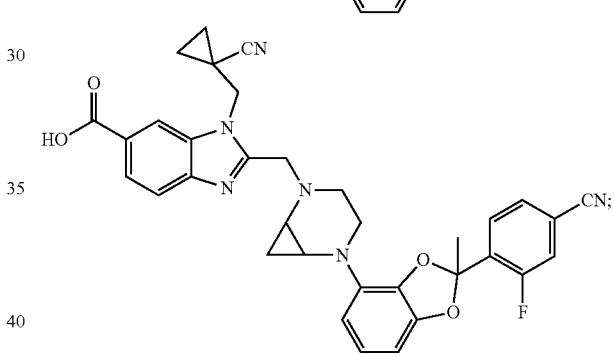
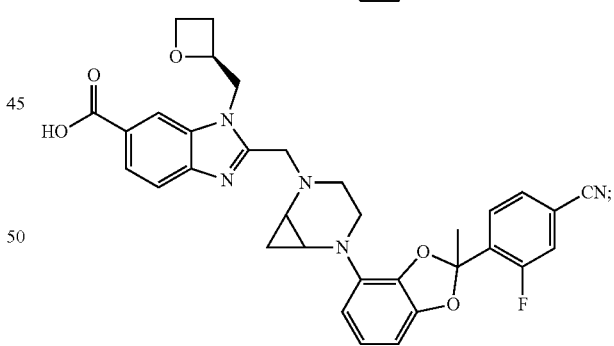
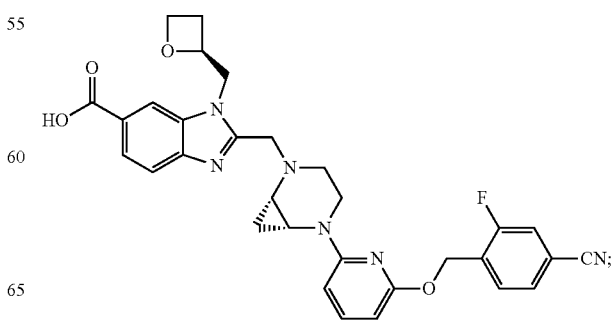

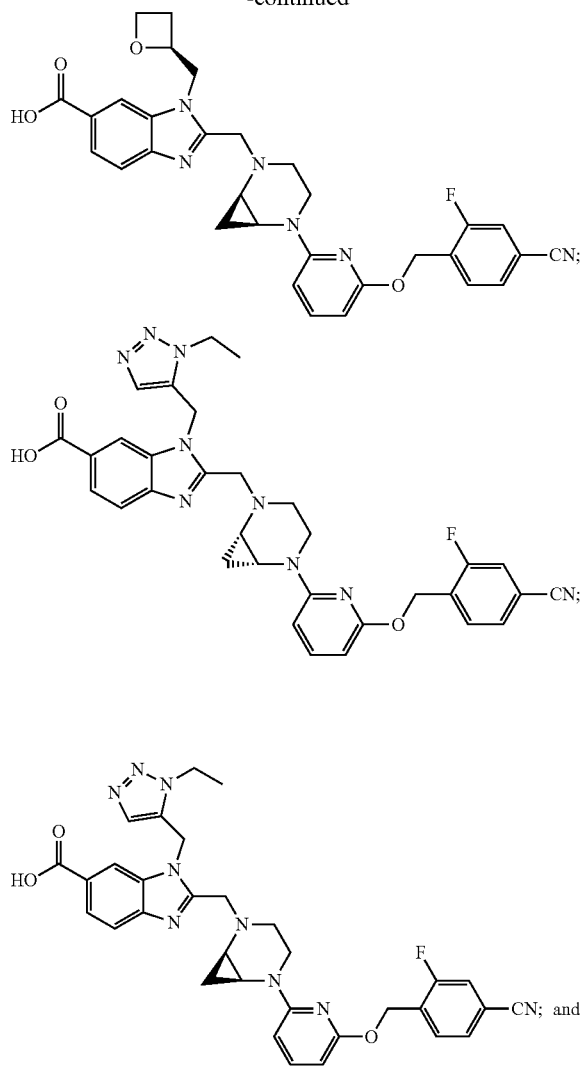

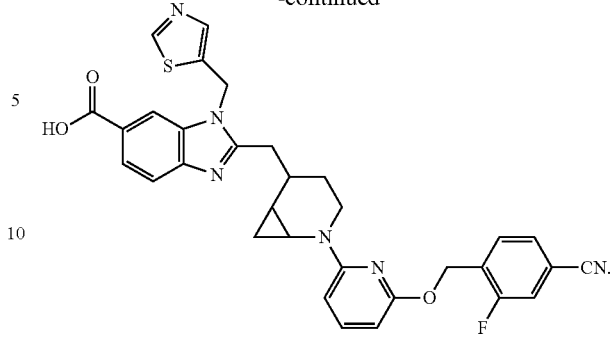

19. A pharmaceutical composition comprising the compound of claim 1, or a pharmaceutically acceptable salt thereof, and a pharmaceutically acceptable excipient.

20. A method of treating a disease mediated by glucagon-like peptide-1 receptor (GLP-1R) in an individual in need thereof, comprising administering to the individual a therapeutically effective amount of the compound of claim 1, or a pharmaceutically acceptable salt thereof.

21. The method of claim 20, wherein the disease is a liver disease.

22. The method of claim 21, wherein the liver disease is primary biliary cirrhosis (PBC), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, viral hepatitis, alcoholic liver disease, nonalcoholic fatty liver disease (NAFLD), nonalcoholic steatohepatitis (NASH), graft versus host disease, transplant liver regeneration, congenital hepatic fibrosis, choledocholithiasis, granulomatous liver disease, intra- or extrahepatic malignancy, Sjogren's syndrome, sarcoidosis, Wilson's disease, Gaucher's disease, hemochromatosis, or oti-antitrypsin deficiency.

23. The method of claim 20, wherein the disease is:
    (i) diabetes;
    (ii) a cardiometabolic disease; and/or
    (iii) obesity.

* * * * *